United States Patent [19]

Naka et al.

[11] Patent Number: 5,583,141
[45] Date of Patent: Dec. 10, 1996

[54] HETEROCYCLIC COMPOUNDS AND THEIR USE AS ANGIOTENSIN ANTAGONISTS

[75] Inventors: Takehiko Naka; Yoshiyuki Inada, both of Hyogo, Japan

[73] Assignee: Takeda Chemical Industries, Ltd., Osaka, Japan

[21] Appl. No.: 291,435

[22] Filed: Aug. 16, 1994

Related U.S. Application Data

[62] Division of Ser. No. 80,259, Jun. 23, 1993, Pat. No. 5,354,766, which is a division of Ser. No. 904,452, Jun. 25, 1992, Pat. No. 5,243,054.

[30] Foreign Application Priority Data

| Jun. 27, 1991 | [JP] | Japan | 3-157194 |
| Jul. 29, 1991 | [JP] | Japan | 3-188882 |
| Jul. 31, 1991 | [JP] | Japan | 3-192054 |
| Aug. 12, 1991 | [JP] | Japan | 3-288217 |
| Sep. 19, 1991 | [JP] | Japan | 3-239766 |
| Dec. 24, 1991 | [JP] | Japan | 3-341107 |

[51] Int. Cl.$^6$ .......... A61K 31/435; A61K 31/42; C07D 471/04; C07D 285/08
[52] U.S. Cl. .......... 514/303; 514/291; 514/361; 514/364; 544/236; 544/280; 544/281; 546/80; 548/122; 548/129; 548/132
[58] Field of Search .......... 546/118, 80; 548/122, 548/129, 132; 544/236, 281, 280; 514/291, 303, 361, 364

[56] References Cited

U.S. PATENT DOCUMENTS

| 4,880,804 | 11/1989 | Carini et al. | 546/199 |
| 5,196,444 | 3/1992 | Naka et al. | 514/381 |
| 5,268,375 | 12/1993 | Bernhart et al. | 514/269 |
| 5,354,766 | 10/1994 | Naka et al. | 514/364 |
| 5,412,097 | 5/1995 | Chakravarty et al. | 546/118 |

FOREIGN PATENT DOCUMENTS

| 28833 | 5/1981 | European Pat. Off. |
| 28834 | 5/1981 | European Pat. Off. |
| 149543 | 7/1985 | European Pat. Off. |
| 245637 | 11/1987 | European Pat. Off. |
| 253310 | 1/1988 | European Pat. Off. |
| 291969 | 11/1988 | European Pat. Off. |
| 323841 | 7/1989 | European Pat. Off. |
| 392317 | 10/1990 | European Pat. Off. |
| 399732 | 11/1990 | European Pat. Off. |
| 400835 | 12/1990 | European Pat. Off. |
| 0407102 | 1/1991 | European Pat. Off. |
| 411766 | 2/1991 | European Pat. Off. |
| 0411507 | 2/1991 | European Pat. Off. |
| 420237 | 4/1991 | European Pat. Off. |
| 425921 | 5/1991 | European Pat. Off. |
| 0425921 | 5/1991 | European Pat. Off. |
| 432737 | 6/1991 | European Pat. Off. |
| 430300 | 6/1991 | European Pat. Off. |
| 0434038 | 6/1991 | European Pat. Off. |
| 0432737 | 6/1991 | European Pat. Off. |
| 0430300 | 6/1991 | European Pat. Off. |
| 501892 | 9/1992 | European Pat. Off. |
| 234744 | 9/1992 | New Zealand . |
| 234742 | 10/1992 | New Zealand . |
| 241659 | 3/1993 | New Zealand . |

*Primary Examiner*—Bernard Dentz
*Attorney, Agent, or Firm*—Foley & Lardner

[57] ABSTRACT

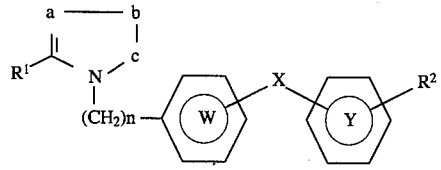

Compounds shown by the above formula or salt thereof show a strong angiotensin II antagonistic activity and hypotensive action and CNS activity, and are useful as therapeutic agents of circulatory diseases such as hypertensive diseases and heart diseases (e.g. hypercardia, heart failure, cardiac infarction), strokes, cerebral apoplexy, nephritis, atherosclerosis, Alzheimer's disease, senile dementia, etc.

32 Claims, No Drawings

HETEROCYCLIC COMPOUNDS AND THEIR USE AS ANGIOTENSIN ANTAGONISTS

This application is a divisional of Ser. No. 08/080,259 filed Jun. 23, 1993 now U.S. Pat. No. 5,354,766, which is a divisional of Ser. No. 07/904,452 filed Jun. 25, 1992 now U.S. Pat. No. 5,243,054 issued Sep. 7, 1993.

FIELD OF THE INVENTION

This invention relates to novel heterocyclic compounds having excellent pharmacological actions and intermediates for the synthesis thereof.

More specifically, the present invention relates to compounds of the general formula

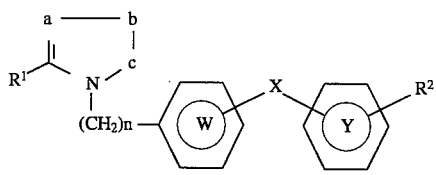

[wherein $R^1$ is an optionally substituted hydrocarbon residue which is optionally bonded through a hetero-atom; $R^2$ is an optionally substituted 5–7 membered heterocyclic residue having, as a group capable of constituting the ring, a carbonyl group, a thiocarbonyl group, an optionally oxidized sulfur atom or a group convertible into them; X is a direct bond or a spacer having an atomic length of two or less between the ring Y and the ring W; W and Y are independently an optionally substituted aromatic hydrocarbon residue optionally containing a hetero-atom or an optionally substituted heterocyclic residue; n is an integer of 1 or 2; a and b forming the heterocyclic residue are independently one or two optionally substituted carbon or hetero atoms; c is an optionally substituted carbon or hetero atom; and, in the group of the formula

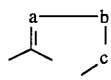

substituents on adjacent two atoms forming the ring are optionally bonded to each other to form a 5–6 membered ring together with the two atoms forming the ring] or a salt thereof.

BACKGROUND OF THE INVENTION

The renin-angiotensin system is involved in the homeostatic function to control systemic blood pressure, the volume of body fluid, balance among the electrolytes, etc., associated with the aldosterone system. The relationship between the renin-angiotensin system and hypertension has been clarified by the development of angiotensin II (AII) converting enzyme inhibitors (ACE inhibitor) which counteract angiotensin II with its strong vasoconstrictive action. Since angiotensin II constricts blood vessel to elevate blood pressure via the angiotensin II receptors on the cellular membranes, angiotensin II antagonists, like the ACE inhibitors, can be used for treating hypertension caused by angiotensin. It has been reported that a number of angiotensin II analogues such as saralasin, [Sar¹, Ile⁸]AII and the like possess potent angiotensin II antagonist activity. It has, however, been reported that, when peptide antagonists are administered non-orally, their actions are not prolonged and, when administered orally, they are ineffective [M. A. Ondetti and D. W. Cushman, Annual Reports in Medicinal Chemistry, 13, 82–91 (1978)].

On the other hand, for solving the problems observed in these peptide angiotensin II antagonists, studies on non-peptide angiotensin II antagonists have been developed. In the earliest studies in this field, imidazole derivatives having angiotensin II antagonist activity have been disclosed in JPA S56(1981)-71073, S56(1981)-71074, S57(1982)-98270 and S58(1983)-157768, U.S. Pat. Nos. 4,355,040 and 4,340,598, etc. Later, improved imidazole derivatives are disclosed in EP-0253310, EP-0291969, EP-0324377, EP-403158, WO-9100277, JPA S63(1988)-23868 and JPA H1(1989)-117876; pyrrole, pyrazole and triazole derivatives in EP-0323841, EP-0409332 and JPA H1(1989)-287071; benzimidazole derivatives in U.S. Pat. No. 4,880,804, EP-0392317, EP-0399732, EP-0400835 and JPA H3(1991)-63264; azaindene derivatives in EP-0399731; pyrimidone derivatives in EP-0407342; and quinazolinone derivatives in EP-0411766; as angiotensin II antagonists.

However, in order to become a therapeutically useful drug, angiotensin II antagonists are required to have a strong and long-lasting angiotensin II antagonistic action by oral administration. As shown in so far known literature references, the preferable angiotensin II antagonist is considered to have an acid group, for example, tetrazole group or carboxyl group on the biphenyl side chain, especially tetrazole group as the most preferable one. Clinical tests of compounds having the tetrazole group for anti-hypertension agents are being conducted [Y. Christen, B. Waeber, J. Nussberger, R. J. Lee, P. B. M. W. M. Timmermans, and H. R. Brunner, Am. J. Hypertens., 4, 350S (1991)]. However, compounds having tetrazole ring and azide compounds to be used for synthesizing them have been known as involving a danger of explosion, which becomes a serious problem to the large scale preparation and production.

OBJECT OF THE INVENTION

The present invention is to provide a novel compound having a heterocyclic residue substitutable for the tetrazole or carboxylic group which has strong angiotensin II antagonistic action and anti-hypertensive action when administered orally and which becomes a therapeutically useful drug.

The present inventors considered that compounds blocking renin-angiotensin system as well as being clinically useful for the treatment of circulatory diseases such as hypertensive diseases, heart diseases (hypercardia, heart failure, cardiac infarction, etc.), cerebral apoplexy, nephritis, atherosclerosis, etc. are required to have potent angiotensin II receptor antagonistic activity and to show a strong and long-lasting angiotensin II antagonistic and hypotensive action by oral administration, and they have made extensive and intensive studies on a compound having angiotension II antagonistic activity for years.

As a result, the present inventors have found that novel heterocyclic compounds (I) have a potent angiotensin II receptor antagonistic activity as well as strong and long-lasting angiotensin II antagonistic and anti-hypertensive actions by oral administration.

SUMMARY OF THE INVENTION

More specifically, the present invention relates to (1) a compound of the formula

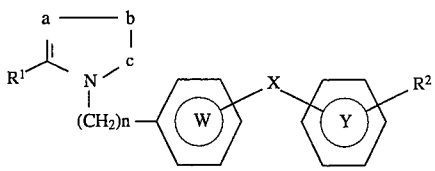 (I)

[wherein R¹ is an optionally substituted hydrocarbon residue which is optionally bonded through a heteroatom; R² is an optionally substituted 5–7 membered heterocyclic residue having, as a group capable of constituting the ring, a carbonyl group, a thiocarbonyl group, an optionally oxidized sulfur atom or a group convertible into them; X is a direct bond or a spacer having an atomic length of two or less between the ring Y and the ring W; W and Y are independently an optionally substituted aromatic hydrocarbon residue optionally containing a hetero-atom or an optionally substituted heterocyclic residue; n is an integer of 1 or 2; a and b forming the heterocyclic residue are independently one or two optionally substituted carbon or hetero atoms; c is an optionally substituted carbon or hetero atom; and, in the group of the formula

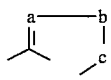

substituents on adjacent two atoms forming the ring are optionally bonded to each other to form a 5–6 membered ring together with the two atoms forming the ring] or a salt thereof, more preferably, (2) a compound of the formula

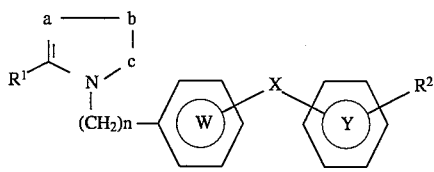 (Iᵃ)

[wherein R¹ is an optionally substituted hydrocarbon residue which is optionally bonded through a heteroatom; R² is an optionally substituted 5–7 membered heterocyclic residue having, as a group capable of constituting the ring, a carbonyl group, a thiocarbonyl group, an optionally oxidized sulfur atom or a group convertible into them; X is a direct bond or a spacer having an atomic length of two or less between the ring Y and the ring W; W and Y are independently an optionally substituted aromatic hydrocarbon residue optionally containing a hetero-atom or an optionally substituted heterocyclic residue; n is an integer of 1 or 2; a and b forming the heterocyclic residue are independently one or two optionally substituted carbon or hetero atoms; c is an optionally substituted carbon or hetero atom; and, when a is an optionally substituted carbon atom, R¹ and a may optionally be bonded to each other to form a group of the formula

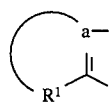

forming a ring] or a slat thereof, or (3) a compound represented of the formula

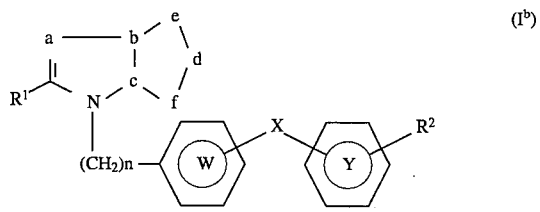 (Iᵇ)

[wherein R¹ is an optionally substituted hydrocarbon residue which is optionally bonded through a heteroatom; R² is an optionally substituted 5–7 membered heterocyclic residue having, as a group capable of constituting the ring, a carbonyl group, a thiocarbonyl group, an optionally oxidized sulfur atom or a group convertible into them; X is a direct bond or a spacer having an atomic length of two or less between the ring Y and the ring W; W and Y are independently an optionally substituted aromatic hydrocarbon residue optionally containing a hetero-atom or an optionally substituted heterocyclic residue; a and e forming the heterocyclic residue are independently one or two optionally substituted carbon or hetero atoms; d and f forming the heterocyclic residue are independently one optionally substituted carbon or hetero atom; b and c are independently one optionally substituted carbon or nitrogen atom; n denotes an integer of 1 or 2; and, when a is an optionally substituted carbon atom, R¹ and a may optionally be bonded to each other to form a group of the formula

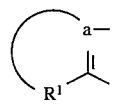

forming a ring] or a salt thereof.

DETAILED DESCRIPTION OF THE INVENTION

Referring to the general formula (I), examples of the hydrocarbon residue represented by R¹ include alkyl, alkenyl, alkynyl, cycloalkyl, aryl and aralkyl groups. Among them, alkyl, alkenyl and cycloalkyl groups are preferable. The hydrocarbon residue may be bonded to the ring through a hetero atom or further substituted with, for example, an optionally substituted hydrocarbon residue which may be bonded through a hetero-atom.

The alkyl group represented by R¹ is a straight or branched lower alkyl group having 1 to about 8 carbon atoms, as exemplified by methyl, ethyl, propyl, isopropyl, butyl, isobutyl, sec-butyl, t-butyl, pentyl, i-pentyl, hexyl, heptyl or octyl.

The alkenyl group represented by R¹ is straight or branched lower alkenyl group having 2 to about 8 carbon atoms, as exemplified by vinyl, propenyl, 2-butenyl, 3-butenyl, isobutenyl or 2-octenyl.

The alkynyl group represented by R¹ is a straight or branched lower alkynyl group having 2 to about 8 carbon atoms, as exemplified by ethynyl, 2-propinyl, 2-butynyl, 2-pentynyl or 2-octynyl.

The cycloalkyl group represented by R¹ is a lower cycloalkyl group having 3 to about 6 carbon atoms, as exemplified by cyclopropyl, cyclobutyl, cyclopentyl or cyclohexyl.

The above-mentioned alkyl, alkenyl, alkynyl or cycloalkyl group may optionally be substituted with, for example, hydroxyl group, an optionally substituted amino group [e.g. amino, N-lower (1–4C) alkylamino, or N,N-di-lower (1–4C)alkylamino], halogen, a lower (1–4C) alkoxy group or a lower (1–4C) alkylthio group.

The aralkyl group represented by $R^1$ is, for example, a phenyl-lower (1–4C) alkyl such as benzyl or phenethyl, and the aryl group represented by $R^1$ is, for example, phenyl.

The above-mentioned aralkyl or aryl group may optionally have, on an optional position of its benzene ring, for example, halogen (e.g. F, Cl or Br), nitro, an optionally substituted amino group [e.g. amino, N-lower(1–4C) alkyl amino, or N,N-di-lower(1–4C) alkylamino], lower(1–4C) alkoxy (e.g. methoxy, or ethoxy), lower(1–4C) alkylthio (e.g. methylthio or ethylthio) or lower(1–4C) alkyl (e.g. methyl or ethyl).

Among the above-exemplified groups represented by $R^1$, optionally substituted alkyl or alkenyl groups (e.g. a lower(1–5C) alkyl or lower(2–5C) alkenyl group optionally substituted with hydroxyl group, amino group, halogen or a lower(1–4C) alkoxy group) are preferable.

The above-mentioned $R^1$ may optionally be bonded through a hetero-atom [e.g. nitrogen [$N(R^9)$] ($R^9$ stands for hydrogen or a lower(1–4C) alkyl], oxygen or sulfur [—S(O)m— (m denotes an integer of 0 to 2)], etc.], and, among them, optionally substituted alkyl or alkenyl groups bonded through a hetero-atom (e.g. methylamino, ethylamino, propylamino, propenylamino, isopropylamino, allylamino, butylamino, isobutylamino, dimethylamino, methylethylamino, methoxy, ethoxy, propoxy, isopropoxy, propenyloxy, allyloxy, butoxy, isobutoxy, sec-butoxy, t-butoxy, 2-butenyloxy, 3-butenyloxy, isobutenyloxy, pentoxy, isopentoxy, hexyloxy, methylthio, ethylthio, propylthio, isopropylthio, allylthio, butylthio, isobutylthio, sec-butylthio, t-butylthio, 2-butenylthio, 3-butenylthio, isobutenylthio, pentylthio, isopentylthio, hexylthio, etc.) are preferable.

Examples of optionally substituted aromatic hydrocarbon or heterocyclic residues optionally containing a hetero-atom, which are represented by Y and W, include aromatic hydrocarbon residues such as phenyl, and 4- to 7-membered monocyclic or condensed heterocyclic residues containing one or more of N, S and O, for example, pyridyl, pyrimidinyl, pyridazinyl, pyrazinyl, thienyl, furyl, pyrrolyl, imidazolyl, pyrazolyl, isothiazolyl, isooxazolyl, benzofuranyl, isobenzofuranyl, indolizinyl, isoindolyl, 3H-indolyl, indolyl, 1H-indazolyl, purinyl, 4H-quinolizinyl, isoquinolyl, quinolyl, phthalazinyl, naphthyridinyl, quinoxalinyl, quinazolinyl, cinnolinyl and pteridinyl (preferably phenyl).

The above-mentioned aromatic hydrocarbon or heterocyclic residues optionally containing a heteroatom, which are represented by Y, have a substituent represented by $R^2$ as exemplified by an optionally substituted 5- to 7-membered (preferably 5- to 6-membered) monocyclic heterocyclic residue containing one or more of N, S and O (preferably N-containing heterocyclic residue having hydrogen atom capable of being protonated) or a group convertible thereinto. The group represented by $R^2$ are shown below:

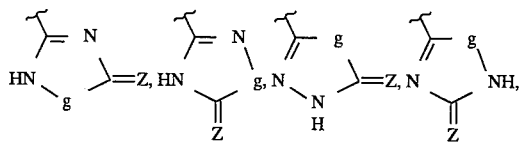

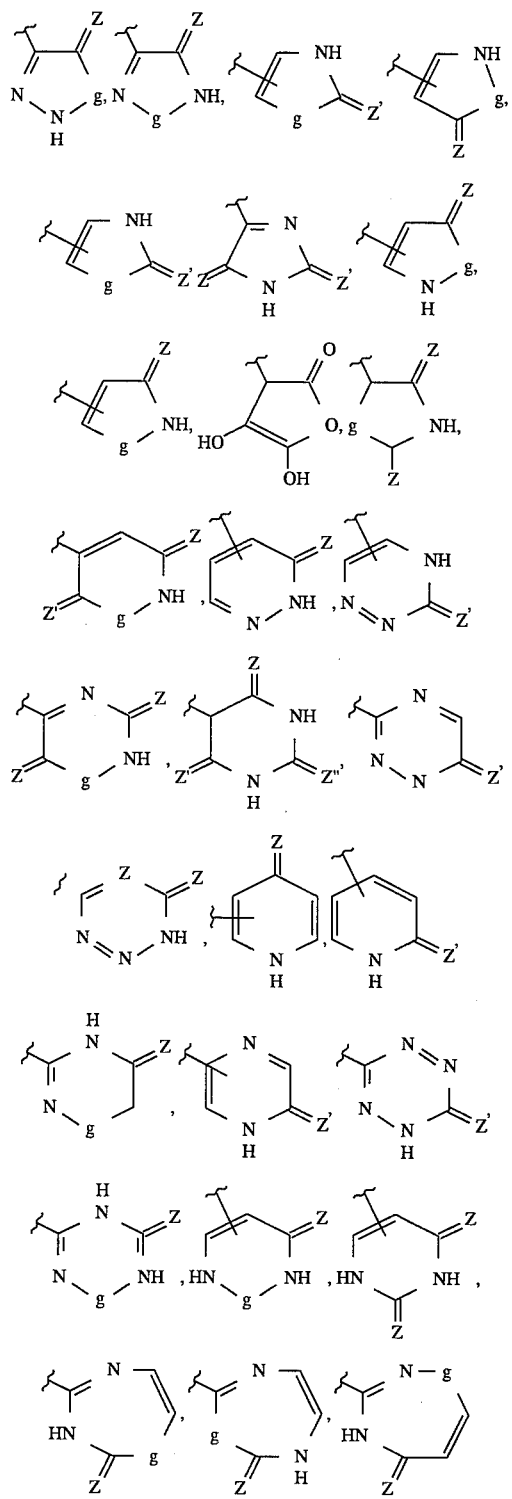

And, besides the case of carbon—carbon linkage as in the above, a group represented by $R^2$ may optionally be bonded with an optionally substituted aromatic hydrocarbon or heterocyclic residue optionally containing a hetero-atom, which is represented by Y, in the case of g=—NH— in the above formula, through one of the plural number of existing nitrogen atoms.

For example, when

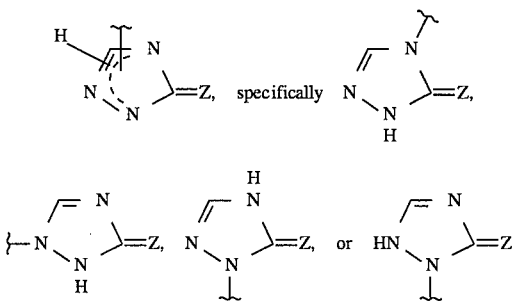

represents that group.

Other examples of $R^2$ bonded through the nitrogen atom include

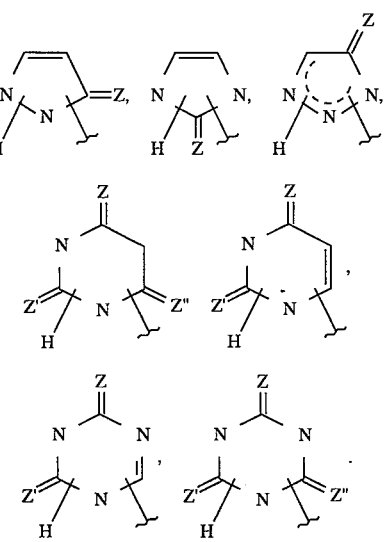

In the above formulae, g=—$CH_2$—, —$NR^9$—, O atom or $$-\overset{(O)_m}{\underset{|}{S}}-;$$

>=Z, >=Z' and >=Z" respectively stand for a carbonyl group, a thiocarbonyl group or an optionally oxidized sulfur atom (e.g. S, S(O), and $S(O)_2$) (preferably a carbonyl or thiocarbonyl group, more preferably a carbonyl group), m denotes an integer of 0, 1 or 2, and $R^9$ stands for hydrogen atom or an optionally substituted lower alkyl group.

Preferable groups represented by $R^2$ are, like oxadiazole or thiadiazole ring, those having —NH or —OH group as proton-donor and a carbonyl group, a thiocarbonyl group or sulfinyl group as proton acceptor simultaneously. And, while the heterocyclic residue represented by $R^2$ may optionally form a condensed ring by the linkage of substituents on the ring, the preferable ones are 5- to 6-membered heterocyclic residues, more preferably 5-membered ones. Among others, as $R^2$, as a group of the formula:

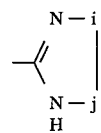

[wherein i is —O— or —S—, j is >=0, >=S or >S(O)m, and m is of the same meaning as defined above] is preferable. In case where Y is, for example, phenyl, $R^2$ may be substituted on any of the ortho-, meta- or para-positions, preferably the ortho-position.

And, while the above-mentioned heterocyclic residue ($R^2$) can exist in tautomeric forms as shown below, for example, three tautomers, a', b' and c',

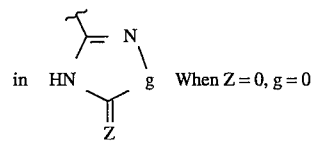

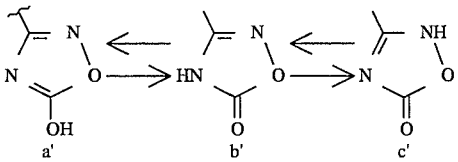

the heterocyclic residue represented by the formula

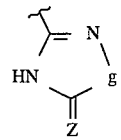

includes all of the above-mentioned a', b' and c'. And, the above-mentioned heterocyclic residue ($R^2$) may optionally be substituted with the group represented by $R^{10}$, as shown below.

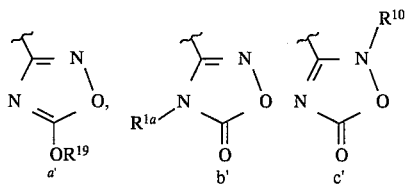

Examples of the group represented by $R^{10}$ mentioned above include groups represented by the formula— $CH(R^4)$—$OCOR^5$ [wherein $R^4$ stands for hydrogen, a 1–6C straight-chain or branched lower alkyl group (e.g. methyl, ethyl, n-propyl, isopropyl, n-butyl, isobutyl, t-butyl, n-pentyl, isopentyl, or neopentyl), a 2–6C straight-chain or branched lower alkenyl group or a 3–8C cycloalkyl group (e.g. cyclopentyl, cyclohexyl or cycloheptyl); $R^5$ stands for a 1–6C straight-chain or branched lower alkyl group (e.g. methyl, ethyl, n-propyl, isopropyl, n-butyl, isobutyl, secbutyl, t-butyl, n-pentyl, isopentyl or neopentyl), a 2–6C straight-chain or branched lower alkenyl group, a 3–8C cycloalkyl group (e.g. cyclopentyl, cyclohexyl or cycloheptyl), a 1–3C lower alkyl group substituted with a 3–8C cycloalkyl group (e.g. cyclopentyl, cyclohexyl or cycloheptyl) or an optionally substituted aryl group such as phenyl (e.g. benzyl, p-chlorobenzyl, phenethyl, cyclpentylmethyl or cyclohexylmethyl), a 2–3C lower alkenyl group substituted with a 3–8C cycloalkyl or an optionally substituted aryl group such as phenyl (e.g. a group having alkenyl moiety such as vinyl (e.g. cinnamyl), propenyl, allyl or isopropenyl), an optionally substituted aryl group such as phenyl (e.g. phenyl, p-tolyl or naphthyl), a 1–6C straight-chain or branched lower alkoxy group (e.g. methoxy, ethoxy, n-propoxy, isopropoxy, n-butoxy, isobutoxy, sec-butoxy, t-butoxy, n-pentyloxy, isopentyloxy or neopentyloxy), a 2–8C straight-chain or branched lower alkenyloxy group (e.g. allyloxy, or isobutenyloxy), a 3–8C cycloalkyloxy group (e.g. cyclopentyloxy, cyclohexyloxy or cycloheptyloxy), a 1–3C lower alkoxy group substituted with a 3–8C cycloalkyl (e.g. cyclopentyl, cyclohexyl, or cycloheptyl) or with an optionally substituted aryl such as phenyl (e.g. a group having alkoxy moiety such as methoxy, ethoxy, n-propoxy or isopropoxy, e.g. benzyloxy, phenethyloxy, cyclopentylmethyloxy, or cyclohexylmethyloxy), a 2–3C lower alkenyloxy group substituted with a 3–8C cycloalkyl (e.g. cyclopentyl, cyclohexyl, or cycloheptyl) or with an optionally substituted aryl such as phenyl (e.g. a group having alkenyloxy moiety such as vinyloxy (e.g. cinnamyloxy), propenyloxy, allyloxy or isopropenyloxy), an aryloxy group including optionally substituted phenoxy (e.g. phenoxy, p-nitrophenoxy or naphthoxy)], and an optionally substituted alkyl (e.g. lower (1–4C) alkyl) or acyl (e.g. lower (2–5C) alkanoyl or optionally substituted benzoyl). Examples of $R^{10}$ include methyl, ethyl, propyl, t-butyl, methoxymethyl, triphenylmethyl, cyanoethyl, acetyl, propionyl, pivaloyloxymethyl, 1-(cyclohexyloxycarbonyloxy) ethyl, 5-methyl-2-oxo-1,3-dioxolen-4-ylmethyl, acetoxymethyl, propionyloxymethyl n-butyryloxymethyl, isobutyryloxymethyl, 1-(ethoxycarbonyloxy)ethyl, 1-acetyloxy)ethyl, 1-(isobutyryloxy)ethyl, cyclohexylcarbonyloxymethyl, benzoyloxymethyl, cinnamyl, and cyclopentylcarbonyloxymethyl. Such groups may include substituents which are capable of easily converting into the initial heterocyclic residue represented by the formula

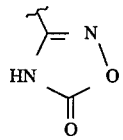

either chemically or biologically i.e. under physiological conditions (for example, an in vivo reaction such as oxidation, reduction or hydrolysis catalyzed by in vivo enzymes (what is called prodrug).

As the above-mentioned tautomers of heterocyclic residues (a', b' and c') and the heterocyclic residue (a", b" and c") substituted with $R^{10}$ are included in the heterocyclic residues represented by the substituent $R^2$ in the present invention, so the tautomers and their substituted compounds of various heterocyclic residues described in the foregoing are, as a matter of course, included in the substituent $R^2$ in the present invention. And, the substituent $R^2$ may have further substituents other than those represented by $R^{10}$ described above, as exemplified by an optionally substituted alkyl group (e.g. methyl and triphenylmethyl), halogen (e.g. F, Cl and Br), nitro, cyano, lower (1–4C) alkoxy, and an optionally substituted amino group (e.g. amino, methylamino, and dimethylamino), among others.

The aromatic hydrocarbon residue and the heterocyclic residue optionally containing one or more of N, O, and S atom may optionally have substituents as exemplified by halogen (e.g. F, Cl and Br), nitro, cyano, lower (1–4C) alkoxy, an optionally substituted amino group (e.g. amino, methylamino and dimethylamino).

X show that the adjacent ring W (e.g. phenylene group) is bonded to the ring Y (e.g. phenyl group) directly or through a spacer with an atomic chain of 2 or less (preferably a direct bond). As the spacer, any one can be exemplified, so long as it is a divalent chain in which the number of atoms constituting the straight chain is 1 or 2, and it may have a side chain, more specifically, lower (1–4C) alkylene, —CO—, —O—, —S—, —NH—, —CO—NH—, —O—$CH_2$—, —S—$CH_2$—, and —CH=CH—.

n denotes an integer of 1 or 2 (preferably 1).

Among the compounds shown by $R^2$, W, X, Y and n described above, those shown by the following formulae, for example, are preferable:

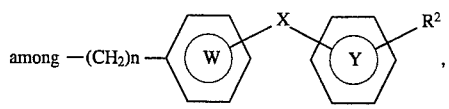

compounds shown by the formula, e.g.

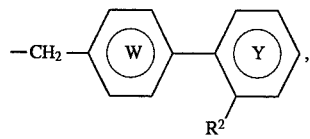

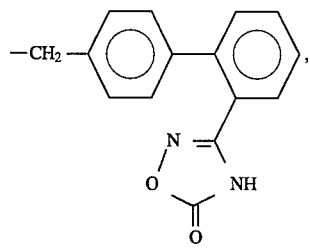

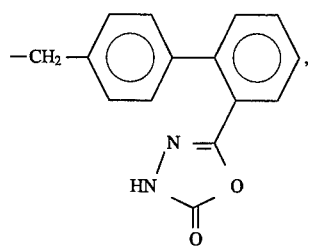

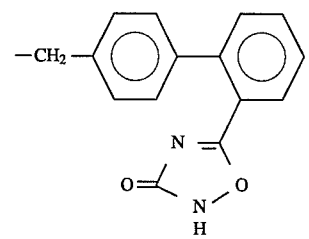

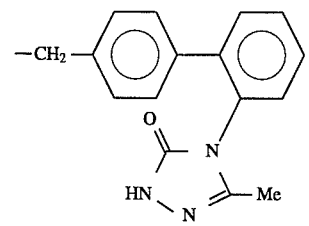

are preferable.

Typical examples of heterocyclic compounds represented by the formula

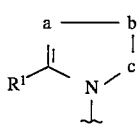 (II)

are specifically shown as follows. Incidentally, in the following formulae, $R^1$ is of the same meaning as defined above, and R stands for the formula:

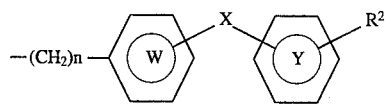

Examples of compounds shown by the formula (II), as compounds shown by formula,

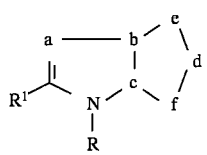 (II$^b$)

include the following, but are not limited thereto:

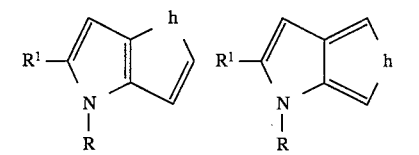

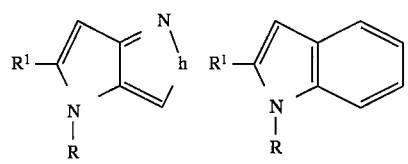

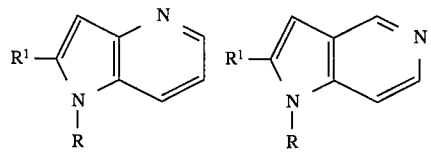

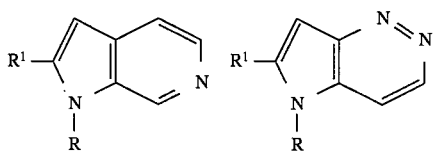

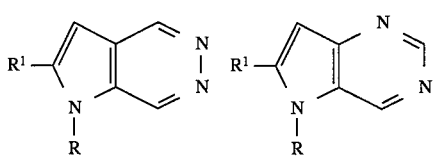

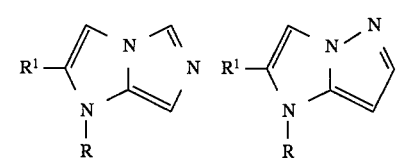

-continued

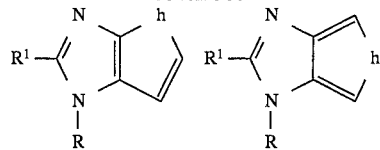

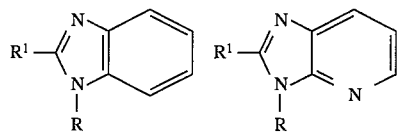

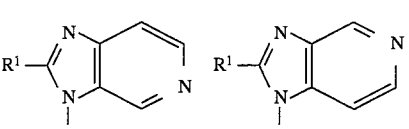

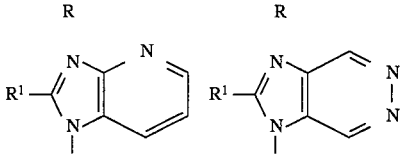

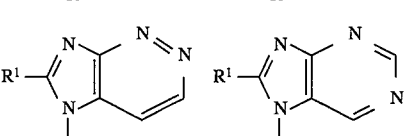

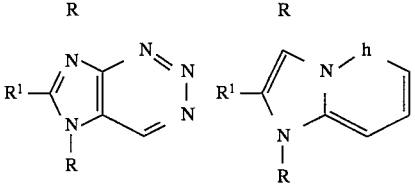

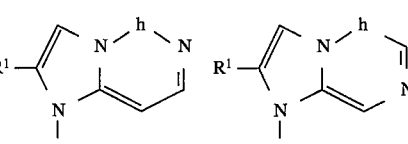

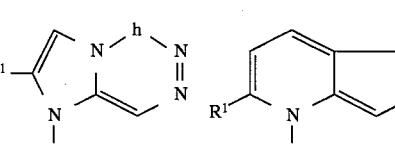

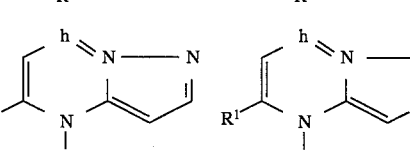

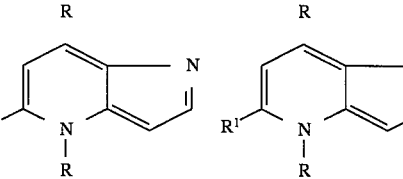

-continued
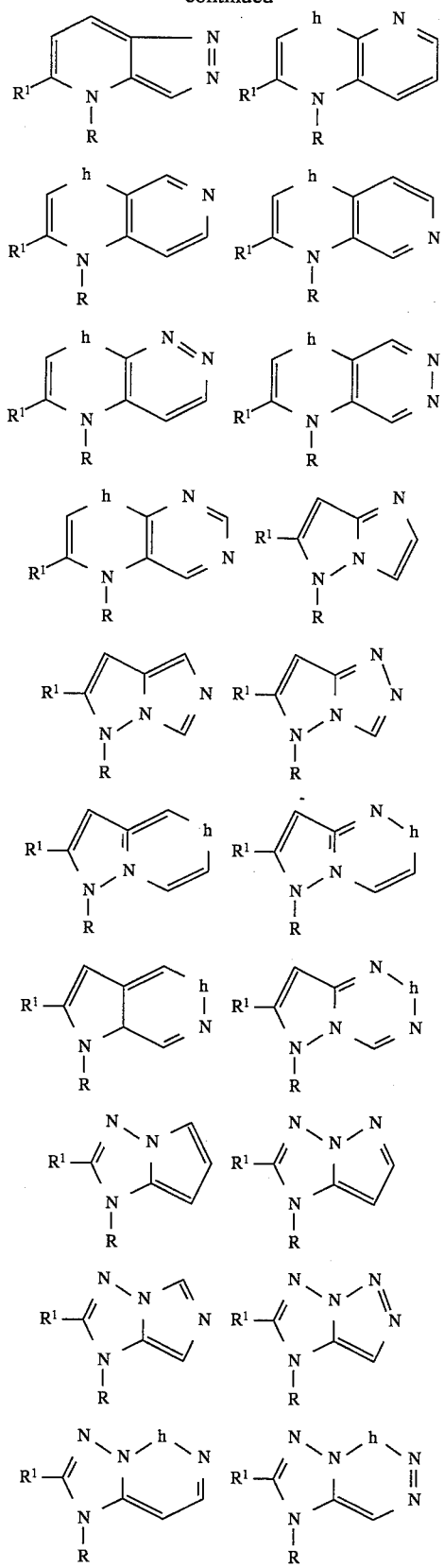
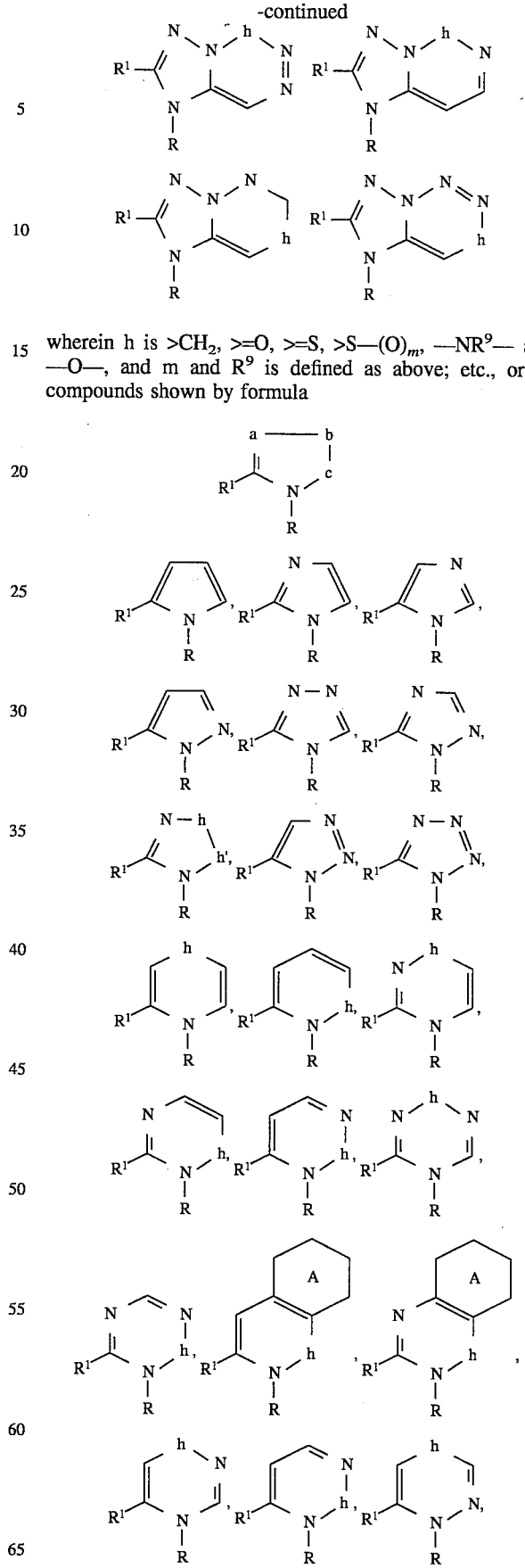
wherein h is >CH$_2$, >=O, >=S, >S—(O)$_m$, —NR$^9$— and —O—, and m and R$^9$ is defined as above; etc., or as compounds shown by formula
(II$^a$)

-continued

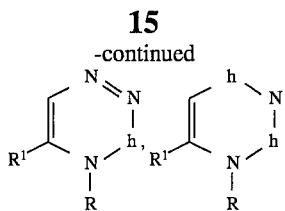

[wherein A stands for an optionally substituted aromatic hydrocarbon residue, optionally containing a hetero-atom, or heterocyclic residue (preferably aromatic hydrocarbon residue such as phenyl), h and h' each shows $>CH_2$, $>=O$, $>=S$, $>S-(O)_m$, $-NR^9-$ and $-O-$ and, m and $R^9$ are of the same meaning as defined above] are exemplified. These examples may further include the following:
formula the

may stand for a heterocyclic ring, and tricyclic hetercyclic compounds as shown below

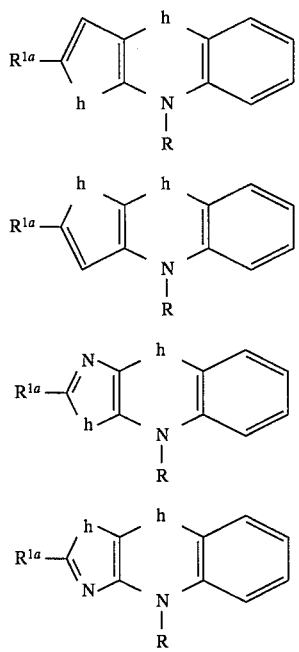

[wherein R, b and c are of the same meaning as defined above, $R^{1a}$ stands for an optionally substituted hydrocarbon residue] or bicyclic heterocyclic compounds

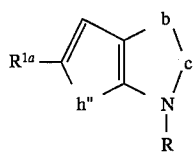

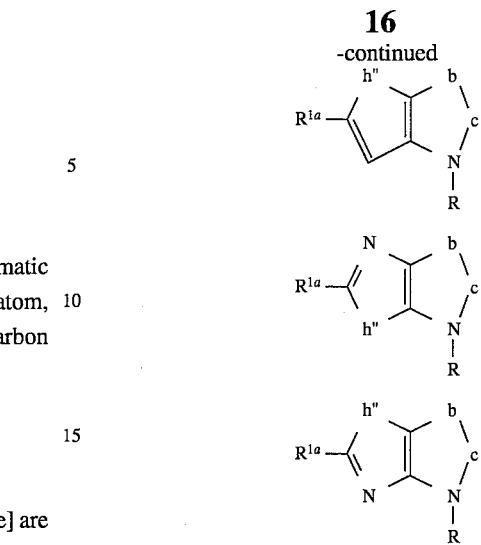

[wherein R, b and c are of the same meaning as defined above, $R^{1a}$ stands for an optionally substituted hydrocarbon residue and h" stands for $-O-$ or $-S-$].

The heterocyclic compound represented by the above-mentioned formula $II^b$ may optionally be substituted with, besides the groups represented by R, $R^1$ and $R^{1a}$, a group represented by $R^3$ capable of forming an anion or a group convertible thereinto. The substitution position of $R^3$ is on the ring adjacent to the ring to which R is bonded, preferably the position adjacent to R (position of f atom).

Examples of the group $R^3$ capable of forming anion or a group convertible thereinto include optionally esterified or amidated carboxyl, tetrazolyl, trifluoromethanesulfonic acid amide ($-NHSO_2CF_3$), phosphoric acid and sulfonic acid. These groups may optionally be protected by an optionally substituted lower alkyl group or acyl group, and may be any one as long as they are capable of forming anion under biological or physiological conditions (for example, an in vivo reaction such as oxidation, reduction or hydrolysis by in vivo enzymes) or chemically.

Examples of optionally esterified or amidated carboxyl represented by $R^3$ include groups represented by the formula $-CO-D$ [wherein D stands for hydroxyl group, optionally substituted amino (e.g. amino, N-lower (1–4C) alkylamino, and N,N-di-lower (1–4C) alkylamino) or optionally substituted alkoxy {e.g. a lower (1–6C) alkoxy group, whose alkyl moiety is optionally substituted with hydroxyl group, optionally substituted amino (e.g. amino, dimethylamino, diethylamino, piperidino and morpholino), halogen, lower (1–6C)alkoxy, lower (1–6C) alkylthio or optionally substituted dioxolenyl (e.g. 5-methyl-2-oxo-1,3-dioxolen-4-yl), or groups represented by the formula $-O-CH(R^4)-OCOR_5$ [wherein $R^4$ stands for hydrogen, a 1–6C straight-chain or branched lower alkyl group (e.g. methyl, ethyl, n-propyl, isopropyl, n-butyl, isobutyl, t-butyl, n-pentyl, isopentyl and neopentyl), a 2–6C straight-chain or branched lower alkenyl group or a 3–8C cycloalkyl group (e.g. cyclopentyl, cyclohexyl and cycloheptyl), and $R^5$ stands for a 1–6C straight-chain or branched lower alkyl group (e.g. methyl, ethyl, n-propyl, isopropyl, n-butyl, sec-butyl, t-butyl, n-pentyl, isopentyl and neopentyl), a 2–6C straight-chain or branched lower alkenyl group, a 3–8C cycloallyl group (e.g. cyclopentyl, cyclohexyl and cycloheptyl), a 1–3C lower alkyl group substituted with 3–8C cycloalkyl (e.g. cyclopentyl, cyclohexyl and cycloheptyl) or an optionally substituted aryl group such as phenyl (e.g. benzyl, p-chlorobenzyl, phenethyl, cyclopentylmethyl and cyclohexylmethyl), a 2–3C lower alkenyl group optionally substituted with 3–8C cycloalkyl or an optionally substituted aryl group such as phenyl (e.g. cinnamyl, etc. having alkenyl moiety such as vinyl, propenyl, allyl and isopropenyl), an aryl group such as optionally substituted phenyl (e.g. phenyl, p-tolyl and naphthyl), a 1–6C straight-chain or branched lower alkoxy group (e.g. methoxy, ethoxy, n-propoxy, isopropoxy, n-butoxy, isobutoxy, sec-butoxy, n-pentyloxy, isopentyloxy and neopentyloxy), a 2–8C straight-chain or branched lower alkenyloxy group (e.g. allyloxy and isobutenyloxy), a 3–8C cycloallyloxy group (e.g. cyclopentyloxy, cyclohexyloxy, and cycloheptyloxy), a 1–3C lower lower alkoxy group substituted with 3–8C cycloalkyl (e.g. cyclopentyl, cyclohexyl and cycloheptyl) or an aryl group such as optionally substituted phenyl (e.g. benzyloxy, phenethyloxy, cyclopentylmethyloxy and cyclohexylmethyloxy having alkoxy moiety such as methoxy, ethoxy, n-propoxy and isopropoxy), a 2–3C lower alkenyloxy group substituted with 3–8C cycloalkyl (e.g. cyclopentyl, cyclohexyl and cycloheptyl) or an aryl group such as optionally substituted phenyl (e.g. cinnamyloxy having an alkenyloxy moiety such as vinyloxy, propenyloxy, allyloxy and isopropenyloxy) and an aryloxy group such as optionally substituted phenoxy (e.g. phenoxy, p-nitrophenoxy and naphthoxy)]}]. And, examples of the substituent represented by $R^3$ may also include a group capable of forming anion or a group convertible thereinto (e.g. tetrazolyl, trifluoromethanesulfonic acid amide, phosphoric acid or sulfonic acid optionally protected with alkyl (e.g. at lower (1–4C) alkyl) or acyl (e.g. lower (2–5C) alkanoyl and optionally substituted benzoyl).

Examples of the substituent $R^3$ include —COOH and a salt thereof, —COOMe, —COOEt, —COOtBu, —COOPr, pivaloyloxymethoxycarbonyl, 1-(cyclohexyloxycarbonyloxy)ethoxycarbonyl, 5-methyl-2-oxo-1,3-dioxolen-4-yl-methoxycarbonyl, acetoxymethyloxycarbonyl, propionyloxymethoxycarbonyl, n-butyryloxymethoxycarbonyl, isobutyryloxymethoxycarbonyl, 1-(ethoxycarbonyloxy) ethoxycarbonyl, 1-(acetyloxy)ethoxycarbonyl, 1-(isobutyryloxy)ethoxycarbonyl, cyclohexylcarbonyloxymethoxycarbonyl, benzoyloxymethoxycarbonyl, cinnamyloxycarbonyl and cyclopentylcarbonyloxymethoxycarbonyl. As such groups as above, any one capable of forming anion (e.g. $COO^-$ and its derivatives) or a group convertible thereinto under biological or physiological conditions (e.g. in vivo reaction such as oxidation, reduction or hydrolysis catalyzed by in vivo enzymes) or chemically is mentioned. $R^3$ may be carboxyl or a prodrug thereof. $R^3$ may also be groups convertible into anion in vivo, for example, biologically or chemically.

And, a compound, in which $R^3$ is a group capable of forming anion or a group convertible thereinto (e.g. optionally protected carboxyl group, tetrazolyl group, carboaldehyde group, and hydroxymethyl group; and cyano group) chemically (e.g. oxidation, reduction or hydrolysis), is useful as a synthetic intermediate.

Among the groups described as $R^3$, preferable ones include carboxyl, esterified carboxyl (e.g. methyl ester, ethyl ester or an ester formed by bonding of a group represented by the above-mentioned formula —O—CH($R^4$)—OCOR$^5$ to carbonyl) and optionally protected tetrazolyl, carbaldehyde and hydroxymethyl.

The heterocyclic compound represented by the formula II may optionally have, besides the groups represented by R, $R^1$, $R^{1a}$ and $R^3$, further substituents as exemplified by halogen (e.g. F, Cl and Br), nitro, cyano, an optionally substituted amino group [e.g. amino, N-lower (1–4C) alkylamino (e.g. methylamino), N,N-di-lower (1–4C) alkylamino (e.g. dimethylamino), N-arylamino (e.g. phenylamino), alicyclic amino (e.g. morpholino, piperidino, piperazino and N-phenylpiperazino)], groups represented by the formula —U—$R^6$ [wherein U stands for a bond, —O—, —S— or —CO—, and $R^6$ stands for hydrogen, an optionally substituted lower alkyl group (e.g. lower (1–4C) alkyl optionally substituted with hydroxyl group, an optionally substituted amino group (e.g. amino), halogen, nitro, cyano or a lower (1–4C) alkoxy group], groups represented by the formula —(CH$_2$)$_1$—CO-D' [wherein D' stands for hydrogen, hydroxyl group, optionally substituted amino (e.g. amino, N-lower (1–4C) alkylamino and N-N-di-lower (1–4C) alkylamino), or optionally substituted alkoxy (e.g. a lower (1–6C) alkoxy group whose alkyl moiety is optionally substituted with hydroxyl group, optionally substituted amino (e.g. amino, dimethylamino, diethylamino, piperidino and morpholino), halogen, lower (1–6C) alkoxy, lower (1–6C) alkylthio, or optionally substituted dioxolenyl (e.g. 5-methyl-2-oxo-1,3-dioxolen-4-yl) or groups represented by the formula —OCH($R^7$)OCOR$^8$ [wherein $R^7$ stands for hydrogen, 1–6C straight-chain or branched lower alkyl group (e.g. methyl, ethyl, n-propyl, isopropyl, n-butyl, isobutyl, t-butyl, n-pentyl, isopentyl and neopentyl) or a 5–7C cycloalkyl group (cyclopentyl cyclohexyl and cycloheptyl), and $R^8$ stands for a 1–6C straight-chain or branched lower alkyl group (e.g. methyl, ethyl, n-propyl, isopropyl, n-butyl isobutyl, sec-butyl, t-butyl, n-pentyl, isopentyl and neopentyl), a 2–8C lower alkenyl group (vinyl, propenyl allyl and isopropenyl), a 5–7C cycloalkyl group (e.g. cyclopentyl cyclohexyl and cycloheptyl), a 1–3C lower alkyl group substituted with a 5–7C cycloalkyl group (e.g. cyclopentyl, cyclohexyl and cycloheptyl) or an aryl group such as phenyl (e.g. benzyl, p-chlorobenzyl, phenethyl, cyclopentylmethyl and cyclohexylmethyl), a 2–3C lower alkenyl group substituted with 5–7C cycloalkyl (e.g. cyclopentyl, cyclohexyl and cycloheptyl)' or an aryl group such as phenyl (e.g. cinnamyl having an alkenyl moiety such as vinyl, propenyl, allyl or isopropenyl), an optionally substituted aryl group such as phenyl (e.g. phenyl, p-tolyl and naphthyl), a 1–6C straight-chain or branched lower alkoxy group (e.g. methoxy, ethoxy, n-propoxy, isopropoxy, n-butoxy, isobutoxy, sec-butoxy, t-butoxy, n-pentyloxy, isopentyloxy and neopentyloxy), a 2–8C straight-chain or branched lower alkenyloxy group (e.g. allyloxy and isobutenyloxy), a 5–7C cycloalkyloxy group (e.g. cyclopentyloxy, cyclohexyloxy and cycloheptyloxy), a 1–3C lower alkoxy group substituted with 5–7C cycloalkyl (e.g. cyclopentyl, cyclohexyl and cycloheptyl) or an aryl group such as optionally substituted phenyl (e.g. benzyloxy, phenethyloxy, cyclopentylmethyloxy and cyclohexylmethyloxy having alkoxy moiety such as methoxy, ethoxy, n-propoxy and isopropoxy), a 2–3C alkenyloxy group substituted with 5–7C cycloalkyl (e.g. cyclopentyl, cyclohexyl and cycloheptyl) or an optionally substituted aryl group such as phenyl (e.g. cinnamyloxy having alkenyloxy moiety such as vinyloxy, propenyloxy, allyloxy and isopropenyloxy) and an aryloxy group such as optionally substituted phenoxy (e.g. phenoxy, p-nitrophenoxy and naphthoxy)], and 1 denotes 0 or 1] or tetrazolyl, trifluoromethanesulfonic acid amide, phosphoric acid or sulfonic acid, each optionally protected with alkyl (e.g. lower (1–4C) alkyl) or acyl (e.g. lower (2–5C) alkanoyl and optionally substituted benzoyl).

One or two of these substituents may optionally be substituted simultaneously on optional positions of the ring. When two or more of these substituents exist, (preferably the case where two substituents exist on two ring-forming atoms adjacent to each other in a, b and c for ring-forming groups), they may be bonded to each other to form a 5- to 6-membered optionally substituted aromatic hydrocarbon residue or a heterocyclic residue (preferably an aromatic ring such as phenyl) optionally containing hetero atom, taken together with the two ring-forming atoms. These rings may further substituted with any of the above-described substituents.

Among the compounds shown by formula

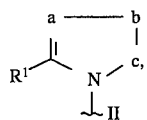

as condensed heterocyclic ring shown by formula

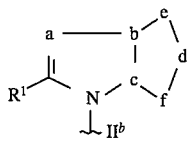

preferable examples are

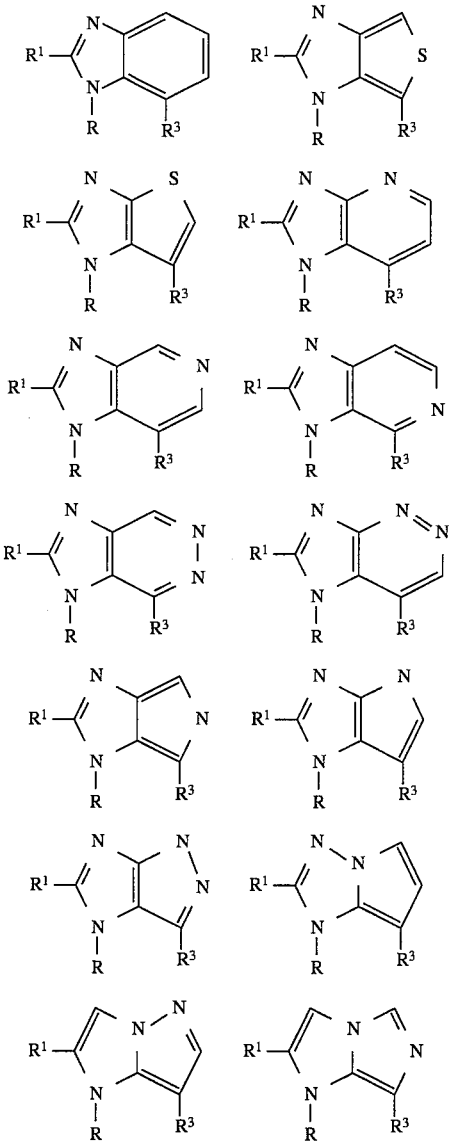

-continued

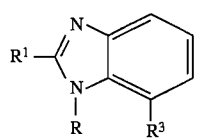 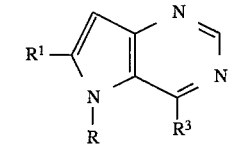

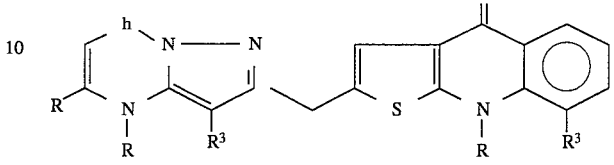

[wherein R, R¹, R³ and h are of the same meaning as defined above] and as heterocyclic ring represented by the formula

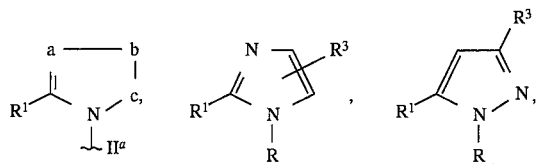

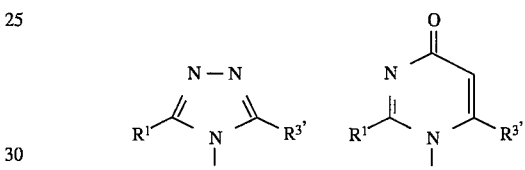

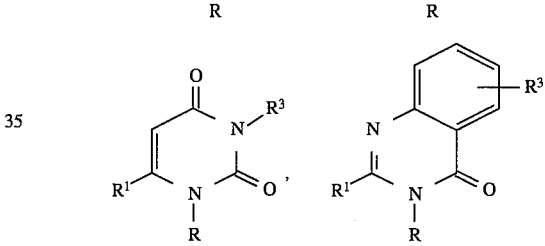

[wherein R, R¹, and R⁹ are of the same meaning as defined above] are preferable.

Among the compounds represented by the above-mentioned formula (Iᵃ), preferable ones are represented by the formula

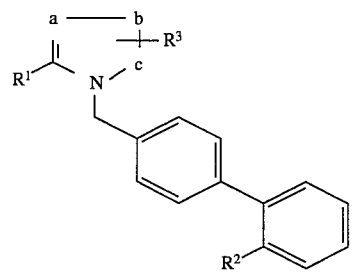

[wherein $R^1$ stands for optionally substituted lower (1–5C) alkyl which may be bonded through a hetero-atom (e.g. O, N(H) and S) (preferably lower (2–4C) alkyl), $R^2$ stands for oxadiazole or thiadiazole optionally protected with oprionally substituted lower (1–4C) alkyl (e.g. methyl, triphenylmethyl, methoxymethyl, acetyloxymethyl, methoxycarbonyloxymethyl, ethoxycarbonyloxymethyl, cyclohexyloxycarbonyloxyethyl and pivaloyloxymethyl) or an acyl (e.g. lower (2–5C) alkanoyl and benzoyl), $R^3$ stands for groups represented by the formula —CO-D" [wherein D" stands for hydroxyl group, amino, N-lower (1–4C) alkylamino, N,N-di-lower (1–4C) alkylamino or lower (1–4C) alkoxy whose alkyl moiety may optionally be substituted with hydroxyl group, amino, halogen, lower (2–6C) alkanoyloxy (e.g. acetyloxy and pivaloyloxy), 1-lower (1–6C) alkoxycarbonyl (e.g. methoxycarbonyloxy, ethoxycarbonyloxy and cyclohexyloxycarbonyloxy) or lower (1–4C) alkoxy] or tetrazolyl optionally protected with lower (1–4C) alkyl or acyl group (e.g. lower (2–5C) alkanoyl and benzoyl), and
heterocyclic ring represented by

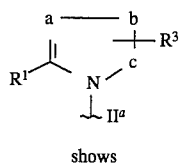

shows

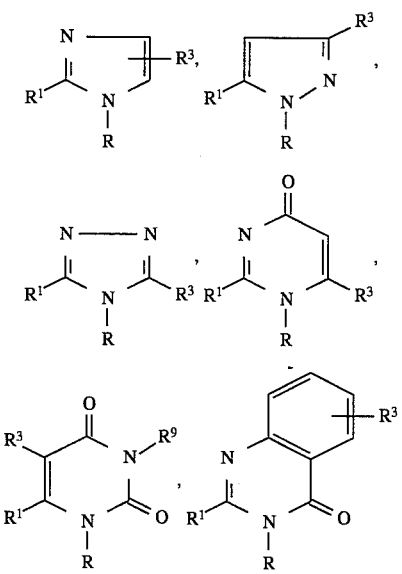

Among the compounds represented by the above-mentioned formula (I$^b$), preferable ones are represented by the formula

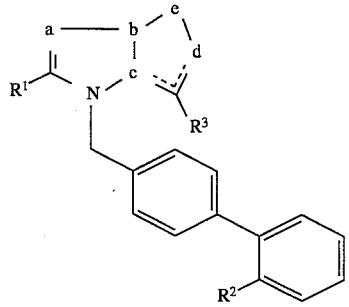

[wherein R$^1$ stands for optionally substituted lower (1–5C) alkyl which may be bonded through a hetero-atom (e.g. O, N(H) and S) (preferably lower (2–4C) alkyl), R$^2$ stands oxadiazole or thiadiazole optionally protected with optionally substituted lower (1–4C) alkyl (e.g. methyl, triphenylmethyl, methoxymethyl, acetyloxymethyl, methoxycarbonyloxymethyl, ethoxycarbonyloxymethyl, cyclohexyloxycarbonyloxyethyl and pivaloyloxymethyl) or an acyl (e.g. lower (2–5C alkanoyl and benzoyl), R$^3$ stands for hydrogen, groups represented by the formula —CO-D"

[wherein D" stands for hydroxyl group, amino, N-lower (1–4C) alkylamino, N,N-di-lower (1–4C) alkylamino or lower (1–4C) alkoxy whose alkyl moiety may optionally be substituted with hydroxyl group, amino, halogen, lower (2–6C) alkanoyloxy (e.g. acetyloxy and pivaloyloxy), 1-lower (1–6C) alkoxycarbonyl (e.g. methoxycarbonyloxy, ethoxycarbonyloxy and cyclohexyloxycarbonyloxy) or lower (1–4C) alkoxy] or tetrazolyl optionally protected with lower (1–4C) alkyl or acyl group (e.g. lower (2–5C) alkanoyl and benzoyl), and the condensed heterocyclic ring represented by

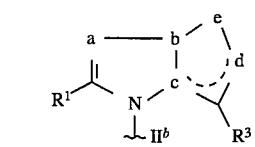

shows

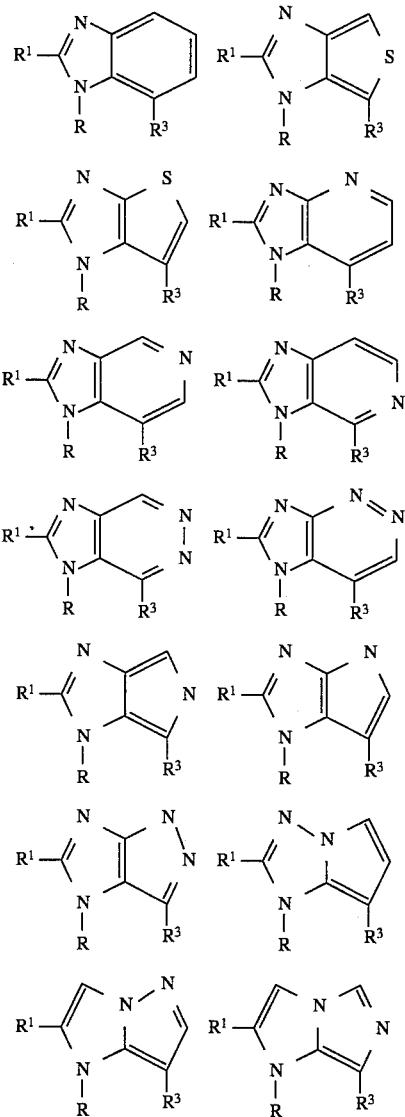

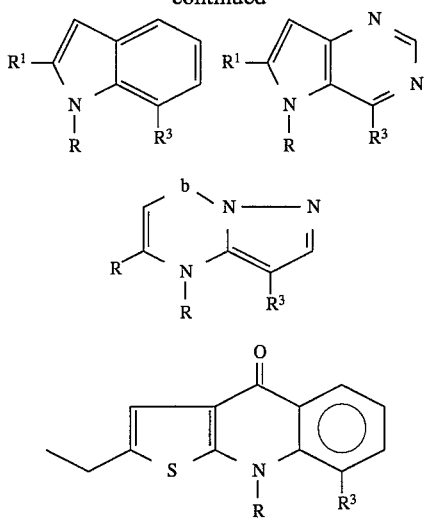

which may be further substituted with the above-mentioned substituents in addition to groups of R, $R^1$ and $R^3$]. As a compound of the formula ($I^b$), compounds having benzimidazole, thienoimidazole or imidazopyridine structure are preferable (more preferably, benzimidazole or thienoimidazole). And, compounds represented by the formula ($I^a$) or ($I^b$) wherein $R^2$ is hydroxyiminocarboxamide (—C(NH$_2$)=N—OH) are useful intermediates for synthesizing compounds of the formula ($I^a$) or ($I^b$) wherein $R^2$ is oxadiazole or thiadiazole.

Production Method

The compounds represented by the above-mentioned general formula (I), or ($I^a$) or ($I^b$) can be produced by, for example, methods as illustrated below.

Reaction (a)

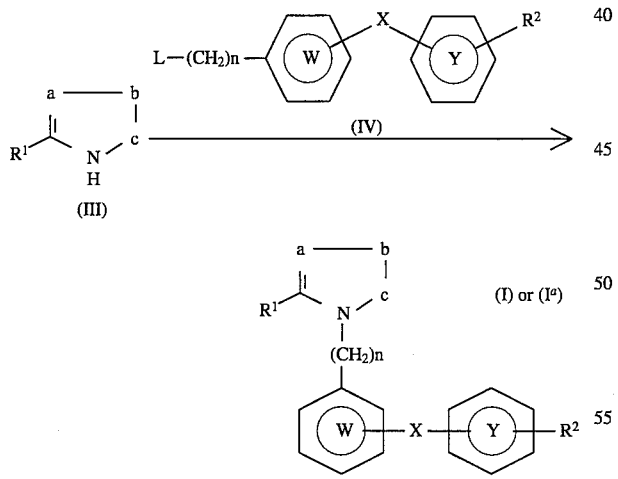

[wherein $R^1$, $R^2$, W, X, Y, a, b, c and n are of the same meaning as defined above, and L stands for a halogen atom].

The above-illustrated reaction (a) is alkylation using an alkylating agent in the presence of a base.

The alkylation is conducted, employing approximately 1 to 3 moles each of the base and the alkylating agent relative to one mole of the compound (III), usually in a solvent such as dimethylformamide, dimethylacetamide, dimethyl sulfoxide, acetonitrile, acetone or ethyl methyl ketone.

Examples of the base include sodium hydride, potassium t-butoxide, potassium carbonate and sodium carbonate.

As the alkylating agent, use is made of, for example, substituted halides (e.g. chlorides, bromides and iodides) and substituted sulfonic acid esters (e.g. p-toluenesulfonic acid ester).

While the reaction conditions vary with the combination of the base and the alkylating agent then employed, it is preferable to conduct the reaction usually at 0° C. to room temperature for about 1–10 hours.

In the alkylation, a mixture of regioisomers is obtained depending on the position of the N atom. While the production ratio of these compounds varies with the reaction conditions then employed and the substituents on the heterocyclic ring, these compounds can be obtained easily as pure products respectively by conventional isolation and purification means (e.g. recrystallization and column chromatography).

Reaction (b)

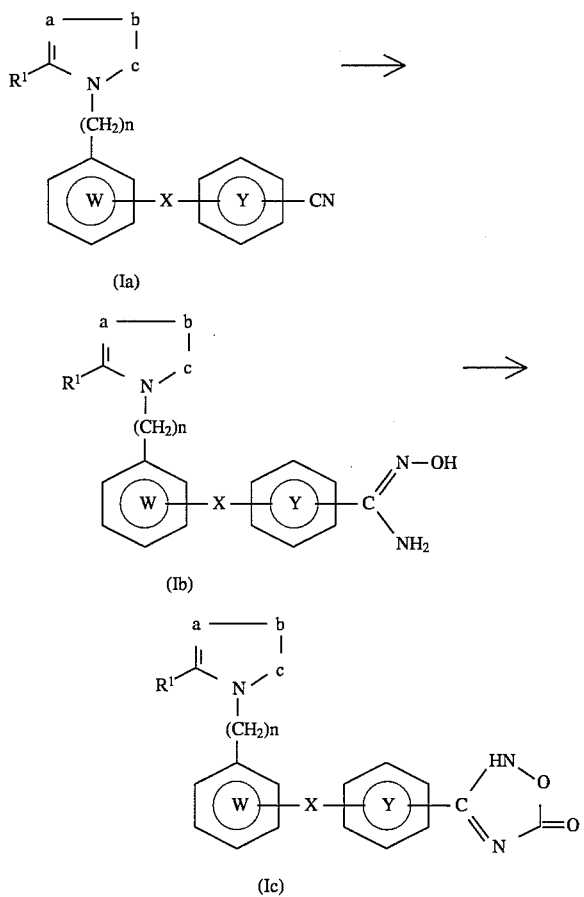

[wherein $R^1$, W, X, Y, a, b, c and n are of the same meaning as defined above]

The above-mentioned reaction (b) is to obtain the oxadiazole compound (Ic) by converting the cyano compound (Ia) into the amidoxime (Ib) followed by closing the ring.

The reaction for obtaining the compound (Ib) is conducted by using approximately 2 to 10 moles of hydroxylamine relative to 1 mole of the compound (Ia) usually in an organic solvent.

Examples of the solvent include amides (e.g. dimethylformamide and dimethylacetamide), sulfoxides (e.g. dimethyl sulfoxide), alcohols (e.g. methanol and ethanol), ethers (e.g. dioxane and tetrahydrofuran) and halogenated hydrocarbons (e.g. methylene chloride and chloroform).

When hydroxylamine is employed, the reaction is conducted in the presence of a suitable base (e.g. potassium carbonate, sodium carbonate, sodium hydroxide, triethylamine, sodium methanolate, sodium ethanolate and sodium hydride) of about equimolar amount, in the case of using an inorganic acid salt (e.g. hydroxylamine hydrochloride or hydroxylamine sulfate) or an organic acid salt (e.g. hydroxylamine oxalate). While the reaction conditions vary with the reagent or solvent then employed, the reaction is preferably conducted at about 50° C. to about 100° C. for about 2–10 hours, after the hydroxylamine hydrochloride is treated with sodium methoxide in dimethyl sulfoxide.

The thus-obtained amidoxime (Ib) is allowed to react with chloroformate (e.g. methyl ester and ethyl ester) in a conventional organic solvent (e.g. chloroform, methylene chloride, dioxane, tetrahydrofuran, acetonitrile and pyridine) in the presence of a base (e.g. triethylamine, pyridine, potassium carbonate and sodium carbonate) to give an o-acyl compound.

Preferably, the reaction is usually conducted by using 2–5 moles of ethyl chloroformate relative to one mole of the amidoxime ($I^b$) in the presence of about 2 to 5 moles of triethylamine in tetrahydrofuran at 0° C. to room temperatures for about 1 to 5 hours.

By heating the thus-obtained o-acyl amidoxime in a conventional organic solvent, the cyclized compound (Ic) is easily obtained.

Examples of the solvent include aromatic hydrocarbons (e.g. benzene, toluene and xylene), ethers (e.g. dioxane and tetrahydrofuran) and halogenated hydrocarbons (e.g. dichloroethane and chloroform). Preferably, oxadiazole is prepared by heating the o-acyl amidoxime compound for about 1 to 3 hours under reflux in xylene.

Reaction (c)

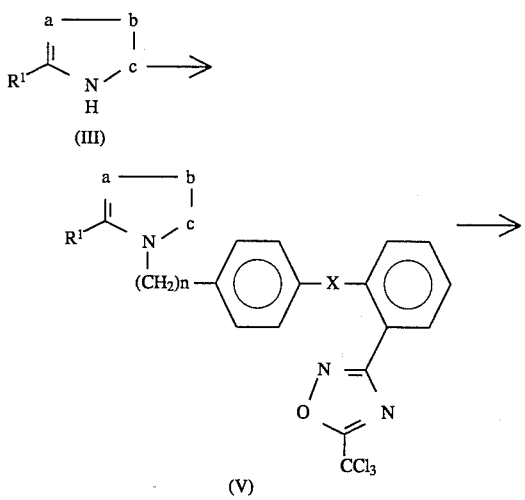

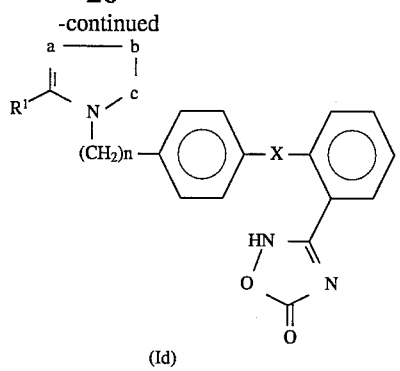

The reaction (c) is to obtain oxadiazolone (Id) by hydrolyzing the compound (V) produced by alkylation of the compound (III) with the alkylating agent obtained in the reaction (m).

Examples of the organic solvent include ethers (e.g. dioxane and tetrahydrofuran) and alcohols (e.g. methanol and ethanol).

As the alkali, mention is made of sodium hydroxide, potassium hydroxide and lithium hydroxide.

Preferably, the compound (V) is reacted at 0° C. to room temperatures for about 0.5 to 2 hours with about 2–10 moles of 0.5 to 1N sodium hydroxide.

Reaction (d)

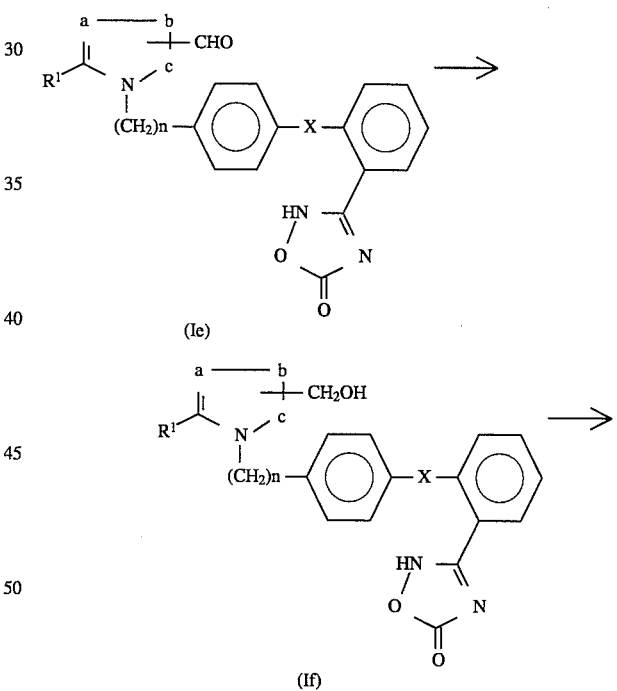

The reaction (d) is to obtain the alcohol compound (Ie) by reducing the aldehyde compound (If).

The reaction is conducted by using about 2 to 5 moles of a reducing agent relative to one mole of the compound (Ie) usually in ethers (e.g. tetrahydrofuran and dioxane) or alcohols (e.g. methanol and ethanol).

As the reducing agent, mention is made of metallic hydrogen complexes such as sodium borohydride.

Preferably, the reaction is carried out by adding a reducing agent to a solution of the compound (Ie) in methanol at 0°

C. to room temperature and allowing to proceed for about 0.5 to 2 hours.

Reaction (e)

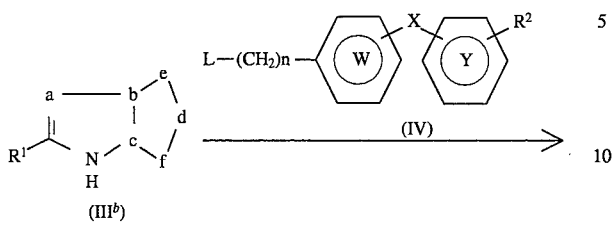

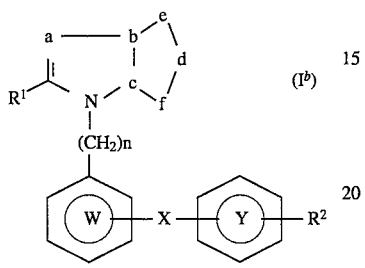

[wherein $R^1$, $R^2$, W, X, Y, a, b, c, d, e, f and n are of the same meaning as defined above, and L stands for halogen atom]

The above reaction (e) is to conduct alkylation by an alkylating agent in the presence of a base.

The reaction is conducted by using 1 to 3 moles of the base and 1 to 3 moles of the alkylating agent relative to 1 mole of the compound (III) usually in a solvent such as dimethylformamide, dimethyl acetamide, dimetyl sulfoxide, acetonitrile, acetone or ethyl methyl ketone.

Examples of the base include sodium hydride, potassium t-butoxide, potassium carbonate and sodium carbonate.

As the alkylating agent, use is made of substituted halogenides (e.g. chloride, bromide and iodide) and substituted sulfonic acid esters (e.g. p-toluenesulfonic acid ester).

While the reaction conditions vary depending on combination of the base with the alkylating agent then employed, it is preferable to conduct the reaction usually at 0° C. to room temperature for about 1 to 10 hours.

By the said alkylation, a mixture of regioisomers is sometimes obtained depending on the position of the N atom to be alkylated. While the production ratio of the compounds varies with the reaction conditions then employed and the substituents on the heterocyclic ring, the compound ($I^b$) can be easily obtained as pure product by subjecting the mixture to conventional isolation and purification means (e.g. recrystallization and column chromatography).

Reaction (f)

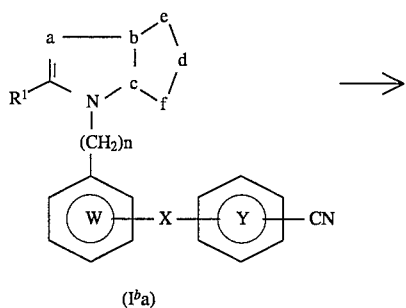

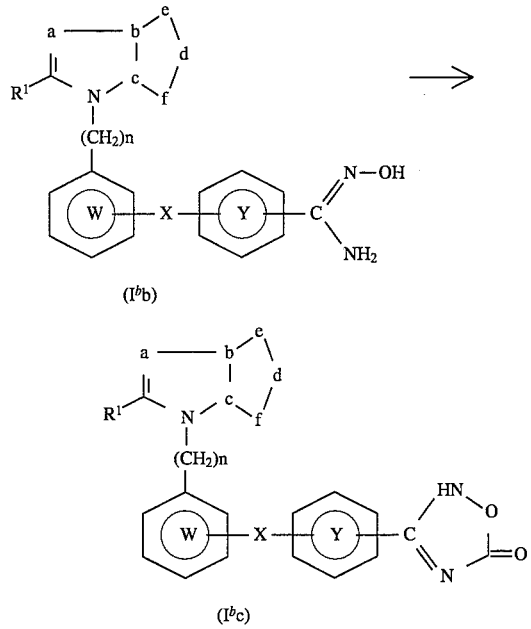

[wherein $R^1$, W, X, Y, a, b, c, d, e, f and n are of the same meaning as defined above]

The reaction (f) is to obtain the oxadiazole compound ($I^bc$) by converting the cyano compound ($I^ba$) to the amidoxime ($I^bb$), followed by cyclization.

The reaction for obtaining the compound ($I^bb$) is conducted by using hydroxylamine in an amount of about 2 to 10 moles relative to 1 mole of the compound ($I^ba$) in a conventional organic solvent.

Examples of the solvent include amides (e.g. dimethylformamide and dimethylacetamide), sulfoxides (e.g. dimethyl sulfoxide), alcohols (e.g. methanol and ethanol), ethers (e.g. dioxane and tetrahydrofuran) and halogenated hydrocarbons (e.g. methylene chloride and chloroform).

When hydroxylamine is employed, the reaction is conducted in the presence of a suitable base (e.g. potassium carbonate, sodium carbonate, sodium hydroxide, triethylamine, sodium methanolate, sodium ethanolate and sodium hydride) of about equimolar amount, in the case of using an inorganic acid salt (e.g. hydroxylamine hydrochloride or hydroxylamine sulfate) or an organic acid salt (e.g. hydroxylamine oxalate). While the reaction conditions vary with the reagent or solvent then employed, the reaction is preferably conducted at about 50° C. to about 100° C. for about 2 to 10 hours, after the hydroxylamine hydrochloride is treated with sodium methoxide in dimethyl sulfoxide.

The thus-obtained amidoxime ($I^bb$) is allowed to react with chloroformic acid ester (e.g. methyl ester and ethyl ester) in a conventional organic solvent (e.g. chloroform, methylene chloride, dioxane, tetrahydrofuran, acetonitrile and pyridine) in the presence of a base (e.g. triethylamine, pyridine, potassium carbonate and sodium carbonate) to give an o-acyl compound.

Preferably, the reaction is usually conducted by using 2–5 moles of ethyl chloroformate relative to one mole of the amidoxime compound ($I^bb$) in the presence of about 2 to 5 moles of triethylamine in tetrahydrofuran at 0° C. to room temperatures for about 1 to 5 hours.

By heating the thus-obtained o-acyl amidoxime compound in a conventional organic solvent, the cyclized compound (Ic) is easily obtained.

Examples of the solvent include aromatic hydrocarbons (e.g. benzene, toluene and xylene), ethers (e.g. dioxane and tetrahydrofuran) and halogenated hydrocarbons (e.g. dichloroethane and chloroform). Preferable reaction conditions are heating the o-acyl amidoxime compound for about 1 to 3 hours under reflux in xylene.

Reaction (g)

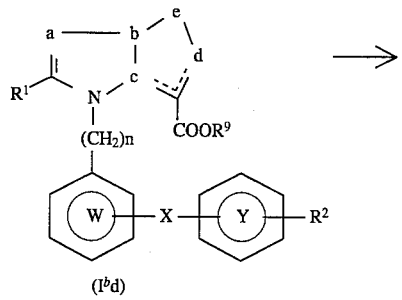

(I$^b$d)

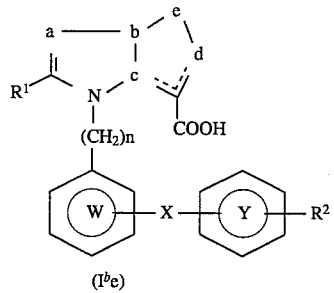

(I$^b$e)

[wherein R$^1$, R$^2$, R$^9$, W, X, Y, a, b, c, d, e and n are of the same meaning as defined above]

The reaction (g) is to obtain the carboxylic acid (I$^b$e) by alkali hydrolysis of the ester compound (I$^b$d).

This reaction is conducted by using alkali in an amount of about 1 to 3 moles relative to one mole of the compound (I$^b$d) usually in a solvent such as aqueous alcohols (e.g. methanol, ethanol and methyl cellosolve).

Examples of the alkali include lithium hydroxide, sodium hydroxide and potassium hydroxide.

The reaction is conducted at room temperature to about 100° C. for about 1 to 10 hours, preferably at about the boiling point of the solvent for about 3 to 5 hours.

Reaction (h)

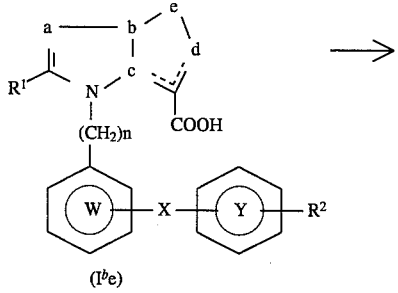

(I$^b$e)

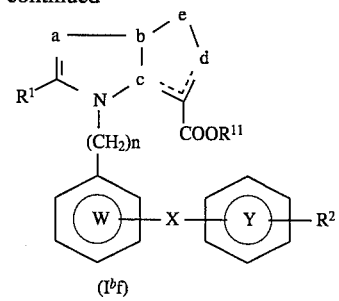

(I$^b$f)

[wherein R$^1$, R$^2$, W, X, Y, a, b, c, d, e and n are of the same meaning as defined above, and R$^{11}$ stands for optionally substituted alkyl group shown by the aforementioned R$^{10}$]

The above reaction (h) is alkylation by an alkylating agent in the presence of a base.

The alkylation is conducted by using 1 to 3 moles of the base and about 1 to 3 moles of the alkylating agent relative to 1 mole of the compound (I$^b$e) usually in a solvent such as dimethylformamide, dimethylacetamide, dimethyl sulfoxide, acetonitrile, acetone and ethyl methyl ketone.

Examples of the base include sodium hydride, potassium t-butoxide, potassium carbonate and sodium carbonate.

Examples of the alkylating agent include substituted halides (e.g. chloride, bromide and iodide) and substituted sulfonic acid esters (e.g. p-toluenesulfonic acid ester).

While the reaction conditions vary with combinations of the base and the alkylating agent then employed, it is preferable to conduct the reaction at 0° C. to room temperatures for about 1 to 10 hours.

And, when chloride or bromide is employed as the alkylating agent, it is preferable to add potassium iodide or sodium iodide to the reaction system to accelerate the reaction.

Reaction (i)

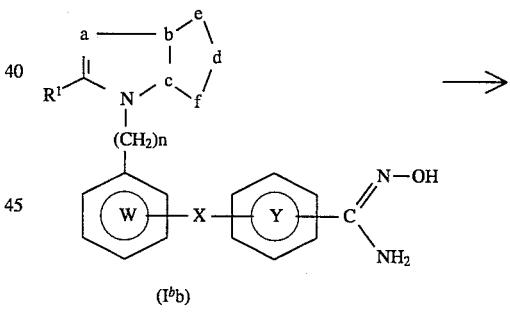

(I$^b$b)

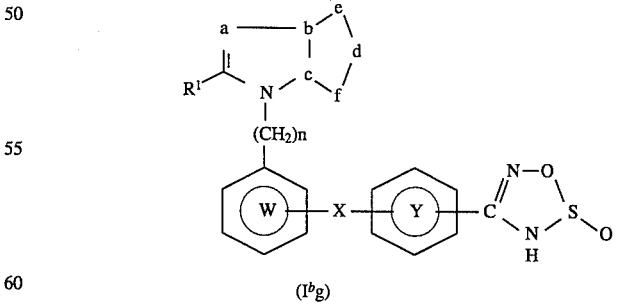

(I$^b$g)

[wherein R¹, W, X, Y, a, b, c, d, e, f and n are of the same meaning as defined above]

The reaction (i) is to obtain the oxathiadiazole (I^bg) by cyclization of the aldoxime compound (I^bb) obtained by the reaction (f).

The compound (I^bg) is obtained by cyclizing aldoxime (I^bb) with thionyl chloride in a conventional organic solvent (e.g. dichloromethane, chloroform, dioxane and tetrahydrofuran) in the presence of a base (e.g. pyridine and triethylamine).

It is preferable to conduct the reaction, adding about 2 to 10 moles of thionyl chloride to the reaction system, under cooling at 0° C. to −30° C., in the presence of about 1 to 3 moles of pyridine to one mole of the aldoxime compound (I^bb), using dichloromethane as the solvent, for about 0.5 to 1 hour.

Reaction (j)

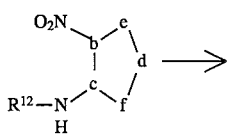

(VI)

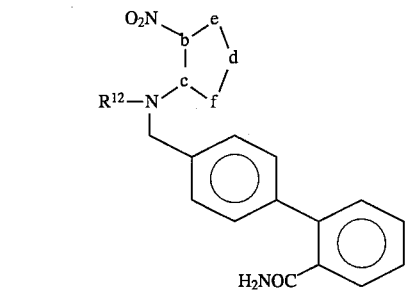

(VII)

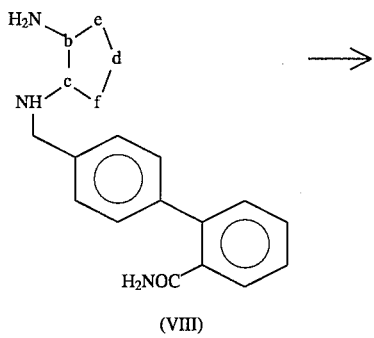

(VIII)

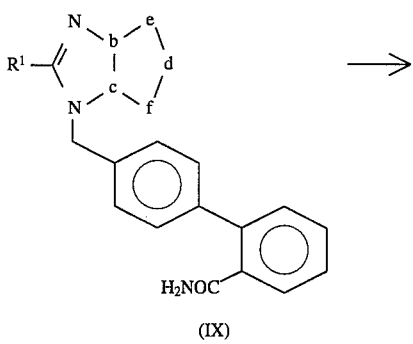

(IX)

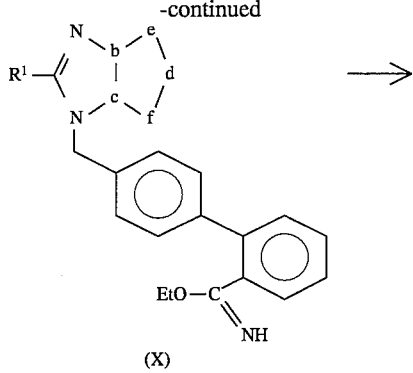

(X)

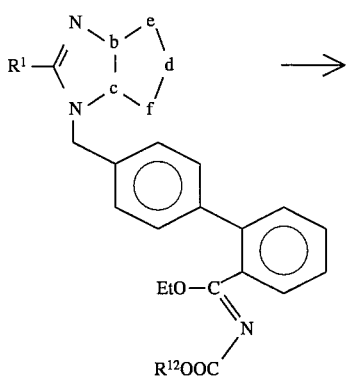

(XI)

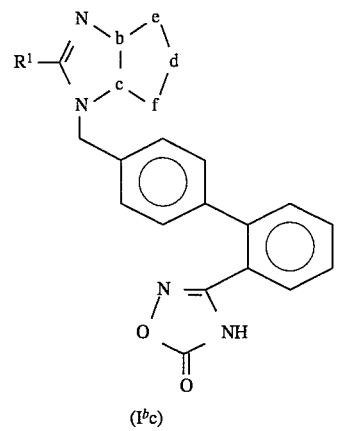

(I^bc)

The above reaction (j) is to obtain the diamino derivative (VIII), which comprises subjecting the nitro derivative (VII) prepared in accordance with the procedure described in EP-434038 and EP-459136 to deprotection by a conventional process, then allowing a reducing agent (e.g. catalytic reduction using Raney nickel or palladium-carbon, iron-hydrochloric acid, ferric chloride-hydrazine, stannic chloride, sodium borohydride-nickel chloride, etc.) to act on the thus deprotected compound. Then the the diamino derivative (VIII) is allowed to react with carboxylic acid or a derivative thereof (e.g. ester, acid anhydride or acid halide), orthoester, imino ether or imino thioether to cause condensing ring-closure to thereby convert the diamino derivative (VIII) into the compound (IX).

Thus-obtained compound (IX) is allowed to react with about 1 to 2 times as many moles of triethyloxonium tetrafluoroborate in halogenated hydrocarbon (e.g. methylene chloride or chloroform) at 0° C. to room temperature for about 30 minutes to about 2 hours to give the imino-ether derivative (X) in a good yield.

Then, the imino-ether derivative (X) is allowed to react with 1 to 2 times as many moles of chloroformic acid ester (e.g. chloromethyl formate or chloroethyl formate) in a conventional organic solvent (e.g. benzene, toluene, methylene chloride, chloroform, dioxane or pyridine) in the presence of about 1 to 2 times as many moles of a base (e.g. 2,4,6-trimethylpyridine, triethylamine, dimethylpyridine, methylpyridine, diethylaniline, etc.). More specifically, the reaction is conducted in toluene at 80° to 100° C. for about 1–3 hours to obtain the N-alkoxycarbonyl derivative (XI) in a good yield.

The thus-obtained acyliminoether derivative (XI) is allowed to react with about two times as many moles of hydroxylamine hydrochloride and a base (e.g. sodium methoxide, sodium ethoxide potassium carbonate) in alcohol (e.g. methanol or ethanol) to cause ring-closure. This reaction is conducted preferably at about 50° C. to the boiling point of the solvent used for about 3–10 hours.

Reaction (k)

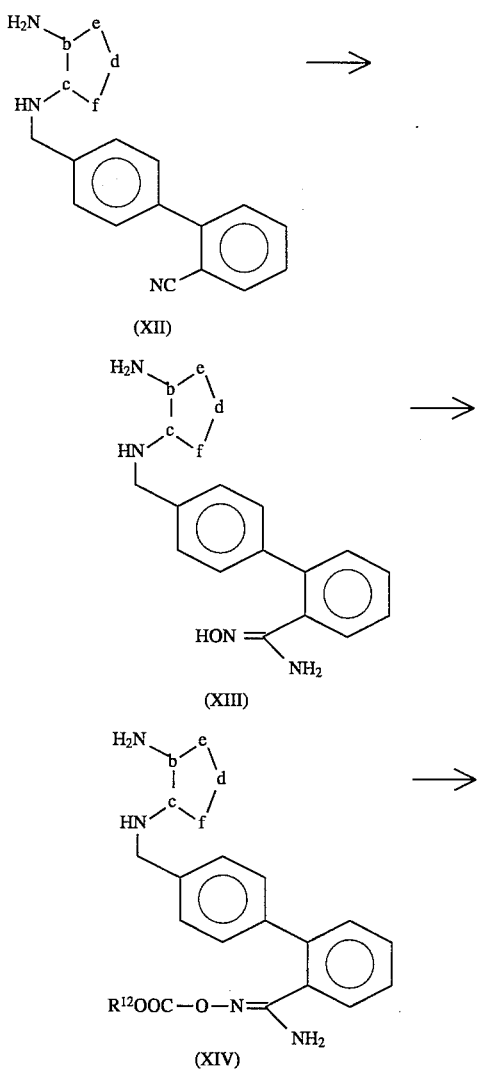

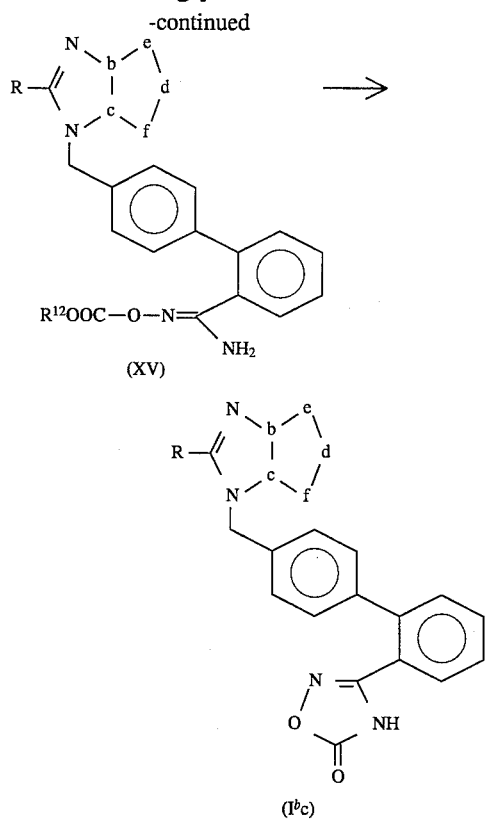

The reaction (k) comprises leading the nitrile derivative (XII) synthesized in accordance with the methods disclosed in EP-434038 and EP-459136 to the aldoxime derivative (XIII) obtained by the similar precedure described in the afore-mentioned reaction (b), followed by allowing the aldoxime derivative (XIII) to react with about 1 to 2 times as many moles of chloroformic acid ester (e.g. chloromethyl formate or chloroethyl formate) in the presence of about 1 to 2 times as many moles of a base (e.g. triethylamine or pyridine) in a conventional non-protomic organic solvent (e.g. benzene, toluene, methylene chloride, chloroform, dioxane or pyridine) in substantially the same manner as in the afore-mentioned reaction (j). In the case of conducting this reaction in tetrahydrofuran, the reaction is allowed to proceed at 0° C. to about room temperature to thereby obtain the O-alkoxycarbonyl derivative (XV) in a good yield.

The thus-obtained compound (XV) is allowed to react in a conventional organic solvent (e.g. methanol, ethanol, ethyl acetate, benzene, acetonitrile, acetone or N,N-dimethylformamide) in the presence of a base (e.g. potassium carbonate, sodium carbonate, sodium hydride, potassium tert-butoxide or 1,8-diazabicyclo[5.4.0]undec-7-ene (DBU)). This reaction is conducted preferably at room temperature to the boiling point of the solvent used for about 1–20 hours. When the reaction is allowed to proceed in ethyl acetate using DBU at about 50° to 80° C. for about 1–2 hours, the ring-closed derivative ($I^b$c) can be obtained in a good yield.

Reaction (l)

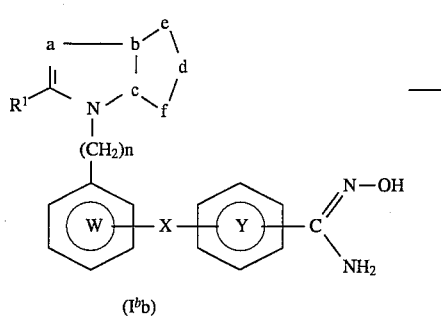

(I^bb)

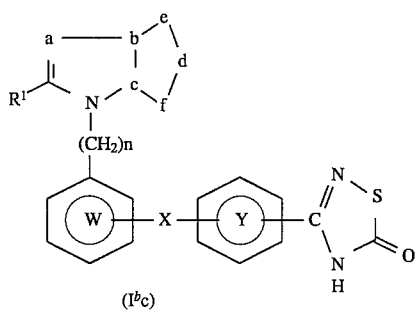

(I^bc)

The reaction (l) is to obtain the thiadiazole derivative (I^bc) by subjecting the aldoxime (I^bb) to ring-closure reaction.

This reaction is conducted in a conventional organic solvent using about 1 to 2 moles of 1,1'-thiocarbonyl diimidazole relative to 1 mole of the compound (I^bb).

As the solvent, use is made of, for example, ethers (e.g. dioxane or tetrahydrofuran) or halogenated hydrocarbons (e.g. methylene chloride or chloroform).

The reaction is preferably conducted by dissolving the compound (I^bb) in the above-mentioned solvent, adding to the solution 1,1'-thiocarbonyl dimidazole while stirring at 0° C. to room temperature, followed by stirring with silica gel in a mixture of methanol and chloroform for about 30 minutes to 2 hours at room temperature.

The reaction products obtained as above by the reactions (a) to (l) can be easily isolated by conventional isolation and purification methods, for example, column chromatography and recrystallization.

Incidentally, these compounds (I) can be converted, by conventional methods, to salts with physiologically acceptable acids or bases. These salts include, for example, salts with an inorganic acid such as hydrochloric acid, sulfuric acid and nitric acid and, depending on the compounds, salts with an organic acid such as acetic acid, nitric acid, succinic acid and maleic acid, salts with an alkali metal such as sodium and potassium, and salts with an alkaline earth metal such as calcium.

The starting compounds can be synthesized by the methods described as follows.

Reaction (m)

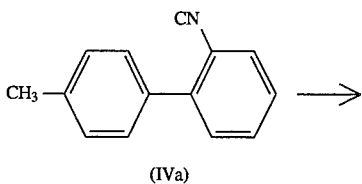

(IVa)

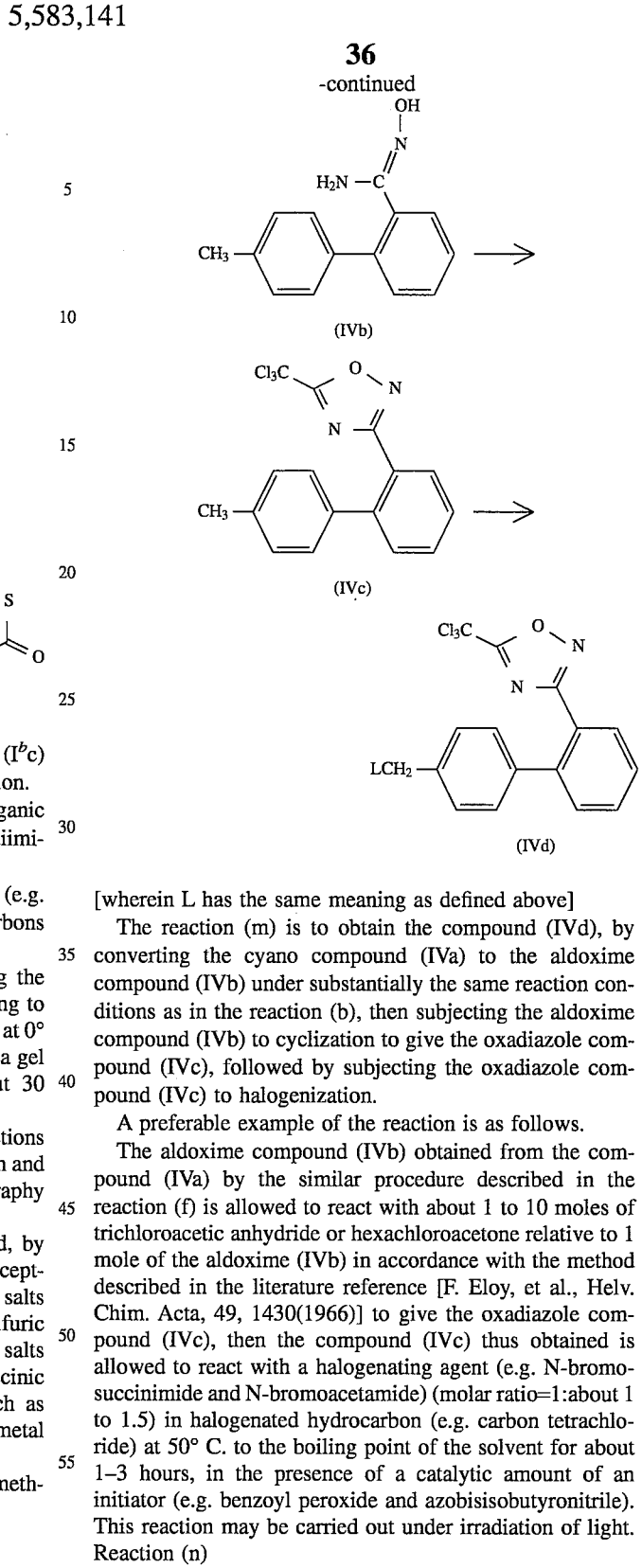

[wherein L has the same meaning as defined above]

The reaction (m) is to obtain the compound (IVd), by converting the cyano compound (IVa) to the aldoxime compound (IVb) under substantially the same reaction conditions as in the reaction (b), then subjecting the aldoxime compound (IVb) to cyclization to give the oxadiazole compound (IVc), followed by subjecting the oxadiazole compound (IVc) to halogenization.

A preferable example of the reaction is as follows.

The aldoxime compound (IVb) obtained from the compound (IVa) by the similar procedure described in the reaction (f) is allowed to react with about 1 to 10 moles of trichloroacetic anhydride or hexachloroacetone relative to 1 mole of the aldoxime (IVb) in accordance with the method described in the literature reference [F. Eloy, et al., Helv. Chim. Acta, 49, 1430(1966)] to give the oxadiazole compound (IVc), then the compound (IVc) thus obtained is allowed to react with a halogenating agent (e.g. N-bromosuccinimide and N-bromoacetamide) (molar ratio=1:about 1 to 1.5) in halogenated hydrocarbon (e.g. carbon tetrachloride) at 50° C. to the boiling point of the solvent for about 1–3 hours, in the presence of a catalytic amount of an initiator (e.g. benzoyl peroxide and azobisisobutyronitrile). This reaction may be carried out under irradiation of light.

Reaction (n)

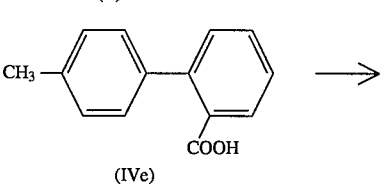

(IVe)

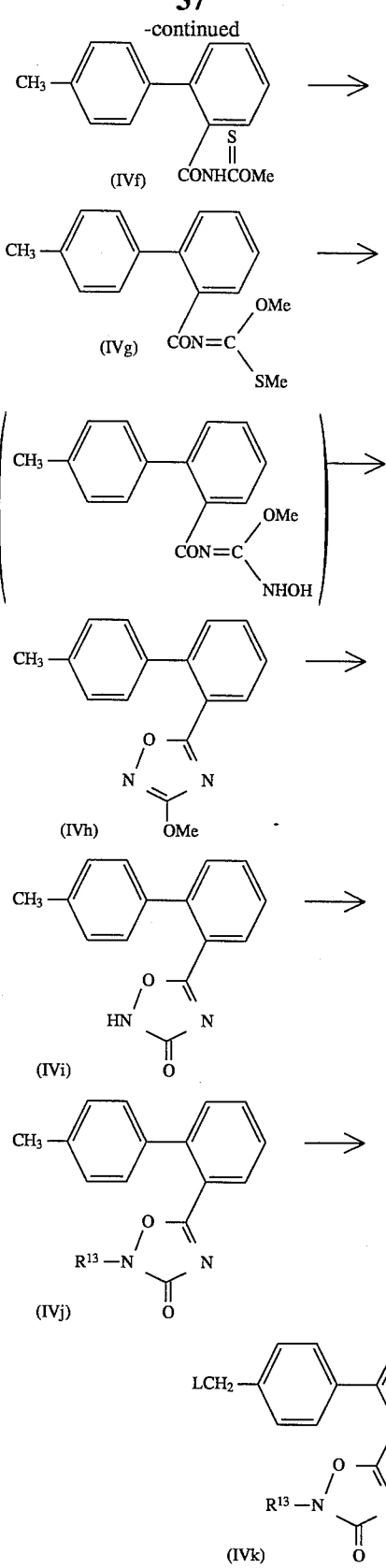

[wherein $R^{13}$ stands for the optionally substituted alkyl group shown by the above-mentioned $R^{10}$ (e.g. triphenyl methyl, methoxy methyl and cyanoethyl) or t-butyldimethyl silyl group; and L is of the same meaning as defined above].

The reaction (n) is to obtain the oxadiazole compound (IVh), which comprises leading carboxylic acid (IVe) to acyl isothiocyanate by a conventional method, allowing the latter to react with alcohol to give the carbonyl thiocarbamate (IVf), subjecting the compound (IVf) to methylation to give carbonate (IVg), then allowing the compound (IVg) to react with hydroxylamine, followed by cyclization under heating.

In the reaction for obtaining carbonyl thiocarbamate (IVf) from carboxylic acid (IVe), the compound (IVe) is allowed to react with a halogenating agent (e.g. thionyl chloride) (molar ratio=1:about 2 to 5) in halogenated hydrocarbon (e.g. chloroform and methylene chloride) for about 1–5 hours at about 50° C. to the boiling point of the solvent then employed. The acid chloride thus obtained is allowed to react with about 2–5 moles of thiocyanate (e.g. sodium salt and potassium salt) in ether (e.g. dioxane and tetrahydrofuran) at from about 50° C. to the boiling point of the solvent then employed for about 1–3 hours to give isocyanate. It is preferable to subject the isothiocyanate thus obtained to heating together with about 2–10 moles of alcohol (e.g. methanol and ethanol) at about 50° C. to the boiling point of the solvent then employed for about 15 minutes to one hour.

In the reaction for obtaining iminomonothiocarbonate (IVg) from the compound (IVf), it is preferable to allow the compound (IVf) to react with methyl iodide (molar ratio=1:1 to 2) in an organic solvent (e.g. methanol, ethanol, dimethylformamide (DMF) and acetonitrile), in the presence of about 1 to 2 moles, relative to one mole of (IVf), of a base (e.g. NaOMe, $Na_2CO_3$ and $K_2CO_3$) at room temperature to about 50° C. for about 10–24 hours.

In the reaction for obtaining the oxadiazole compound (IVh) from the compound (IVg), it is preferable to allow (IVg) to react with hydroxylamine (molar ratio=1:about 1 to 2) in alcohol (e.g. methanol and ethanol) at room temperature to 50° C. for about 10–20 hours, followed by subjecting the reaction mixture to heating in an organic solvent (e.g. toluene and benzene) in the presence of about a catalytic amount of an acid (e.g. p-toluenesulfonic acid) at 50° C. to the boiling point of the solvent then employed for about 1–3 hours.

In the reaction for obtaining demethylated compound (IVi) from the compound (IVh), it is preferable to subject an excess amount of pyridine hydrochloride and (IVh) to fuse under nitrogen atmosphere at about 150° C. to 160° C. for about 30 minutes–one hour.

In the reaction for obtaining the compound (IVj) from the compound (IVi), it is preferable to allow the compound (IVi) to react with an alkylating agent (e.g. triphenylmethyl chloride, methoxymethyl chloride and cyanoethyl chloride) (molar ratio=1:about 1 to 2) in an organic solvent (e.g. chloroform, methylene chloride, dioxane, tetrahydrofuran and pyridine) in the presence of about 1 to 2 moles of a base (e.g. potassium carbonate, sodium carbonate, triethylamine and pyridine) at 0° C. to room temperature for about 1–3 hours.

The reaction for obtaining the compound (IVk) by halogenating the compound (IVj) can be conducted in substantially the same manner as in the reaction for obtaining the compound (IVd) from the compound (IVc) in the reaction (m).

Reaction (o)

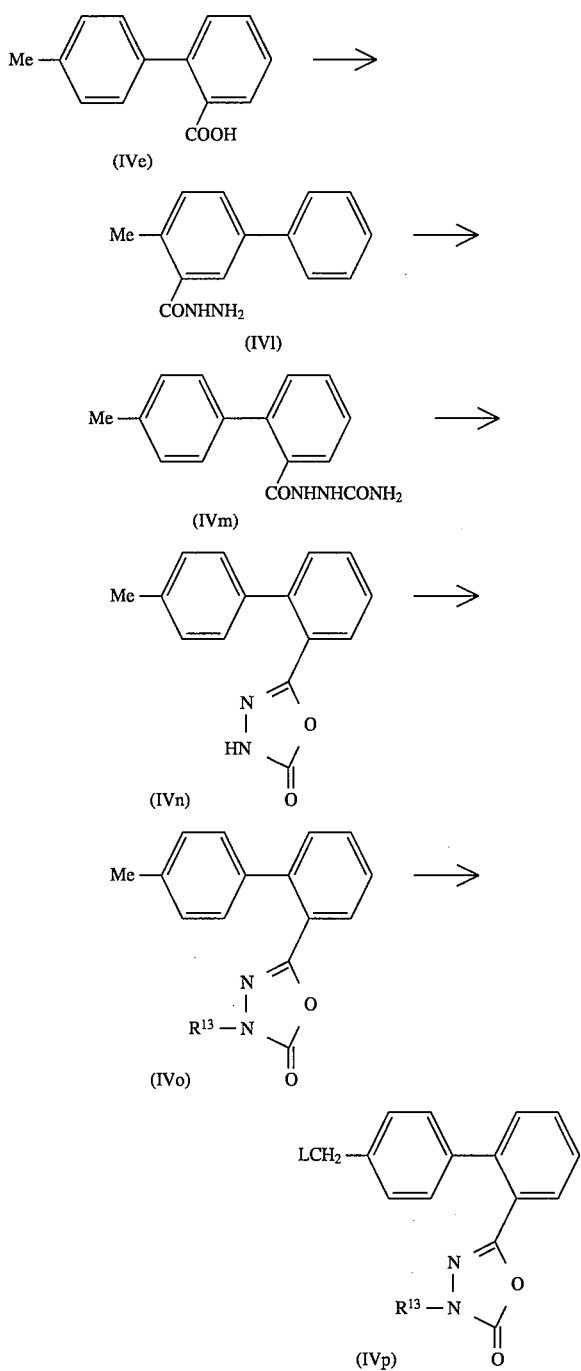

[wherein R[13] and L are of the same meaning as defined above]

The reaction (o) comprises converting carboxylic acid (IVe) to semicarbazide (IVm) via hydrazide (IVl) by a conventional manner, then subjecting (IVm) to dehydrocyclization to give oxadiazolone (IVn), followed by leading (IVn) to the halogeno compound (IVp).

In the reaction for obtaining hydrazide (IVl) from carboxylic acid (IVe), (IVe) is allowed to react with about 2 to 5 moles of a halogenating agent (e.g. oxalyl chloride and thionyl chloride) in an organic solvent (e.g. tetrahydrofuran, chloroform and methylene chloride) at room temperature to the boiling point of the solvent then employed for about 1–20 hours. In this case, it is preferable to add a catalytic amount of dimethylformamide to accelerate the reaction. The acid chloride obtained is allowed to react with about 2 to 5 moles of hydrazine hydrate in an organic solvent (e.g. tetrahydrofuran and dioxane) at room temperature to about 50° C. for about 1–10 hours to obtain compound (IVl). In the reaction for producing semicarbazide (IVm) from the hydrazide (IVl), it is preferable to allow (IVe) to react with about 2–5 moles of isocyanate (e.g. sodium or potassium salt) in aqueous solution in the presence of an acid (e.g. hydrochloric acid or sulfuric acid) in an amount equal to that of the isocyanate employed at 0° C. to room temperature for about 1–5 hours.

In the reaction for producing oxadiazolone (IVn) from the semicarbazide (IVm), it is preferable to heat (IVm) in an organic solvent (e.g. benzene and xylene) at the boiling point of the solvent for about 5–20 hours.

The reaction for producing the halogenated compound (IVp) from the oxadiazolone (IVn) is preferably conducted in a manner similar to that described in the reaction (n).

Reaction (p)

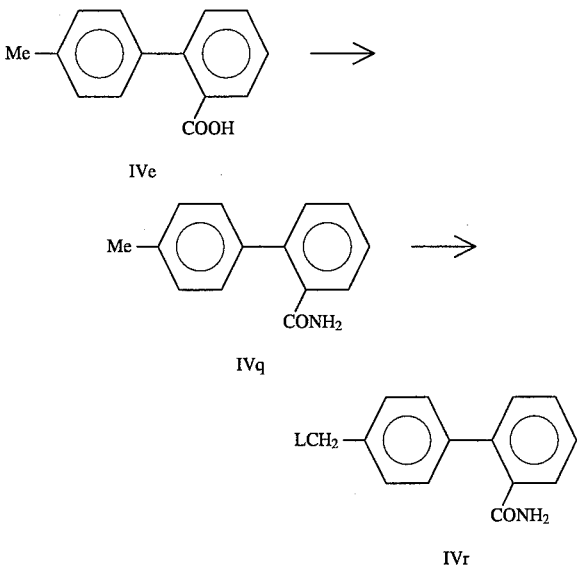

The reaction (p) is to obtain the amide (IVq) in substantially the same manner as in the reaction (o).

The carboxylic acid (IVe) is allowed to react with about 2–5 mole of a halogenating agent (e.g. oxalyl chloride or thionyl chloride) in an organic solvent (e.g. tetrahydrofuran, chloroform or methylene chloride) at room temperature to the boiling point of the solvent used for about 1–20 hours. It is preferable to accelerate this reaction by the addition of a catalytic amount of dimethylformamide. The acid halide obtained is preferably allowed to react with an excess amount of aqueous ammonium hydroxide in an organic solvent (e.g. tetrahydrofuran or dioxane) at 0° C. to room temperature for about 1–10 hours, so that the amide derivative (IVq) can be obtained in a good yield.

The reaction to obtain the halide (IVr) from the amide derivative (IVq) obtained is preferably conducted in substantially the same manner as shown by the reaction (m) or (n).

The compounds (I) and salts thereof are less toxic, strongly inhibit the vasoconstrictive and hypertensive actions of angiotensin II, exert a hypotensive effect in animals, especially mammals (e.g. human, dog, rabbit and rat), and therefore they are useful as therapeutic agents for not only hypertension but also circulatory diseases such as heart failure (hypertrophy of the heart, cardiac insufficiency, cardiac infarction or the like), cerebral apoplexy and nephropathy. The compounds (I) also have CNS activity for treating Alzheimer's disease and senile dementia, and anxiolytic and antidepressant properties.

For such therapeutic use as above, the compound (I) and salts thereof can be administered orally, non-orally, by inhalation, rectally or topically as pharmaceutical compositions or formulations (e.g. powders, granules, tablets, pills, capsules, injections, syrups, emulsions, elixir, suspensions or solutions), comprising at least one species of the compounds of this invention alone or in admixture with pharmaceutically acceptable carriers, adjuvants, vehicles and/or diluents.

Pharmaceutical compositions can be formulated in accordance with conventional procedures. In the present specification, "non-orally" includes subcutaneous injection, intravenous injection, intramuscular injection, intraperitoneal injection or instillation. Injectable preparations, for example, sterile injectable aqueous suspensions or oil suspensions can be prepared by known procedures in the fields concerned, using a suitable dispersant or wetting agent and suspending agent. The sterile injections may be in the state of, for example, a solution or a suspension, which is prepared with a nontoxic diluent administrable non-orally, e.g. an aqueous solution, or with a solvent employable for sterile injection. Examples of usable vehicles or acceptable solvents include water, Ringer's solution and an isotonic aqueous saline solution. Further, a sterile non-volatile oil can usually be employed as solvent or suspending agent. Any non-volatile oil and a fatty acid can be sued for this purpose, which includes natural, synthetic or semi-synthetic fatty oil or fatty acid and natural or synthetic or semi-synthetic mono- or di- or tri-glycerides.

Rectal suppositories can be prepared by mixing the drug with a suitable non-irritable vehicle, for example, cocoa butter and polyethylene glycol, which is in the solid state at ordinary temperatures, in the liquid state at temperatures in the intestinal tubes and melts in the rectum to release the drug.

As a solid formulation for oral administration, mention is made of powders, granules, tablets, pills and capsules as referred to above. In such formulations as exemplified above, the active component compound can be mixed with at least one additive, for example, sucrose, lactose, cellulose sugar, mannitol, maltitol, dextrin, starch, agar, alginate, chitin, chitosan, pectin, tragacanth gum, gum arabic, gelatin, collagen, casein, albumin, synthetic or semi-synthetic polymer or glyceride. These formulations can contain further additives, for example, an inactive diluent, a lubricant such as magnesium stearate, a preservative such as paraben or sorbic acid, an anti-oxidant such as ascorbic acid, α-tocopherol or cysteine, a disintegrator, a binder, a thickening agent, a buffer, a sweetener, a flavoring agent and a perfuming agent. Tablets and pills can further be applied with enteric coating. Examples of liquid preparations for oral administration include pharmaceutically acceptable emulsions, syrups, elixirs, suspensions and solution, which may contain an inactive diluent, for example, water, which is conventionally employed in the field concerned.

The dose of a specific patient is decided in accordance with the age, body weight, general health conditions, sex, diet, dose interval, administration routes, excretion rate, combinations of drugs and conditions of the diseases then treated, while taking them and any other necessary factors into consideration.

The dose varies with the diseases to be treated, conditions of such diseases, subject patients and administration routes, and it is preferable that a daily dose of 1 to 50 mg for oral administration or 1 to 30 mg for intravenous injection is given once or divided into 2 to 3 administrations when used as an agent for the therapy of essential hypertension of an adult human.

WORKING EXAMPLES

By the following formulation examples, working examples, experimental examples and reference examples, the present invention will be illustrated more concretely, and it is needless to say that they should not be construed as limiting the invention thereto.

Formulation Examples

When the compound (I) of the present invention is used as a therapeutic agent for circulatory disturbances such as hypertension, heart diseases, cerebral apoplexy and nephritis, it can be used in accordance with, for example, the following formulations.

1. Capsules

| | | |
|---|---|---|
| (1) | 2-ethoxy-1-[[2'-(2,5-dihydro-5-oxo-1,2,4-oxadiazol-3-yl)biphenyl-4-yl]methyl]benzimidazole-7-carboxylic acid | 10 mg |
| (2) | lactose | 90 mg |
| (3) | microcrystalline cellulose | 70 mg |
| (4) | magnesium stearate | 10 mg |
| | one capsule | 180 mg |

(1), (2), (3) and a half of (4) are mixed and granulated. To the granules is added the remainder of (4), and the whole is filled into gelatin capsules.

2. Tablets

| | | |
|---|---|---|
| (1) | 2-ethoxy-1-[[2'-(2,5-dihydro-5-oxo-1,2,4-oxadiazol-3-yl)biphenyl-4-yl]methyl]benzimidazole-7-carboxylic acid | 10 mg |
| (2) | lactose | 35 mg |
| (3) | corn starch | 150 mg |
| (4) | microcrystalline cellulose | 30 mg |
| (5) | magnesium stearate | 5 mg |
| | one tablet | 230 mg |

(1), (2), (3), two thirds of (4) and a half of (5) are mixed and granulated. To the granules are added the remainders of (4) and (5), followed by subjecting the mixture to compression molding.

3. Injections

| | | |
|---|---|---|
| (1) | 2-ethoxy-1-[[2'-(2,5-dihydro-5-oxo-1,2,4-oxadiazol-3-yl)biphenyl-4-yl]methyl]benzimidazole-7-carboxylic acid disodium salt | 10 mg |
| (2) | inositol | 100 mg |
| (3) | benzyl alcohol | 20 mg |
| | one ampoule | 130 mg |

(1), (2) and (3) are dissolved in distilled water for injection to make the whole volume 2 ml, which is filled into an ampoule. The whole process is conducted under sterile conditions.

| 4. | Capsules | |
|---|---|---|
| (1) | 2-butyl-4-chloro-5-hydroxymethyl-1-[[2'-(2,5-dihydro-5-oxo-1,2,4-oxadiazol-3-yl)biphenyl-4-yl]methyl]imidazole | 10 mg |
| (2) | lactose | 90 mg |
| (3) | microcrystalline cellulose | 70 mg |
| (4) | magnesium stearate | 10 mg |
| | one capsule | 180 mg |

(1), (2), (3) and a half of (4) are mixed and granulated. To the granules is added the remainder of (4), and the whole is filled into gelatin capsules.

| 5. | Tablets | |
|---|---|---|
| (1) | 2-butyl-4-chloro-5-hydroxymethyl-1-[[2'-(2,5-dihydro-5-oxo-1,2,4-oxadiazol-3-yl)biphenyl-4-yl]methyl]imidazole | 10 mg |
| (2) | lactose | 35 mg |
| (3) | corn starch | 150 mg |
| (4) | microcrystalline cellulose | 30 mg |
| (5) | magnesium stearate | 5 mg |
| | one tablet | 230 mg |

(1), (2), (3), two thirds of (4) and a half of (5) are mixed and granulated. To the granules are added the remainders of (4) and (5), followed by subjecting the mixture to compression molding.

| 6. | Injections | |
|---|---|---|
| (1) | 2-butyl-4-chloro-5-hydroxymethyl-1-[[2'-(2,5-dihydro-5-oxo-1,2,4-oxadiazol-3-yl)biphenyl-4-yl]methyl]imidazole sodium salt | 10 mg |
| (2) | inositol | 100 mg |
| (3) | benzyl alcohol | 20 mg |
| | one ampoule | 130 mg |

(1), (2) and (3) are dissolved in distilled water for injection to make the whole volume 2 ml, which is filled into an ampoule. The whole process is conducted under sterile conditions.

| 7. | Capsules | |
|---|---|---|
| (1) | 2-ethoxy-1-[[2'-(2,5-dihydro-5-oxo-1,2,4-thiadiazol-3-yl)biphenyl-4-yl]methyl]-benzimidazole-7-carboxylic acid | 10 mg |
| (2) | lactose | 90 mg |
| (3) | microcrystalline cellulose | 70 mg |
| (4) | magnesium stearate | 10 mg |
| | one capsule | 180 mg |

(1), (2), (3) and a half of (4) are mixed and granulated. To the granules is added the remainder of (4), and the whole is filled into gelatin capsules.

| 8. | Tablets | |
|---|---|---|
| (1) | 2-ethoxy-1-[[2'-(2,5-dihydro-5-oxo-1,2,4-thiadiazol-3-yl)biphenyl-4-yl]methyl]-benzimidazole-7-carboxylic acid | 10 mg |
| (2) | lactose | 35 mg |
| (3) | corn starch | 150 mg |
| (4) | microcrystalline cellulose | 30 mg |
| (5) | magnesium stearate | 5 mg |
| | one tablet | 230 mg |

(1), (2), (3), two thirds of (4) and a half of (5) are mixed and granulated. To the granules are added the remainders of (4) and (5), followed by subjecting the mixture to compression molding.

| 9. | Injections | |
|---|---|---|
| (1) | 2-ethoxy-1-[[2'-(2,5-dihydro-5-oxo-1,2,4-thiadiazol-3-yl)biphenyl-4-yl]methyl]benzimidazole-7-carboxylic acid disodium salt | 10 mg |
| (2) | inositol | 100 mg |
| (3) | benzyl alcohol | 20 mg |
| | one ampoule | 130 mg |

(1), (2) and (3) are dissolved in distilled water for injection to make the whole volume 2 ml, which is filled into an ampoule. The whole process is conducted under sterile conditions.

WORKING EXAMPLE 1

2-Ethoxy-1-[[2'-(2,5-dihydro-5-oxo-1,2,4-oxadiazol-3-yl)biphenyl-4-yl]methyl]benzimidazole-7-carboxylic Acid 1a) Methyl 3-Amino-2-[[2'-cyanobiphenyl-4-yl]methyl Amino]benzoate A mixture of methyl 2-[[2'-cyanobiphenyl-4-yl)methyl]amino]-3-nitrobenzoate (10 g) synthesized in accordance with the method described in official gazette of EP-0425921, $FeCl_3 \cdot 6H_2O$ (0.1 g) and activated charcoal (1 g) in a mixture of methanol (100 ml) and THF (50 ml) were heated under reflux for 30 minutes. To the reaction mixture was added dropwise hydrazine hydrate (7.2 ml), followed by heating for 14 hours under reflux. Insoluble materials were filtered off, and the filtrate was concentrated to dryness. To the residue was added an aqueous solution of sodium hydrogencarbonate, and the mixture was extracted with ethyl acetate. The extract was washed with water and dried, then the solvent was evaporated to dryness, followed by purifying the residue by column chromatography on silica gel. Crystals thus obtained were recrystallized from isopropyl ether to afford pale yellow needles (6.0 g, 64%), m.p. 110°–111° C.

$^1$H-NMR(200 MHz,CDCl$_3$) δ: 3.81(3H,s), 3.97(2H,br s), 4.23(2H,d), 6.39(1H,t), 6.84–6.93(2H,m), 7.26–7.55(8H, m), 7.64(1H,dt), 7.77(1H,dd).

1b) Methyl 1-[(2'-cyanobiphenyl-4-yl)methyl]-2-ethoxybenzimidazole-7-carboxylate To a solution of methyl 3-amino-2-[[(2'-cyanobiphenyl-4-yl)methyl]amino]benzoate (2.03 g) in ethyl orthocarbonate (5 ml) was added acetic acid (0.37 g), and the mixture was stirred for one hour at 80° C. The reaction mixture was concentrated, and the residue was dissolved in ethyl acetate. The solution was washed with an aqueous solution of sodium hydrogencarbonate and water. The solvent was evaporated to dryness to give crystals. Recrystallization of the crystals from ethyl acetate-hexane afforded colorless crystals (2.01 g, 86%).

m.p.168.5°–169.5° C., Elemental Analysis for $C_{25}H_{21}N_3O_3$:

|  | C(%) | H(%) | N(%) |
|---|---|---|---|
| Calcd.: | 72.98; | 5.14; | 10.21 |
| Found: | 72.71; | 5.12;. | 9.97 |

$^1$H-NMR(200 MHz, CDCl$_3$) δ: 1.42(3H,t,J=7.1 Hz), 3.71(3H,s), 4.63 (2H,q,J=7.1 Hz), 5.59(2H,s), 7.09(2H,d,J=8.4 Hz), 7.20(1H,t,J=7.9 Hz), 7.45–7.59(5H,m), 7.69–7.80(2H,m), 7.92(1H,dd,J=1.4,7.8 Hz). IR(KBr)cm: 2225, 1725, 1550, 1480, 1430, 1350, 1280, 1250, 1040, 760, 750.

1c) Methyl 2-Ethoxy-1-[[2'-hydroxycarbamimidoyl)biphenyl)-4-yl]methyl]-1H-benzimidazole-7-carboxylate To a mixture of hydroxylamine hydrochloride (6.95 g) in dimethyl sulfoxide (DMSO) (80 ml) was added a solution of 28% NaOMe in methanol (5.2 g) while stirring at room temperature. The mixture was stirred for 10 minutes at room temperature, to which was added the compound (8.22 g) obtained in Working Example (1b), and then the mixture was stirred for 4 hours at 90° C. To the stirred reaction mixture was added water (50 ml) at room temperature. Resulting crystalline precipitates were collected by filtration, washed with water and dried to give white powder (8.0 g, 90%)

$^1$H-NMR(90 MHz,CDCl$_3$) δ: 1.43(3H,t), 3.73(3H,s), 4.67(2H,q), 5.63(2H,s), 6.97–7.80(11H,m). IR(Nujol)cm$^{-1}$: 3420, 3320, 1720, 1545, 1430, 1280, 1040, 750.

1d) Methyl 2-Ethoxy-1-[[2'-(2,5-dihydro-5-oxo-1,2,4-oxadiazol-3-yl)biphenyl-4-yl]methyl]benzimidazole-7-carboxylate To a stirred suspension of the compound obtained in Working Example 1c) and triethylamine (0.2 g) in tetrahydrofuran (THF) (30 ml) was added dropwise a methylene chloride (2 ml) solution of ethyl chlorocarbonate (0.22 g) under ice-cooling. The mixture was stirred for two hours at room temperature, then insolubles were filtered off, and the filtrate was concentrated to dryness. To the concentrate was added ethyl acetate (5 ml), then insolubles were filtered off, and the filtrate was concentrated to dryness. The mixture of the residue in xylene (10 ml) was heated for 1.5 hour under reflux. To the reaction mixture was added ethyl acetate, which was washed with water, dried, and concentrated to dryness. The residue was purified by column chromatography on silica gel to give crude crystals. Recrystallization from ethyl acetate isopropyl ether afforded colorless prisms (0.22 g, 23%), m.p. 195°–197° C.

Elemental Analysis for $C_{26}H_{22}N_4O_5$:

|  | C(%) | H(%) | N(%) |
|---|---|---|---|
| Calcd.: | 66.38; | 4.71; | 11.91 |
| Found: | 66.17; | 4.66; | 11.84 |

$^1$H-NMR(90 MHz,CDCl$_3$)δ: 1.43(3H,t), 3.77(3H,s), 4.60(2H,q), 5.63(2H,s), 7.00–7.73(11H,m). IR(Nujol)cm$^{-1}$: 2740, 2670, 1775, 1720, 1545, 1450, 1435, 1275, 1040, 750.

1e) 2-Ethoxy-1-[[2'-2,5-dihydro-5-oxo-1,2,4-oxadiazol-3-yl)biphenyl-4-yl]methyl]benzimidazole-7-carboxylic Acid The compound obtained in Working Example 1d) (0.165 g) was dissolved in methanol (12 ml), to which was added a 2N aqueous solution of LiOH (1 ml), followed by heating for 3 hours under reflux. The reaction was adjusted to pH 3 with 2N HCl, then the solvent was evaporated to dryness. The residue was partitioned between water (20 ml) and chloroform (50 ml), then the organic layer was washed with water and dried. The solvent was evaporated to dryness, and the crystalline product was crystallized from ethyl acetate to give colorless prisms (0.135 g, 84%), m.p.156°–157° C.

Elemental Analysis for $C_{25}H_{20}N_4O_5 \cdot \frac{1}{2}C_4H_8O_2 \cdot \frac{1}{5}H_2O$:

|  | C(%). | H(%) | N(%) |
|---|---|---|---|
| Calcd.: | 64.33; | 4.88; | 11.11 |
| Found: | 64.37; | 4.89; | 11.04 |

$^1$H-NMR(90 MHz,CDCl$_3$) δ: 1.47(3H,t), 4.60(2H,q), 5.67(2H,s), 6.97–7.77(11H,m). IR(Nujol)cm$^{-1}$: 1775, 1730, 1685, 1540, 1425, 1270, 1030, 750.

WORKING EXAMPLE 2

Methyl 2-butyl-1-[[2,-(2-oxo-3H-1,2,3,5-oxathiadiazol-4-yl)biphenyl]methyl]benzimidazole-7-carboxylate In DMSO (3 ml) were dissolved methyl 2-butyl-1-[(2'-cyanobiphenyl-4-yl)methyl]benzimidazole-7-carboxylate (1.27 g) synthesized in accordance with the disclosure in a known literature reference (official gazette of EP-0425921) and hydroxylamine hydrochloride (0.35 g). To the solution was added a solution of 28% sodium methoxide in methanol (0.965 g), and the mixture was stirred for 3 hours at 90°–100° C. To the reaction mixture was added water (20 ml), and then resulting precipitates were filtered off. The filtrate was concentrated to dryness, and the residue was purified by means of a silica gel column chromatography to give a pale brown powdery product. The product (0.427 g) and pyridine (0.183 g) were dissolved in methylene chloride (3 ml). To the solution was added dropwise, while cooling at 20° to 25° C. thionyl chloride (1.19 g). The mixture was stirred for a while, to which was added water (3 ml) dropwise at −5° to −10° C. To the reaction mixture was added water (15 ml), and the mixture was extracted with methylene chloride (20 ml). The organic layer was washed with water, dried and concentrated to dryness. The residue was purified by column chromatography on silica gel. Crude crystals thus obtained were recrystallized from isopropyl ether to afford colorless prisms (0.12 g, 7%), m.p.124°–125°C.

Elemental Analysis for $C_{27}H_{26}N_4O_4S \cdot \frac{1}{5}C_6H_{14}O \cdot \frac{1}{5}H_2O$:

|  | C(%) | H(%) | N(%) |
|---|---|---|---|
| Calcd.: | 64.02; | 5.56; | 10.59 |
| Found: | 64.11; | 5.52; | 10.51 |

$^1$H-NMR(90 MHz, CDCl$_3$) δ: 0.90(3H,t), 1.20–2.00(4H,m), 2.63(2H,t), 3.70(3H,s), 5.63(2H,s), 6.73(2H,d), 7.00–7.70(8H,m), 7.83–7.93(1H,m). IR(Nujol)cm$^{-1}$: 1725, 1520, 1435, 1410, 1290, 1180. MS m/z: 502(M$^+$), 438, 423, 381, 192, 64.

WORKING EXAMPLE 3

Methyl 2-Ethoxy-1-[[2'-(2-oxo-3H-1,2,3,5-oxathiadiazol-4-yl)biphenyl]methyl]benzimidazole-7-carboxylate To a solution of the compound (2.0 g) obtained in Working Example (1c) in THF (100 ml) was added pyridine (0.711 g). The mixture was added dropwise over a period of 45 minutes, under ice-cooling, to a methylene chloride (20 ml) solution containing thionyl chloride (0.536 g). To the mixture was added water (15 ml) dropwise under ice-cooling. The solvent was evaporated to dryness. To the residue was added water (50 ml), and the mixture was extracted with chloroform (100 ml). The extract was concentrated to dryness, and the residue was purified by column chromatography. Resultant crystals were recrystallized from ethyl acetate to give colorless prisms (0.35 g, 16%), m.p.109°–111° C.

Elemental Analysis for $C_{25}H_{22}N_4O_5S \cdot \frac{1}{5}H_2O$:

|  | C(%) | H(%) | N(%) | S(%) |
| --- | --- | --- | --- | --- |
| Calcd.: | 60.77; | 4.53; | 11.34; | 6.49 |
| Found: | 60.76; | 4.49; | 11.11; | 6.48 |

$^1$H-NMR (90 MHz, CDCl$_3$) δ: 1.47(3H,t), 3.73(2H,s), 4.53(2H,q), 5.60(2H,s), 6.90–7.93(11H,m). IR(Nujol)cm$^{-1}$: 1720, 1545, 1430, 1280, 1040, 750.

WORKING EXAMPLE 4

1-(Cyclohexyloxycarbonyloxy)ethyl 2-Ethoxy-1-[[2'-(2,5-dihydro-5-oxo-1,2,4-oxadiazol-3-yl)biphenyl-4-yl]methyl]benzimidazole-7-carboxylate The compound (0.51 g) obtained in Working Example (1e) was dissolved in dimethylformamide (8 ml). To the solution were added 1-(cyclohexyloxycarbonyloxy)ethyl chloride (0.3 g), anhydrous potassium carbonate (0.4 g) and potassium iodide (0.04 g). The mixture was stirred for 15 hours at 80° C. The solvent was evaporated to dryness. To the residue were added chloroform (100 ml), water (5 ml) and ethanol (5 ml), and the mixture was shaken. The lower layer was concentrated to dryness under reduced pressure, and the residue was purified by column chromatography on silica gel. Recrystallization from isopropyl ether afforded the title compound as colorless prisms (0.2 g, 36%), m.p.108°–109° C.

Elemental Analysis for $C_{34}H_{34}N_4O_8 \cdot 0.5H_2O$:

|  | C(%) | H(%) | N(%) |
| --- | --- | --- | --- |
| Calcd.: | 64.24; | 5.55; | 8.81 |
| Found: | 64.43; | 5.50; | 8.79 |

$^1$H-NMR(90 MHz,CDCl$_3$) δ: 1.07–2.00(16H,m), 4.03–4.67(3H,m), 5.63(2H,s), 6.57–7.90(12H,m), 10.57(1H,broad). IR(Nujol)cm$^{-1}$: 1780, 1750, 1545, 1275, 1235, 1070, 1030.

WORKING EXAMPLE 5

2-Ethylthio-4-methyl-1-[[2'-(2,3-dihydro-3-oxo-1,2,4-oxadiazol-5-yl)biphenyl-4-yl]methyl]-1H-thieno[3,4-d]imidazole-6-carboxylic Acid

5a) O-methyl (4'-methylbiphenyl-2-yl)carbonylthiocarbamate

In chloroform (40 ml) was dissolved (4'-methylbiphenyl-2-yl)carboxylic acid (10 g). To the solution was added thionyl chloride (7 ml), and the mixture was heated for 3 hours under reflux. The reaction mixture was poured into ice-water, then the organic layer was separated, washed with water and concentrated to dryness to give a syrup, which was dissolved in dioxane (80 ml). To the solution was added powdered potassium thiocyanate (9.16 g), and the mixture was heated for one hour under reflux. The reaction mixture was allowed to cool, and then insolubles were filtered off. After addition of methanol (15 ml) to the filtrate, the solution was heated for 15 minutes under reflux. The reaction solution was concentrated to dryness, and the resulting crystals were crystallized from isopropyl ether to afford the title compound as white plates (7.4 g, 55%), m.p.149°–150° C.

$^1$H-NMR(200 MHz,CDCl$_3$): 2.40(3H,s), 4.01(3H,s), 7.23–7.34(4H,m), 7.38–7.60(3H,m), 7.74(1H,dd), 8.37(1H, br s).

5b) Dimethyl (4'-Methylbiphenyl-2-yl)carbonylimino Monothiocarbonate

To a solution of the compound (7.4 g) obtained in Working Example (5a) in methanol (35 ml) were added methyl iodide (4.0 g) and a solution of 28% sodium methoxide in methanol (5.5 g), and then the mixture was stirred for 24 hours at room temperature. The reaction mixture was concentrated to dryness, and the residue was extracted with ethyl acetate—water. The organic layer was washed with water and concentrated to dryness. The residue was purified by column chromatography on silica gel to give a colorless syrup (4.4 g, 57%).

$^1$H-NMR(200 MHz,CDCl$_3$) δ: 2.29(3H,s), 3.36(3H, s), 2.37(3H,s), 7.13–7.27(4H,m), 7.32–7.53(3H,m), 7.93(1H, m).

5c) 3-Methoxy-5-(4'-methylbiphenyl-2-yl)-1,2,4-oxadiazole

To a solution of potassium hydroxide (1.1 g) in methanol (20 ml) was added powdered hydroxylamine hydrochloride (1.2 g), and the mixture was shaken well. The mixture was added to a solution of the compound (4.4 g) obtained in Working Example (5b) in 95% ethanol (10 ml), and the resultant mixture was stirred for 18 hours at room temperature. The reaction mixture was concentrated to dryness, and to the residue was added chloroform. Insoluble materials were filtered off, and the filtrate was concentrated to dryness, and the residue was dissolved in toluene (50 ml). The solution was heated for 2 hours under reflux together with a catalytic amount of p-toluenesulfonic acid, followed by concentration to dryness. The residue was purified by column chromatography on silica gel to afford a colorless syrup (2.5 g, 64%).

$^1$H-NMR(200 MHz,CDCl$_3$) δ: 2.38(3H,s), 4.08(3H,s), 7.11–7.21(4H,m), 7.41–7.62(3H,m), 7.96(1H,dd).

5d) 5-(4'-Methylbiphenyl-2-yl)-1,2,4-oxadiazolin-3(2H)-one

A mixture of the compound (0.5 g) obtained in Working Example (5c) and pyridinium chloride (5 g) was heated for 30 minutes at 155° C. in nitrogen atmosphere. The reaction mixture was extracted with ethyl acetate—water. The organic layer was washed with water and concentrated to dryness to, give pale yellow prisms (0.5 g, 100%), m.p.145°–150° C.

$^1$H-NMR(200 MHz, CDCl$_3$) δ: 2.36(3H,s), 7.09–7.20(4H,m), 7.44–7.53(2H,m), 7.58–7.67(1H,m), 7.88(1H,dd). IR(Nujol)cm$^{-1}$: 1605, 1590, 1480, 1340, 815, 750.

5e) 5-(4'-Methylbiphenyl-2-yl)-2-trityl-1,2,4-oxadiazol-3(2H)-one

To a solution of the compound (1 g) obtained in Working Example (5d) and trityl chloride (1.0 g) in dichloromethane (20 ml) was added dropwise with stirring. The mixture was then stirred for one hour at room temperature. The reaction mixture was concentrated to dryness, and the residue was purified by column chromatography on silica gel to afford colorless prisms (0.9 g, 45%), m.p.181°–184° C.

$^1$H-NMR(200 MHz,CDCl$_3$) δ: 2.37(3H,s), 7.06(4H,s), 7.16–7.43(17H,m), 7.52–7.60(1H,m), 7.79(1H,dd). IR(Nujol)cm$^{-1}$: 1745, 1595, 1580, 1440, 1335, 1160.

5f) 5-(4-Bromomethylbiphenyl-2-yl)-2-trityl-1,2,4-oxadiazol-3(2H)-one

A mixture of the compound (0.9 g) obtained in Working Example (5e), N-bromosuccinimide (0.3 g) and a catalytic amount of benzoyl peroxide was heated under reflux for one hour in carbon tetrachloride (20 ml) under irradiation of light. The reaction mixture was allowed to cool, and then precipitates were filtered off. The filtrate was concentrated to dryness to give the title compound as pale yellow amorphous powder (1.0 g, 99%).

$^1$H-NMR(200 MHz,CDCl$_3$) δ: 4.47(2H,s), 7.06–7.63(22H,m), 7.85(1H,dd).

5g) Methyl 2-Ethylthio-4-methyl-1-[[2'-(2,3-dihydro-3-oxo-2-trityl-1,2,4-oxadiazol-5-yl)biphenyl-4-yl]methyl]-1H-thieno[3,4-d]imidazole-6-carboxylate To a stirred solution of methyl 2-ethylthio-4-methyl-1H-thieno[3,4-d]imidazole-6-carboxylate (0.4 g) in dimethylformamide (10 ml) was added, in portions, sodium hydride (60% dispersion in meneral oil; 70 mg) under ice-cooling. The mixture was stirred for further 30 minutes at room temperature. To the reaction mixture was added the compound (1 g) obtained in Working Example (5f), and the mixture was stirred for 1.5 hour. The reaction mixture was concentrated to dryness, and the residue was extracted with ethyl acetate—water. The organic layer was washed with water, and then concentrated to dryness. The residue was purified by column chromatography on silica gel to afford the title compound as yellow amorphous powder (0.6 g, 51%).

$^1$H-NMR(200 MHz, CDCl$_3$) δ: 1.32(3H,t), 2.66(3H,s), 3.61(3H,s), 3.25(2H,q), 5.75(2H,s), 7.10(4H,s), 7.19(15H,s), 7.26–7.43(2H,m), 7.52–7.60(1H,m), 7.70(1H,dd). IR(Nujol)cm$^{-1}$: 1740, 1685, 1595, 1330, 1315, 1160, 1080

5h) Methyl 2-Ethylthio-1-[[2'-(2,3-dihydro-3-oxo-1,2,4-oxadiazol-5-yl)-biphenyl-4-yl]methyl]-4-methyl-1H-thieno[3,4-d]imidazole-6-carboxylate The compound (0.6 g) obtained in Working Example (5g) was dissolved in methanol (15 ml) and chloroform (10 ml). To the solution was added 1N—HCl (0.9 ml), and the mixture was stirred for one hour at room temperature. The reaction mixture was concentrated to dryness, and the residue was partitioned between chloroform-water. The organic layer was washed with water and concentrated to dryness. The resulting residue was purified by column chromatography on silica gel to afford the title compound as pale yellow amorphous powder (0.4 g, 95%).

Elemental Analysis for $C_{25}H_{22}N_4O_4S_2 \cdot \frac{2}{5}CH_2Cl_2$:

|  | C(%) | H(%) | N(%) |
| --- | --- | --- | --- |
| Calcd.: | 56.44; | 4.25; | 10.36 |
| Found: | 56.56; | 4.18; | 10.26 |

$^1$H-NMR(200 MHz,d$_6$-DMSO) δ: 1.35(3H,t), 2.56(3H,s), 3.70(3H,s), 3.26(2H,s), 5.67(2H,s), 7.12(2H,d), 7.21(2H,d), 7.41–7.68(3H,m), 7.80(1H,d). IR(Nujol)cm$^{-1}$: 1685, 1590, 1530, 1355, 1315, 1230, 1160, 1085.

5i) 2-Ethylthio-1-[[2'-(2,3-dihydro-3-oxo-1,2,4-oxadiazol-5-yl)biphenyl-4-yl]methyl]-4-methyl-1H-thieno[3,4-d]imidazole-6-carboxylic Acid The compound (0.1 g) obtained in Working Example (5h) was dissolved in tetrahydrofuran (2 ml) and water (1 ml). To the solution was added lithium hydroxide monohydrate (25 mg), and the mixture was heated for 17 hours under reflux. The reaction mixture was concentrated to dryness, to which was added water, and then insoluble materials were filtered off. The filtrate was made acid with 1N—HCl, and then resulting precipitates were collected by filtration to obtain the title compound as pale yellow powder (60 mg, 62%), m.p. 144°–147° C.

Elemental Analysis for $C_{24}H_{20}N_4O_4S_2$:

|  | C(%) | H(%) | N(%) |
| --- | --- | --- | --- |
| Calcd.: | 58.52; | 4.09; | 11.37 |
| Found: | 58.47; | 4.25; | 11.33 |

$^1$H-NMR(200 MHz,d$_6$-DMSO) δ: 1.34(3H,t), 2.54(3H,s), 3.25(2H,q), 5.70(2H,s), 7.16(2H,d), 7.20(2H,d), 7.45–7.73(3H,m), 7.88(1H,d). IR(Nujol)cm$^{-1}$: 1650, 1590, 1525, 1310, 1160, 1085.

WORKING EXAMPLE 6

2-Butyl-1-[[2'-(2,3-dihydro-2-oxo-1,3,4-oxadiazol-5yl)-biphenyl-4-yl]methyl]benzimidazole-7-carboxylic Acid

6a) 4'-Methylbiphenyl-2-carbohydrazide

To a solution of 4'-methylbiphenyl-2-carboxylic acid (6.4 g) in tetrahydrofuran (50 ml) were added N,N-dimethylformamide (two drops) and oxalyl chloride (4.4 g). The mixture was stirred for 16 hours at room temperature. The solvent was evaporated to dryness under reduced pressure to give an oil, which was added dropwise to a solution of hydrazine monohydrate (7.5 g) in tetrahydrofuran (50 ml) with stirring, followed by stirring for further 6 hours. The reaction mixture was diluted with water, which was extracted with ethyl acetate. The extract was washed with water and dried. The solvent was evaporated to dryness under reduced pressure. The residue was purified by column chromatography on silica gel to give crude crystals. Recrystallization from chloroform-isopropyl ether afforded the title compound as colorless needles (4.3 g, 63%), m.p.98°–99° C.

Elemental Analysis for $C_{14}H_{14}N_2O$:

|  | C(%) | H(%) | N(%) |
|---|---|---|---|
| Calcd.: | 74.31; | 6.24; | 12.38 |
| Found: | 74.17; | 6.17; | 12.46 |

$^1$H-NMR(200 MHz,CDCl$_3$) δ: 2.39(3H,s), 2.65(2H,br), 6.52(1H,br), 7.20–7.31(4H,m), 7.35–7.55(3H,m), 7.67(1H, dd). IR(KBr)cm$^{-1}$: 3280, 3220, 1670, 1610, 1520, 1320, 1185, 1100, 820, 755.

6b) 1-[2-(4'-Methylphenyl)benzoyl]semicarbazide

To a solution of the compound (4.3 g) obtained in Working Example (6a) in 1N—HCl (20 ml) was added dropwise an aqueous solution (20 ml) of sodium isocyanate (1.7 g), and the mixture was stirred for 3.5 hours. Resulting crystalline precipitates were collected by filtration and recrystallized from ethyl acetate—methanol to give colorless needles (4.5 g, 87%), m.p.183°–184° C. (decomp.).

Elemental Analysis for $C_{15}H_{15}N_3O_2.0.3H_2O$:

|  | C(%) | H(%) | N(%) |
|---|---|---|---|
| Calcd.: | 65.59; | 5.72; | 15.30 |
| Found: | 65.79; | 5.61; | 15.38 |

$^1$H-NMR(200 MHz,DMSO-d$_6$) δ: 2.33(3H,s), 5.71(2H,br), 7.18(2H,d), 7.33–7.56(6H,m), 7.84(1H,s), 9.84(1H,br). IR(KBr)cm$^{-1}$: 3460, 3230, 1700, 1650, 1520, 1305, 820, 765.

6c) 2,3-Dihydro-5-(4'-methylbiphenyl-2-yl)-1,3,4-oxadiazol-2(3H)-one

The compound (4.0 g) obtained in Working Example (6b) was suspended in xylene (100 ml), and the mixture was heated for 18 hours under reflux. The solvent was evaporated to dryness under reduced pressure, and the residue was purified by column chromatography on silica gel to give crude crystals. Recrystallization from ethyl acetate—hexane afforded the title compound as colorless needles (2.0 g , 53%), m.p. 130°–131° C.

Elemental Analysis for $C_{15}H_{12}N_2O_2$:

|  | C(%) | H(%) | N(%) |
|---|---|---|---|
| Calcd.: | 71.42; | 4.79; | 11.10 |
| Found: | 71.45; | 4.79; | 11.05 |

$^1$H-NMR(200 MHz,CDCl$_3$) δ: 2.39(3H,s), 7.19(4H,s), 7.37–7.60(3H,s), 7.77(1H,dd), 8.89 (1H,br). IR(KBr)cm$^{-1}$: 1765, 1600, 1490, 1330, 1240, 1035, 960, 925, 815, 770, 750, 715, 700.

6d) 2,3-Dihydro-5-(4'-methylbiphenyl-2-yl)-3-triphenyl Methyl-1,3,4-oxadiazol-2(3H)-one To a solution of the compound (2.0 g) obtained in Working Example (6c) in methylene chloride (25 ml) were added triethylamine (0.89 g) and triphenylmethyl chloride (2.5 g), and the mixture was stirred for one hour. The reaction mixture was washed with water, then dried. The solvent was evaporated to dryness under reduced pressure, and the residue was purified by column chromatography on silica gel to afford the title compound as colorless amorphous powder (4.0 g, 100%), m.p.60°–63° C.

Elemental Analysis for $C_{34}H_{26}N_2O_2$:

|  | C(%) | H(%) | N(%) |
|---|---|---|---|
| Calcd.: | 82.57; | 5.30; | 5.66 |
| Found: | 82.67; | 5.37; | 5.20 |

$^1$H-NMR(200 MHz,CDCl$_3$) δ: 2.31(3H,S), 7.00(2H,d), 7.05–7.54(20H,m), 7.68(1H,dd). IR(KBr)cm$^{-1}$: 1780, 1490, 1445, 1335, 1280, 1005, 875, 820, 770, 755, 740, 700.

6e) 5-(4'-Bromomethylbiphenyl-2-yl)-2,3-dihydro-3-triphenylmethyl-1,3,4-oxadiazole-2(3H)-one To a solution of the compound (4.0 g) obtained in Working Example (6d) in carbon tetrachloride (50 ml) were added N-bromosuccinimide (1.4 g) and benzoyl peroxide (19 mg), and the reaction mixture was heated for one hour under reflux under irradiation of light. Insoluble materials were filtered off, and the filtrate was concentrated under reduced pressure. The resulting residue was purified by column chromatography on silica gel to afford the title compound as colorless amorphous powder (4.3 g, 93%).

$^1$H-NMR(200 MHz,CDCl$_3$) δ: 4.42(2H,s), 7.10–7.56(22H,m), 7.72(1H,dd). IR(KBr)cm$^{-1}$: 1780, 1490, 1440, 1335, 1260, 1215, 1000, 870, 765, 740, 700.

6f) Methyl-2-[N-[2'-(2,3-dihydro-2-oxo-1,3,4-oxadiazol-5-yl)biphenyl-4-yl]methyl-N-valeryl]amino-3-nitrobenzoate To a solution of the compound (0.86 g) obtained in Working Example (6e) in acetonitrile (10 ml) were added methyl 3-nitro-2-valerylaminobenzoate (0.42 g) and potassium carbonate (0.26 g), and the mixture was heated for 36 hours under reflux. The reaction mixture was diluted in water, which was extracted with ethyl acetate. The extract was washed with water and dried. The solvent was evaporated to dryness under reduced pressure, and the residue was purified by column chromatography on silica gel. The oily product thus obtained was dissolved in trifluoroacetic acid (5 ml), and the solution was stirred for 30 minutes at 60° C. Trifluoroacetic acid was evaporated to dryness under reduced pressure. The residue was dissolved in ethyl acetate, which was washed with an aqueous solution of sodium hydrogencarbonate and dried. The solvent was evaporated to dryness under reduced pressure, and the residue was purified by column chromatography on silica gel to afford the title compound as a yellow oily product (0.50 g, 63%).

$^1$H-NMR(200 MHz,CDCl$_3$) δ: 0.85(3H,t), 1.18–1.36(2H, m), 1.58–1.71(2H,m), 2.05–2.15(2H,m), 3.69(3H,s), 4.58(1H,d), 4.95(1H,d), 7.06–7.16(4H,m), 7.34(1H,dd), 7.41–7.54(2H,m), 7.62(1H,t), 7.77(1H,dd), 8.02(1H,dd), 8.17(1H,dd), 8.97(1H,br). IR(neat)cm$^{-1}$: 1815, 1780, 1730, 1660, 1530, 1445, 1390, 1370, 1340, 1285, 1260, 1230, 750.

6g) Methyl 2-Butyl-1-[[2'-(2,3-dihydro-2-oxo-1,3,4-oxadiazol-5-yl)biphenyl-4-yl]methyl]benzimidazole-7-carboxylate To a solution of the compound (0.50 g) obtained in Working Example 6f) in methanol (10 ml) were added conc.

HCl (1 ml) and iron powder (0.34 g). The mixture was heated for 24 hours under reflux. Insoluble materials were filtered off, and the filtrate was concentrated to dryness. The residue was diluted with water and extracted with ethyl acetate. The extract was washed with water and dried. The solvent was evaporated to dryness under reduced pressure, and the residue was purified by column chromatography on silica gel. Crude crystals thus obtained were recrystallized from ethyl acetate—chloroform to afford the title compound as colorless crystals (73 mg, 16%), m.p. 204°–205° C.

Elemental Analysis for $C_{28}H_{26}N_4O_4$:

|  | C(%) | H(%) | N(%) |
|---|---|---|---|
| Calcd.: | 69.70; | 5.43; | 11.61 |
| Found: | 69.43; | 5.49; | 11.59 |

$^1$H-NMR(200 MHz,CDCl$_3$) δ: 0.94(3H,t), 1.36–1.55 (2H, m), 1.79–1.94(2H,m), 2.94(2H,t), 3.73(3H,s), 5.78(2H,s), 6.84(2H,d), 7.16(2H,d), 7.21–7.36(2H,m), 7.41–7.57(2H, m), 7.64(1H,dd), 7.77(1H,dd), 7.96(1H,dd), 9.35(1H,br). IR(KBr)cm$^{-1}$: 1760, 1710, 1600, 1430, 1405, 1335, 1270, 750.

6h)
2-Butyl-1-[[2'-(2,3-dihydro-2-oxo-1,3,4-oxadiazol-5-yl)biphenyl-4-yl]methyl]benzimidazole-7-carboxylic Acid To a solution of the compound (30 mg) obtained in Working Example (6g) in methanol (1 ml) was added 1N—NaOH (0.5 ml), and the mixture was heated for 1.5 hour under reflux. After evaporation of the solvent, the residue was diluted with water, which was then adjusted to pH 3-4 with 1N—HCl to precipitate crystals. The crystals were collected by filtration and recrystallized from ethyl acetate—methanol to afford the title compound as colorless needles (16 mg, 54%), m.p. 247°–248° C.

Elemental Analysis for $C_{27}H_{24}N_4O_4 \cdot 0.5H_2O$:

|  | C(%) | H(%) | N(%) |
|---|---|---|---|
| Calcd.: | 67.91; | 5.28; | 11.73 |
| Found: | 68.19; | 5.21; | 11.89 |

$^1$H-NMR(200 MHz,CDCl$_3$) δ: 0.98(3H,t), 1.40–1.60(2H, m), 1.81–1.97(2H,m), 3.05(2H,t), 5.87(2H,s), 6.86(2H,d), 7.17(2H,d), 7.28(1H,t), 7.36–7.62(3H,m), 7.67(1H,dd), 7.83(1H,dd), 7.99(1H,dd). IR(KBr)cm$^{-1}$: 1770, 1700, 1600, 1410, 1230, 740.

WORKING EXAMPLE 7

2-Ethylthio-1-[[2'-(2,3-dihydro-2-oxo-1,3,4-oxadiazol-5-yl)biphenyl-4-yl]methyl]-4-methylthieno[3,4-d]imidazole-6-carboxylic Acid 7a) Methyl 2-Ethylthio-1-[[2'-2,3-dihdyro-2-oxo-1,3,4-oxadiazol-5-yl)biphenyl-4-yl]methyl]-4-methylthieno[3,4-d]imidazole-6-carboxylate To an ice-cooling solution of methyl 2-ethylthio- 4-methylthieno[3,4-d]imidazole-6-carboxylate (0.26 g) in N,N-dimethyl formamide (2 ml) was added sodium hydride (60% dispersion in meneral oil; 44 mg), and the mixture was stirred for 15 minutes, to which was then added 5-(4'-bromomethylbiphenyl-2-yl)-2,3-dimethyl-3-triphenylmethyl-1,3,4-oxadiazol-2-one (0.57 g). The reaction mixture was stirred for 2 hours at room temperature, which was diluted with water and extracted with ethyl acetate. The extract was washed with water and dried. The solvent was evaporated to dryness under reduced pressure, and the residue was dissolved in trifluoroacetic acid (5 ml). The solution was stirred for 30 minutes at 60° C. and concentrated to dryness under reduced pressure, and the residue was dissolved in ethyl acetate. The solution was washed with an aqueous solution of sodium hydrogencarbonate and dried. The solvent was evaporated to dryness under reduced pressure, and the residue was purified by column chromatography on silica gel to give crude crystals. Recrystallization from ethyl acetate afforded the title compound as yellow prisms (0.17 g, 33%), m.p. 220°–221° C.

Elemental Analysis for $C_{25}H_{22}N_4O_4S_2$:

|  | C(%) | H(%) | N(%) |
|---|---|---|---|
| Calcd.: | 59.27; | 4.38; | 11.06 |
| Found: | 59.18; | 4.50; | 10.91 |

$^1$H-NMR(200 MHz,CDCl$_3$) δ: 1.42(3H,t), 2.62(3H,s), 3.30(2H,q), 3.75(3H,s), 5.70(2H,s), 7.13–7.23(4H,m), 7.34–7.58(3H,m), 7.77(1H,dd), 8.83(1H,br). IR(neat)cm$^{-1}$: 1770, 1695, 1600, 1530, 1445, 1340, 1320, 1240, 1195, 1165, 1085, 1000, 750.

7b)
2-Ethylthio-1-[[2'-(2,3-dihydro-2-oxo-1,3,4-oxadiazol-5-yl)biphenyl-4-yl]methyl]-4-methylthieno[3,4-d]imidazole-6-carboxylic Acid To a solution of the compound (0.12 g) obtained in Working Example (7a) in tetrahydrofuran (6 ml) was added a solution of lithium hydroxide monohydride (60 mg) in water (3 ml). The mixture was stirred for 60 minutes at 50°–60° C. The solvent was evaporated to dryness under reduced pressure. The residue was diluted with water, and the solution was adjusted to pH 3–4 with 1N—HCl to precipitate crystals. The crystals were collected by filtration and recrystallized from ethyl acetate—methanol to afford the title compound as yellow prisms (72 mg, 60%), m.p. 195°–196° C. (decomp.).

Elemental Analysis for $C_{24}H_{20}N_4O_4S_2 \cdot 0.2H_2O$:

|  | C(%) | H(%) | N(%) |
|---|---|---|---|
| Calcd.: | 58.10; | 4.14; | 11.29 |
| Found: | 58.13; | 4.22; | 11.22 |

$^1$H-NMR(200 MHz,DMSO-d$_6$) δ: 1.34(3H,t), 2.55(3H,s), 3.25(2H,q), 5.72(2H,s), 7.19(2H,d), 7.28(2H,d), 7.42(1H, dd), 7.49–7.67(2H,m), 7.76(1H,dd), 12.40(1H,br). IR(KBr)cm$^{-1}$: 1760, 1685, 1600, 1440, 1330, 1185, 1160, 1080, 960, 925, 760, 750.

WORKING EXAMPLE 8

2-Ethylthio-1-[[2'-(2,5-dihydro-5-oxo-1,2,4-oxadiazol-3-yl)biphenyl-4-yl]methyl]-4-methylthieno[3,4-d]imidazole-6-carboxylic Acid 8a) Methyl 2-Ethylthio-4-methyl-1-[2'-(5-trichloromethyl-1,2,4-oxadiazol-3-yl)biphenyl-4-yl]methylthieno[3,4-d]imidazole-6-carboxylate To an ice-cooling solution of methyl 2-ethylthio-4-methylthieno[3,4-d]imidazole-6-carboxylate (3 g) in DMF (20 ml) was added sodium hydride (60%, oil) (0.56 g), and the mixture was stirred for 10 minutes. To the ice-cooling mixture was added [2'-(5-trichloromethyl-1,2,4-oxadiazol-3-yl)biphenyl-4-yl]methyl bromide (6.1 g), and the mixture was stirred for two hours at room temperature. To the reaction mixture was added water, and the mixture was extracted with ethyl acetate. The organic layer was washed with a saturated aqueous saline solution. The solvent was distilled off under reduced pressure, and the residue was purified by column chromatography on silica gel to afford the title compound as a pale yellow syrupy product (4.15 g, 58%).

$^1$H-NMR(200 MHz,CDCl$_3$) δ: 1.42(3H,t), 2.62(3H,s), 3.29(2H,q), 3.77(3H,s), 5.71(2H,s), 7.16(4H,s), 7.42–7.62(3H,m), 7.83–7.88(1H,m). IR (neat) cm$^{-1}$: 1690, 1600, 1450, 1430, 1345; 1330, 1315, 1230, 1190, 1160, 1090, 840, 820, 800, 755, 730.

8b) Methyl 2-Ethylthio-1-[[2'-(2,5-dihydro-5-oxo-1,2,4-oxadiazol-3-yl)biphenyl-4-yl]methyl]-4methylthieno[3,4-d]imidazole-6-carboxylate To a solution of the compound (4.15 g) obtained in Working Example (8a) in MeOH (50 ml)—CHCl$_3$ (10 ml) was added 1N—NaOH (10 ml), and the mixture was stirred for 30 minutes at room temperature. The reaction mixture was adjusted to pH 4 with 1N—HCl, to which was added water, followed by extraction with CHCl$_3$. The extract was washed with water, dried, and then the solvent was evaporated to dryness under reduced pressure to give crude crystals. Recrystallization from ethyl acetate—methanol—hexane afforded the title compound as colorless prisms (3.15 g, 91%), m.p. 240°–241° C. (decomp.).

Elemental Analysis for C$_{25}$H$_{22}$N$_4$O$_4$S$_2$:

|  | C(%) | H(%) | N(%) |
|---|---|---|---|
| Calcd.: | 59.27; | 4.38; | 11.06 |
| Found: | 59.07; | 4.26; | 11.00 |

$^1$H-NMR(200 MHz ,CDCl$_3$) δ: 1.42(3H,t), 2.61(3H,s), 3.29(2H,q), 3.75(3H,s), 5.74(2H,s), 7.26(4H,s), 7.42(1H,dt), 7.51(1H,dd), 7.61(1H,dt), 7.85(1H,dd), 7.90(1H, br s). IR(KBr)cm$^{-1}$: 1760, 1680, 1595, 1455, 1450, 1430, 1315, 1230, 1160, 1085, 755.

8c) 2-Ethylthio-1-[[2'-(2,5-dihydro-5-oxo-1,2,4-oxadiazol-3-yl)biphenyl-4-yl]methyl]-4-methylthieno[3,4-d]imidazole-6-carboxylic Acid To a solution of the compound (0.5 g) obtained in Working Example (8b) in tetrahydrofuran (THF) (5 ml)—H$_2$O (2.5 ml) was added sodium hydroxide monohydrate (0.12 g), and the mixture was heated for 7 hours under reflux. To the reaction mixture was added water, and the mixture was adjusted to pH 3 with 1N—HCl. Resultant crystals were collected by filtration and recrystallized from chloroform-methanol to give the titled compound as colorless needles (0.36 g, 73%), m.p. 217°–219° C. (decomp.).

Elemental Analysis for C$_{24}$H$_{20}$N$_4$O$_4$S.0.3H$_2$O:

|  | C(%) | H(%) | N(%) |
|---|---|---|---|
| Calcd.: | 57.89; | 4.17; | 11.25 |
| Found: | 57.89; | 4.02; | 11.08 |

$^1$H-NMR(200 MHz,DMSO-d$_6$) δ: 1.34(3H,t), 2.55(3H,s), 3.24(3H,q), 5.71(2H,s), 7.19(2H,d), 7.28(2H,d), 7.49–7.72(4H,m). IR(KBr)cm$^{-1}$: 1750, 1640, 1620, 1585, 1520, 1450, 1305, 1250, 1235, 1155, 760, 750.

WORKING EXAMPLE 9

2-Methoxy-1-[[2'-(2,5-dihydro-5-oxo-1,2,4-oxadiazol-3-yl)biphenyl-4-yl]methyl]-4-methylthieno[3,4-d]imidazole-6-carboxylic Acid 9a) Methyl 2-Ethylsulfinyl-1-[[2'-(2,5-dihydro-5-oxo-1,2,4-oxadiazol-3-yl)biphenyl-4-yl]methyl]-4-methylthieno[3,4-d]imidazole-6-carboxylate To a solution of the compound (3.15 g) obtained in Working Example (8b) in methylene chloride (100 ml) was added m-chloro perbenzoate (1.3 g), and the mixture was stirred for 20 minutes at room temperature. To the reaction mixture was added a saturated aqueous solution of sodium hydrogencarbonate, and the mixture was extracted with ethyl acetate. The extract was washed with water and dried. The solvent was evaporated to dryness and the residue was purified by silica gel column chromatography to give crude crystals. Recrystallization from ethyl acetate—methanol—hexane afforded the title compound as colorless needles (2.60 g, 80%), m.p. 206°–208° C. (decomp.).

Elemental Analysis for C$_{25}$H$_{22}$N$_4$O$_5$S$_2$:

|  | C(%) | H(%) | N(%) |
|---|---|---|---|
| Calcd.: | 57.46; | 4.24; | 10.72 |
| Found: | 57.28; | 4.27; | 10.45 |

$^1$H-NMR(200 MHz,CDCl$_3$) δ: 1.27(3H,t), 2.71 (3H,s), 3.38(2H,q), 3.82(3H, s), 5.98(1H,d), 6.40(1H,d), 7.26(4H, m), 7.41–7.64(3H,m), 7.81(1H,dd), 8.75(1H,br s). IR(KBr)cm$^{-1}$: 1770, 1685, 1450, 1420, 1315, 1235, 1090, 1050, 1040, 1020, 780, 750.

9b) Methyl-1-[[2'-(2,5-dihydro-5-oxo-1,2,4-oxadiazol-3-yl)biphenyl-4-yl]methyl]-2-methoxy-4-methylthieno[3,4-d]imidazole-6-carboxylate To a suspension of the compound (0.79 g) obtained in Working Example (9a) in methanol (20 ml) was added sodium methoxide (28%, methanol solution) (0.88 g), and the mixture was stirred for 30 minutes at room temperature. To the reaction mixture was added water, and the mixture was adjusted to pH 4 with 1N—HCl and extracted with ethyl acetate, followed by washing with a saturated aqueous saline solution and drying. The solvent was evaporated to dryness under reduced pressure to give crude crystals. Recrystallization from ethyl acetate—hexane afforded the title compound as colorless needles (0.71 g, 98%), m.p. 207°–209° C. (decomp.).

Elemental Analysis for $C_{24}H_{20}N_4O_5S$:

|  | C(%) | H(%) | N(%) |
|---|---|---|---|
| Calcd.: | 60.49; | 4.23; | 11.76 |
| Found: | 60.23; | 4.29; | 11.49 |

$^1$H-NMR(200 MHz,CDCl$_3$) δ: 2.37(3H,s), 3.73(3H,s), 3.99(3H,s), 5.59(2H,s), 7.25(4H,s), 7.38 (1H,dd), 7.50(1H, dt), 7.61 (1H,dt), 7.83(1H,dd), 8.79(1H,br s). IR(KBr)cm$^{-1}$: 1750, 1685, 1610, 1570, 1525, 1450, 1440, 1430, 1375, 1330, 1230, 1055, 750.

9c) 1-[[2'-(2,5-Dihydro-5-oxo-1,2,4-oxadiazol-3-yl)biphenyl-4-yl]methyl]-2-methoxy-4-methylthieno[3,4-d]imidazole-6-carboxylic Acid To a mixture of the compound (0.6 g) obtained in Working Example (9b) in a mixture of THF (10 ml)—water (5 ml) was added lithium hydroxide monohydrate (0.16 g). The mixture was heated for 8 hours under reflux. To the reaction mixture was added water, and the mixture was adjusted to pH 4 with 1N—HCl and extracted with chloroform. The extract was washed with water and dried. The solvent was evaporated to dryness under reduced pressure to give crude crystals. Recrystallization from ethyl acetate—methanol afforded the title compound as colorless needles (0.35 g, 54%), m.p. 183°–186° C. (decomp.).

Elemental Analysis for $C_{23}H_{18}N_4O_5S \cdot 0.5AcOEt$:

|  | C(%) | H(%) | N(%) |
|---|---|---|---|
| Calcd.: | 59.28; | 4.38; | 11.06 |
| Found: | 58.94; | 4.15; | 11.18 |

$^1$H-NMR(200 MHz,DMSO-d$_6$) δ: 2.48(3H,s), 4.06(3H,s), 5.56(2H,s), 7.21–7.31(4H,m), 7.49–7.72(4H,m). IR(KBr)cm$^{-1}$: 1800, 1660, 1650, 1570, 1450, 1380, 1370, 1330, 1240, 760, 730.

WORKING EXAMPLE 10

2-Ethoxy-1-[[2'-(2,5-dihydro-5-oxo-1,2,4-oxadiazol-3-yl)biphenyl-4-yl]methyl]-4-methylthieno[3,4-d]imidazole-6-carboxylic Acid

10a) Methyl 2-ethoxy-1-[[2'-f2,5-dihydro-5-oxo-1,2,4-oxadiazol-3-yl)biphenyl-4-yl]methyl]-4-methylthieno[3,4-d]imidazole-6-carboxylate To a solution of sodium (0.1 g) in ethanol (20 ml) was added the compound (0.7 g) obtained in Working Example (9a), and the mixture was stirred for 30 minutes at room temperature. To the reaction mixture was added water, and the mixture was adjusted to pH 4 with 1N—HCl, followed by extraction with ethyl acetate. The extract was washed with water and dried. The solvent was evaporated to dryness under reduced pressure to give crystals, which were suspended in methanol. To the suspension was added sodium methoxide (28%, methanol solution) (0.65 g), and the mixture was heated for 7 hours under reflux. After addition of water, the mixture was adjusted to pH 4 with 1N—HCl, followed by extraction with ethyl acetate. The extract was washed with water and dried, and the solvent was evaporated to dryness under reduced pressure to give crude crystals. Recrystallization from ethyl acetate—methanol—hexane afforded the title compound as pale yellow prisms (0.5 g, 76%), m.p. 215°–217° C. (decomp.).

Elemental Analysis for $C_{25}H_{22}N_4O_5S$:

|  | C(%) | H(%) | N(%) |
|---|---|---|---|
| Calcd.: | 61.21; | 4.52; | 11.42 |
| Found: | 61.02; | 4.32; | 11.28 |

$^1$H-NMR(200 MHz,CDCl$_3$) δ: 1.42(3H,t), 2.45(3H,s), 3.75(3H,s), 4.45(2H,q), 5.59(2H,s), 7.23–7.33(4H,m), 7.38(1H,dd), 7.49(1H,dt), 7.60(1H,dt), 7.84(1H,dd), 8.27(1H,br s). IR(KBr)cm$^{-1}$: 1760, 1685, 1610, 1570, 1530, 1460, 1445, 1435, 1410, 1380, 1330, 1230, 1100, 1060, 760.

10b) 2-Ethoxy-1-[[2'-(2,5-dihydro-5-oxo-1,2,4-oxadiazol-3-yl)biphenyl-4-yl]methyl]-4methylthieno[3,4-d]imidazole-6-carboxylic Acid To a suspension of the compound (0.4 g) obtained in Working Example (10a) in a mixture of THF (10 ml) and water (5 ml) was added lithium hydroxide monohydrate (0.1 g), and the mixture was heated for 12 hours under reflux. To the reaction mixture was added water, and the mixture was adjusted to pH 4 with 1N—HCl. Recrystallization of the resulting crystals from ethyl acetate—methanol afforded the title compound as colorless prisms (0.31 g, 79%), m.p. 206°–208° C. (decomp.).

Elemental Analysis for $C_{24}H_{20}N_4O_5S$:

|  | C(%) | H(%) | N(%) |
|---|---|---|---|
| Calcd.: | 60.49; | 4.23; | 11.76 |
| Found: | 60.27; | 4.15; | 11.70 |

$^1$H-NMR(200 MHz,DMSO-d$_6$) δ: 1.32(3H,t), 2.46(3H,s), 4.47(2H,q), 5.56(2H,s), 7.27(4H,s), 7.49–7.72(4H,m) IR(KBr)cm$^{-1}$: 1760, 1650, 1640, 1600, 1570, 1525, 1460, 1445, 1330, 1240, 760.

WORKING EXAMPLE 11

1-[2'-(2,5-Dihydro-5-oxo-1,2,4-oxadiazol-3-yl)biphenyl-4-yl]methyl-4-methyl-2-n-propoxythieno[3,4-d]imidazole-6-carboxylic Acid

11a) Methyl 1-[[2'-(2,5-dihydro-5-oxo-1,2,4-oxadiazol-3-yl]biphenyl-4-yl]methyl-4-methyl-2-n-propoxythieno[3,4-d]imidazole-6-carboxylate To a solution of sodium (0.1 g) in n-propanol (20 ml) was added the compound (0.7 g) obtained in Working Example (9a), and the mixture was stirred for 30 minutes at room temperature. To the reaction mixture was added water, and the reaction mixture was adjusted to pH 4 with 1N—HCl, followed by extraction with ethyl acetate. The extract was washed with water and dried. The solvent was evaporated to dryness under reduced pressure to give crystals. The crystals were suspended in methanol, and to the suspension was added sodium methoxide (28%, methanol solution) (0.65 g). The mixture was heated for 7 hours under reflux. To the reaction mixture was added water, and the mixture was adjusted to pH 4 with 1N HCl, followed by extraction with ethyl acetate. The extract was washed with water and dried. The solvent was evaporated to dryness under reduced pressure to give crude crystals. Recrystallization from ethyl acetate—methanol—hexane afforded the title compound as pale yellow prisms (0.5 g, 74%), m.p. 213°–215° C. (decomp.).

Elemental Analysis for $C_{26}H_{24}N_4O_5S$:

|  | C(%) | H(%) | N(%) |
|---|---|---|---|
| Calcd.: | 61.89; | 4.79; | 11.10 |
| Found: | 61.73; | 4.63; | 10.93 |

$^1$H-NMR(200 MHz,CDCl$_3$) δ: 0.98(3H,t), 1.71–1.91(2H, m), 2.47(3H,s), 3.76(3H,s), 4.37(2H,t), 5.59(2H,s), 7.23–7.34(4H,m), 7.37(1H, dd), 7.49(1H,dt), 7.60(1H,dt), 7.83(1H,dd), 8.22(1H,br s). IR(KBr)cm$^{-1}$: 1760, 1690, 1615, 1570, 1530, 1460, 1445, 1430, 1410, 1360, 1330, 1230, 1100, 1060, 755.

11b) 1-[2'-(2,5-Dihydro-5-oxo-1,2,4-oxadiazol-3-yl)biphenyl-4-yl]methyl-4-methyl-2-n-propoxythieno[3,4-d]imidazole-6-carboxylic Acid To a suspension of the compound (0.4 g) obtained in Working Example (11a) in a mixture of THF (10 ml) and water (5 ml) was added lithium hydroxide monohydrate (0.1 g), and the mixture was heated for 12 hours under reflux. To the reaction mixture was added water, and the mixture was adjusted to pH 4 with 1N—HCl. Resulting crystals were collected by filtration and recrystallized from chloroform-methanol-ether to afford the title compound as colorless needles (0.28 g, 72%), m.p. 208°–209° C. (decomp.).

Elemental Analysis for $C_{25}H_{22}N_4O_5S \cdot 0.3H_2O$:

|  | C(%) | H(%) | N(%) |
|---|---|---|---|
| Calcd.: | 60.55; | 4.59; | 11.30 |
| Found: | 60.58; | 4.43; | 11.39 |

$^1$H-NMR(200 MHz,DMSO-d$_6$) δ: 0.89(3H,t), 1.65–1.82(2H,m), 2.48(3H,s), 4.38(2H,t), 5.59(2H,s), 7.28(4H,s), 7.49–7.74(4H,m). IR(KBr)cm$^{-1}$: 1760, 1650, 1645, 1605, 1570, 1530, 1460, 1445, 1325, 1240, 760.

WORKING EXAMPLE 12

2-Ethylamino-1-[[2'-(2,5-dihydro-5-oxo-1,2,4-oxadiazol-3-yl)biphenyl-4-yl]methyl]-4-methylthieno[3,4-d]imidazole-6-carboxylic Acid

12a) Methyl 2-Ethylamino-1-[[2'-(2,5,dihydro-5-oxo-1,2,4-oxadiazol-3-yl)biphenyl-4-yl]methyl]-4-methylthieno[3,4-d]imidazole-6-carboxylate A mixture of the compound (0.60 g) obtained in Working Example (9a) and a 70% aqueous solution of ethylamine (10 ml) was heated at 80° C. in an autoclave for two hours. The reaction mixture was concentrated to dryness and adjusted to pH 4 with 1N—HCl. The mixture was extracted with chloroform, and the extract was washed with water and dried. The solvent was evaporated to dryness under reduced pressure, and the residue was purified by column chromatography on silica gel to give crude crystals. Recrystallization from ethyl acetate—methanol—hexane afforded the title compound as pale orange needles (0.28 g, 45%), m.p. 219°–221° C. (decomp.).

Elemental Analysis for $C_{25}H_{23}N_5O_4S \cdot 0.5AcOEt$ (533.60):

|  | C(%) | H(%) | N(%) |
|---|---|---|---|
| Calcd.: | 60.78; | 5.10; | 13.12 |
| Found: | 60.52; | 5.15; | 12.93 |

$^1$H-NMR(200 MHz,CDCl$_3$) δ: 1.26(3H,t), 2.40(3H,s), 3.31(2H,q), 3.67(3H 5.61(2H,s), 7.16(2H,d), 7.23(2H,d), 7.38(1H ,dt), 7.47(1H,dd), 7.58(1H,dt), 7.72(1H ,dd). IR(KBr)cm$^{-1}$: 3325, 1740, 1690, 1610, 1590, 1540, 1460, 1435, 1335, 1230, 1090, 765.

12b) 2-Ethylamino-1-[[2'-(2,5-dihydro-5-oxo-1,2,4-oxadiazol-3-yl)biphenyl-4-yl]methyl]-4-methylthieno[3,4-d]imidazole-6-carboxylic Acid To a suspension of the compound (0.2 g) obtained in Working Example (12a) in a mixture of THF (5 ml) and water (2.5 ml) was added lithium hydroxide monohydrate (51 mg), and the mixture was heated for 24 hours under reflux. To the reaction mixture was added water, and the mixture was adjusted to pH 4 with 1N—HCl. Crystals precipitated were collected by filtration and recrystallized from chloroform-methanol to afford the title compound as pale yellow crystals (0.12 g, 67% ), m.p. 189°–192° C. (decomp.).

Elemental Analysis for $C_{24}H_{21}N_5O_4S \cdot 1.0MeOH$ (507.56):

|  | C(%) | H(%) | N(%) |
|---|---|---|---|
| Calcd.: | 59.16; | 4.96; | 13.80 |
| Found: | 59.34; | 4.76; | 14.00 |

$^1$H-NMR(200 MHz,DMSO-d$_6$) δ: 1.13(3H,t), 2.34(3H,s), 3.28(2H,q), 5.84(2H,s), 7.06(2H,s), 7.22(2H,d), 7.28(1H, dd), 7.34–7.43(2H,m), 7.47(1H,dd). IR(KBr)cm$^{-1}$: 1770, 1700, 1680, 1670, 1650, 1635, 1560, 1540, 1510.

WORKING EXAMPLE 13

Acetoxymethyl 1-[[2'-(4-Acetoxymethyl-4,5-dihdyro-5-oxo-4H-1,2,4-oxadiazol-3-yl)biphenyl-4-yl]methyl]-2-ethoxybenzimidazole-7-carboxylate To a solution of the compound (1.02 g) obtained in Working Example 1 in DMF (4 ml) was added triethylamine (413 mg). To the stirred mixture was added acetoxymethyl chloride (444 mg) at room temperature, followed by stirring for 20 hours under the same conditions. To the reaction mixture were added dichloromethane (40 ml), water (25 ml) and 2N—HCl (3 ml), and the mixture was shaken. The organic layer was separated and concentrated to dryness under reduced pressure. The residue was purified by column chromatography on silica gel to give crude crystals. Recrystallization from ether—isopropyl ether afforded the title compound as colorless prisms (356 mg, 30%), m.p. 132°–133° C.

Elemental Analysis for $C_{31}H_{28}N_4O_9$:

|  | C(%) | H(%) | N(%) |
| --- | --- | --- | --- |
| Calcd.: | 62.00; | 4.70; | 9.33 |
| Found: | 62.08; | 4.60; | 9.29 |

$^1$H-NMR(90 MHz,CDCl$_3$) δ: 1.47(3H,t), 1.77 (3H,s), 2.10(3H,s), 4.67(2H,q), 4.87(2H,s), 5.70(2H,s), 5.87(2H,s), 7.00–7.83(11H,m). IR(Nujol)cm$^{-1}$: 1790, 1760, 1730, 1200, 1035, 980.

WORKING EXAMPLE 14

Acetoxymethyl 2-Ethoxy-1-[[2'-(2,5-dihydro-5-oxo-1,2,4-oxadiazol-3-yl)biphenyl-4-yl]methyl]benzimidazole-7-carboxylate The same reaction as in Working Example 13 was conducted, and the reaction mixture was purified by silica gel column chromatography to give crude crystals. Recrystallization from ethyl acetate—isopropyl ether afforded the title compound as colorless prisms (250 mg, 29%), m.p. 111°–112° C.

Elemental Analysis for $C_{28}H_{24}N_4O_7 \cdot 1/30 C_6H_{14}O \cdot 1/5 H_2O$:

|  | C(%) | H(%) | N(%) |
| --- | --- | --- | --- |
| Calcd.: | 63.24; | 4.68; | 10.46 |
| Found: | 63.31; | 4.64; | 10.20 |

$^1$H-NMR(90 MHz,CDCl$_3$) δ: 1.40(3H,t), 2.00(3H,s), 4.40(2H,q), 5.67(2H,s), 5.70(2H,s), 6.87–7.90(11H,m). IR(Nujol)cm$^{-1}$: 1780, 1730, 1545.

WORKING EXAMPLE 15

1-[[2'-(4-Acetoxymethyl-4,5-dihydro-5-oxo-4H-1,2,4-oxadiazol-3-yl)biphenyl-4-yl]methyl-2-ethoxybenzimidazole-7-carboxylate The same reaction as in Working Example 13 was conducted, and the reaction mixture was purified by column chromatography on silica gel to give crude crystals, followed by recrystallization from ethyl acetate to afford the title compound as colorless prisms (50 mg, 5%), m.p. 177°–179° C.

Elemental Analysis for $C_{28}H_{24}N_4O_7 \cdot 1/3 H_2O$:

|  | C(%) | H(%) | N(%) |
| --- | --- | --- | --- |
| Calcd.: | 62.92; | 4.65; | 10.48 |
| Found: | 62.86; | 4.44; | 10.35 |

$^1$H-NMR(90 MHz,CDCl$_3$) δ: 1.47(3H,t), 1.77(3H,s), 4.70(2H,q), 4.80(2H,s), 5.70(2H,s), 6.97–7.83(11H,m) IR(Nujol)cm$^{-1}$: 1785, 1760, 1690, 1550, 1205, 1035.

WORKING EXAMPLE 16

1-[[2'-(2,5-Dihydro-5-oxo-1,2,4-oxadiazol-3-yl)biphenyl-4-yl]methyl]-2-propylpyrazolo[1,5-b][1,2,4]triazole-7-carboxylic Acid 16a) Ethyl 1-[[2'-(5-Trichloromethyl-1,2,4-oxadiazol-3-yl)biphenyl-4-yl]methyl]-2-propylpyrazolo[1,5-b][1,2,4]triazole-7-carboxylate To an ice-cooling solution of ethyl 2-propyl-1H-pyrazolo[1,5-b][1,2,4]triazole-7-carboxylate (0.4 g) in N,N-dimethylformamide (7 ml) was added sodium hydride (60% oil; 72 mg) under nitrogen atmosphere, and the mixture was stirred for 30 minutes at the same temperature. To the reaction mixture was added a solution of the compound (1.15 g) obtained in Working Example (22c) in N,N-dimethylformamide (7 ml). The mixture was stirred for one hour under ice-cooling, then for 3 hours at room temperature. The reaction mixture was concentrated to dryness under reduced pressure. To the residue was added water, and the mixture was extracted with ethyl acetate. The organic layer was washed with water and dried, and then the solvent was evaporated to dryness under reduced pressure. The residue was purified by column chromatography on silica gel to afford the title compound as white amorphous powder (0.92 g, 89%).

$^1$H-NMR(200 MHz,CDCl$_3$) δ: 1.01(3H,t), 1.30(3H,t), 1.70–1.88(2H,m), 2.67(2H,t), 4.27(2H,q), 5.72(2H,s), 7.14(2H,d), 7.24(2H,d), 7.40–7.60(3H,m), 7.90–7.94(1H, m), 8.00(1H,s). IR(KBr)cm$^{-1}$: 2970, 1692, 1600, 1538, 1470.

16b) Ethyl-1-[[2'-(2,6-dihydro-5-oxo-1,2,4-oxadiazol-3-yl)biphenyl-4-yl]methyl]-2-propylpyrazolo[1,5-b][1,2,4]-triazole-7-carboxylate To an ice-cooling solution of the compound (0.92 g) obtained in Working Example (16a) in a mixture of dioxane (8 ml) and water (2 ml) was added 1N—NaOH (1.7 ml), and the mixture was stirred for 15 minutes under ice-cooling. To the reaction mixture were added 1N—HCl (2.5 ml) and water, and the mixture was extracted with ethyl acetate. The organic layer was washed with water and dried, then the solvent was evaporated to dryness under reduced pressure. The residue was crystallized from ethyl acetate—ether to afford the title compound as colorless crystals (0.666 g, 88%), m.p. 227°–228° C.

Elemental Analysis for $C_{25}H_{24}N_6O_4$:

|  | C(%) | H(%) | N(%) |
| --- | --- | --- | --- |
| Calcd.: | 63.55; | 5.12; | 17.79 |
| Found: | 63.53; | 5.20; | 17.67 |

$^1$H-NMR(200 MHz,DMSO-d$_6$) δ: 0.91(3H,t), 1.16(3H,t), 1.54–1.73(2H,m), 2.73(2H,t), 4.16(2H,q), 5.75(2H,s), 7.26(2H,d), 7.32(2H,d), 7.48–7.73(4H,m), 7.96(1H,s). IR(KBr)cm$^{-1}$: 3100, 2980, 1795, 1702, 1602, 1540, 1468.

16c) 1-[[2'-(2,5-Dihydro-5-oxo-1,2,4-oxadiazol-3-yl)biphenyl-4-yl]methyl]-2-propylpyrazolo[1,5-b][1,2,4]-triazole-7-carboxylic Acid To a mixture of the compound (0.2 g) obtained in Working Example (16b) in a mixture of methanol(5 ml), tetrahydrofuran (5 ml) and water (5 ml) was added 2N—NaOH (2.1 ml), and the mixture was heated for 3 hours under reflux. The reaction mixture was cooled, to which were added 2N—HCl (3.0 ml) and water, followed by extraction with ethyl acetate. The organic layer was washed with water and dried, and the solvent was evaporated to dryness under reduced pressure. The residue was recrystallized from ethyl acetate to afford the title compound as colorless crystals (0.17 g, 90%), m.p.223°–225° C.

Elemental Analysis for $C_{23}H_{20}N_6O \cdot 0.2AcOEt$:

|  | C(%) | H(%) | N(%) |
|---|---|---|---|
| Calcd.: | 61.87; | 4.71; | 18.19 |
| Found: | 61.81; | 4.66; | 18.28 |

$^1$H-NMR (200 MHz, DMSO-$d_6$) δ: 0.90(3H,t), 1.52–1.70(2H,m), 2.71(2H,t), 5.79(2H,s ), 7.32(4H,s), 7.50–7.73(4H,m), 7.92(1H,s), 12.35 (1H,br s). IR (KBr) cm$^{-1}$: 3060, 2960, 2700–2200, 1783, 1668, 1590, 1540, 1483.

WORKING EXAMPLE 17

1-[[2'-(2,5-Dihydro-5-oxo-1,2,4-oxadiazol-3-yl)biphenyl-4-yl]methyl-2-propylimidazo[1,2-b]pyrazole-7-carboxylic Acid

17a) Ethyl 2-propyl-1-[[2'-(5-trichloromethyl-1,2,4-oxadiazole-3-yl]biphenyl-4-yl]methyl]imidazo[1,2-b]-pyrazole-7-carboxylate By the similar reaction procedure as in Working Example (16a), the title compound was obtained as a pale yellow oil (0.16 g, 47%) from ethyl 2-propyl-1H-imidazo[1,2-b]pyrazole-7-carboxylate (0.132 g).

$^1$H-NMR(200 MHz,CDCl$_3$) δ: 0.98(3H,t), 1.28(3H,t), 1.53–1.72(2H,m), 2.46(2H,t), 4.23(2H,q), 5.75(2H,s), 7.05(2H,d), 7.14(1H,s), 7.18(2H,d), 7.41–7.63(3H,m), 7.86–7.91(1H,m), 8.01(1H,s). IR(Neat)cm$^{-1}$: 2975, 1702, 1690, 1603, 1582, 1562, 1495.

17b) Ethyl 1-[[2,5-Dihydro-5-oxo-1,2,4-oxadiazol-3-yl)biphenyl-4-yl]methyl]-2-propylimidazo[1,2-b]pyrazole-7-carboxylate By the similar reaction procedure as in Working Example (16b), the title compound was obtained as colorless crystals (84 mg, 68%), m.p. 204°–206° C. (ethyl acetate-ether) from the compound obtained in Working Example (17a) (0.15 g).

Elemental Analysis for $C_{26}H_{25}N_5O_4 \cdot 0.5H_2O$:

|  | C(%) | H(%) | N(%) |
|---|---|---|---|
| Calcd.: | 64.99; | 5.45; | 14.57 |
| Found: | 65.27; | 5.50; | 14.38 |

1H-NMR(200 MHz,CDCl$_3$) δ: 0.99(3H,t), 1.27(3H,t), 1.53–1.72(2H,m), 2.48(2H,t), 4.18(2H,q), 5.74 (2H, s), 7.13(2H,d), 7.13(1H,s), 7.27(2H,d), 7.38–7.65 (3H,m), 7.80–7.84(1H,m), 7.92(1H,s), 8.31(1H,br). IR(KBr)cm$^{-1}$: 3125, 2960, 1780, 1705, 1600, 1587, 1492, 1470.

17c) 1-[[2'-(2,5-Dihydro-5-oxo-1,2,4-oxadiazol-3-yl)biphenyl-4-yl]methyl]-2-propylimidazo[1,2-b]pyrazole-7-carboxylic Acid By the similar reaction procedure as in Working Example (16c), the title compound was obtained as colorless crystals (48 mg, 57%), m.p. 191°–196° C. (decomp.) (methanol-water), from the compound obtained in Working Example (17b) (90 mg).

Elemental Analysis for $C_{24}H_{21}N_5O$:

|  | C(%) | H(%) | N(%) |
|---|---|---|---|
| Calcd.: | 65.00; | 4.77; | 15.79 |
| Found: | 65.28; | 4.68; | 15.72 |

$^1$H-NMR(200 MHz,DMSO-$d_6$) δ: 0.89(3H,t), 1.43–1.62(2H,m), 2.43–2.51(2H,m), 5.80(2H,s), 7.18(2H, d), 7.29(2H,d), 7.50–7.72(5H,m), 11.87(1H,br s), 12.36(1H, br s). IR(KBr)cm$^{-1}$: 3025, 2960, 1700–2200, 1780, 1643, 1595, 1580, 1498.

WORKING EXAMPLE 18

Ethyl 2-Ethyl-4,7-dihydro-7-[[2'-(2,5-dihydro-5-oxo-1,2,4-oxadiazol-3-yl)biphenyl-4-yl]methyl]-4-oxothieno[2,3-b]pyridine-5-carboxylate

18a) Ethyl 7-[[2'-(5-Trichloromethyl-1,2,4-oxadiazol-3-yl)biphenyl-4-yl]methyl]-2-ethyl-4,7-dihydro-4-oxothieno[2,3-b]pyridine-5-carboxylate To an ice-cooling solution of ethyl 2-ethyl-4-hydroxythieno[2,3-b]pyridine-5-carboxylate (0.252 g) in N,N-dimethylformamide (DMF) (7 ml) was added, under nitrogen atmosphere, sodium hydride (60% in oil; 40 mg), and the mixture was stirred for 30 minutes. To the reaction mixture was added a solution of the compound obtained in Working Example (22c) (0.6 g) in N,N-dimethylformamide (4 ml), and the mixture was stirred for 2 hours at room temperature. The reaction mixture was concentrated to dryness under reduced pressure. To the residue was added water, and the mixture was extracted with ethyl acetate. The organic layer was washed with water and dried, and the solvent was evaporated to dryness under reduced pressure, The residue was purified by column chromatography on silica gel to afford the tile compound as white powder (0.5 g, 83%).

$^1$H-NMR(200 MHz,CDCl$_3$) δ: 1.32(3H,t), 1.41(3H,t), 2.82(2H,d-q), 4.40(2H,q), 5.22(2H,s), 7.23–7.33(5H,m), 7.43–7.65(3H,m), 7.93–7.98(1H,m), 8.39(1H,s). IR(KBr)cm$^{-1}$: 2975, 1672, 1620, 1580, 1493.

18b) Ethyl 2-Ethyl-4,7-dihydro-7-[[2'-(2,5-dihydro-5-oxo-1,2,4-oxadiazol-3-yl)biphenyl-4-yl]methyl]-4-oxothieno[2,3-b]pyridine-5-carboxylate To an ice-cooling solution of the compound (0.49 g) obtained in Working Example (18a) in a mixture of dioxane (8 ml), tetrahydrofuran (THF) (8 ml) and water (4 ml) was added 1N—NaOH (0.9 ml). After stirring for 40 minutes under ice-cooling, to the mixture was added 1N—NaOH (0.4 ml), and the mixture was stirred for 20 minutes under ice-cooling. To the reaction mixture were added 1N—HCl (2,0 ml) and water, followed by extraction with ethyl acetate. The organic layer was washed with water and dried, then the solvent was evaporated to dryness under reduced pressure. The residue was crystallized from methanol to afford the titled compound as colorless crystals (0.278 g, 68%), m.p. 243°–235° C.

Elemental Analysis for $C_{27}H_{23}N_3O_5S$:

|  | C(%) | H(%) | N(%) |
|---|---|---|---|
| Calcd.: | 64.66; | 4.62; | 8.38 |
| Found: | 64.70; | 4.70; | 8.33 |

$^1$H-NMR(200 MHz,DMSO-$d_6$) δ: 1.22(3H,t), 1.29(3H,t), 2.79(2H,d-q), 4.23(2H,q), 5.50(2H,s), 7.10(1H,t), 7.31–7.40(4H,m), 7.50–7.73(4H,m), 8.77(1H,s), 12.37 (1H, br s). IR(KBr)cm$^{-1}$: 3430, 2980, 1782, 1727, 1602, 1542, 1500.

WORKING EXAMPLE 19

3-[[2'-(2,5-Dihydro-5-oxo-1,2,4-oxadiazol-3-yl)biphenyl-4-yl]methyl]-2-propyl-4(3H)-quinazolinone

19a) 3-[[2'-(5-Trichloromethyl-1,2,4-oxadiazol-3-yl)biphenyl-4-yl]methyl]-2-propyl-4(3H)-quinazolinone To an ice-cooling solution of 2-propyl-4(3H)-quinazoline (0.283 g) in N,N-dimethylformamide (8 ml) was added sodium hydride (60% in oil; 60 mg) under nitrogen atmosphere, and the mixture was stirred for 30 minutes at the same temperature. To the reaction mixture was added a solution of the compound (0.78 g) obtained in Working Example (22c) in N,N-dimethylformamide (5 ml) and stirred for 4 hours at room temperature. The reaction mixture was concentrated to dryness under reduced pressure, and to the mixture was added water, followed by extraction with ethyl acetate. The organic layer was washed with water and dried, and the solvent was evaporated to dryness under reduced pressure. The residue was purified by column chromatography on silica gel to afford the title compound as a colorless oil (0.5 g, 62%).

$^1$H-NMR(200 MHz,CDCl$_3$) δ: 1.02(3H,t), 1.75–1.94(2H, m), 2.75(2H,t), 5.44(2H,s), 7.16(2H,d), 7.22(2H,d), 7.41–7.79(6H,m), 7.87–7.92(1H,m), 8.28–8.32(1H,m). IR(neat)cm$^{-1}$: 2960, 1668, 1595, 1567.

19b) 3-[[2'-(2,5-Dihydro-5-oxo-1,2,4-oxadiazol-3-yl)-biphenyl-4-yl]methyl]-2-propyl-4(3H)-quinazolinone To a mixture of the compound (0.42 g) obtained in Working Example (19a) in a mixture of dioxane (6 ml) and water (1.5 ml) was added 1N—NaOH (1.0 ml) under ice-cooling. The mixture was stirred for 30 minutes under ice-cooling. To the reaction mixture were added 1N—HCl (2.0 ml) and water, and the mixture was extracted with ethyl acetate. The organic layer was washed with water and dried, and the solvent was evaporated to dryness under reduced pressure. The residue was crystallized from ethyl acetate—ether to afford the title compound as colorless crystals (0.311 g, 91%), m.p. 251°–253° C.

Elemental Analysis for $C_{26}H_{22}N_4O_3$:

|  | C(%) | H(%) | N(%) |
|---|---|---|---|
| Calcd.: | 71.22; | 5.06; | 12.78 |
| Found: | 70.93; | 5.04; | 12.72 |

$^1$H-NMR (200 MHz, DMSO-$d_6$) δ: 0.91(3H,t), 1.63–1.82(2H,m), 2.74(2H,t), 5.45(2H,s ), 7.24(2H,d), 7.31(2H,d), 7.49–7.74(6H,m), 7.80–7.88 (1H,m), 8.16–8.20(1H,m), 12.38(1H,br s). IR(KBr)cm$^{-1}$: 3120, 2970, 1768, 1638, 1605, 1590.

WORKING EXAMPLE 20

Methyl 2-Butyl-1-[[2'-(4,5-dihydro-5-oxo-6H-1,2,4-oxadiazin-3-yl)biphenyl-4-yl]methyl]benzimidazole-7-carboxylate

20a) Methyl 2-Butyl-1-[[[2'-(O-ethoxycarbonylmethyl)-hydroxycarbamimidoyl]biphenyl-4-yl]methyl]-benzimidazole-7-carboxylate A mixture of the compound (2.20 g) obtained in Working Example (1c), ethyl bromoacetate (0.84 g) and potassium carbonate (0.67 g) in acetonitrile (20 ml) was stirred for 15 hours at room temperature. To the reaction mixture was added a saturated aqueous saline solution, and mixture was extracted with ethyl acetate. The extract was washed with water and dried (MgSO$_4$), then the solvent was evaporated in vacuo. The residue was purified by silica gel (80 g) column chromatography to give the title compound (1.10 g, 42%) as an oil.

$^1$H-NMR(200 MHz,CDCl$_3$) δ: 0.96(3H,t,J=7.4 Hz), 1.28(3H,t,J=7.2 Hz), 1.48(2H,m), 1.89(2H,m), 2.94(2H,t,J= 7.6 Hz), 3.74(3H,s), 4.20(2H,q,J=7.2 Hz), 4.45(2H,br s), 4.56(2H,s), 5.77(2H,s), 6.89(2H,d,J=8.0 Hz), 7.19–7.70(8H, m), 7.94(1H,dd,J=1.2 Hz,7.8 Hz). IR(Neat)cm$^{-1}$: 3480, 3375, 3150, 1750, 1725, 1715, 1635, 1600.

20b) Methyl 2-Butyl-1-[[2'-(4,5-dihydro-5-oxo-6H-1,2,4-oxadiazin-3-yl)biphenyl-4-yl]methyl]benzimidazole-7-carboxylate A mixture of the compound (1.10 g) obtained in Working Example (20a) and p-toluenesulfonic acid chloride (0.1 g) in toluene (20 ml) was heated for 18 hours under reflux. The reaction mixture was concentrated to dryness, and the residue was extracted with chloroform. The extract was washed with water and dried (MgSO$_4$), and the solvent was evaporated in vacuo. The residue was purified by silica gel (80 g) column chromatography to give the title compound as colorless crystals (0.25 g, 25%), m.p. 226°–227° C.

Elemental Analysis for $C_{29}H_{28}N_4O_4 \cdot \frac{1}{2}H_2O$:

|  | C(%) | H(%) | N(%) |
|---|---|---|---|
| Calcd.: | 68.90; | 5.78; | 11.08 |
| Found: | 69.06; | 5.78; | 10.73 |

$^1$H-NMR(200 MHz,DMSO-$d_6$) δ: 0.90(3H,t,J=7.2 Hz), 1.40(2H,m), 1.77(2H,m), 2.88(2H,t,J=7.4 Hz), 3.65(3H,s), 4.15(2H,s), 5.72(2H,s), 6.89(2H,d,J=8.4 Hz), 7.27–7.64(8H, m), 7.87(1H,dd,J=100 Hz,8.0 Hz), 10.91(1H,br s). IR(Nujol)cm$^{-1}$: 1720, 1710, 1605.

WORKING EXAMPLE 21

2-Butyl-1-[[2'-(2,4-dioxothiazolidin-5-yl)biphenyl-4-yl]methyl]benzimidazole

21a) 2-Butyl-1-[[2'-hydroxymethylbiphenyl-4-yl]methyl]benzimidazole

A stirred solution of 2-butyl-1-[(2'-carboxybiphenyl-4-yl)methyl]benzimidazole (1.50 g) in benzene (30 ml) was added dropwise to sodium dihydro-bis(2-methoxyethoxy- )aluminate (70% toluene solution). The mixture was stirred for one hour at room temperature, and then heated for 10 minutes under reflux. The reaction mixture was cooled and poured into 2N—HCl, followed by extraction with dichloromethane. The extract was washed with water and dried ($MgSO_4$), and the solvent was evaporated in vacuo. The residue was purified by silica gel (80 g) column chromatography to give the title compound (0.67 g, 46%) as an oil, which was crystallized from ethyl acetate—ether to afford pale yellow prisms, m.p. 162°–163° C.

Elemental Analysis for $C_{25}H_{26}N_2O\cdot\frac{1}{3}H_2O$:

|  | C(%) | H(%) | N(%) |
|---|---|---|---|
| Calcd.: | 79.75; | 7.14; | 7.44 |
| Found: | 79.75; | 7.01; | 7.29 |

$^1$H-NMR(200 MHz,$CDCl_3$) δ: 0.92(3H,t,J=7.2 Hz), 1.43(2H,m), 1.83(2H,m), 1.86(1H,s), 2.87(2H,t,J=7.4 Hz), 4.57(2H,s), 5.39(2H,s), 7.09(2H,d,J=8.4 Hz), 7.19–7.61(9H, m), 7.72–7.81(1H,m). IR(Nujol)$cm^{-1}$: 3170.

21b) 2-Butyl-1-[(2'-formylbiphenyl-4-yl)methyl]benzimidazole

A mixture of the alcohol (0.65 g) obtained in Working Example (21a) and pyridinium dichromate (0.67 g) in dichloromethane (20 ml) was stirred for 15 hours at room temperature. Insoluble materials were filtered off, and the filtrate was concentrated to dryness. The residue was purified by silica gel (60 g) column chromatography to give the title compound as an oil (0.52 g, 80%), which was crystallized from isopropyl ether to afford colorless crystals (0.46 g, 71%), m.p. 117°–118° C.

Elemental Analysis for $C_{25}H_{24}N_2O\cdot\frac{1}{5}H_2O$:

|  | C(%) | H(%) | N(%) |
|---|---|---|---|
| Calcd.: | 80.72; | 6.61; | 7.53 |
| Found: | 80.73; | 6.55; | 7.41 |

$^1$H-NMR(200 MHz,$CDCl_3$) δ: 0.94(3H,t,J=7.2 Hz), 1.45(2H,m), 1.86(2H,m), 2.88(2H,t,J=7.4 Hz), 5.42(2H,s), 7.14(2H,d,J=7.8 Hz), 7.21–7.68(8H,m), 7.76–7.83(1H,m), 8.01(1H,dd,J=1.6 Hz,7.6 Hz), 9.94(1H,s). IR(Nujol)$cm^{-1}$: 1690, 1655, 1615, 1595.

21c) 2-Butyl-1-[[2'-(2,4-dioxothiazolin-5-yl)biphenyl-4-yl]methyl]benzimidazole To a stirred mixture of the aldehyde (0.44 g) obtained in Working Example (21b) in ethyl acetate (4 ml) and tetrahydrofuran (4 ml) were added an aqueous solution (2 ml) of sodium sulfite and an aqueous solution (1.2 ml) of potassium cyanate (0.78 g). The reaction mixture was stirred for 4 hours at room temperature and for further one hour at 60° C. The reaction mixture was concentrated in vacuo, and to the residue was added water, followed by extraction with chloroform. The extract was washed with water and dried ($MgSO_4$), and the solvent was evaporated in vacuo. The residue was crystallized from ether to give cyanohydrin (0.43 g, 91%) as colorless crystals. The product was used for the subsequent reaction without further purification.

$^1$H-NMR(200 MHz,$CDCl_3$) δ: 0.78(3H,t,J=7.4 Hz), 1.25(2H,m), 1.61(2H,m), 2.69(2H,t,J=7.6 Hz), 5.32(2H,s), 5.51(1H,s), 7.03(2H,d,J=8.0 Hz), 7.11–7.60(9H,m), 7.92(1H,dd,J=1.8 Hz, 7.6 Hz). IR(Nujol;)$cm^{-1}$: 3420, 2230, 1615.

To a solution of the cyanohydrin (0.41 g) obtained by the above-mentioned reaction in chloroform (2.5 ml) was added thionyl chloride (0.11 ml). The mixture was heated for 1.5 hour under reflux with stirring. The reaction mixture was concentrated to dryness to give an oil. The mixture of the oil and thiourea (88 mg) in ethanol (10 ml) were heated for one hour under reflux. To the reaction mixture was added 2N—HCl (10 ml), and the mixture was heated overnight (16 hours) under reflux. The reaction mixture was cooled and then diluted with water, followed by extraction with chloroform. The extract was washed with water and dried ($MgSO_4$), and the solvent was evaporated in vacuo. The residue was purified by silica gel (70 g) column chromatography to give crystals. Recrystallization from ethyl acetate afforded the title compound (0.31 g, 66%) as colorless prisms, m.p. 249°–250° C.

Elemental Analysis for $C_{27}H_{25}N_3O_2S$:

|  | C(%) | H(%) | N(%) |
|---|---|---|---|
| Calcd.: | 71.18; | 5.53; | 9.22 |
| Found: | 70.93; | 5.51; | 9.09 |

$^1$H-NMR(200 MHz,DMSO-$d_6$) δ: 0.88(3H,t,J=7.4 Hz), 1.38(2H,m), 1.74(2H,m ), 2.87(2H,t,J=7.4 Hz), 5.52(1H,s), 5.56(2H,s), 7.13–7.64 (12H,m), 12.20(1H,br). IR(Nujol)$cm^{-1}$: 1690.

WORKING EXAMPLE 22

2-Butyl-4-chloro-5-formyl-1-[[2'-(2,5-dihydro-5-oxo-1,2,4-oxadiazol-3-yl)biphenyl-4-yl]methyl]imidazole

22a) 4'-Methylbiphenyl-2-carboxamidoxime

To a solution of hydroxylamine hydrochloride (17.9 g) in dimethyl sulfoxide (120 ml) was added a methanol solution of sodium methoxide prepared from metallic sodium (5.92 g) and anhydrous methanol (50 ml). The mixture was stirred for 10 minutes at room temperature, to which was added 2'-cyano-4-methylbiphenyl (10 g). The reaction mixture was stirred for 5 hours at 100° C. The reaction mixture was partitioned between ethyl acetate and water. The aqueous layer was extracted with ethyl acetate. Organic layers were combined, washed with water and dried, then the solvent was evaporated in vacuo. The residue was purified by column chromatography on silica gel to afford the title compound as a white amorphous product (11.2 g, 96%).

$^1$H-NMR(200 MHz,$CDCl_3$) δ: 2.39(3H,s), 4.42(2H,br s), 7.22(2H,d), 7.31–7.50(5H,m), 7.56–7.60(1H,m). IR(KBr)$cm^{-1}$: 3490, 3380, 1642, 1575, 1568.

22b) 5-Trichloromethyl-3-(4'-methylbiphenyl-2-yl)-1,2,4-oxadiazole

To a solution of the compound (10 g) obtained by Working Example (22a) in benzene (100 ml) was added dropwise trichloroacetic anhydride (16.4 g), and the reaction mixture was heated for two hours under reflux. The reaction mixture was cooled and concentrated to dryness. The residue was partitioned between ether and water. The aqueous layer was extracted with ether. Organic layers were combined, washed with water and dried, and the solvent was evaporated under reduced pressure. The residue was purified by column chromatography on silica gel to afford the title compound as a pale yellow oil (12 g, 77%).

$^1$H-NMR(200 MHz,CDCl$_3$) δ: 2.38(3H,s), 7.16(4H,s), 7.44–7.64(3H,m), 7.88–7.93(1H,m). IR(neat)cm$^{-1}$: 3025, 1600, 1580, 1561, 1508.

22c)
3-(4'-Bromomethylbiphenyl-2-yl)-5-trichloromethyl-1,2,4-oxadiazole

To a solution of the compound (24.8 g) obtained in Working Example (22b) in carbon tetrachloride (300 ml) were added N-bromosuccinimide (12.5 g) and α,α'-azobisisobutyronitrile (1.15 g), and the mixture was heated for two hours under reflux. The reaction mixture was cooled, and white insoluble materials were filtered off. The filtrate was diluted with dichloromethane. The organic layer was washed with water and dried, and the solvent was evaporated in vacuo under reduced pressure. The residue was recrystallized from ether-hexane to afford the title compound as colorless crystals (23.0 g, 76%), m.p. 77°–79° C.

Elemental Analysis for $C_{16}H_{10}N_2OBrCl_3 \cdot 0.5H_2O$:

|  | C(%) | H(%) | N(%) |
|---|---|---|---|
| Calcd.: | 43.52; | 2.51; | 6.34 |
| Found: | 43.76; | 2.33; | 6.31 |

$^1$H-NMR(200 MHz,CDCl$_3$) δ: 4.52(2H,s), 7.23(2H,d), 7.38(2H,d), 7.44–7.65(3H,m), 7.91–7.95(1H,m). IR(KBr)cm$^{-1}$: 1600, 1560, 1475, 1428, 1332.

22d) 2-Butyl-4-chloro-1-[[2'-(5-trichloromethyl-1,2,4-oxadiazol-3-yl)biphenyl-4-yl]methyl]-5-formylimidazole To a cooled solution of metallic sodium (25 mg) in anhydrous methanol (2 ml) was added dropwise a solution of 2-butyl-4-chloro-5-formylimidazole (0.2 g) in methanol (3 ml) under nitrogen atmosphere. The mixture was stirred for one hour at room temperature and concentrated to dryness. To a solution of the residue in N,N-dimethylformamide (2 ml) was added dropwise a solution of the compound (0.56 g) obtained in Working Example (22c) in N,N-dimethylformamide (3 ml) under ice-cooling. The reaction mixture was stirred for 2.5 hours at room temperature and concentrated to dryness under reduced pressure. Water was added to the residue, and the mixture was extracted with ethyl acetate. The organic layer was washed with water and dried, and the solvent was evaporated under reduced pressure. The residue was purified by column chromatography on silica gel to afford the title compound as a colorless oil (0.44 g, 76%).

$^1$H-NMR(200 MHz,CDCl$_3$) δ: 0.91(3H,t), 1.28–1.46(2H, m), 1.63–1.78(2H,m), 2.65(2H,t), 5.59(2H,s), 7.05(2H,d), 7.23(2H,d), 7.41–7.65(3H,m), 7.90–7.95(1H,m), 9.77(1H, s). IR(neat)cm$^{-1}$: 2960, 1670, 1652, 1580, 1565, 1510.

22e) 2-Butyl-4-chloro-1-[[2'-(2,5-dihydro-5-oxo-1,2,4-oxadiazol-3-yl)biphenyl-4-yl]methyl]-5-formylimidazole To a solution of the compound obtained in Working Example (22d) in a mixture of dioxane (4 ml) and water (1 ml) was added 1N—NaOH (0.75 ml) under ice-cooling. The mixture was stirred for 30 minutes under ice-cooling. To the reaction mixture were added 1N—HCl (1 ml) and water, followed by extraction with ethyl acetate. The organic layer was washed with water and dried, and the solvent was evaporated under reduced pressure. The residue was recrystallized from isopropyl ether—hexane to afford the title compound as white crystals (0.225 g, 87%), m.p. 181°–183° C.

Elemental Analysis for $C_{23}H_{21}N_4O_3Cl \cdot 0.2H_2O$:

|  | C(%) | H(%) | N(%) |
|---|---|---|---|
| Calcd.: | 62.71; | 4.90; | 12.72 |
| Found: | 62.71; | 4.79; | 12.62 |

$^1$H-NMR(200 MHz,CDCl$_3$) δ: 0.91(3H,t), 1.29–1.48(2H, m), 1.63–1.79(2H,m), 2.68 (2H,t), 5.55(2H,s), 7.10(2H,d), 7.31(2H,d), 7.38–7.67 (3H,m), 7.80(1H,dd), 8.50(1H,br), 9.68(1H,s). IR(KBr)cm$^{-1}$: 2960, 1772, 1673, 1522, 1490, 1460.

WORKING EXAMPLE 23

2-Butyl-4-chloro-1-[[2'-(2,5-dihydro-5-oxo-1,2,4-oxadiazol-3-yl)biphenyl-4-yl]methyl]-5-hydroxymethylimidazole To a solution of the compound (0.15 g) obtained in Working Example (22e) in a mixture of methanol (3 ml) and tetrahydrofuran (2 ml) was added sodium borohydride (16 mg), and the mixture was stirred for one hour at room temperature. To the reaction mixture was added ice-water, and the mixture was extracted with ethyl acetate. The organic layer was washed with water and dried, and the solvent was evaporated in vacuo under reduced pressure. The residue was recrystallized from ether-hexane to afford the title compound as white crystals (67 mg, 45%), m.p. 202°–205° C.

Elemental Analysis for $C_{23}H_{23}N_4O_3Cl \cdot 0.1Et_2O \cdot 0.5H_2O$:

|  | C(%) | H(%) | N(%) |
|---|---|---|---|
| Calcd.: | 61.73; | 5.53; | 12.30 |
| Found: | 61.81; | 5.56; | 12.07 |

$^1$H-NMR(200 MHz,DMSO-d$_6$) δ: 0.80(3H,t), 1.16–1.34(2H,m), 1.40–1.55(2H,m), 2.45 –2.52(2H,m), 4.34–4.36(2H,m), 5.25(1H,br), 5.29(2H ,s), 7.14(2H,d), 7.30(2H,d), 7.48–7.72(4H,m). IR(KBr)cm$^{-1}$: 3470, 2960, 1755, 1501, 1463.

WORKING EXAMPLE 24

5-Butyl-3-ethoxycarbonyl-1-[[2'-(2,5-dihydro-5-oxo-1,2,4-oxadiazol-3-yl)biphenyl-4-yl]methylpyrazole

24a)
5-Butyl-3-ethoxycarbonyl-1-[[2'-(5-trichloromethyl-1,2,4-oxadiazol-3-yl]biphenyl-4-yl]methyl]pyrazole To an ice-cooling solution of 3-butyl-5ethoxycarbonylpyrazole (0.3 g) and the compound (0.95 g) obtained in Working Example (22c) in anhydrous tetrahydrofuran (10 ml) was added sodium hydride (60%, 61 mg) under nitrogen atmosphere. The mixture was stirred for 10 minutes at room temperature, and then heated for 3 hours under reflux. The reaction mixture was cooled, to which was added water, followed by extraction with ethyl acetate. The organic layer was washed with water and dried, and the solvent was evaporated under reduced pressure. The residue was purified by column chromatography on silica gel to afford the title compound as a pale yellow oil (0.29 g, 35%).

$^1$H-NMR(200 MHz,CDCl$_3$) δ: 0.89(3H,t), 1.26–1.44(2H, m), 1.40(3H,t), 1.50–1.68(2H,m), 2.49(2H,t), 4.41(2H,q), 5.41(2H,s), 6.64(1H,s), 7.08(2H,d), 7.20(2H,d), 7.40–7.63(3H,m), 7.88–7.92(1H,m). IR(neat)cm$^{-1}$: 2950, 1715, 1578, 1565.

24b)

5-Butyl-3-ethoxycarbonyl-1-[[2'-(2,5-dihydro-5-oxo-1,2,4-oxodiazol-3-yl)biphenyl-4-yl]methyl]pyrazole To a solution of the compound (0.27 g) obtained in Working Example (24a) in a mixture of dioxane (4 ml) and water (1 ml) was added 1N—NaOH (0.6 ml) under ice-cooling. The mixture was stirred for 20 minutes under ice-cooling. To the reaction mixture were added 1N—HCl (0.9 ml) and water, and the mixture was extracted with ethyl acetate. The organic layer was washed with water, dried, and concentrated to dryness under reduced pressure. The residue was recrystallized from isopropyl ether—hexane to afford the title compound as colorless crystals (0.176 g, 80%), m.p. 166°–168° C.

Elemental Analysis for C$_{25}$H$_{26}$N$_4$O$_4$:

|  | C(%) | H(%) | N(%) |
| --- | --- | --- | --- |
| Calcd.: | 67.25; | 5.87; | 12.55 |
| Found: | 66.99; | 5.91; | 12.45 |

$^1$H-NMR(200 MHz,CDCl$_3$) δ: 0.91(3H,t), 1.28–1.46(2H, m), 1.37(3H,t), 1.53–1.68(2H,m), 2.56(2H,t), 4.35(2H,q), 5.36(2H,s), 6.64(1H, s), 7.15(2H,d), 7.30(2H,d), 7.37–7.65(3H,m), 7.79–7.83(1H,m), 8.49(1H,br). IR(KBr)cm$^{-1}$: 2960, 1777, 1725, 1600, 1485.

WORKING EXAMPLE 25

2-Butyl-4-chloro-1-[[2-1-(2,5-dihydro-5-oxo-1,2,4-oxadiazol-3-yl)biphenyl-4-yl]methyl]imidazole-5-carboxylic Acid To a solution of the compound (0.27 g) obtained in Working Example (22e) in pyridine (5 ml) was added an aqueous solution (2.5 ml) of potassium permanganate (0.147 g). The mixture was stirred for 3 hours at room temperature. The reaction mixture was concentrated to dryness under reduced pressure. To the residue were added ethyl acetate and dilute hydrochloric acid. The resulting suspension was filtrated through celite. The filtrate was extracted with ethyl acetate. The organic layer was washed with water, dried, and concentrated to dryness under reduced pressure. The residue was purified by silica gel column chromatography and the product was crystallized from ethyl acetate—isopropyl ether to afford the title compound as colorless crystals (0.17 g, 61 %), m.p. 188°–189° C. (decomp.).

Elemental Analysis for C$_{23}$H$_{21}$N$_4$O$_4$Cl.0.1AcOEt.2.9H$_2$O:

|  | C(%) | H(%) | N(%) |
| --- | --- | --- | --- |
| Calcd.: | 54.69; | 5.41; | 10.90 |
| Found: | 54.91; | 5.17; | 10.62 |

$^1$H-NMR(200 MHz,DMSO-d$_6$) δ: 0.80(3H,t), 1.16–1.35(2H,m), 1.43–1.58(2H,m), 2.46–2.53(2H,m), 5.80(2H,s), 6.95(2H,d), 7.25(2H,d), 7.29–7.51(4H,m). IR(KBr)cm$^{-1}$: 3390, 2960, 1765, 1648, 1590, 1525, 1488.

WORKING EXAMPLE 26

2-Butyl-4-chloro-1-[[2'-(2,3-dihydro-2-oxo-1,3,4-oxadiazol-5-yl)biphenyl-4-yl]methyl]imidazole-5-carbaldehyde To an ice-cooling solution of 2-butyl-4-chloroimidazole-5-carbaldehyde (0.19 g) in N,N-dimethylformamide (1 ml) was added sodium hydride (60% in oil; 44 mg), and the mixture was stirred for 10 minutes. To the mixture was then added 5-(4'-bromomethylbipenyl-2-yl)-2,3-dihydro-3-triphenylmethyl-1,3,4-oxadiazol-2-one (0.57 g). The reaction mixture was stirred for 1.5 hour at room temperatures, which was diluted with water and extracted with ethyl acetate. The extract was washed with water and dried. The solvent was evaporated under reduced pressure, and the residue was purified by column chromatography on silica gel. The crude product thus obtained was dissolved in trifluoroacetic acid (4 ml), and the solution was stirred for 30 minutes at 60° C. Trifluoroacetic acid was evaporated under reduced pressure. The residue was dissolved in ethyl acetate, and the solution was washed with an aqueous solution of sodium hydrogencarbonate and dried. The solvent was evaporated under reduced pressure, and the residue was purified by column chromatography on silica gel. Crude crystals thus obtained was recrystallized from ethylacetate-hexane to afford the title compound as colorless prisms (0.12 g, 27%), m.p. 178°–179° C.

Elemental Analysis for C$_{23}$H$_{21}$N$_4$ClO$_3$:

|  | C(%) | H(%) | N(%) |
| --- | --- | --- | --- |
| Calcd.: | 63.23; | 4.84; | 12.82 |
| Found: | 63.07; | 4.87; | 12.69 |

$^1$H-NMR(200 MHz,CDCl$_3$) δ: 0.90(3H,t), 1.28–1.46(2H, m), 1.62–1.78(2H,m), 2.68(2H,t), 5.59(2H,s), 7.08(2H,d), 7.26(2H,d), 7.35(1H,dd), 7.43–7.60(2H,m), 7.79(1H,dd), 8.85(1H,br), 9.76(1H,s). IR(neat)cm$^{-1}$: 1810, 1775, 1660, 1455, 1340, 1275, 900, 840, 770, 750.

WORKING EXAMPLE 27

2-Butyl-4-chloro-1-[[2'-(2,3-dihydro-2-oxo-1,3,4-oxadiazol-5-yl)biphenyl-4-yl]methyl]-5-imidazolemethanol To a solution of the compound (50 mg) obtained in Working Example 26 in methanol (5 ml) was added sodium borohydride (4 mg), and the mixture was stirred for one hour at 0° C. The solvent was evaporated under reduced pressure, and the residue was adjusted to pH 3–4 with N—HCl. Crystalline precipitate was collected by filtration and recrystallized from ethyl acetate—hexane to afford the title compound as colorless prisms (47 mg, 94%), m.p. 163°–164° C.

Elemental Analysis for C$_{23}$H$_{23}$N$_4$ClO$_3$:

|  | C(%) | H(%) | N(%) |
| --- | --- | --- | --- |
| Calcd.: | 62.94; | 5.28; | 12.76 |
| Found: | 62.76; | 5.16; | 12.54 |

$^1$H-NMR(200 MHz,CDCl$_3$) δ: 0.88(3H,t), 1.25–1.41 (2H, m), 1.58–1.70(2H,m), 2.62(2H,t), 4.50(2H,s), 5.24(2H,s), 7.06(2H,d), 7.27(2H,d), 7.37(1H,dd), 7.43–7.59(2H,m), 7.81(1H,dd), 9.93(1H,br). IR(KBr)cm$^{-1}$: 3400, 1800, 1775, 1455, 1410, 1340, 1260, 1000, 900, 770, 750.

WORKING EXAMPLE 28

2-Butyl-5-ethoxycarbonyl-3-[[2,-(2,5-dihdyro-5-oxo-1,2,4-oxadiazol-3-yl)biphenyl-4-yl]methyl]-4(3H)-pyrimidinone

28a)
2-Butyl-5-ethoxycarbonyl-3-[[2,-(5-trichloromethyl-1,2,4-oxadiazol-3-yl)biphenyl-4-yl]methyl]-4(3H)-pyrimidinone To an ice-cooling solution of 2-butyl-5-ethoxycarbonyl-4-hydroxypyrimidine (0.36 g) in anhydrous tetrahydrofuran (8 ml) was added sodium hydride (60% in oil; 65 mg) under nitrogen atmosphere, and the mixture was stirred for 15 minutes at room temperatures. To the reaction mixture was added a solution of the compound (1.02 g) obtained in Working Example (22c) in anhydrous tetrahydrofuran (5 ml), and the mixture was heated for 6 hours under reflux. The reaction mixture was cooled, to which was added water, followed by extraction with ethyl acetate. The organic layer was washed with water and dried, and the solvent was evaporated under reduced pressure. The residue was purified by column chromatography on silica gel to afford the title compound as a colorless oil (0.18 g, 20%).

$^1$H-NMR(200 MHz,CDCl$_3$) δ: 0.92(3H,t), 1.29–1.47(2H, m), 1.39(3H,t), 1.64–1.79(2H,m), 2.75(2H,t), 4.39(2H,q), 5.38(2H,s), 7.19(2H,d), 7.25(2H,d), 7.41–7.65(3H,m), 7.93(1H,dd), 8.64(1H,s). IR(neat)cm$^{-1}$: 2960, 1748, 1705, 1685, 1580, 1521.

28b)
2-Butyl-5-ethoxycarbonyl-3-[[2'-(2,5-dihydro-5-oxo-1,2,4-oxadiazol-3-yl)biphenyl-4-yl]methyl]-4(3H)-pyrimidinone The compound (0.18 g) obtained in Working Example (28a) was dissolved in a mixture of dioxane (4 ml) and water (1 ml). To the ice-cooling solution was added 1N—NaOH (0.4 ml), and the reaction solution was stirred for 30 minutes under ice-cooling. After addition of 1N—HCl (0.6 ml) and water, the reaction mixture was extracted with ethyl acetate. The organic layer was washed with water and dried, and the solvent was evaporated under reduced pressure. The residue was purified by column chromatography on silica gel. The crude product thus obtained was recrystallized from ethyl acetate—isopropyl ether to afford the title compound as colorless crystals (62 mg, 42%), m.p. 151°–154° C.

Elemental Analysis for C$_{26}$H$_{26}$N$_4$O$_5$·0.1H$_2$O:

|  | C(%) | H(%) | N(%) |
| --- | --- | --- | --- |
| Calcd.: | 65.56; | 5.54; | 11.76 |
| Found: | 65.41; | 5.68; | 11.62 |

$^1$H-NMR (200 MHz, CDCl$_3$) 67 : 0.91(3H,t), 1.28–1.48(2H, m), 1.34(3H,t), 1.65–1.80(2H,m), 2.79(2H,t), 4.31(2H,q), 5.30(2H,s), 7.22(2H,d), 7.32(2H,d), 7.37–7.65(3H,m), 7.78 (1H,dd), 8.61(1H,s). IR (KBr) cm$^{-1}$: 3210, 2960, 1795, 1705, 1660, 1523.

WORKING EXAMPLE 29

1-[[2'-(2,5-Dihydro-5-oxo-1,2,4-oxadiazol-3-yl)biphenyl-4-yl]methyl]-6-propoxy-3-propyluracil

29a)
6-Chloro-1-[[2'-(5-trichloromethyl-1,2,4-oxadiazol-3-yl)biphenyl-4-yl]methyl]-3-propyluracil To an ice-cooling solution of 6-chloro-3-propyluracil (0.2 g) in N,N-dimethylformamide (4 ml) was added sodium hydride (60% in oil; 43 mg) under nitrogen atmosphere. The mixture was stirred for 30 minutes at the same temperature. To the reaction mixture was added a solution of the compound (0.64 g) obtained in Working Example (22c) in N,N-dimethylformamide (4 ml). The mixture was stirred for 2.5 hours at room temperature. The reaction mixture was concentrated to dryness under reduced pressure, and to the residue was added water, followed by extraction with ethyl acetate. The organic layer was washed with water, dried, and concentrated to dryness under reduced pressure. The residue was purified by column chromatography on silica gel to afford the title compound as a colorless oil (0.43 g, 75%).

$^1$H-NMR(200 MHz,CDCl$_3$) δ: 0.95(3H,t), 1.56–1.76(2H, m), 3.91(2H,t), 5.29(2H,s), 5.93(1H,s), 7.24(2H,d), 7.31(2H,d), 7.43–7.64(3H,m), 7.89–7.93(1H,m). IR(neat)cm$^{-1}$: 2960, 1712, 1668, 1608, 1582, 1568, 1508.

29b) 
1-[[2'-(2,4-Dihydro-5-oxo-1,2,4-oxadiazol-3-yl)biphenyl-4-yl]methyl]-6-propoxy-3-propyluracil To a solution of the compound (0.42 g) obtained in Working Example (29a) in a mixture of dioxane (4 ml) and water (1 ml) was added 1N—NaOH (1.0 ml) under ice-cooling. The mixture was stirred for 30 minutes under ice-cooling, and to the reaction mixture were added 1N—HCl (1.5 ml) and water, followed by extraction with ethyl acetate. The organic layer was washed with water, dried, and concentrated to dryness under reduced pressure. The residue was dissolved in a mixture of propanol (4 ml) and N,N-dimethylformamide (4 ml). To the ice-cooling solution were added dropwise a solution of sodium propoxide prepared from metallic sodium (72 mg) and propanol (2 ml), and the solution was heated for 1.5 hour at 100°–110° C. The reaction mixture was cooled, and then concentrated to dryness under reduced pressure. To the residue was added dilute hydrochloric acid, and the mixture was extracted with ethyl acetate. The organic layer was washed with water, dried, and evaporated to dryness under reduced pressure. The residue was purified by column chromatography on silica gel. The crude product thus obtained was recrystallized from ethyl acetate—hexane to afford the title compound as colorless crystals (0.223 g, 63%), m.p.129°–132° C.

Elemental Analysis for C$_{25}$H$_{26}$N$_4$O$_5$:

|  | C(%) | H(%) | N(%) |
| --- | --- | --- | --- |
| Calcd.: | 64.92; | 5.67; | 12.11 |
| Found: | 64.82; | 5.77; | 11.91 |

$^1$H-NMR(200 MHz,CDCl$_3$) δ: 0.92(3H,t), 1.00(3H,t), 1.56–1.73(2H,m), 1.74–1.93(2H,m), 3.85(2H,t), 3.98(2H,t), 5.11(2H,s), 5.15(1H,s), 7.28–7.67(7H,m), 7.81–7.86(1H,m), 8.15(1H,br s). IR(KBr)cm$^{-1}$: 3120, 2970, 1775, 1705, 1638, 1472.

WORKING EXAMPLE 30

1-[[2'-(2,5-Dihydro-5-oxo-1,2,4-oxadiazol-3-yl)biphenyl-4-yl]methyl]-2-propylbenzimidazole-7-carboxylic Acid

30a) Methyl 1-[(2'-cyanobiphenyl-4-yl)methyl]-2-propyl Benzimidazole-7-carboxylate To a solution of methyl 3-amino-2-[(2'-cyanobiphenyl-4-yl)methyl]benzoate (1.43 g) in dioxane (8 ml) was added butyric anhydride (950 mg), and the mixture was stirred for 3 hours at room temperature, and then for two hours at 110° C. To the reaction mixture was added conc. HCl (1 ml), and the mixture was 10 stirred for 15 hours at 80° C. The reaction mixture was partitioned between ethyl acetate (150 ml) and an aqueous solution of sodium hydrogencarbonate (70 ml). The upper layer was washed twice with water (50 ml) and concentrated under reduced pressure. The crystalline product was recrystallized from ethyl acetate—ether to afford the title compound as colorless prisms (1.4 g, 85%), m.p. 128°–129° C.

$^1$H-NMR(90 MHz,CDCl$_3$) δ: 1.10(3H,t), 1.77–2.10(2H, m), 2.87(3H,t), 3.67(3H,s), 5.77(2H,s), 6.93(2H,d), 7.13–7.77(8H,m), 7.93(1H,d). IR(Nujol)cm$^{-1}$: 2225, 1710, 1450, 1280, 1270, 1200, 1130, 760.

30b) Methyl 1-[(2'-(hydroxycarbamimidoyl)biphenyl-4-yl)methyl]-2-propylbenzimidazole-7-carboxylate To a solution of hydroxylamine hydrochloride (2.78 g) in DMSO (12 ml) was added triethylamine (4.04 g) and tetrahydrofuran (15 ml), and then the resulting crystals were filtered off. The filtrate was concentrated to dryness under reduced pressure. To the residue were added methyl 1-[(2'-cyanobiphenyl-4-yl)methyl]-2-propylbenzimidazole-7-carboxylate (1.6 g) and triethylamine (1 g). The mixture was stirred for 15 hours at 75° C. which was then dissolved in ethyl acetate (200 ml). The solution was washed with water (200 ml and 50 ml×3), dried and evaporated under reduced pressure to afford the title compound as a pale yellow product (1.57 g, 89%).

$^1$H-NMR(90 MHz,CDCl$_3$) δ: 1.10(3H,t), 1.73–2.10(2H, m), 2.90(2H,t), 3.70(3H,s), 4.33(2H,broad), 5.73(2H,s), 6.87(2H,d), 7.10–7.67(8H,m), 7.93(1H,d). IR(Nujol)cm$^{-1}$: 1720, 1440, 1380, 1290, 1265.

30c) Methyl 1-[[2'-(2,5-dihydro-5-oxo-1,2,4-oxadiazol-3-yl)biphenyl-4-yl]methyl]-2-propylbenzimidazol-7-carboxylate To a solution of methyl 1-[(2'-N-hydroxyamidinobiphenyl-4-yl)methyl]-2-propylbenzimidazole-7-carboxylate (1.5 g) in DMF (8 ml) was added pyridine (240 mg) and chloroformic acid 2-ethylhexyl ester (556 mg) with stirring in an ice-bath. The mixture was stirred for 0.5 hour under the same conditions, to which was added methanol (3 ml), and the mixture was stirred for 0.5 hour at room temperature. The reaction mixture was dissolved in ethyl acetate (250 ml), and the solution was washed with water (200 ml and 50 ml×3). Ethyl acetate was evaporated under reduced pressure. The residue was dissolved in xylene (150 ml), and the solution was heated for 4 hours under reflux. The reaction mixture was allowed to stand for 20-hours at room temperature to give the title compound as colorless prisms (1.03 g, 58%), m.p. 224°–226° C.

Elemental Analysis for $C_{27}H_{24}N_4O_4 \cdot \frac{1}{2}C_8H_{10}$:

|  | C(%) | H(%) | N(%) |
|---|---|---|---|
| Calcd.: | 71.46; | 5.60; | 10.74 |
| Found: | 71.41; | 5.44; | 10.53 |

$^1$H-NMR(90 MHz,CDCl$_3$) δ: 0.90(3H,t), 1.13–1.73(2H,m), 2.43(2H,t), 3.57(3H,s), 5.57(2H,s), 6.50–7.93(11H,m). IR(Nujol) cm$^{-1}$: 1770, 1720, 1267.

30d) 1-[[2'-(2,5-Dihydro-5-oxo-1,2,4-oxadiazol-3-yl)biphenyl-4-yl]methyl]-2-propylbenzimidazole-7-carboxylic Acid A mixture of methyl 1-[[2'-(2,5-dihydro-5-oxo-1,2,4-oxadiazol-3-yl)biphenyl-4-yl]methyl]-2 -propylbenzimidazole-7-carboxylate (703 mg) in 0.3N—NaOH (12 ml) was stirred at 60° C. for one hour, and then adjusted to pH 3 with 0.1N—HCl. Resulting precipitates were extracted with a mixture of chloroform-ethanol (10:1; 150 ml). The solvent was evaporated under reduced pressure, and the residue was crystallized from methanol to give the title compound as colorless prisms (550 mg, 90%), m.p. 169°–171° C.

Elemental Analysis for $C_{26}H_{22}N_4O_4$:

|  | C(%) | H(%) | N(%) |
|---|---|---|---|
| Calcd.: | 67.38; | 5.00; | 12.09 |
| Found: | 67.39; | 4.85; | 11.91 |

$^1$H-NMR(90 MHz,DMSOd$_6$-CDCl$_3$) δ: 1.03(3H,t), 1.67–2.10(2H,m), 2.83(2H,t), 5.97(2H,s), 7.00(2H,d), 7.20–8.03(9H,m). IT(Nujol)cm$^{-1}$: 1785, 1710, 1500, 1380, 760.

WORKING EXAMPLE 31

2-Ethyl-1-[[2'-(2,5-dihydro-5-oxo-1,2,4-oxadiazol-3-yl)-biphenyl-4-yl]methyl]benzimidazole-7-carboxylic Acid

31a) Methyl 1-[(2'-cyanobiphenyl-4-yl)methyl]-2-ethylbenzimidazole-7-carboxylate Methyl 3-amino-2-[(2'-cyanobiphenyl-4-yl)methyl]benzoate (1.79 g) was treated with propionic anhydride (1.04 g) in the similar manner as Working Example (30a). The product was recrystallized from ethyl acetate to give the title compound as colorless prisms (1.5 g, 76%), 153°–154° C.

$^1$H-NMR(90 MHz,CDCl$_3$) δ: 1.47(3H,t), 2.90(2H,q), 3.73(3H,s), 5.83(2H,s), 6.97(2H,d), 7.30–7.83(8H,m), 7.97(1H,d). IR(Nujol)cm$^{-1}$: 2225, 1725, 1710, 1480, 1440, 1285, 1250, 1205, 1120.

31b) Methyl 2-ethyl-1-[(2'-(hydroxycarbamimidoyl)-biphenyl-4-yl)methyl]benzimidazole-7-carboxylate Methyl 1-[(2'-cyanobiphenyl-4-yl)methyl]-2 -ethylbenzimidazole-7-carboxylate (2g) was subjected to the similar reaction as in Working Example (30b) to give the title compound as a pale yellow resinous substance (1.85 g, 85%).

¹H-NMR(90 MHz,CDCl₃) δ: 1.43(3H,t), 2.97(2H,q), 3.73(3H,s), 4.40(2H,broad), 5.73(2H,s), 6.90(2H,d), 7.17–7.80(8H,m), 7.97(1H,d). IR(Nujol)cm⁻¹: 1720, 1380, 1290, 1265.

WORKING EXAMPLE 32

2-Cyclopropyl-1-[[2'-(2,5-dihydro-5-oxo-1,2,4-oxadiazol-3-yl)biphenyl-4-yl]methyl]benzimidazole-7-carboxylic Acid

32a) Methyl 1-[l2'-cyanobiphenyl-4-yl)methyl]-2-cyclopropyl-benzimidazole-7-carboxylate Methyl 3-amino-2-[(2'-cyanobiphenyl-4-yl)methyl]benzoate (1.79 g) was treated with cyclopropanecarboxylic anhydride (1.3 g) in the similar manner as in Working Example (30a) to give the title compound as an orange syrup (1.85 g, 91%).

¹H-NMR(90 MHz,CDCl₃) δ: 1.00–1.40(4H,m), 1.87–2.23(1H,m), 3.70(3H,s), 5.93(2H,s), 7.00–7.93(11H, m). IR(Neat)cm⁻¹: 2225, 1720, 1710, 1525, 1440, 1285.

32b) Methyl 2-cyclopropyl-1-[(2'-hydroxycarbamimidoyl)biphenyl-4-yl)methyl]benzimidazole-7-carboxylate Methyl 1-[(2'-cyanobiphenyl-4-yl)methyl]-2-cyclopropylbenzimidazole-7-carboxylate (1.8 g) was subjected to the similar reaction as in Working Example (32b) to give the title compound as a pale yellow syrup (1.75 g, 90%).

¹H-NMR(90 MHz,CDCl₃) δ: 0.97–1.43(4H,m), 1.80–2.17(1H,m), 3.70(3H,s), 4.33(2H,broad), 5.87(2H,s), 6.87(2H,d), 7.10–7.63(8H,m), 7.87(1H,d). IR(Nujol)cm⁻¹: 1720, 1440, 1380, 1290, 1265, 760.

32c) Methyl 2-cyclopropyl-1-[[2'-(2,5-dihydro-5-oxo-1,2,4-oxadiazol-3-yl)biphenyl-4-yl]methyl]-benzimidazole-7-carboxylate Methyl 2-cyclopropyl-1-[(2'-N-hydroxyiminocarboxamidebiphenyl-4-yl)methyl]benzimidazole-7-carboxylate (1.7 g) was subjected to the similar reaction as in Working Example (30c). From the reaction mixture, xylene was evaporated under reduced pressure. The residue was recrystallized from ethyl acetate to give the title compound as colorless prisms (780 mg, 48%), m.p.188°–190° C.

Elemental Analysis for C₂₇H₂₂N₄O₄:

|  | C(%) | H(%) | N(%) |
|---|---|---|---|
| Calcd.: | 69.52; | 4.75; | 12.01 |
| Found: | 69.52; | 4.77; | 11.90 |

¹H-NMR(90 MHz,CDCl₃) δ: 0.87–1.07(4H,m), 1.53–1.80(1H,m), 3.73(3H,s), 5.87(2H,s), 6.83–7.87(11H, m).

IR(Nujol)cm⁻¹: 1778, 1765, 1728, 1716, 1211.

32d) 2-Cyclopropyl-1-[[2'-(2,5-dihydro-5-oxo-1,2,4-oxadiazol-3-yl)biphenyl-4-yl]methyl]benzimidazole-7-carboxylic acid Methyl 2-cyclopropyl-1-[[2'-(2,5-dihydro-5-oxo-1,2,4-oxadiazol-3-yl)biphenyl-4-yl]methyl]benzimidazole-7-carboxylate (550 mg) was subjected to the similar reaction as in Working Example (30d). The product was recrystallized from ethyl acetate to give the title compound as colorless prisms (480 mg, 90%), m.p.199°–200° C.

Elemental Analysis for C₂₈H₂₀N₄O₄·⅓H₂O:

|  | C(%) | H(%) | N(%) |
|---|---|---|---|
| Calcd.: | 68.11; | 4.54; | 12.22 |
| Found: | 68.16; | 4.61; | 12.03 |

¹H-NMR(90 MHz,DMSO-d₆) δ: 0.93–1.30(4H,m), 2.07–2.40(1H,m), 6.07(2H,s), 7.00–7.83(11H,m), 12.27(1H, broad).

IR(Nujol)cm⁻¹: 1755, 1703, 1699, 1257.

Working Example 33

2-Butyl-1-[[2'-(2,5-dihydro-5-oxo-1,2,4-oxadiazol-3-yl)-biphenyl-4-yl]methyl]benzimidazole-7-carboxylic acid The methyl ester (0.53 g) obtained in Working Example 2 was subjected to the similar reaction as in Working Example (30d) to give the title compound as colorless prisms (0.36 g, 64%), m.p.165°–167° C.

Elemental Analysis for C₂₇H₂₄N₄O₄·⅓CHCl₃:

|  | C(%) | H(%) | N(%) |
|---|---|---|---|
| Calcd.: | 64.59; | 4.83; | 11.02 |
| Found: | 64.76; | 4.95; | 10.83 |

¹H-NMR(90 MHz,DMSO-d₆) δ: 0.90(3H,t), 1.13–2.00(4H,m), 2.83(2H,t), 5.93(2H,s), 6.93(2H,d), 7.13–7.90(9H,m).

IR(Nujol)cm⁻¹: 1770, 1700, 1440, 1420, 1250, 765.

Working Example 34

1-[[2'-(2,5-Dihydro-5-oxo-1,2,4-oxadiazol-3-yl)biphenyl-4-yl]methyl]-2-propylthiobenzimidazole-7-carboxylic acid 34a) Methyl 2-(2'-cyanobiphenyl-4-yl)methylamino-3-methoxycarbonylaminobenzoate To an ice-cooling solution of the compound (10.0 g) obtained in Working Example (la) in pyridine (50 ml) was added dropwise methyl chloroformate (9.0 ml), and the mixture was stirred for 3 hours at room temperature. The reaction mixture was concentrated to dryness, and to the residue was added water. After extraction with ethyl acetate, the extract was washed with water, dried and concentrated to dryness. The residue was crystallized from ethyl acetate—hexane to afford pale yellow crystals (10.5 g, 90%), m.p.113°–115° C.

¹H-NMR(200 MHz,CDCl₃) δ: 3.80(3H,s), 3.83(3H,s), 4.11(2H,d), 6.29(1H,br s), 7.09(1H,t), 7.40–7.80(10H,m), 8.19(1H,d).

34b) Methyl-[(2'-cyanobiphenyl-4-yl)methyl]-2,3-dihydro-2-oxobenzimidazole-7-carboxylate To a suspension of the compound (10.5 g) obtained in Working Example (34a) in methanol (100 ml) was added a solution of 28% sodium methoxide in methanol (10 g). The mixture was heated for 21 hours under reflux. The reaction mixture was adjusted to pH 3 with 1N-HCl and concentrated to dryness. After addition of water to the residue, the mixture was extracted with chloroform. The extract was dried and concentrated to dryness. The residue was crystallized from chloroform-methanol to give colorless needles (8.7 g, 90%), m.p.250°–253° C.

¹H-NMR(200 MHz,DMSO-d₆) δ: 3.65(3H,s), 5.35(2H,s), 7.04–7.16(3H,m), 7.24–7.28(2H,m), 7.48–7.59(4H,m), 7.76(1H,dt), 7.92(1H,dd).

IR(KBr)cm⁻¹: 2210, 1720, 1690, 1635, 1430, 1390, 1270, 1255, 760, 750, 730, 690.

34c) Methyl 1-[(2'-cyanobiphenyl-4-yl)methyl]2-propylthiobenzimidazole-7-carboxylate A mixture of the compound (11 g) obtained in Working Example (34b) in phosphorus oxychloride (90 g) was heated for 10 hours under reflux, followed by conventional workup to give methyl 2-chloro-1-(2'-cyanobiphenyl-4-yl)methyl-benzimidazole-7-carboxylate (11.37 g). To a solution of the compound in dioxane (100 ml) was added propyl mercaptane (2.4 g) and a 28% solution of sodium methoxide in methanol (6.4 g). The mixture was stirred for 1.5 hour at room temperature. The reaction mixture was concentrated to dryness under reduced pressure. The residue was partitioned between ethyl acetate (300 ml) and water (150 ml), and then the upper layer was washed with water (50 ml×1). Ethyl acetate was evaporated under reduced pressure. After addition of methanol (50 ml) to the residue, the resulting crystalline precipitate was collected by filtration, washed with methanol and dried to afford the title compound as pale yellow prisms (10 g, 80%), m.p.107°–108° C.

$^1$H-NMR(90 MHz,CDCl$_3$) δ: 1.07(3H,t), 1.63–2.03(2H, m), 3.40(2H,t), 3.73(3H,s), 5.80(2H,s), 7.00–7.93(11H,m).

IR(Nujol)cm$^{-1}$: 2220, 1725, 1280.

34d) Methyl 1-[(2'-(hydroxycarbamimidoyl)biphenyl-4-yl)methyl]-2-propylthiobenzimidazole-7-carboxylate To a solution of hydroxylamine hydrochloride (20.85 g) in DMSO (200 ml) was added triethylamine (3.9 g) and the mixture was stirred for 30 minutes at room temperatures. To the reaction mixture was added the compound (16 g) obtained in Example (34c), and the mixture was stirred for 60 hours at 70° C. To the resultant mixture was added tetrahydrofuran (100 ml). After removal of crystalline precipitate by filtration, the filtrate was concentrated to dryness. The residue was partitioned between water (1.2 liter) and ethyl acetate (350 ml), and the upper layer was washed with water (70 ml×3). Ethyl acetate was evaporated under reduced pressure, and to the residue was added methanol (70 ml). Resulting crystalline precipitate was filtered off. The filtrate was concentrated to dryness under reduced pressure to give the title compound as a pale yellow syrup (13.0 g, 76%).

$^1$H-NMR(90 MHz,CDCl$_3$) δ: 1.07(3H,t), 1.63–2.03(2H, m), 3.40(2H,t), 3.73(3H,s), 4.37(2H,broad), 5.13(1H,broad), 5.73(2H,s), 6.97(2H,d), 7.10–7.60(8H,m), 7.87(2H,d).

IR(Nujol)cm$^{-1}$: 1720, 1645, 1280, 755.

34e) Methyl, 1-[[2'-(2,5-dihydro-5-oxo-1,2,4-oxadiazol-3-yl)bibiphenyl-4-yl]methyl]-2-propylthiobenzimidazole-7-carboxylate To a stirred solution of the compound (13.0 g) obtained in Working Example (34d) in DMF (20 ml) were added pyridine (2.2 g) and 2-ethylhexyl chloroformate (4.83 g) successively under cooling with an ice-bath. The mixture was stirred for 30 minutes under the same conditions, to which was added methanol (5 ml), followed by stirring for 30 minutes at room temperatures. The reaction mixture was partitioned between ethyl acetate (250 ml) and water (250 ml). The upper layer was washed with water (150 ml×3) and concentrated to dryness under reduced pressure. The residue was dissolved in xylene (180 ml), and the solution was stirred for 70 minutes on a bath of 160° C. The solution was concentrated to dryness under reduced pressure. To the residue was added methanol (70 ml) to give the title compound as pale yellow prisms (7.16 g, 57%), m.p.220°–221° C.

Elemental Analysis for C$_{27}$H$_{24}$N$_4$O$_4$S:

|  | C(%) | H(%) | N(%) |
|---|---|---|---|
| Calcd.: | 64.78; | 4.83; | 11.19 |
| Found: | 64.54; | 4.92; | 10.89 |

$^1$H-NMR(90 MHz,CDCl$_3$) δ: 1.03(3H,t), 1.60–2.00(2H, m), 3.27(2H,t), 3.73(3H,s), 5.73(2H,s), 6.90–7.87(11H,m).

IR(Nujol)cm$^{-1}$: 1760, 1720, 1280, 1260.

34f) 1-[[2'-(2,5-Dihydro-5-oxo-1,2,4-oxadiazol-3-yl)biphenyl-4-yl]methyl]-2-propylthiobenzimidazole-7-carboxylic acid To a solution of the compound (0.3 g) obtained in Working Example (34e) in tetrahydrofuran (10 ml) were added 2N-NaOH (2 ml) and methanol (5 ml). The mixture was stirred for 3 hours at 80° C. The reaction mixture was concentrated under reduced pressure. To the residue was added water (20 ml), and the aqueous solution was adjusted to pH 3 with 2N-HCl. Precipitates then formed were collected by filtration and recrystallized from ethyl acetate to give colorless prisms (0.19 g, 65%), m.p.228°–229° C.

Elemental Analysis for C$_{26}$H$_{22}$N$_4$O$_4$S:

|  | C(%) | H(%) | N(%) |
|---|---|---|---|
| Calcd.: | 64.18; | 4.56; | 11.52 |
| Found: | 64.15; | 4.62; | 11.56 |

$^1$H-NMR(90 MHz,CDCl$_3$-CD$_3$OD) δ: 1.07(3H,t), 1.63–2.03(2H,m), 3.37(2H,t), 5.87(2H, s), 6.97–7.90(11H, m).

IR(Nujol)cm$^{-1}$: 1795, 1700, 1455, 1280, 1240, 755.

Working Example 35

1-[[2'-(2,5-Dihydro-5-oxo-1,2,4-oxadiazol-3-yl)biphenyl-4-yl]methyl]-2-methoxybenzimidazole-7-carboxylic acid 35a) Methyl 1-[[2'-(2,5-dihydro-5-oxo-1,2,4-oxadiazol-3-yl)biphenyl-4-yl]methyl]-2-propylsulfinylbenzimidazole-7-carboxylate To a stirred solution of the compound (2.5 g) obtained in Working Example (34e) in dichloromethane (60 ml) was added metachloroperbenzoic acid (1.1 g) in portions under cooling with an ice-bath. The mixture was stirred for one hour under the same conditions, which was washed with a solution of sodium hydrogencarbonate (500 mg) in water (50 ml). The organic layer was washed with water (30 ml×1) and dried over anhydrous magnesium sulfate. The solvent was evaporated under reduced pressure to afford the title compound as a pale yellow syrup (2.58 g, 100%).

$^1$H-NMR(90 MHz,CDCl$_3$) δ: 1.03(3H,t), 1.57–2.00(2H, m), 3.13–3.63(2H,m), 3.77(3H,s), 6.07(1H,d), 6.17(1H,d), 6.93(2H,d), 7.17–8.03(9H,m).

IR(Nujol)cm$^{-1}$: 1780, 1720, 1285, 1260, 755.

35b) Methyl 1-[[2'-(2,5-dihydro-5-oxo-1,2,4-oxadiazol-3-yl)biphenyl-4-yl]methyl]-2-methoxybenzimidazole-7-carboxylate To a solution of the compound (517 mg) obtained in Working Example (35a) in methanol (5 ml) was added a solution of 28% sodium methoxide in methanol solution (579 mg), and the mixture was allowed to stand for one hour at room temperature. To the mixture was added 2N-HCl to adjust to pH 3, and the mixture was concentrated under reduced pressure. The residue was partitioned between water (20 ml) and dichloromethane (50 ml). The organic layer was concentrated to dryness under reduced pressure, and the residue was crystallized from methanol to afford the title compound as prisms (308 mg, 68%), m.p. 215°–216° C.

Elemental Analysis for $C_{25}H_{20}N_4O_5 \cdot 0.1H_2O$:

|  | C(%) | H(%) | N(%) |
|---|---|---|---|
| Calcd.: | 65.53; | 4.44; | 12.23 |
| Found: | 65.38; | 4.56; | 12.12 |

$^1$H-NMR(90 MHz,DMSO-$d_6$) δ: 3.73(3H,s), 4.27(3H,s), 5.63(2H,s), 7.03(2H,d), 7.20–7.77(9H,m).

IR(Nujol)cm$^{-1}$: 1760, 1720, 1560, 1435, 1405, 1285, 1250, 1040, 740.

35c) 1-[[2'-(2,5-Dihydro-5-oxo-1,2,4-oxadiazol-3-yl)biphenyl-4-yl]methyl]-2-methoxybenzimidazole-7-carboxylic acid The compound (228 mg) obtained in Working Example (35b) was subjected to the similar reaction as in Working Example (34f), and the product was recrystallized from ethyl acetate to give the title compound as colorless prisms (133 mg, 60%), m.p.189°–190° C.

Elemental Analysis for $C_{24}H_{18}N_4O_5 \cdot 0.75H_2O$:

|  | C(%) | H(%) | N(%) |
|---|---|---|---|
| Calcd.: | 63.22; | 4.31; | 12.29 |
| Found: | 63.50; | 4.28; | 12.03 |

$^1$H-NMR(90 MHz,DMSO-$d_6$) δ: 4.20(3H,s), 5.73(2H,s), 7.03–7.73(11H,s), 12.17(1H,broad), 12.93(1H,broad).

IR(Nujol)cm$^{-1}$: 1780, 1705, 1560, 1415, 1250, 1040.

Working Example 36
1-[[2'-(2,5-Dihydro-5-oxo-1,2,4-oxadiazol-3-yl)biphenyl-4-yl]methyl]-2-propoxybenzimidazole-7-carboxylic acid 36a) Methyl1-[[2'-(2,5-dihydro-5-oxo-1,2,4-oxadiazol-3-yl)biphenyl-4-yl]methyl]-2-propoxybenzimidazole-7-carboxylate A solution of 28% sodium methoxide in methanol (710 mg) was concentrated to dryness under reduced pressure, and the residue was dissolved in propanol (10 ml). In the solution was dissolved the compound (517 mg) obtained in Working Example (35a), and the solution was allowed to stand for two hours at room temperature. The solution was adjusted to pH 3 with 2N-HCl and concentrated to dryness under reduced pressure. The residue was dissolved in methanol (15 ml), and to the solution was added a solution of 28% sodium methoxide in methanol (710 mg). The mixture was allowed to stand for 15 hours at room temperature and adjusted to pH 3 with 2N-HCl, followed by concentration under reduced pressure. The residue was partitioned between water (25 ml) and dichloromethane (25 ml). The organic layer was concentrated to dryness under reduced pressure. The residue was crystallized from methanol to give the title compound colorless prisms (310 mg, 64%), m.p.172°–174° C.

Elemental Analysis for $C_{27}H_{24}N_4O_5 \cdot 0.2H_2O$:

|  | C(%) | H(%) | N(%) |
|---|---|---|---|
| Calcd.: | 66.44; | 5.04; | 11.48 |
| Found: | 66.57; | 5.01; | 11.55 |

$^1$H-NMR(90 MHz,CDCl$_3$) δ: 1.00(3H,t), 1.60–2.00(2H,m), 3.63(3H,s), 4.23(2H,t), 5.60(2H,s), 6.80–7.93(11H,m).

IR(Nujol)cm$^{-1}$: 1780, 1720, 1550, 1440, 1280, 755.

36b) 1-[[[2'-(2,5-Dihydro-5-oxo-1,2,4-oxadiazol-3-yl)biphenyl-4-yl]methyl]-2-propoxybenzimidazole-7-carboxylic acid The compound (194 mg) obtained in Working Example (36a) was subjected to the similar reaction as in Working Example (34f), and the product was recrystallized from ethyl acetate to give the title compound as colorless prisms (132 mg, 70%), m.p.170°–172° C.

Elemental Analysis for $C_{26}H_{22}N_4O_5 \cdot H_2O$:

|  | C(%) | H(%) | N(%) |
|---|---|---|---|
| Calcd.: | 63.93; | 4.95; | 11.47 |
| Found: | 63.82; | 4.65; | 11.41 |

$^1$H-NMR(90 MHz,CDCl$_3$-CD$_3$OD) δ: 1.00(3H,t), 1.67–2.07(2H,m), 4.50(2H,t), 5.67(2H,s), 7.00–7.80(11H,m).

IR(Nujol)cm$^{-1}$: 1765, 1725, 1550, 1430.

Working Example 37
2-Ethylthio-1-[[2'-(2,5-dihydro-5-oxo-1,2,4-oxadiazol-3-yl]biphenyl-4-yl]methyl]benzimidazole-7-carboxylic acid 37a) Methyl 2-ethylthio-1-[[2'-(2,5-dihydro-5-oxo-1,2,4-oxadiazol-3-yl)biphenyl-4-yl]methyl]benzimidazole-7-carboxylate To a solution of the compound (517 mg) obtained in Working Example (35a) in methanol (3 ml) were added triethylamine (404 mg) and ethyl mercaptan (186 mg). The mixture was allowed to stand for 60 hours at room temperature and concentrated to dryness in vacuo. After addition of water (20 ml) to the residue, the mixture was adjusted to pH 3 with 2N-HCl. The solution was extracted with ethyl acetate (60 ml). The upper layer was washed with water (10 ml×3), and then concentrated to dryness in vacuo. The residue was crystallized from ethyl acetate to give the title compound as colorless prisms (370 mg, 76%), m.p.210°–211° C.

Elemental Analysis for $C_{26}H_{22}N_4O_4S$:

|  | C(%) | H(%) | N(%) |
|---|---|---|---|
| Calcd. | 64.18; | 4.56; | 11.52 |
| Found: | 64.06; | 4.58; | 11.40 |

$^1$H-NMR(90 MHz,CDCl$_3$) δ: 1.40(3H,t), 3.27(2H,q), 3.70(3H,s), 5.70(2H,s), 6.87–7.87(11H,m).

IR(Nujol)cm$^{-1}$: 1760, 1720, 1280, 1260.

37b) 2-Ethylthio-1-[[2'-(2,5-dihydro-5-oxo-1,2,4-oxadiazol-3-yl)biphenyl-4-yl]methyl]benzimidazole-7-carboxylic acid The compound (260 mg) obtained in Working Example (37a) was subjected to the similar reaction as in Working Example (34f), and the product was recrystallized from methanol-water to afford the title compound as colorless needles (160 mg, 63%), m.p.146°–148° C.

Elemental Analysis for $C_{25}H_{20}N_4O_4S$:

|  | C(%) | H(%) | N(%) |
|---|---|---|---|
| Calcd.: | 63.55; | 4.27; | 11.86 |
| Found: | 63.28; | 4.37; | 11.59 |

$^1$H-NMR(90 MHz,CDCl$_3$) δ: 1.43(3H,t), 3.40(2H,q), 5.70(2H,s), 6.90–7.87(11H,m).

IR(Nujol)cm$^{-1}$: 1785, 1765, 1700, 1350, 760.

Working Example 38
1-[[2'-(2,5-Dihydro-5-oxo-1,2,4-oxadiazol-3-yl)biphenyl-4-yl]methyl]-2-methylthiobenzimidazole-7-carboxylic acid 38a) Methyl 1-[[2'-(2,5-dihydro-5-oxo-1,2,4-oxadiazol-3-yl)biphenyl-4-yl]methyl]-2-methylthiobenzimidazole-7-carboxylate The compound (690 mg) obtained in Working Example (35a) was subjected to the similar reaction as in Working Example (37a), and the product was recrystallized from methanol to afford the title compound as colorless prisms (460 mg, 73%), m.p.231°–232° C.

Elemental Analysis for $C_{25}H_{20}N_4O_4S$:

|  | C(%) | H(%) | N(%) |
|---|---|---|---|
| Calcd.: | 63.55; | 4.27; | 11.86 |
| Found: | 63.36; | 4.33; | 11.76 |

$^1$H-NMR(90 MHz,DMSO-$d_6$) δ: 2.77(3H,s), 3.73(3H,s), 5.73(2H,s), 7.00–7.93(11H,m), 12.33(1H,broad).

IR(Nujol)cm$^{-1}$: 1760, 1710, 1430, 1270, 1250, 760.

38b) 1-[[2'-(2,5-Dihydro-5-oxo-1,2,4-oxadiazol-3-yl)biphenyl-4-yl]methyl]-2-methylthiobenzimidazole-7-carboxylic acid The compound (360 mg) obtained in Working Example (38a) was subjected to the similar reaction as in Working Example (34f), and the product was recrystallized from methanol to afford the title compound as colorless prisms (270 mg, 77%), m.p.222°–223° C.

Elemental Analysis for $C_{24}H_{18}N_4S.0.8H_2O$:

|  | C(%) | H(%) | N(%) |
|---|---|---|---|
| Calcd.: | 60.95; | 4.18; | 11.85 |
| Found: | 60.83; | 4.40; | 11.58 |

$^1$H-NMR(90 MHz,DMSO-$d_6$) δ: 2.77(3H,s), 5.83(2H,s), 7.00–7.77(11H,m), 12.60(2H,broad).

IR(Nujol)cm$^{-1}$: 1760, 1270, 760.

Working Example 39

Dipotassium salt of 2-Ethoxy-1-[[2'-(5-oxide-1,2,4-oxadiazol-3-yl)biphenyl-4-yl]methyl]benzimidazole-7-carboxylic acid A solution of 2-ethoxy-1-[[2'-(2,5-dihydro-5-oxo-1,2,4-oxadiazol-3-yl)biphenyl-4-yl]methyl]benzimidazole-7-carboxylic acid (456 mg) in 0.2N-KOH (10 ml) was concentrated to dryness under reduced pressure. To the residue was added acetone (30 ml), and the mixture was stirred for three days at room temperature. Crystals then precipitated were collected by filtration and dried (120° C., 1.5 hour) to give the title compound as colorless needles (470 mg, 89%), m.p.245°–247° C.

Elemental Analysis for $C_{25}H_{18}N_4O_5K_2.3/2H_2O$:

|  | C(%) | H(%) | N(%) |
|---|---|---|---|
| Calcd.: | 53.65; | 3.78; | 10.01 |
| Found: | 53.77; | 3.63; | 9.93 |

$^1$H-NMR(90 MHz,DMSO-$d_6$) δ: 1.40(3H,t), 4.53(2H,q), 5.83(2H,s), 6.90–7.70(11H,m).

IR(Nujol)cm$^{-1}$: 3370, 1660, 1610, 1570, 1540, 1385.

Working Example 40

Disodium salt of 2-ethoxy-1-[[2'-(5-oxide-1,2,4-oxadiazol-3-yl)biphenyl-4-yl]methyl]benzimidazole-7-carboxylic acid In ethanol (500 ml) was dissolved a solution of 28% sodium methoxide in methanol (43.7 g), and the solution was concentrated to dryness under reduced pressure. To the residue were added ethanol (500 ml) and 2-ethoxy-1-[[2'-(2,5-dihydro-5-oxo-1,2,4-oxadiazol-3-yl)biphenyl-4-yl]methyl]benzimidazole-7-carboxylic acid (52.5 g), and the mixture was dissolved. The solution was concentrated to dryness under reduced pressure. The residue was dissolved in ethanol (250 ml) by heating, and then the solution was allowed to stand for 40 hours at room temperature. Crystals then precipitated were collected by filtration, washed with ethanol (30 ml) and dried (140° C., 2 hours) to give colorless prisms (35.5 g), which were allowed to stand for three days in the air at room temperature to afford the titled compound as colorless prisms (42.34 g, 61%), m.p.294°–297° C.

Elemental Analysis for $C_{25}H_{18}N_4O_5Na_2.5.5H_2O$:

|  | C(%) | H(%) | N(%) |
|---|---|---|---|
| Calcd.: | 50.09; | 4.88; | 9.35 |
| Found: | 50.32; | 4.71; | 9.21 |

$^1$H-NMR(90 MHz,DMSO-$d_6$) δ: 1.43(3H,t), 4.57(2H,q), 5.80(2H,s), 6.87–7.63(11H,m).

IR(Nujol)cm$^{-1}$: 3375, 1655, 1615, 1410, 1350, 1280, 1040, 770.

Working Example 41

Methyl 2-ethoxy-1-[[2'-(2,5-dihydro-5-oxo-1,2,4-oxadiazol-3-yl)biphenyl-4-yl]methyl]-4-methylthieno[3,4-d]imidazole-6-carboxylate 41a) Methyl 1,3-dihydro-4-methyl-2-oxo-thieno[3,4-d]imidazole-6-carboxylate Methyl 3,4-diamino-5-methylthiophene-2-carboxylate (3.0 g) was dissolved in a mixture of N,N-dimethyl formamide (5 ml) and dichloromethane (15 ml). To the solution was added triphosgene (2.4 g) in portions. The mixture was stirred for two days at room temperature, and precipitates were collected by filtration, washed with dichloromethane and dried. Resultant white powder (2.4 g) was suspended in N,N-dimethylformamide (25 ml). To the suspension was added sodium hydride (60% in oil; 0.55 g), and the mixture was stirred for three days at room temperature. The solvent was evaporated under reduced pressure. To the residue was added 2N-HCl. Resulting precipitates were collected by filtration, washed with water, ether and methanol successively, followed by drying to afford the title compound (82 g, 53%) as pale brown powder.

$^1$H-NMR(200 MHz,DMSO-$d_6$) δ: 2.32(3H,s), 3.73(3H,s), 10.71(1H,bs), 11.06(1H,bs).

IR(KBr)cm$^{-1}$: 3300, 1735, 1675, 1585, 1440.

41b) Methyl 2-ethoxy-4-methylthieno[3,4-d]imidazole-6-carboxylate

The compound (1.0 g) obtained in Working Example (41a) was suspended in a mixture of dioxane (10 ml) and dichloromethane (20 ml). To the suspension was added an excess amount of triethyl oxonium tetrafluoroborate at room temperatures in nitrogen atmosphere, and the mixture was stirred for 19 hours. The reaction mixture was poured into ice-water, and the mixture was extracted four times with a mixture of chloroform and ethanol. Organic layers were combined, dried, and concentrated to dryness under reduced pressure. The residue was purified by column chromatography on silica gel to afford the title compound (945 mg, 75%) as pale yellow powder, m.p.209°–210° C.

Elemental Analysis for $C_{10}H_{12}N_2O_3S.0.2H_2O$:

|  | C(%) | H(%) | N(%) |
|---|---|---|---|
| Calcd.: | 49.25; | 5.12; | 11.49 |
| Found: | 49.42; | 4.95; | 11.29 |

$^1$H-NMR(200 MHz,CDCl$_3$) δ: 1.44(3H,t), 2.57(3H,s), 3.87(3H,s), 4.54(2H,q), 9.03(1H,bs).

IR(KBr)cm$^{-1}$: 3250, 1670, 1640, 1580, 1540.

41c) Methyl 2-ethoxy-1-[[2'-(5-trichloromethyl-1,2,4-oxadiazol-3-yl)biphenyl-4-yl]methyl]-4-methylthieno[3,4-d]imidazole-6-carboxylate The compound (100 mg) obtained in Working Example (41b) and 4'-bromomethyl-2-(5-trichloromethyl-1,2,4-oxadiazol-3-yl)biphenyl (193 mg) were dissolved in N,N-dimethyl formamide (3.5 ml). To the ice-cooling solution was added sodium hydride (60% in oil; 18 mg) under nitrogen atmosphere. The mixture was stirred for 15 minutes under ice-cooling, then for one hour at room temperature. The reaction mixture was diluted with ethyl acetate, and the solution was washed with dilute hydrochloric acid, water and an aqueous saline solution, successively, followed by drying. The solvent was evaporated under reduced pressure. The residue was purified by column chromatography on silica gel to afford the title compound (121 mg, 55%) as a pale yellow oil.

$^1$H-NMR(200 MHz,CDCl$_3$) δ: 1.42(3H,t), 2.55(3H,s), 3.79(3H,s), 4.52(2H,q), 5.57(2H,s), 7.15(2H,d), 7.23(2H,d), 7.86(1H,d).

IR(neat)cm$^{-1}$: 1690, 1615, 1570, 1535.

41d) Methyl 2-ethoxy-1-[[2'-(2,5-dihydro-5-oxo-1,2,4-oxadiazol-3-yl)biphenyl-4-yl]methyl]-4-methylthieno[3,4-d]imidazole-6-carboxylate The compound (120 mg) obtained in Working Example (41c) was dissolved in a mixture of dioxane (4 ml) and water (1 ml). To the ice-cooling solution was added 1N-NaOH (0.26 ml), and the mixture was stirred for 50 minutes at the same temperature. The reaction mixture was made acid with 2N-HCl and extracted with ethyl acetate. The extract was washed with water and dried, and then the solvent was evaporated under reduced pressure. The residue was purified by silica gel column chromatography to give a yellow oil. The product was crystallized from ether and hexane to afford the title compound (81 mg, 77%) as pale yellow crystals, m.p.208°–210° C.

Elemental Analysis for C$_{25}$H$_{22}$N$_4$O$_5$S:

|  | C(%) | H(%) | N(%) |
|---|---|---|---|
| Calcd.: | 61.21; | 4.52; | 11.42 |
| Found: | 60.98; | 4.55; | 11.27 |

$^1$H-NMR(200 MHz,CDCl$_3$) δ: 1.42(3H,t), 2.42(3H,s), 3.74(3H,s), 4.42(2H,q), 5.58(2H,s), 7.2–7.7 (7H,m), 7.82(1H,dd), 7.68(1H,bs).

IR(KBr)cm$^{-1}$: 1760, 1700, 1620, 1580, 1535.

Working Example 42

Disodium salt of 1-[[2'-(2,5-Dihydro-5-oxo-1,2,4-oxadiazol-3-yl)biphenyl-4-yl]methyl]-2-methoxy-4-methylthieno[3,4-d]imidazole-6-carboxylic acid The compound (0.5 g) obtained in Working Example 9 was suspended in methanol (10 ml). To the suspension was added an aqueous solution (5 ml) of sodium hydroxide (90 mg), and the mixture was stirred for 10 minutes at room temperature. The reaction solution was concentrated to dryness to give crude crystals. Recrystallization from ethanol-ether afforded the title compound as pale yellow crystals (0.28 g, 49%), 263°–266° C. (decomp.).

Elemental Analysis for C$_{23}$H$_{16}$N$_4$O$_5$SNa$_2$·1.0H$_2$O (molecular weight 524.46):

|  | C(%) | H(%) | N(%) |
|---|---|---|---|
| Calcd.: | 52.67; | 3.46; | 10.68 |
| Found: | 52.88; | 3.43; | 10.45 |

$^1$H-NMR(200 MHz,DMSO-d$_6$) δ: 2.37(3H,s), 4.00(3H,s), 5.80(2H,s), 7.16–7.50(8H,m).

IR(KBr)cm$^{-1}$: 1680, 1620, 1575, 1545, 1460, 1395, 1360.

Working Example 43

2-Ethylthio-1-[[3'-(2,5-dihydro-5-oxo-1,2,4-oxadiazol-3-yl)biphenyl-4-yl]methyl]-4-methylthieno[3,4-d]imidazole-6-carboxylic acid 43a) 4'-Methyl-3-cyanobiphenyl This compound was synthesized according to the procedure described in the literature (Y. Hamana, S. Fukushima & T. Hiyama, Chem. Lett., 1989, 1711). M.p.71°–73° C.

$^1$H-NMR(200 MHz,CDCl$_3$) δ: 2.41(3H,s), 7.28(2H,d), 7.46(2H,d), 7.51(1H,t), 7.60(1H,td), 7.79(1H,td), 7.84(1H,t).

IR(KBr)cm$^{-1}$: 2230, 1475, 825, 800.

43b) 4'-Methylbiphenyl-3-carboxamide oxime

To a solution of hydroxylamine hydrochloride (2.61 g) in DMSO (20 ml) was added a solution of 28% NaOMe in methanol (7.25 g), and the mixture was stirred for 10 minutes at room temperature. To the reaction mixture was added the solution of the compound (1.45 g) obtained in Working Example (43a) in DMSO (10 ml). The mixture was stirred for one hour at 100° C. To the reaction mixture was added water, and the mixture was extracted with ethyl acetate. The extract was washed with water and dried. The solvent was evaporated in vacuo, and the residue was purified by column chromatography on silica gel to afford colorless crystals (1.30 g, 76.6%), m.p.134°–136° C.

$^1$H-NMR(200 MHz,CDCl$_3$) δ: 2.39(3H,s), 4.93(2H,br s), 7.25(2H,d), 7.41–7.66(5H,m), 7.85(1H,t).

IR(KBr)cm$^{-1}$: 3495, 3385, 1660, 1585, 1440, 1375, 940, 925, 900, 795.

43c) 5-Trichloromethyl-3-(4'-methylbiphenyl-3-yl)-1,2,4-oxadiazole

To a suspension of the compound (1.30 g) obtained in Working Example (43b) in toluene (30 ml) was added trichloroacetic anhydride (2.13 g). The mixture was stirred for 30 minutes at 80° C. The reaction mixture was concentrated to dryness, and the residue was partitioned between ethyl acetate and water. The organic layer was dried over Na$_2$SO$_4$ and concentrated to dryness. The residue was purified by column chromatography on silica gel to afford a colorless oil (2.09 g, quantitatively).

$^1$H-NMR(200 MHz,CDCl$_3$) δ: 2.41(3H,s), 7.28(2H,d), 7.55(2H,d), 7.56(1H,t), 7.76(1H,td), 8.07(tH,td), 8.32(1H,t).

IR(Neat)cm$^{-1}$: 1570, 1515, 1460, 1355, 1335, 850, 825, 800, 745, 690.

43d) 3-(4'-Bromomethylbiphenyl-3-yl)-5-trichloromethyl-1,2,4-oxadiazole

To a solution of the compound (2.09 g) obtained in Working Example (43c) in CCl$_4$ (50 ml) were added NBS (1.10 g) and BPO (0.20 g). The mixture was irradiated by light. The reaction mixture was cooled to room temperature, and insoluble materials were filtered off. The filtrate was concentrated to dryness. The residue was purified by column chromatography on silica gel (Merck Art.9385 (80 g), AcO-Et:nHex=1:10) to afford a colorless syrup (2.40 g, 60%).

$^1$H-NMR(200 MHz,CDCl$_3$) δ: 4.57(2H,s), 7.49–7.68(5H, m), 7.75–7.79(1H,m), 8.09–8.17(1H,m), 8.33(1H,m).

43e) Methyl 2-ethylthio-1-[[3'-(2,5-dihydro-5-oxo-1,2,4-oxadiazol-3-yl)biphenyl-4-yl]methyl]-4-methylthieno-[3,4-d]imidazole-6-carboxylate To a solution of methyl 2-ethylthio-4-methyl-1H-thieno[3,4-d]imidazole-6-carboxylate (0.80 g) in DMF (10 ml) was added sodium hydride (60% in oil; 0.14 g) under ice-cooling. The mixture was stirred for 10 minutes, to which was added a solution of the compound (1.53 g) obtained in Working Example (43d) in DMF (10 ml) under ice-cooling. The mixture was stirred for one hour at room temperature. The reaction mixture was partitioned between water and ethyl acetate. The organic layer was washed with a saturated aqueous saline solution and dried. The solvent was evaporated in vacuo, and the residue was purified by silica gel column chromatography to give colorless crystals. To a solution of the crystals in chloroform (10 ml)–methanol (10 ml) was added 1N NaOH (3 ml), and the mixture was stirred for one hour at room temperature. The reaction mixture was concentrated and adjusted to pH 3–4 with 1N HCl. The mixture was partitioned between $CHCl_3$ and water. The organic layer was dried over $Na_2SO_4$ and concentrated to dryness, to give crude crystals. Recrystallization from methanol—ethyl acetate afforded colorless crystal (0.74 g, 84%), m.p. 248°–151° C. (decomp.).

Elemental Analysis for $C_{25}H_{22}N_4O4S_2 \cdot 0.5H_2O$:

|  | C(%) | H(%) | N(%) |
|---|---|---|---|
| Calcd.: | 58.24; | 4.50; | 10.87 |
| Found: | 58.24; | 4.38; | 10.77 |

$^1$H-NMR(200 MHz,CDCl$_3$) δ: 1.41(3H,t), 2.63(3H,s), 3.30(2H,q), 3.78(3H,s), 5.75(2H,s), 7.27(2H,d), 7.51–7.60(3H,m), 7.69–7.78(2H,m), 7.98(1H,t).

IR(KBr)cm$^{-1}$: 1780, 1755, 1690, 1460, 1320, 1170, 1090, 760.

43f) 2-Ethylthio-1-[[3'-(2,5-dihydro-5-oxo-1,2,4-oxadiazol-3-yl)biphenyl-4-yl]methyl]-4-methylthieno[3,4-d]imidazole-6-carboxylic acid The compound (0.60 g) obtained in Working Example (43e) was suspended in tetrahydrofuran (20 ml)–H$_2$O (20 ml). To the suspension was added lithium hydride (0.25 g: 5.96 mmol), and mixture was heated for 15 hours under reflux. The reaction mixture was concentrated, and aqueous residue was adjusted to pH 3 with 1N-HCl. Crystals then precipitated were collected by filtration and dried. The crystals were recrystallized to afford colorless crystals (0.33 g, 56.7%), m.p. 177°–179° C. (decomp.).

Elemental Analysis for $C_{24}H_{20}N_4O_4S_2 \cdot 0.5H_2O$:

|  | C(%) | H(%) | N(%) |
|---|---|---|---|
| Calcd.: | 57.47; | 4.22; | 11.17 |
| Found: | 57.63; | 4.04; | 11.17 |

$^1$H-NMR(200 MHz,DMSO-d$_6$) δ: 1.35(3H,t), 2.56(3H,s), 3.26(2H,q), 5.73(2H,s), 7.26(2H,d), 7.65(1H,t), 7.69(2H,d), 7.81(1H,td), 7.90(1H,td), 8.08(1H,t).

IR(KBr)cm$^{-1}$: 1770, 1755, 1650, 1530, 1460, 1165, 765.

Working Example 44
2-Ethylthio-1-[[4'-(2,5-dihydro-5-oxo-1,2,4-oxadiazol-3-yl)biphenyl-3-yl]methyl]-4-methylthieno[3,4-d]-imidazole-6-carboxylic acid 44a) 4'-Methyl-4-cyanobiphenyl This compound was synthesized in the similar procedure as in Working Example (43a), m.p. 108°–109° C.

$^1$H-NMR(200 MHz,CDCl$_3$) δ: 2.42(3H,s), 7.29(2H,d), 7.50(2H,d), 7.64–7.75(4H,m).

IR(KBr)cm$^{-1}$: 2225, 1495, 815.

44b) 4'-Methylbiphenyl-4-carboxamide oxime

This compound was synthesized by the similar procedure as in Working Example (43b).

44c) 3-(4'-Methylbiphenyl-4-yl)-5-trichloromethyl-1,2,4-oxadiazole

This compound was synthesized by the similar procedure as in Working Example (43c), m.p. 126°–127° C. The yield was 75%.

$^1$H-NMR (200 MHz, CDCl$_3$) δ: 2.42(3H,s), 7.29(2H,d), 7.55(2H,d), 7.72(2H,d), 8.17(2H,d).

IR(KBr)cm$^{-1}$: 1610, 1585, 1540, 1470, 1420, 1345, 905, 855, 845, 825, 810, 755, 725.

44d) 3-(4'-Bromomethylbiphenyl-4-yl)-trichloromethyl-1,2,4-oxadiazole

The title compound was obtained as colorless needles (71%) from the compound obtained in Working Example (44c) in the similar manner as in Working Example (43d), m.p. 113°–116° C.

$^1$H-NMR(200 MHz,CDCl$_3$) δ: 4.56 (2H,s), 7.51(2H,d), 7.64(2H,d), 7.73(2H,d), 8.20(2H,d).

IR(KBr) cm$^{-1}$: 1475, 1400, 1350, 845, 830, 800, 760, 725.

44e) Methyl 2-ethylthio--1-[[4'-(2,5-dihydro-5-oxo-1,2,4-oxadiazole-3-yl)biphenyl-4-yl]-4-methylthieno[3,4-d]imidazole-6-carboxylate The title compound was obtained as pale yellow crystals (0.4 g, 25%) from the compound (1.53 g) obtained in Working Example (44d) in the similar manner as in Working Example (43e), m.p. 251°–255° C. (decomp.).

Elemental Analysis for $C_{25}H_{22}N_4O_4S_2$

|  | C(%) | H(%) | N(%) |
|---|---|---|---|
| Calcd.: | 58.85; | 4.43; | 10.98 |
| Found: | 58.89; | 4.35; | 10.81 |

$^1$H-NMR(200 MHz,DMSO-d$_6$) δ: 1.36(3H,t), 2.57(3H,s), 3.27(2H,q), 3.70(3H,s), 5.70(2H,s), 7.22(2H,d), 7.72(2H,d), 7.87(4H,s).

IR(KBr)cm$^{-1}$: 1760, 1690, 1460, 1320, 1305, 1255, 1240, 1160, 1090, 760.

44f) 2-Ethylthio-1-[[4'-(2,5-dihydro-5-oxo-1,2,4-oxadiazole-3-yl)biphenyl-4-yl]methyl]-4-methylthieno[3,4-d]imidazole-6-carboxylic acid The title compound was obtained as colorless crystals (0.29 g, 90%) from the compound (0.33 g) obtained in Working Example (44e) in the similar manner as in Working Example (43f), m.p. 202°–204° C. (decomp.).

Elemental Analysis for $C_{24}H_{20}N_4O_4S_2$

|  | C(%) | H(%) | N(%) |
|---|---|---|---|
| Calcd.: | 57.68; | 4.19; | 11.21 |
| Found: | 57.83; | 4.48; | 11.39 |

$^1$H-NMR(200 MHz,DMSO-d$_6$) δ: 1.35(3H,t), 2.56(3H,s), 3.26(2H,q), 5.72(2H,s), 7.24(2H,d), 7.72(2H,d), 7.87(4H,s).

IR(KBr)cm$^{-1}$: 1760, 1640, 1610, 1600, 1535, 1460, 1165, 770.

Working Example 45
2-Ethylthio-1-[[2'-(2,5-dihydro-5-oxo-1,2,4-oxadiazol-3-yl)methylbiphenyl-4-yl]methyl]-4-methylthieno[3,4-d]imidazole-6-carboxylic acid 45a) 4'-Methyl-2-hydroxymethylbiphenyl To an ice-cooling suspension of lithium aluminium hydride (1.79 g) in tetrahydrofuran (50 ml) was added dropwise a solution of 4'-methylbiphenyl-2-carboxylic acid (5.0 g) in tetrahydrofuran (30 ml). The mixture was stirred for 17 hours at room temperature. To the reaction mixture were added ethyl acetate (10 ml) and water (50 ml), and insoluble materials were removed by filtration through celite. The filtrate was concentrated to dryness, and the residue was dissolved in ethyl acetate. The solution was washed with a saturated aqueous solution of sodium hydrogencarbonate and dried. The solvent was evaporated under reduced pressure, and the residue was purified by column chromatography on silica gel to afford the title compound as colorless syrup (3.95 g, 84%).

¹H-NMR(200 MHz,CDCl₃) δ: 2.41(3H,s), 4.62(2H,s), 7.20–7.41(7H,m), 7.51–7.56(1H,m).

IR(Neat)cm⁻¹: 3350, 3020, 2920, 1480, 1440, 1030, 1000, 820, 755.

45b) 4'-Methyl-2-chloromethylbiphenyl

To an ice-cooling solution of the compound (3.95 g) obtained in Working Example (45a) in chloroform (50 ml) was added dropwise thionyl chloride (3.56 g). To the mixture was further added one drop of dimethylformamide, and the mixture was heated for one hour under reflux. The reaction mixture was concentrated to dryness, and the residue was suspended with a saturated aqueous solution of sodium hydrogen carbonate and extracted with ethyl acetate. The extract was washed with water and dried, and the solvent was evaporated under reduced pressure to afford the title compound as a pale yellow oil (4.15 g, 96%).

¹H-NMR(200 MHz,CDCl₃) δ: 2.41(3H,s), 4.53(2H,s), 7.23–7.41(7H,m), 7.50–7.56(1H,m).

IR(Neat)cm⁻¹: 1480, 1440, 1260, 1000, 825, 820, 755, 690, 665.

45c) 4'-Methyl-2-cyanomethylbiphenyl

To a solution of the compound (4.15 g) obtained in Working Example (45b) in acetonitrile (50 ml) were added potassium cyanide (2.5 g) and 18-crown-6 (0.5 g). The mixture was heated for 10 hours under reflux. Insoluble materials were filtered off, and the filtrate was concentrated to dryness. The residue was dissolved in ethyl acetate, washed with water and dried. The solvent was evaporated under reduced pressure, and the residue was purified by column chromatography on silica gel to afford the title compound as a pale yellow oil (3.71 g, 93%).

¹H-NMR(200 MHz,CDCl₃) δ: 2.41(3H,s), 3.62(2H,s), 7.14–7.39(7H,m), 7.50–7.55(1H,m).

IR(Neat)cm⁻¹: 2240, 1480, 820, 760.

45d) 4'-Methylbiphenyl-2-acetamidoxime

To a solution of hydroxylamine hydrochloride (1.68 g) in dimethyl sulfoxide (10 ml) was added a solution of 28% sodium methoxide in methanol solution (4.65 g), and the mixture was stirred for 20 minutes at room temperature. To this mixture was added a solution of the compound obtained in Working Example (45c) in dimethyl sulfoxide (3 ml), and the mixture was stirred for 1.5 hour at 100° C. The reaction mixture was partitioned between water and ethyl acetate. The organic layer was washed with water and dried, and then the solvent was evaporated under reduced pressure. The residue was purified by column chromatography on silica gel to afford the title compound as colorless crystals (0.92 g, 79%), m.p.127–128° C.

¹H-NMR(200 MHz,CDCl₃) δ: 2.40(3H,s), 3.46(2H,s), 4.33(2H,br s), 7.18–7.43(8H,m).

IR(KBr)cm⁻¹: 3450, 3350, 1670, 1590, 1480, 1380, 940, 820, 760.

45e) 3-(4'-Methylbiphenyl-2-yl)methyl-5-trichloromethyl-1,2,4-oxadiazole

The compound obtained in Working Example 45d) (0.92 g) was suspended in toluene (20 ml). To the suspension was added trichloroacetic anhydride (1.42 g), and the mixture was stirred for one hour at 80°–90° C. The reaction mixture was concentrated to dryness, and the residue was dissolved in ethyl acetate, followed by washing with water and dried. The solvent was evaporated under reduced pressure. The residue was purified by column chromatography on silica gel to afford the title compound as a colorless oil (1.25 g, 88%).

¹H-NMR(200 MHz,CDCl₃) δ: 2.40(3H,s), 4.11(2H,s), 7.19–7.42(8H,m).

IR(Neat)cm⁻¹: 1580, 1490, 1355, 1050, 860, 820, 800, 760, 735, 705.

45f) 3-(4'-Bromomethylbiphenyl-2-yl)methyl-5-trichloromethyl-1,2,4-oxadiazole

To a solution of the compound (1.25 g) obtained in Working Example (45e) in carbon tetrachloride (20 ml) were added N-bromosuccinimide (0.67 g) and α,α'-azobis isobutyronitrile (0.1 g), and the mixture was heated for one hour under reflux. Insoluble materials were filtered off, and the filtrate was concentrated to dryness. The residue was purified by column chromatography on silica gel to afford a pale yellow syrup (0.91 g, 60%).

¹H-NMR(200 MHz,CDCl₃) δ: 4.10(2H,s), 4.55(2H,s), 7.23–7.47(8H,m).

45g) Methyl 2-ethylthio-1-[[2'-(2,5-dihydro-5-oxo-1,2,4-oxadiazol-3-yl)methylbiphenyl-4-yl]methyl]thieno[3,4-d]imidazole-4-methyl-6-carboxylate To an ice-cooling solution of methyl 2-ethylthio-4-methylthieno-[3,4-d]imidazole-6-carboxylate (0.75 g) in dimethylformamide (5 ml) was added sodium hydride (60% in oil; 0.13 g), and the mixture was stirred for 10 minutes. To the ice-cooling mixture was added dropwise a solution of the compound (0.91 g) obtained in Working Example (45f) in dimethylformamide (5 ml), followed by stirring for one hour at room temperature. To the reaction mixture was added water, and the mixture was extracted with ethyl acetate. The extract was washed with a saturated aqueous saline solution and dried. The solvent was evaporated in vacuo, and the residue was purified by silica gel column chromatography to give a pale yellow syrup. The syrup was dissolved in chloroform (5 ml)–methanol (10 ml), and to the solution was added 1N-NaOH (2 ml), followed by stirring for 30 minutes at room temperature. The reaction mixture was concentrated to dryness, and the residue was diluted with water. The aqueous solution was adjusted to pH 3 with 1N-HCl and extracted with chloroform. The extract was washed with water and dried, and the solvent was evaporated under reduced pressure. The residue was purified by column chromatography on silica gel. Crude crystals thus obtained were recrystallized from ethyl acetate—methanol to afford the title compound as pale yellow needles (0.31 g, 20%), m.p.172–173° C. (decomp.).

Elemental Analysis for $C_{26}H_{24}N_4O_4S_2$ (Molecular weight 520.63):

|  | C(%) | H(%) | N(%) |
| --- | --- | --- | --- |
| Calcd.: | 59.98; | 4.65; | 10.76 |
| Found: | 59.78; | 4.55; | 10.41 |

¹H-NMR(200 MHz,CDCl₃) δ: 1.41(3H,t), 2.61(3H,s), 3.28(2H,q), 3.76(3H,s), 3.83(2H,s), 5.72(2H,s), 7.16–7.39(8H,m), 8.68(1H,br s).

IR(KBr)cm⁻¹: 1765, 1695, 1685, 1600, 1540, 1460, 1430, 1320, 1240, 1170, 1090, 760.

45h) 2-Ethylthio-1-[[2'-(2,5-dihydro-5-oxo-1,2,4-oxadiazol-3-yl)methylbiphenyl-4-yl]methyl]thieno[3,4-d]imidazole-4-methyl-6-carboxylic acid To a solution of the compound (0.25 g) obtained in Working Example (45g) in tetrahydrofuran (10 ml)–water (5 ml) was added lithium hydroxide monohydrate (0.10 g), and the mixture was heated for 30 hours under reflux. The reaction mixture was adjusted to pH 3 with 1N-HCl and extracted with chloroform. The extract was washed with water and dried, and the solvent was evaporated under reduced pressure to give crude crystals. Recrystallization from ethyl acetate—methanol-hexane afforded the title compound as pale yellow needles (0.18 g, 74%), m.p.184°–186° C. (decomp.).

Elemental Analysis for $C_{25}H_{22}N_4O_4S_2$ (molecular weight 506.61):

|  | C(%) | H(%) | N(%) |
|---|---|---|---|
| Calcd.: | 59.27; | 4.38; | 11.06 |
| Found: | 59.10; | 4.22; | 10.91 |

$^1$H-NMR(200 MHz,DMSO-$d_6$) δ: 1.35(3H,t), 2.55(3H,s), 3.26(2H,q), 3.80(2H,s), 5.73(2H,s), 7.20–7.40(8H,m).

IR(KBr)cm$^{-1}$: 1810, 1790, 1650, 1535, 1460, 1325, 1170, 760.

Working Example 46
2-Ethylthio-1-[[2'-(1,4-dihydro-3-trifluoromethyl-5-oxo-1,2,4-triazol-4-yl)biphenyl-4-yl]methyl]thieno[3,4-d]imidazole-4-methyl-6-carboxylic acid 46a) 4-(4'-Methylbiphenyl-2-yl)semicarbazide To an ice-cooling solution of (4'-methylbiphenyl-2-yl)carboxylic acid (3.0 g) and triethylamine (2.2 ml) in N,N-dimethylformamide (10 ml) was added DPPA (3.4 ml) under nitrogen atmosphere, and the mixture was stirred for 4 hours at the same temperature. To the reaction mixture was added water, and the mixture was extracted with ethyl acetate. The organic layer was washed with water and dried. The solution was added dropwise to benzene (150 ml) heated at 80° C. The mixture was then stirred for 20 minutes at the same temperature. The isocyanate solution thus prepared was added dropwise to a solution of hydrazine (2.0 ml) in benzene (50 ml) heated at 70° C. during the period of 90 minutes. The powdery product obtained by evaporating the solvent under reduced pressure was washed with ethyl acetate and dried to afford the title compound as white power (2.9 g, 85%), m.p.148°–151° C.

Elemental Analysis for $C_{14}H_{15}N_3O.0.5H_2O$:

|  | C(%) | H(%) | N(%) |
|---|---|---|---|
| Calcd.: | 68.66; | 6.33; | 17.16 |
| Found: | 68.80; | 6.34; | 17.18 |

$^1$H-NMR(200 MHz,CDCl$_3$) δ: 2.40(3H,s), 3.55(2H,bs), 6.11(1H,bs), 7.0–7.4(7H,m), 8.21(1H,d), 8.32(1H,bs).

IR(KBr)cm$^{-1}$: 1690, 1615, 1580, 1520.

46b) 3-Trifluoromethyl-4-(4'-methylbiphenyl-2-yl)-1,2,4-tiazol-5-one

To an ice-cooling solution of the compound (700 mg) obtained in Working Example (46a) in dichloromethane (10 ml) were added trifluoroacetic anhydride (0.43 ml) and pyridine (0.32 ml) under nitrogen atmosphere. The mixture was stirred for one hour under ice-cooling, and then for 20 hours at room temperature. To the reaction mixture was added water, and the mixture was extracted with chloroform. The extract was dried and the solvent was evaporated under reduced pressure. The residue was dissolved in benzene (8 ml), and to the solution was added phosphorus oxychloride (1.5 ml). The mixture was stirred for 4 hours at 80° C. The solvent was evaporated under reduced pressure, and the residue was dissolved in ethyl acetate (30 ml). The solution was washed with water and an aqueous saline solution, and the solution was concentrated to dryness under reduced pressure. The residue was purified by column chromatography on silica gel to afford the title compound as a pale brown oil (620 mg, 66%).

$^1$H-NMR(200 MHz,CDCl$_3$) δ: 2.42(3H,s), 7.1–7.5(7H, m), 8.17(1H,d).

IR(KBr)cm$^{-1}$: 1620, 1590, 1520, 1510.

46c) 4-(4'-Methylbiphenyl-2-yl)-3-methoxymethoxy-5-trifluoromethyl-1,2,4-triazole To an ice-cooling solution of the compound (600 mg) obtained in Working Example (46b) and triethylamine (0.34 ml) in dichloromethane (12 ml) was added chloromethyl ether (0.17 ml) under nitrogen atmosphere. The mixture was stirred for 9 hours, and to the mixture were added triethylamine (0.15 ml) and chloromethyl ether (0.17 ml). The mixture was stirred for 13 hours under ice-cooling. The solvent was evaporated under reduced pressure. To the residue was added dilute hydrochloric acid, and the mixture was extracted with ethyl acetate. The extract was dried and concentrated to dryness under reduced pressure. The residue was purified by column chromatography on silica gel to afford the title compound as a pale yellow oil (395 mg, 57%).

$^1$H-NMR(200 MHz,CDCl$_3$) δ: 2.34(3H,s), 3.40(3H,s), 4.91(2H,s), 7.0–7.5(8H,m).

IR(Neat)cm$^{-1}$: 1620, 1600, 1580, 1520.

46d) 4-(4'-Bromomethylbiphenyl-2yl)-3-methoxymethoxy-5 trifluoromethyl-1,2,4-triazole To a solution of the compound (390 mg) obtained in working Example (46c) in carbon tetrachloride (15 ml) were added N-bromosuccimide (230 mg) and α,α'-azobisisobutyronitrile (20 mg). The mixture was stirred for 4.5 hours at 80° C. The reaction mixture was diluted with chloroform, and the solution was washed with an aqueous solution of sodium hydrogencarbonate and dried. The solvent was evaporated under reduced pressure. The residue was purified by silica gel column chromatography to afford the title compound (380 mg, 80%) as a pale yellow oil.

$^1$H-NMR(200 MHz,CDCl$_3$) δ: 3.39(3H,s), 4.48(2H,s), 4.94(2H,s), 7.2–7.6(8H,m)

IR(Neat)cm$^{-1}$: 1615, 1600, 1575.

46e) Methoxymethyl 2-ethylthio-4-methylthieno[3,4-d]imidazole-6-carboxylate

A mixture of methyl 2-ethylthio-4-methylthieno[3,4-d]imidazole-6-carboxylate (2.15 g) in a mixture of 4N-LiOH (8 ml) and methanol (25 ml) was stirred for 60 hours at 70° C. Methanol was evaporated under reduced pressure. To the residue was added 1N-HCl. Resulting precipitates were collected by filtration, washed with chloroform and dried. The brownish powder (560 mg) thus obtained was suspended in dichloromethane (10 ml). To the suspension were added triethylamine (0.35 ml) and chloromethyl methyl ether (0.19 ml). The mixture was stirred for two hours. To the reaction mixture was added dilute hydrochloric acid, and the mixture was extracted with chloroform. The extract was dried and concentrated to dryness under reduced pressure. The residue was purified by column chromatography on silica gel to afford the title compound (445 mg, 19%) as white powder, m.p.128°–130° C.

Elemental Analysis for $C_{11}H_{14}N_2O_3S_2$:

|  | C(%) | H(%) | N(%) |
|---|---|---|---|
| Calcd.: | 46.14; | 4.93; | 9.78 |
| Found: | 45.90; | 4.93; | 9.56 |

$^1$H-NMR(200 MHz,CDCl$_3$) δ: 1.45(3H,t), 2.64(3H,s), 3.31(2H,q), 3.53(3H,s), 5.43(2H,s), 9.29(1H,bs).

IR(KBr)cm$^{-1}$: 1640, 1620, 1540.

46f) 2-Ethylthio-1-[[2'-(1,4-dihydro-3-trifluoromethyl-5-oxo-1,2,4-triazol-4-yl)biphenyl]methyl]thieno[3,4-d]imidazole-4-methyl-6-carboxylic acid The compound (280 mg) obtained in Working Example (46e) and the compound (450 mg) obtained in Working Example (46d) were dissolved in N,N-dimethylformamide (12 ml). To the ice-cooling solution was added sodium hydride (60% in oil; 47 mg) under nitrogen atmosphere. The mixture was stirred for two hours at the same temperature. To the reaction mixture was added dilute hydrochloric acid, and the mixture was extracted with ethyl acetate. The extract was washed with water and an aqueous saline solution and dried. The solvent was evaporated under reduced pressure. The residue was purified by silica gel column chromatography to give a yellow oil (464 mg). The oil was dissolved in a mixture of trifluroacetic acid (4 ml) and chloroform (5 ml). The solution was stirred for 5 hours at 70° C. The reaction mixture was diluted with chloroform, washed with water and dried, and the solvent was evaporated under reduced pressure. The residue was purified by column chromatography on silica gel to afford the title compound (60 mg, 10%) as pale brown powder, m.p.178°–180° C. (decomp.).

Elemental Analysis for $C_{25}H_{20}N_5O_3S_2F_3 \cdot 0.5H_2O$:

|  | C(%) | H(%) | N(%) |
|---|---|---|---|
| Calcd.: | 52.81; | 3.72; | 12.32 |
| Found: | 52.83; | 3.54; | 12.20 |

$^1$H-NMR(200 MHz,CDCl$_3$) δ: 1.41(3H,t), 2.60(3H,s), 3.30(2H,q), 5.67(2H,s), 7.0–7.5(7H,m), 8.06(1H,d).

IR(KBr)cm$^{-1}$: 1655, 1620, 1595, 1580, 1530.

Working Example 47
Methyl 2-ethylthio-1-[[2'-[1,4-dihydro-3-methyl-5-oxo-1,2,4-triazol-4-yl]biphenyl-4-yl]methyl]thieno[3,4-d]imidazole-4-methyl-6-carboxylate 47a) 1-Acetyl-4-(4'-methylbibiphenyl-2-yl)semicarbazide To a solution of the compound (300 mg) obtained in Working Example (31a) in dichloromethane (5 ml) were added acetic anhydride (0.12 ml) and pyridine (0.10 ml). The mixture was stirred for 15 hours at room temperature. The reaction mixture was poured into ice-water and extracted with a mixture of chloroform and ethanol. The extract was washed with water and dried, and the solvent was evaporated under reduced pressure to afford the title compound (320 mg, 90%) as white powder, m.p.203°–205° C.

Elemental Analysis for $C_{16}H_{17}N_3O_2$:

|  | C(%) | H(%) | N(%) |
|---|---|---|---|
| Calcd.: | 67.83; | 6.05; | 14.83 |
| Found: | 67.53; | 5.90; | 14.84 |

$^1$H-NMR (200 MHz, DMSO-d$_6$) δ: 1.75(3H,s), 2.37(3H,s), 7.0–7.4(7H,m), 7.55(1H,s), 7.94(1H,d), 8.33(1H,s), 9.59(1H,s).

IR(KBr)cm$^{-1}$: 1660, 1615, 1595, 1540.

47b) 3-Methyl-4-[4'-methylbiphenyl-2-yl)-1,2,4-triazol-5(4H)-one

To a solution of the compound (950 mg) obtained in Working Example (31a) in benzene (20 ml) was added phosphorus oxychloride (1.2 ml), and the mixture was stirred for 20 hours at 90° C. The solvent was evaporated under reduced pressure, and the residue was diluted with ethyl acetate, washed with water and dried. The solvent was evaporated under reduced pressure. The residue was purified by column chromatography on silica gel to afford the title compound (460 mg, 51%) as white powder, m.p.102°–104° C.

Elemental Analysis for $C_{16}H_{15}N_3O$:

|  | C(%) | H(%) | N(%) |
|---|---|---|---|
| Calcd.: | 72.43; | 5.70; | 15.84 |
| Found: | 72.37; | 5.68; | 15.95 |

$^1$H-NMR(200 MHz,CDCl$_3$) δ: 2.40(3H,s), 2.42(3H,s), 6.83(1H,bs), 7.0–7.5(7H,m), 8.20(1H,d).

IR(KBr)cm$^{-1}$: 1640, 1575, 1530.

47c) 3-Methyl-4-(4'-methylbiphenyl-2-yl)-1-methoxymethyl-1,2,4-triazol-5(4H)-one To an ice-cooling solution of the compound (250 ml) obtained in Working Example (31b) in dichloromethane (8 ml) were added chloromethyl ether (0.18 ml) and triethylamine (0.20 ml) under nitrogen atmosphere. The mixture was stirred for 23 hours at room temperature. The solvent was evaporated under reduced pressure. The residue was purified by column chromatography on silica gel to afford the title compound (75 mg, 25%) as a pale yellow oil.

$^1$H-NMR(200 MHz,CDCl$_3$) δ: 2.09(3H,s), 2.34(3H,s), 3.28(3H,s), 4.95(2H,s), 7.0–7.4(8H,m).

IR(Neat)cm$^{-1}$: 1715, 1640, 1590, 1570, 1515.

47d) Methyl 2-ethylthio-1-[[2'-[1,4-dihydro-1-methoxymethyl-3-methyl-5-oxo-1,2,4-triazol-4-yl]biphenyl-4-yl]methyl]thieno[3,4-d]imidazole-4-methyl-6-carboxylate To a solution of the compound obtained in Working Example (31c) in carbon tetrachloride (5 ml) were added N-bromosuccinimide (48 mg) and α,α'-azobisisobutyronitrile (5 mg). The mixture was stirred for 5 hours at 80° C. The reaction mixture was poured into an aqueous solution of sodium hydrogencarbonate and extracted with chloroform. The extract was dried and concentrated to dryness under reduced pressure. The residue was purified by column chromatography on silica gel to give a pale yellow oil (34 mg). This oil (34 mg) and methyl 2-ethylthio-4-methylthieno[3,4-d]imidazole-6-carboxylate (30 mg) were dissolved in N,N-dimethylformamide (4 ml). To the ice-cooling solution was added sodium hydride (60% in oil; 5 mg) under nitrogen atmosphere. The mixture was stirred overnight at room temperature and concentrated to drynes under reduced pressure. The residue was diluted with ethyl acetate, and the solution was washed with water and an aqueous saline solution, and then dried. The solvent was evaporated under reduced pressure. The residue was purified by column chromatography on silica gel to afford the title compound (42 mg, 85%) as a pale yellow oil.

$^1$H-NMR(200 MHz,CDCl$_3$) δ: 1.42(3H,t), 2.05(3H,d), 2.62(3H,s), 3.18(3H,s), 3.30(2H,q), 3.77(3H,s), 4.91(2H,d), 5.69(2H,s), 7.0–7.4(8H,m).

IR(Neat)cm$^{-1}$: 1720, 1695, 1645, 1605, 1540.

47e) Methyl 2-ethylthio-1-[[2'-[1,4-dihydro-3-methyl-5-oxo-1,2,4-triazol-4-yl]biphenyl-4-yl]methyl]thieno[3,4-d]imidazole-4-methyl-6-carboxylate The compound (42 mg) obtained in Working Example (31d) was dissolved in a mixture of trifluoroacetic acid (1 ml) and chloroform (1.5 ml), and the solution was stirred for 12 hours at 60° C. The reaction mixture was diluted with chloroform, and the solution was washed with water, dried and concentrated to dryness under reduced pressure. The residue was purified by column chromatography on silica gel to give a pale yellow oil. Crystallization from chloroform and ether afforded the title compound (34 mg, 87%) as pale yellow crystals, m.p.204°–206° C.

Elemental Analysis for $C_{26}H_{25}N_5O_3S_2 \cdot 0.4CHCl_3$:

|  | C(%) | H(%) | N(%) |
|---|---|---|---|
| Calcd.: | 55.88; | 4.51; | 12.34 |
| Found: | 55.73; | 4.49; | 12.57 |

$^1$H-NMR(200 MHz,CDCl$_3$) δ: 1.44(3H,t), 2.41(3H,s), 2.63(3H,s), 3.33(2H,q), 3.80(3H,s), 5.77(2H,s), 6.83(1H, bs), 7.0–7.6(7H,m), 8.18(1H,t).

IR(KBr)cm$^{-1}$: 1685, 1630, 1600, 1570, 1535, 1520.

Working Example 48

1-[[2'-(2,4-Dihydro-4-methyl-3-oxo-1,2,4-triazol-5-yl)biphenyl-4-yl]methyl]-2-ethylthio-4-methylthieno[3,4-d]imidazole-6-carboxylic acid 48a) 4-Methyl-1-[2-(4-phenyl)benzoyl]semicarbazide To a solution of 4'-methylbiphenyl-2-carbonyl hydrazide (2.3 g) in chloroform (20 ml) was added methyl isocyanate (10 ml), and the mixture was stirred for one hour at room temperature. The resulting crystalline precipitate was collected by filtration, which was purified by column chromatography on silica gel. Crude crystals thus obtained were recrystallized from chloroform-methanol to afford colorless needles (0.86 g, 31%), m.p.181°–182° C.

Elemental Analysis for $C_{16}H_{17}N_3O_2$:

|  | C(%) | H(%) | N(%) |
|---|---|---|---|
| Calcd.: | 67.83; | 6.05; | 14.83 |
| Found: | 67.65; | 6.90; | 14.85 |

$^1$H-NMR (200 MHz, DMSO-d$_6$) δ: 2.34(3H,s), 3.30(3H, d), 5.55(1H,br), 7.21(2H,d), 7.32–7.56(6H,m), 7.85(1H,s), 9.79(1H,s).

IR(KBr)cm$^{-1}$: 3380, 3250, 3220, 1690, 1645, 1540, 820, 760.

48b) 2,4-Dihydro-5-(4'-methylbiphenyl-2-yl)-4-methyl-1,2,4-triazol-3-one

The compound (0.86 g) obtained in Working Example (48a) was dissolved in 1N-NaOH (8 ml), and the solution was heated for 15 hours under reflux. The reaction mixture was adjusted to pH 3–4 with 1N-HCl and extracted with ethyl acetate. The extract was washed with water and dried. The solvent was evaporated under reduced pressure, The residue was purified by column chromatography on silica gel to give crude crystals. Recrystallization from ethyl acetate—hexane afforded the title compound as colorless needles (0.60 g, 74%), m.p.181°–182° C.

Elemental Analysis for $C_{16}H_{15}N_3O$:

|  | C(%) | H(%) | N(%) |
|---|---|---|---|
| Calcd.: | 72.43; | 5.70; | 15.84 |
| Found: | 72.54; | 5.74; | 15.95 |

$^1$H-NMR(200 MHz,CDCl$_3$) δ: 2.37(3H,s), 2.55(3H,s), 7.16(2H,d), 7.22(2H,d), 7.42–7.65(4H,m), 9.72(1H,s).

IR(KBr)cm$^{-1}$: 3180, 3060, 1700, 1490, 1465, 1330, 1080, 1040, 960. 820, 800, 780, 760, 750, 700, 650.

48c) 2,4-Dihydro-2-methoxymethyl-5-(4'-methylbiphenyl-2-yl)-4-methyl-1,2,4-triazol-3-one To an ice-cooling solution of the compound (0.40 g) obtained in Working Example (48b) in DMF (1 ml) was added sodium hydride (60% in oil; 72 mg). The mixture was stirred for 30 minutes, and to the reaction mixture was added chloromethyl methyl ether (0.14 g). The reaction mixture was stirred for further 1.5 hour at 0° C. and diluted with water, followed by extraction with acetic acid. The extract was washed with water and dried. The solvent was removed under reduced pressure. The residue was purified by column chromatography on silica gel to afford the title compound as a colorless oil (0.40 g, 87%).

$^1$H-NMR(200 MHz,CDCl$_3$) δ: 2.35(3H,s), 2.55(3H,s), 3.43(3H,s), 5.20(2H,s), 7.14(2H,d), 7.21(2H,d), 7.40–7.64(4H,m).

IR(Neat)cm$^{-1}$: 1720, 1490, 1460, 1440, 1395, 1380, 1330, 1295, 1175, 1095, 1040, 920, 820, 785, 760.

48d) 5-(4'-Bromomethylbiphenyl-2-yl)-4,5-dihydro-1-methoxymethyl-4-methyl-1,2,4-triazol-3-one The compound (0.40 g) obtained in Working Example (48c), NBS(0.23 g) and benzoyl peroxide (17 mg) were added to carbon tetrachloride (10 ml). The mixture was refluxed under irradiation of light for one hour. Insoluble materials were filtered off, and the filtrate was concentrated under reduced pressure. The residue was purified by silica gel column chromatography to give crude crystals. Recrystallization from ethyl acetate—hexane afforded the title compound as colorless prisms (0.38 g, 73%), m.p.137°–138° C.

Elemental Analysis for $C_{18}H_{18}N_3BrO_2 \cdot 0.5H_2O$:

|  | C(%) | H(%) | N(%) |
|---|---|---|---|
| Calcd.: | 54.42; | 4.82; | 10.58 |
| Found: | 54.50; | 4.66; | 10.51 |

$^1$H-NMR(200 MHz,CDCl$_3$) δ: 2.60(3H,s), 3.41(3H,s), 4.49(2H,s), 5.19(2H,s), 7.29(2H,d), 7.38(2H,d), 7.45–7.67(4H,m).

IR(KBr)cm$^{-1}$: 1710, 1490, 1470, 1455,.1440, 1375, 1330, 1295, 1235, 1180, 1090, 915, 860, 855, 790, 765, 755, 610.

48e) Methyl-[[2'-(2,4-dihydro-2-methoxymethyl-4-methyl-3-oxo-1,2,4-triazol-5-yl)biphenyl-4-yl]methyl]-2-ethylthio-4-methylthieno[3,4-d]imidazole-6-carboxylate To an ice-cooling solution of methyl 2-ethylthio-4-methylthieno-[3,4-d]imidazole-6-carboxylate (0.26 g) in DMF (1 ml) was added sodium hydride (60% in oil; 48 mg). The mixture was stirred for 20 minutes. To the reaction mixture was added the compound (0.38 g) obtained in Working Example (36d), and the reaction mixture was stirred for further 1.5 hour at room temperature. The reaction mixture was diluted with water and extracted with ethyl acetate. The extract solution was washed with water and dried. The solvent was removed under reduced pressure. The residue was purified by column chromatography on silica gel to afford the title compound as a colorless oil (0.30 g, 55%).

$^1$H-NMR(200 MHz,CDCl$_3$) δ: 1.42(3H,s), 2.55(3H,s), 2.63(3H,s), 3.30(2H,q), 3.37(3H,s), 3.77(3H,s), 5.18(2H,s), 5.71(2H,s), 7.19(2H,d), 7.25(2H,d), 7.42–7.64(4H,m).

IR(Neat)cm$^{-1}$: 1705, 1605, 1540, 1460, 1440, 1320, 1240, 1170, 1095, 755.

48f) Methyl 2-ethylthio-1-[[2'-(2,4-dihydro-4-methyl-3-oxo-1,2,4-triazol-5-yl)biphenyl-4-yl]methyl]-4-methylthieno[3,4-d]imidazole-6-carboxylate The compound (0.30 g) obtained in Working Example (48e) was dissolved in a mixture of trifluoroacetic acid (2 ml) and chloroform (2 ml). The solution was stirred for 5.5 days at 60° C. The reaction mixture was concentrated under reduced pressure. The residue was purified by column chromatography on silica gel to afford the title compound as a colorless oil (0.27 g, 96%).

$^1$H-NMR(200 MHz,CDCl$_3$) δ: 1.42(3H,t), 2.53(3H,s), 2.63(3H,s), 3.30(2H,q), 3.77(3H,s), 5.71(2H,s), 7.15(2H,d), 7.23(2H,d), 7.42–7.65(4H,m).

IR(Neat)cm$^{-1}$: 1700, 1600, 1540, 1460, 1435, 1320, 1240, 1195, 1170, 1095, 750.

48g) 2-Ethylthio-1-[[2'-(2,4-dihydro-4-methyl-3-oxo-1,2,4-triazol-5-yl)biphenyl4-yl]methyl]-4-methylthieno[3,4d]imidazole-6-carboxylic acid The compound (0.27 g) obtained in Working Example (48f) and lithium hydroxide monohydrate (0.11 g) were dissolved in a mixture of THF (2 ml) and water (2 ml), and the solution was stirred for 8 hours at 60°–70° C. The reaction mixture was diluted with water, and insoluble materials were filtered off, and the filtrate was adjusted to pH 3–4 with 1N-HCl. Crystalline precipitate was collected by filtration and purified by silica gel column chromatography to give crude crystals. Recrystallization from chloroform-methanol afforded the title compound as pale yellow prisms (70 mg, 27%), m.p.228°–229° C. (decomp.).

Elemental Analysis for $C_{25}H_{23}N_5O_3S_2 \cdot 5H_2O$:

|  | C(%) | H(%) | N(%) |
| --- | --- | --- | --- |
| Calcd.: | 58.35; | 4.70; | 13.61 |
| Found: | 58.64; | 4.59; | 13.71 |

$^1$H-NMR (200 MHz, CDCl$_3$) δ: 1.46(3H,t), 2.44 (3H,s), 2.63(3H,s), 3.35(2H,q), 5.61(2H,s), 7.10(2H,d), 7.20(2H,d), 7.46–7.64(4H,m).

IR(KBr)cm$^{-1}$: 1690, 1605, 1540, 1490, 1460, 1415, 1315, 1240, 1200, 1170, 1100, 940, 805, 780, 760.

Working Example 49
2-Ethylthio-1-[[2'-(5-hydroxy-2-methyl-1,2,4-triazol-3-yl)biphenyl-4-yl]methyl]-4-methylthieno[3,4-d]imidazole-6-carboxylic acid 49a) 1-Methyl-1-(4'-methylbiphenyl-2-carbonyl)hydrazide To a solution of 4'-methylbiphenyl-2-carboxylic acid (3.2 g) and DMF (one drop) in THF (35 ml) was added dropwise oxalyl chloride (2.9 g), and the mixture was stirred for further 18 hours. The reaction mixture was concentrated under reduced pressure. The residue was added dropwise to a solution of monomethyl hydrazine (6.9 g) in THF (80 ml). The reaction mixture was stirred for one hour at room temperature and concentrated to dryness under reduced pressure. The residue was partitioned between water and ethyl acetate. The ethyl acetate layer was separated, washed with water and dried. The solvent was evaporated under reduced pressure. The residue was purified by column chromatography on silica gel to afford the title compound as a yellow oil (3.6 g, 100%).

$^1$H-NMR(200 MHz,CDCl$_3$) δ: 2.39(3H,s), 2.62(3H,s), 4.39(2H,br), 7.19–7.47(8H,m).

IR(Neat)cm$^{-1}$: 3300, 3200, 1630.

49b) 1-Methyl-1-[2-(4-methylphenyl)benzoyl]semicarbazide

To a solution of the compound (3.6 g) obtained in Working Example (49a) in 1N-HCl (37 ml) was added dropwise an aqueous solution (30 ml) of sodium isocyanate (2.6 g), and the mixture was stirred for 3 hours at room temperature. Crystalline precipitate was collected by filtration and recrystallized from methanol—ethyl acetate to afford the title compound as colorless prisms (3.1 g, 74%), m.p.217°–218° C.

Elemental Analysis for $C_{16}H_{17}N_3O_2$:

|  | C(%) | H(%) | N(%) |
| --- | --- | --- | --- |
| Calcd.: | 67.83; | 6.05; | 14.83 |
| Found: | 67.99; | 6.02; | 15.03 |

$^1$H-NMR(200 MHz,DMSO-d$_6$) δ: 2.34(3H,s), 3.00(3H,s), 6.08(1H,br), 7.19(2H,d), 7.24–7.50(6H,m), 8.15(1H,s).

IR(KBr)cm$^{-1}$: 3470, 3330, 1680, 1645, 1610, 1520, 1460, 1390, 1340, 825, 755.

49c) 1-Methyl-5-(4'-methylbiphenyl-2-yl)-3-hydroxy-1,2,4-triazole

According to the procedure described in Working Example (48b), the title compound was obtained as colorless prisms (2.7 g, 93%) from the compound (3.1 g) prepared in Working Example (49b). M.p.271°–172° C.

Elemental Analysis for $C_{16}H_{15}N_3O$:

|  | C(%) | H(%) | N(%) |
| --- | --- | --- | --- |
| Calcd.: | 72.43; | 5.70; | 15.84 |
| Found: | 72.30; | 5.74; | 15.79 |

$^1$H-NMR(200 MHz,DMSO-d$_6$) δ: 2.31(3H,s), 2.95(3H,s), 7.06(2H,d), 7.18(2H,d), 7.51–7.68(4H,m), 10.84(1H,s).

IR(KBr)cm$^{-1}$: 1580, 1510, 1490, 1440, 1400, 1325, 1275, 890, 880, 840, 820, 760, 620.

49d) 3-Ethoxycarbonyloxy-1-methyl-5-(4'-methylbiphenyl-2-yl)-1,2,4-triazole

To a suspension of the compound (0.65 g) obtained in Working Example (49c) and triethylamine (0.29 g) in methylene chloride (10 ml) was added ethyl chloroformate (0.31 g), and the mixture was stirred for 3 hours at room temperature. The reaction mixture was washed with water and dried. The solvent was removed under reduced pressure, and the residue was purified by column chromatography on silica gel to afford the title compound as a colorless oil (0.55 g, 68%).

$^1$H-NMR(200 MHz,CDCl$_3$) δ: 1.40(3H,t), 2.34(3H,s), 3.02(3H,s), 4.37(2H,q), 7.09(2H,d), 7.16(2H,d), 7.41–7.64(4H,m).

IR(Neat)cm$^{-1}$: 1780, 1505, 1360, 1230.

49e) 5-(4-Bromomethylbiphenyl-2-yl)-3-ethoxycarbonyloxy-1-methyl-1,2,4-triazole

According to the procedure described in Working Example (48d), the title compound was obtained as a colorless oil (0.63 g, 94%) from the compound (0.55 g) obtained in Working Example (49d).

$^1$H-NMR(200 MHz,CDCl$_3$) δ: 1,41(3H,t), 3.05(3H,s), 4.37(2H,q), 4.48(2H,s), 7.19(2H,d), 7.38(2H,d), 7.45–7.66(4H,m).

IR(Neat)cm$^{-1}$: 1770, 1500, 1470, 1435, 1400, 1360, 1230, 760.

49f) Methyl 1-[[2'-(3-ethoxycarbonyloxy-1-methyl-1,2,4-triazol-5-yl)biphenyl-4-yl]methyl]-2-ethylthio-4-methylthieno[3,4-d]imidazole-6-carboxylate According to the procedure described in Working Example (48e), the title compound was obtained as a colorless oil (0.22 g, 25%) from the compound (0.63 g) obtained in Working Example (49e).

$^1$H-NMR(200 MHz,CDCl$_3$): 1.40(3H,t), 1.41(3H,t), 2.63(3H,s), 2.97(3H,s), 3.29(2H,q), 3.76(3H,s), 4.36(2H,q), 5.69(2H,s), 7.14(4H,s), 7.42–7.64(4H,m).

IR(Neat)cm$^{-1}$: 1780, 1690, 1605, 1540, 1510, 1460, 1440, 1365, 1320, 1240, 1170, 1090, 760.

49g) 2-Ethylthio-1-[[2'-(3-hydroxy-1-methyl-1,2,4-triazol-5-yl)biphenyl-4-yl]methyl]-4-methylthieno[3,4-d]-imidazole-6-carboxylic acid According to the procedure described in Working Example (48g), the title compound was obtained as colorless prisms (40 mg, 21%) from the compound (0.22 g) obtained in Working Example (49e). M.p.236°–237° C.

Elemental Analysis for $C_{25}H_{23}N_5O_3S_2 \cdot 0.2H_2O$:

|  | C(%) | H(%) | N(%) |
|---|---|---|---|
| Calcd.: | 58.97; | 4.63; | 13.75 |
| Found: | 59.00; | 4.76; | 13.68 |

$^1$H-NMR(200 MHz,DMSO-$d_6$) δ: 1.33(3H,t), 2.55(3H,s), 2.92(3H,s), 3.24(2H,q), 5.69(2H,s), 7.12(4H,s-like), 7.50–7.68(4H,m).

IR(KBr)cm$^{-1}$: 1690, 1640, 1600, 1585, 1540, 1460, 1415, 1370, 1305, 1270, 1235, 1200, 1170, 1095, 935, 775, 765.

Working Example 50
1-[[2'-(2,4-Dihydro-3-oxo-1,2,4-triazol-5-yl)biphenyl-4-yl]methyl]-2-ethylthio-4-methylthieno[3,4-d]imidazole-6-carboxylic acid

50a) 2,5-Dihydro-5-(4'-methylbiphenyl-2-yl)-1,2,4-triazol-3-one

1-[2-(4-Methylphenyl)benzoyl]semicarbazide (4.6 g) and phosphorus oxychloride (10.3 g) were suspended in benzene (100 ml), and the suspension was heated for 3 hours under reflux. The reaction mixture was concentrated to dryness under reduced pressure. To the residue was added water, and resulting crystalline precipitate was collected by filtration. Recrystallization from methanol afforded the title compound as colorless needles (3.4 g, 79%), m.p.245°–246° C. (decomp.).

Elemental Analysis for $C_{15}H_{13}N_3O$:

|  | C(%) | H(%) | N(%) |
|---|---|---|---|
| Calcd.: | 71.70; | 5.21; | 16.72 |
| Found: | 71.37; | 5.42; | 16.72 |

$^1$H-NMR(200 MHz,CDCl$_3$) δ: 2.39(3H,s), 4.84(2H,br s), 7.17(4H,s), 7.39–7.58(3H,m), 7.85–7.89(1H,m).

IR(KBr)cm$^{-1}$: 3260, 3080, 1670, 1655, 1605, 1580, 1025, 820, 765, 750.

50b) 1,2-(& 2,4-)Dihydro-1,2-(& 2,4-bis(methoxymethyl)-3-(4'-methylbiphenyl-2-yl)-1,2,4-triazol-3-one Accoding to the procedure described in Working Example (48c), a mixture of the isomers (1:2) of the title compound was obtained as a colorless oil (1.6 g, 73%) from the compound (1.6 g) obtained in Working Example (50a).

$^1$H-NMR (200 MHz, CDCl$_3$) δ: 2.38(3H,s), 3.09(3H,s), 3.30(1H,s), 3.40(2H,s), 4.30(2H,s), 4.56(2H,s), 7.20–7.30(4H,m), 7.39–7.54(4H,m).

IR(Neat)cm$^{-1}$: 2220, 1685, 1480, 1440, 1360, 1290, 1240, 1190, 1090, 915, 820, 760.

50c) 3-(4'-Bromomethylbiphenyl-2-yl)-1,2-(& 2,4-)dihydro-1,2-(& 2,4-)bis(methoxymethyl)-1,2,4-triazol-3-one According to the procedure described in Working Example (48d), a mixture of the isomers (1:2) of the title compound was obtained as a colorless oil (2.0 g, 100%) from the compound (1.6 g) obtained in Working Example (50b).

$^1$H-NMR(200 MHz,CDCl$_3$) δ: 3.10(3H,s), 3.23(1H,s), 3.41(2H,s), 4.31(2H,s), 4.51 (2H,s), 4.54(2H,s), 7.35–7.65(8H,m).

IR(Neat)cm$^{-1}$: 2210, 1680, 1440, 1360, 1285, 1240, 1230, 1190, 1090, 915, 760.

50d) Methyl 2-ethylthio-1-[[2'-(1,2-(& 2,4-]dihydro-1,2-(& 2,4-)bis-methoxymethyl)-5-oxo-1,2,4-triazol-3-yl)biphenyl-4-yl)methyl]-4-methylthieno[3,4-d]imidazole-6-carboxylate According to the procedure described in Working Example (48e), a mixture of the isomers of the title compound was obtained as a pale yellow oil (0.65 g, 43%) from the compound (1.0 g) obtained in Working Example (50c).

$^1$H-NMR(200 MHz,CDCl$_3$) δ: 1.42(3H,t), 2.62(3H,s), 3.05(3H,s), 3.16(1H,s), 3.30(2H,q), 3.36(⅔H,s), 3.77(3H,s), 4.22(2H,s), 4.42(2H,s), 5.72(2H,s), 7.21–7.57(8H,m).

IR(Neat)cm$^{-1}$: 2220, 1690, 1600, 1540, 1460, 1430, 1360, 1320, 1285, 1240, 1195, 1165, 1090, 755.

50e) Methyl 2-ethylthio-1-[[2'-(4,5-dihydro-5-oxo-1,2,4-triazol-3-yl)biphenyl-4-yl]methyl]-4-methylthieno[3,4-d]imidazole-6-carboxylate According to the procedure described in Working Example (48f), the title compound was obtained as yellow prisms (0.28 g, 50%) from the compound (0.65 g) obtained in Working Example (50d). M.p.272°–273° C. (decomp.)

Elemental Analysis for $C_{25}H_{23}N_5O_3S_2$:

|  | C(%) | H(%) | N(%) |
|---|---|---|---|
| Calcd.: | 59.39; | 4.58; | 13.85 |
| Found: | 58.17; | 4.74; | 13.81 |

$^1$H-NMR(200 MHz,DMSO-$d_6$) δ: 1.36(3H,t), 2.56(3H,s), 3.26(2H,q), 3.70(3H,s), 5.66(2H,s), 6.96(2H,br s), 7.12(2H, d), 7.22(2H,d), 7.41–7.63 (3H,m), 7.69 (1H,dd).

IR(KBr)cm$^{-1}$: 3275, 3100, 1680, 1660, 1535, 1450, 1430, 1320, 1235, 1160, 1090, 755.

50f) 2-Ethylthio-1-[[2'-(4,5-dihydro-5-oxo-1,2,4-triazol-3-yl)biphenyl-4-yl]methyl]-4-methylthieno[3,4-d]imidazole-6-carboxylic acid According to the procedure described in Working Example (48g), the title compound was obtained as colorless needles (0.17 g, 65%) from the compound (0.27 g) obtained in Working Example (50e). M.p.205°–207° C. (decomp.)

Elemental Analysis for $C_{24}H_{21}N_5O_3S_2$:

|  | C(%) | H(%) | N(%) |
|---|---|---|---|
| Calcd.: | 58.64; | 4.31; | 14.25 |
| Found: | 58.30; | 4.16; | 14.12 |

$^1$H-NMR(200 MHz,DMSO-$d_6$) δ: 1.35(3H,t), 2.54(3H,s), 3.24(2H,q), 5.70(2H,s), 6.95(2H,s), 7.15(2H,d), 7.22(2H,d), 7.41–7.63(3H,m), 7.69(1H,dd).

IR(KBr)cm$^{-1}$: 1660, 1650, 1595, 1535, 1450, 1305, 1240, 1160.

Working Example 51
Methyl 2-n-butyl-1-[[2'-(2,4-dioxoimidazolidin-1-yl)beiphenyl-4-yl]methyl]benzimidazole-7-carboxylate

51a) Methyl 2-n-butyl-1-[[2'-(t-butoxycarbonylamino)biphenyl-4-yl]methyl]benzimidazole-7-carboxylate Methyl 2-butyl-1-[[2'-(t-butoxycarbonyl)biphenyl-4-yl]methyl]benzimidazole-7-carboxylate (600 mg) and triethylamine (0.2 ml) were dissolved in N,N-dimethylformamide (3 ml). To the ice-cooling solution was added dropwise diphenyl phosphoryl azide (DPPA) (0.32 ml) under nitrogen atmosphere. The mixture was stirred for 4.5 hours at the same temperature. The reaction mixture was diluted with ethyl acetate, washed with water three times, and dried. The solution thus obtained was concentrated under reduced pressure to a volume of 20 ml. The concentrate was added dropwise to toluene (25 ml) with stirring at 80° C. The mixture was stirred for further 20 minutes at the same temperature. To the reaction mixture was added t-butanol (15 ml), and the mixture was stirred for 17 hours. The solvent was evaporated under reduced pressure, and the residue was purified by column chromatography on silica gel to afford the title compound (510 mg, 73%) as a pale yellow oil.

51b) Methyl 2-n-butyl-1-[(2'-aminobiphenyl-4-yl)methyl]-benzimidazole-7-carboxylate The compound (510 mg) obtained in Working Example (51a) was dissolved in conc. HCl (0.8 ml) and methanol (10 ml), and the solution was stirred for 70 minutes at 80° C. The solvent was removed under reduced pressure. To the residue was added an aqueous solution of sodium hydrogencarbonate, and the mixture was extracted with ethyl acetate. The extract was washed with water and dried. The solvent was evaporated under reduced pressure to give a pale yellow oil, which was crystallized from ether to afford the title compound (370 mg, 90%) as white crystals, m.p.97°–99° C.

Elemental Analysis for $C_{26}H_{27}N_3O_2$:

|  | C(%) | H(%) | N(%) |
| --- | --- | --- | --- |
| Calcd.: | 75.52; | 6.58; | 10.16 |
| Found: | 75.27; | 6.81; | 9.99 |

$^1$H-NMR(200MHz,CDCl$_3$) δ: 0.95(3H,t), 1.4–1.6(2H,m), 1.8–2.0(2H,m), 2.92(2H,t), 3.65(2H,bs), 3.73(3H,s), 5.79(2H,s), 6.7–7.5(9H,m), 7.64(1H,dd), 7.95(1H,dd).

IR(KBr)cm$^{-1}$: 1720, 1630, 1600, 1575, 1520.

51c) Methyl 2-n-butyl-1-[[2'-(ethoxycarbonylmethylamino) biphenyl-4-yl]methyl]benzimidazole-7-carboxylate The compound (408 mg) obtained in Working Example (51b) and ethyl bromoacetate (0.13 ml) were dissolved in N,N-dimethylformamide (12 ml), and to the solution was added potassium carbonate (150 mg) at room temperature. The mixture was stirred for 63 hours at room temperature, then the solvent was removed under reduced pressure. The residue was partitioned between water and ethyl acetate. The organic layer was dried and concentrated to dryness under reduced pressure. The residue was purified by column chromatography on silica gel to afford the title compound (139 mg, 28%) as a pale yellow oil.

$^1$H-NMR(200 MHz,CDCl$_3$) δ: 0.96(3H,t), 1.24(3H,t), 1.4–1.6(2H,m), 1.8–2.0(2H,m), 2.93(2H,t), 3.73(3H,s), 3.85(2H,d), 4.17(2H,q), 4.51(1H,bt), 5.79(2H,s), 6.55(1H, d), 6.7–7.5(8H,m), 7.64(1H,dd), 7.95(1H,dd).

IR(Neat)cm$^{-1}$: 1745, 1720, 1600, 1580, 1520, 1505.

51d) Methyl 2-n-butyl-1-[[2'-[(N-chloroacetylcarbamoyl)-((N-ethoxycarbonyl-methyl)amino]biphenyl-4-yl]methyl]benzimidazole-7-carboxylate To an ice-cooling solution of the compound (260 mg) obtained in Working Example (51c) in dichloromethane (10 ml) was added dropwise chloroacetyl isocyanate (80 micro 1) under nitrogen atmosphere. The mixture was stirred for two hours at the same temperature and concentrated to dryness. The residue was purified by column chromatography on silica gel to afford the title compound (193 mg, 60%) as white powder, m.p.149°–151° C.

Elemental Analysis for $C_{33}H_{35}N_4O_6Cl.0.2H_2O$:

|  | C(%) | H(%) | N(%) |
| --- | --- | --- | --- |
| Calcd.: | 63.65; | 5.73; | 9.00 |
| Found: | 63.46; | 5.65; | 8.72 |

$^1$H-NMR(200 MHz,CDCl$_3$) δ: 0.98(3H,t), 1.25(3H,t), 1.3–1.6(2H,m), 1.7–2.0(2H,m), 2.91(2H,t), 3.32(1H,d), 3.75(3H,s), 4.0–4.3(2H,m), 4.38(1H,d), 4.40(1H,d), 4.58(1H,d), 5.79(2H,s), 6.91(2H,d), 7.11(2H,d), 7.2–7.7(6H,m), 7.95(1H,d).

IR(KBr)cm$^{-1}$: 1750, 1720, 1690, 1520.

51e) Methyl 2-n-butyl-1-[[2'-(2,4-dioxoimidazolidin-1-yl) biphenyl-4-yl]methyl]benzimidazole-7-carboxylate The compound (180 mg) obtained in Working Example (51d) was dissolved in a mixture of methanol (10 ml) and chloroform (3 ml). To the solution was added sodium N-methyldithiocarbamate (48 mg) at room temperature under nitrogen atmosphere. The mixture was stirred for 5 hours at room temperature, and the solvent was removed under reduced pressure. The residue was purified by column chromatography on silica gel to give a colorless oil (137 mg). To an ice-cooling solution of the oil in N,N-dimethylformamide (3 ml) was added sodium hydride (60% in oil; 13 mg) under nitrogen atmosphere. The mixture was stirred for two hours under ice-cooling, then 4 hours at room temperature. After evaporation of the solvent, the residue was diluted with chloroform, and the solution was washed with dilute hydrochloric acid and dried. The solvent was removed under reduced pressure, and the residue was purified by column chromatography on silica gel to give a yellow oil. This product was crystallized from chloroform and ether to afford the title compound (40 mg, 32%) as pale yellow powder, m.p.175°–178° C.

Elemental Analysis for $C_{29}H_{28}N_4O_4.0.3H_2O$:

|  | C(%) | H(%) | N(%) |
| --- | --- | --- | --- |
| Calcd.: | 69.39; | 5.74; | 11.16 |
| Found: | 69.47; | 5.83; | 10.98 |

$^1$H-NMR(200 MHz,CDCl$_3$) δ: 0.95(3H,t), 1.3–1.6(2H, m), 2.95(2H,t), 3.68(2H,s), 3.71(3H,s), 5.79(2H,s), 6.89(2H, d), 7.1–7.5(7H,m), 7.63(1H,d), 7.97(1H,dd), 8.14(1H,bs).

IR(KBr)cm$^{-1}$: 3450, 2960, 2740, 1770, 1730, 1610, 1525.

Working Example 52

Methyl 2-butyl-1-[[2'-(2,4-dioxo-3H-thiazolidin-5-yl)biphenyl-4-yl]methyl]benzimidazole-7-carboxylate 52a) Methyl 2-[N-(2'-tert-butoxycarbonylbiphenyl-4-yl)methyl-N-valeryl]amino-3-nitrobenzoate To a solution of methyl 3-nitro-2-valerylaminobenzoate (2.79 g) in DMF (20 ml) was added sodium hydride (60% in oil; 0.40 g) with stirring under ice-cooling. After stirring for fifteen minutes, 2'-tert-butoxycarbonyl biphenyl methyl bromide (4.51 g, 13 mmol) was added to the mixture. The reaction mixture was stirred for two hours at 70° C. and extracted with ethyl acetate. The extract was washed with water and dried (MgSO$_4$), and the solvent was evaporated in vacuo. The residue was purified by column chromatography on silica gel to give crude crystals. Recrystallization from isopropyl ether afforded the title compound (4.41 g, 81%) as colorless crystals, m.p.127°–128° C.

Elemental Analysis for $C_{31}H_{34}N_2O_7$:

|  | C(%) | H(%) | N(%) |
| --- | --- | --- | --- |
| Calcd.: | 68.12; | 6.27; | 5.12 |
| Found: | 68.27; | 6.27; | 4.85 |

$^1$H-NMR(200 MHz,CDCl$_3$) δ: 0.80(3H,t), 1.20(2H,m), 1.23(9H,s), 1.53(2H,m), 2.05(2H,t), 3.62(3H,s), 4.56 and 4.77(2H,each d), 7.05(2H,d), 7.13(2H,d), 7.27–7.83(5H,m), 8.12(1H,dd), 8.23(1H,dd).

IR(Nujol)cm$^{-1}$: 1740, 1710, 1675, 1600.

52b) Methyl 2-butyl-1-[2'-tert-butoxycarbonylbiphenyl-4-yl]methylbenzimidazole-7-carboxylate Iron powder (1.35 g) was added to a mixture of the compound (3.20 g) obtained in working Example (52a) in a mixture of conc. HCl (0.5 ml) and methanol (30 ml). The mixture was heated for 1.5 hour under reflux. Insoluble materials were filtered off through celite. The filtrate was concentrated to dryness, and to the residue were added conc. HCl (0.5 ml) and methanol (50 ml). The mixture was heated for 1.5 hour under reflux and concentrated to dryness. The residue was partitioned between water and chloroform. The organic layer was dried and concentrated to dryness. The residue was purified by column chromatography on silica gel to afford the title compound (2.38 g, 82%) as an oil.

Elemental Analysis for $C_{31}H_{34}N_2O_4 \cdot \frac{1}{2}H_2O$:

|  | C(%) | H(%) | N(%) |
|---|---|---|---|
| Calcd.: | 73.35; | 6.95; | 5.52 |
| Found: | 73.42; | 6.98; | 5.45 |

$^1$H-NMR(200 MHz,CDCl$_3$) δ: 0.97(3H,t), 1.19(9H,s), 1.48(2H,m), 2.93(2H,t), 3.76(3H,s), 5.83(2H,s), 6.87(2H,d), 7.16–7.51(6H,m), 7.64–7.77(2H,m), 7.95(1H,dd).

IR(Neat)cm$^{-1}$: 1715, 1700, 1595.

52c) Methyl 2-butyl-1-[2'-carboxylbiphenyl-4-yl]methylbenzimidazole-7-carboxylate Trifluoroacetic acid (10 ml) was added to a solution of the compound (2.35 g) obtained in Working Example (52b) in dichloromethane (8 ml). The mixture was stirred for one hour at room temperature, diluted with water and extracted with chloroform. The extract was washed with water and dried (MgSO$_4$), and the solvent was evaporated in vacuo. The residue was purified by column chromatography on silica gel to give crystals. Recrystallization from diethyl ether afforded the title compound (2.04 g, 98%) as colorless prisms, m.p.192°–194° C.

$^1$H-NMR(200 MHz,DMSO-d$_6$) δ: 0.90(3H,t), 1.40(2H,m), 1.78(2H,m), 2.94(2H,t), 3.65(3H,s), 3.84(1H,br), 5.73(2H,s), 6.87(2H,d), 7.22–7.57(7H,m), 7.70(1H,dd), 7.88(1H,dd).

IR(Nujol)cm$^{-1}$: 3420, 1725, 1690, 1600.

52d) Methyl 2-butyl-1-[2'-hydroxymethylbiphenyl-4-yl]methylbenzimidazole-7-carboxylate A mixture of methyl 2-butyl-1-[2'-carboxybiphenyl-4-yl]methylbenzimidazole-7-carboxylate (0.44 g) and thionyl chloride (0.15 ml) in chloroform (4 ml) was heated for 30 minutes under reflux with stirring. The reaction mixture was concentrated, and the resulting product was used for the subsequent reaction without purification. A stirred solution of the above product in tetrahydrofuran (6 ml) was added dropwise to a suspension of aluminium lithium hydride (40 mg) in tetrahydrofuran (6 ml) under ice-cooling. The reaction mixture was stirred for one minutes at the same temperature, and to the mixture were added 2N-HCl and, then water, followed by extraction with chloroform. The extract was washed with water and dried (MgSO$_4$), and the solvent was evaporated in vacuo. The residue was purified by column chromatography on silica gel to give an oil. Crystallization of this product from isopropyl ether afforded colorless prisms (0.13 g, 31%), m.p.126°–127° C.

Elemental Analysis for $C_{27}H_{28}N_2O_3$:

|  | C(%) | H(%) | N(%) |
|---|---|---|---|
| Calcd.: | 75.68; | 6.59; | 6.54 |
| Found: | 75.20; | 6.66; | 6.55 |

52e) Methyl 2-butyl-1-[2'-formylbiphenyl-4-yl]methylbenzimidazole-7-carboxylate

A mixture of the compound (0.73 g) obtained in Working Example (52d), pyridinium dichromate (0.75 g) and dichloromethane (20 ml) was stirred for 15 hours at room temperature. Insoluble materials were filtered off through celite, and the filtrate was concentrated to dryness. The residue was purified by column chromatography on silica gel to give crude crystals. Recrystallization from ethyl acetate—diethyl ether afforded colorless prisms (0.62 g, 85%), m.p.103°–104° C.

Elemental Analysis for $C_{27}H_{26}N_2O_3$:

|  | C(%) | H(%) | N(%) |
|---|---|---|---|
| Calcd.: | 76.03; | 6.14; | 6.57 |
| Found: | 79.95; | 6.07; | 6.56 |

$^1$H-NMR(200 MHz,CDCl$_3$) δ: 0.96(3H,t), 1.48(2H,m), 1.89(2H,m), 2.93(2H,t), 3.74(3H,s), 5.84(2H,s), 6.96(2H,d), 7.22–7.72(7H,m), 7.94–8.06(2H,m), 9.91(1H,s).

IR(Nujol)cm$^{-1}$: 1720, 1695, 1595.

52f) Methyl 2-butyl-1-[2'-cyanohydroxymethylbiphenyl-4-yl]methylbenzimidazole-7-carboxylate To a solution of the compound (0.61 g) obtained in Working Example (52e) in ethyl acetate (6 ml) were added an aqueous solution (1.5 ml) of sodium hydrogensulfate (0.74 g) and an aqueous solution (1.5 ml) of potassium cyanide (0.47 g). The reaction mixture was stirred for two hours at room temperature, and then for one hour at 60° C. The mixture was diluted with water and extracted with ethyl acetate. The extract was washed with water and dried (MgSO$_4$) and concentrated to dryness. The residue was purified by column chromatography on silica gel to afford the title compound (0.61 g, 94%) as a syrup.

$^1$H-NMR(200 MHz,CDCl$_3$) δ: 0.87(3H,t), 1.36(2H,m), 1.71(2H,m), 2.80(2H,t), 3.74(3H,s), 5.47(1H,s), 5.75(2H,s), 6.85(2H,d), 7.16–7.93(9H,m).

IR(Neat)cm$^{-1}$: 3420, 2360, 1720, 1605.

52g) Methyl 2-butyl-1-[2'-(2,4-dioxothiazolidin-5-yl)biphenyl-4-yl]methylbenzimidazole-7-carboxylate Thionyl chloride (0.15 ml, 2.1 mmol) was added to a solution of the compound (0.60 g) obtained in Working Example (52f) in chloroform (6 ml). The solution was heated for one hour under reflux. The reaction mixture was concentrated, and the residue was used in the subsequent reaction without purification.

A mixture of the compound obtained above and thiourea (0.11 g) in methanol (10 ml) was heated for one hour under reflux. After addition of 2N-HCl (13 ml), the reaction mixture was heated for 12 hours under reflux. The reaction mixture was diluted with water and extracted with chloroform. The extract was washed with water and dried (MgSO$_4$), and the solvent was evaporated in vacuo. The residue was purified by column chromatography on silica gel to give crystals. Recrystallization from dichloromethane—ethyl acetate afforded the title compound (0.40 g, 59%) as colorless prisms, m.p.241°–142° C.

Elemental Analysis for $C_{29}H_{27}N_3O_4S$:

|  | C(%) | H(%) | N(%) |
|---|---|---|---|
| Calcd.: | 67.82; | 5.30; | 8.18 |
| Found: | 67.71; | 5.62; | 8.14 |

$^1$H-NMR(200 MHz,DMSO-d$_6$) δ: 0.89(3H,t), 1.40(2H,m), 1.78(2H,m), 2.91(2H,t ), 3.69(3H,s), 5.46(1H,s), 5.76(2H,s), 6.93(2H, 7.15–7.61(8H,m), 7.87(1H,d), 12.28(1H,br).

IR(Nujol)cm$^{-1}$: 1745, 1725, 1700, 1605.

Working Example 53

2-Ethylthio-1-[[3'-(2,5-dihydro-5-oxo-1,2,4-oxadiazol-3-yl) biphenyl-4-yl]methyl]thieno[3,4]imidazole-4-methyl-6-carboxylic acid 53a) Methyl 4'-methylbiphenyl-3-carboxylate To a mixture of methyl 3-iodobenzoate (26.1 g) in 4-iodotoluene (21.9 g) was added copper powder (31.8 g) gradually at 180°–190° C. The mixture was then stirred for 6 hours at 200–210° C. The reaction mixture was cooled to room temperature, to which was added toluene. Insoluble materials were filtered off, and the filtrate was concentrated to dryness. The residue was purified by column chromatography on silica gel to afford the title compound as a colorless oil (6.61 g, 29%).

$^1$H-NMR(200 MHz,CDCl$_3$) δ: 2.40(3H,s), 3.94(3H,s), 7.26(2H,d), 7.49(1H,t), 7.52(2H,d), 7.77(1H,m), 7.99(1H, td), 8.26(1H,t).

53b) 4'-Methylbiphenyl-3-carboxylic acid

To a solution of the compound (2.36 g) obtained in Working Example (53a) in tetrahydrofuran (20 ml)–water (10 ml) was added lithium hydroxide monohydrate (1.31 g). The mixture was stirred for 3 hours at room temperature. The reaction mixture was concentrated, diluted with water and washed with ethyl acetate. The aqueous layer was adjusted to pH 3 with 1N-HCl. Crystalline precipitate was collected by filtration and dried to afford the title compound as colorless needles (1.73 g, 78%), m.p.182°–187° C.

$^1$H-NMR(200 MHz,CDCl$_3$) δ: 2.41(3H,s), 7.28(2H,d), 7.54(1H,t), 7.54(2H,d), 7.83(1H,m), 8.08(1H,td), 8.35(1H, t).

$^1$R(KBr)cm$^{-1}$: 1700, 1450, 1415, 1310, 1300, 1270, 1260, 810, 755, 720.

53c) 4'-Methylbiphenyl-3-carboxamide

To a suspension of the compound (1.73 g) obtained in Working Example (53b) in chloroform (25 ml) were added thionyl chloride (1.94 g) and dimethylformamide (two drops). The mixture was heated for 4 hours under reflux. The reaction mixture was concentrated to dryness and to the residue was added toluene. The mixture was again concentrated to dryness. This procedure was repeated four times to give a pale yellow oil, which was added dropwise to 25% aqueous ammonia (20 ml) under ice-cooling. The mixture was stirred for 30 minutes at room temperature. Crystalline precipitate then formed was collected by filtration and dried to afford the title compound as colorless crystals (1.73 g, quantitatively), m.p.200°–205° C.

$^1$H-NMR(200 MHz,DMSO-d$_6$) δ: 2.36(3H,s), 7.30(2H, d), 7.41(1H,br s), 7.51(1H,t), 7.63(2H,d), 7.76–7.86(2H,m), 8.10(1H,br s), 8.14(1H,t).

IR(KBr)cm$^{-1}$: 3300, 3150, 1670, 1630, 1605, 1580, 1450, 1410, 1390, 1125, 800, 685.

53d) 4'-Methyl-3-cyanobiphenyl

A mixture of the compound (1.70 g) obtained in Working Example (53c) in thionyl chloride (10 ml) was heated for 4.5 hours under reflux. The reaction mixture was concentrated to dryness and to the residue was added toluene. The mixture was again concentrated to dryness. This procedure was repeated three times, then the residue was purified by column chromatography on silica gel to afford the title compound as colorless crystals (1.50 g, 96%), m.p.71°–73° C.

$^1$H-NMR(200 MHz,CDCl$_3$) δ: 2.41(3H,s), 7.28(2H,d), 7.46(2H,d), 7.51(1H,t), 7.60(1H,td), 7.79(1H,td), 7.84(1H, t).

$^1$IR(KBr)cm$^{-1}$: 2230, 1475, 825, 800.

53e) 4'-Methylbiphenyl-3-carboxyamidoxime

To a solution of hydroxylamine hydrochloride (2.61 g) in dimethyl sulfoxide (20 ml) was added a solution of 28% sodium methoxide in methanol (7.25 g). The mixture was then stirred for 10 minutes at room temperature, to which was added a solution of the compound (1.45 g) obtained in Working Example (53d) in dimethyl sulfoxide (10 ml). The mixture was stirred for one hour at 100° C. and water was added to the mixture. The mixture was extracted with ethyl acetate. The extract was washed with water, dried and concentrated to dryness in vacuo. The residue was purified by column chromatography on silica gel to afford the title compound as colorless crystals (1.30 g, 76%), m.p.134°–136° C.

$^1$H-NMR(200 MHz,CDCl$_3$) δ: 2.39(3H,s), 4.93(2H,br s), 7.25(2H,d), 7.41–7.66(5H,m), 7.85(1H,t).

IR(KBr)cm$^{-1}$: 3495, 3385, 1660, 1585, 1440, 1375, 940, 925, 900, 795.

53f) 3-(4'-Methylbiphenyl-3-yl)-5-trichloromethyl-1,2,4-oxadiazole

To a suspension of the compound (1.30 g) obtained in Working Example (53e) in toluene (30 ml) was added trichloroacetic anhydride (2.13 g), and the mixture was stirred for 30 minutes at 80° C. The reaction mixture was concentrated to dryness and dissolved in ethyl acetate. The solution was washed with water, dried and concentrated to dryness in vacuo. The residue was purified by column chromatography on silica gel to afford the title compound as an oil (2.09 g, quantitatively).

$^1$H-NMR(200 MHz,CDCl$_3$) δ: 2.41(3H,s), 7.28(2H,d), 7.55(2H,d), 7.56(1H,t), 7.76(1H,td), 8.07(1H,td), 8.32(1H, t),

IR(Neat)cm$^{-1}$: 1570, 1515, 1460, 1355, 1335, 850, 825, 800, 745, 690.

53g) 3-(4'-Bromomethylbiphenyl-3-yl)-5-trichloromethyl-1,2,4-oxadiazole

To a solution of the compound (2.09 g) obtained in Working Example (53f) in carbon tetrachloride (50 ml) were added N-bromosuccinimide (NBS) (1.10 g) and benzoyl peroxide (BPO) (0.20 g). The mixture was refluxed under irradiation of light for one hour. The reaction mixture was cooled to room temperature, and insoluble materials were filtered off. The filtrate was concentrated to dryness, and the residue was purified by column chromatography on silica gel to afford the title compound as a colorless oil (2.40 g, 59%).

$^1$H-NMR(200 MHz,CDCl$_3$) δ: 4.57(2H,s), 7.49–7.68(5H, m), 7.75–7.79(1H,m), 8.09–8.17(1H,m), 8.33(1H,m).

53h) Methyl 2-ethylthio-1-[[3'-(2,5-dihydro-5-oxo-1,2,4-oxadiazol-3-yl)biphenyl-4-yl]methyl]thieno[3,4-d]imidazole-4-methyl-6-carboxylate To an ice-cooling solution of methyl 2-ethylthio-4-methylthieno[3,4-d]imidazole-6-carboxylate (0.80 g) in dimethylformamide (10 ml) was added sodium hydride (60% in oil; 0.14 g). After stirring for 10 minutes, a solution of the compound (1.53 g) obtained in Working Example (53g) in dimethylformamide (10 ml) was added to the mixture under ice-cooling, followed by stirring for one hour at room temperature. To the reaction mixture was added water, and the mixture was extracted with ethyl acetate. The extract was washed with a saturated aqueous saline solution, dried and concentrated to dryness. The residue was purified by column chromatography on silica gel to give a colorless crystalline product. To a solution of the crystals in a mixture of chloroform (10 ml)–methanol (10 ml) was added 1N-NaOH (3 ml), and the mixture was stirred for one hour at room temperature. The reaction mixture was concentrated and adjusted to pH 3–4 with 1N HCl. The aqueous mixture was partitioned between chloroform and water. The organic layer was dried and the solvent was removed in vacuo to give crude crystals. Recrystallization from methanol—ethyl acetate afforded the title compound as colorless needles (0.74 g, 83%), m.p.248°–251° C. (decomp.).

Elemental Analysis for $C_{25}H_{24}N_4S_2 \cdot 0.5H_2O$:

|  | C(%) | H(%) | N(%) |
|---|---|---|---|
| Calcd.: | 58.24; | 4.50; | 10.87 |
| Found: | 58.24; | 4.38; | 10.77 |

$^1$H-NMR(200 MHz,CDCl$_3$) δ: 1.41(3H,t), 2.63(3H,s), 3.30(2H,q), 3.78(3H,s), 5.75(2H,s), 7.27(2H,d), 7.51–7.60(3H,m), 7.69–7.78(2H,m), 7.98(1H,t).

IR(KBr)cm$^{-1}$: 1780, 1755, 1690, 1460, 1320, 1170, 1090, 760.

53i) 2-Ethylthio-1-[[3'-(2,5-dihydro-5-oxo-1,2,4-oxadiazol-3-yl)biphenyl-4-yl]methyl]thieno[3,4-d]imidazole-4-methyl-6-carboxylic acid To a suspension of the compound (0.60 g) obtained in Working Example (53h) in a mixture of tetrahydrofuran (20 ml)–water (20 ml) was added lithium hydroxide monohydrate (0.25 g). The mixture was heated for 15 hours under reflux. The reaction mixture was concentrated, and the aqueous residue was adjusted to pH 3 with 1N-HCl. Crystalline precipitate was recrystallized to afford colorless needles (0.33 g, 56%), m.p.177–179 C (decomp.).

Elemental Analysis for $C_{24}H_{20}N_4O_4S_2 \cdot 0.5H_2O$:

|  | C(%) | H(%) | N(%) |
|---|---|---|---|
| Calcd.: | 57.47; | 4.22; | 11.17 |
| Found: | 57.63; | 4.04; | 11.17 |

$^1$H-NMR(200 MHz,DMSO-d$_6$) δ: 1.35(3H,t), 2.56(3H,s), 3.26(2H,q), 5.73(2H,s), 7.26(2H,d), 7.65(1H,t), 7.69(2H,d), 7.81(1H,td), 7.90(1H,td), 8.08(1H,t).

IR(KBr)cm$^{-1}$: 1770, 1755, 1650, 1530, 1460, 1165, 765.

Working Example 54
2-Ethoxy-1-[[2'-(2,5-dihydro-5-oxo-1,2,4-oxadiazol-3-yl)biphenyl-4-yl]methyl]benzimidazole-7-carboxylic acid 54a) 4'-bromomethylbiphenyl-2-carboxamide A mixture of 4'-methylbiphenyl-2-carboxamide (2.1 g), N-bromo-succinimide (2.5 g) and azobisisobutyronitrate (AIBN;82 mg) in benzene (20 ml) was stirred for 20 hours at 60° to 70° C. Resulting crystalline precipitates were collected by filtration, washed with isopropylether and suspended in water. The suspension was stirred for 30 minutes, and insoluble materials were collected by filtration and dried to give crude crystals. Recrystallization from ethyl acetate—methanol afforded colorless needles (1.6 g, 55%), m.p. 220°–221° C.(decomp.).

Elemental Analysis for $C_{14}H_{12}BrNO$:

|  | C(%) | H(%) | N(%) |
|---|---|---|---|
| Calcd.: | 57.95; | 4.17; | 4.83 |
| Found: | 57.85; | 4.16; | 4.77 |

$^1$H-NMR (200 MHz, DMSO-d$_6$) δ: 4.75(2H,s), 7.31–7.69(10H,m)

IR(KBr)cm$^{-1}$: 3150, 3000, 1570, 1520, 1500, 1300, 665.

54b) Methyl 2-[N-tert-butoxycarbonyl-N-(2'-carbamoylbiphenyl-4-yl)methylamino]-3-nitrobenzoate A mixture of methyl 2-(N-tert-butoxycarbonylamino)-3-nitrobenzoate (1.8 g), 4'-bromomethylbiphenyl-2-carboxamide (1.8 g) and $K_2CO_3$ (0.86 g) in acetonitrile (25 ml) was heated for 6 hours under reflux. To the reaction mixture was added water, and the mixture was extracted with ethyl acetate. The extract was washed with water and dried over MgSO$_4$. The solvent was removed in vacuo., and the residue was purified by column chromatography on silica gel to afford a yellow syrup (2.3 g, 90%).

$^1$H-NMR (200 MHz, CDCl$_3$) δ: 1.35(9H,s), 3.83(3H,s), 4.48(1H,d), 4.92(1H,d), 5.29(1H,brs), 5.56(1H,brs), 7.13–7.54(8H,m), 7.80–7.91(2H,m), 8.06(1H,dd).

IR(neat)cm$^{-1}$: 1740–1660, 1600, 1535, 1480, 1450, 1160, 1130, 860, 830, 760.

54c) Methyl 2-(2'-carbamoylbiphenyl-4-yl)methylamino-3-nitrobenzoate

A mixture of the compound (2.8 g) obtained in Example (54b) in methanol (15 ml) and 1N-HCl (6 ml) was heated for 2 hours under reflux. After removal of the solvent, the residue was made alkaline with an aqueous solution of NaHCO$_3$, and the mixture was extracted with ethyl acetate. The extract was washed with water, dried over MgSO$_4$ and concentrated to dryness. The residue was purified by column chromatography on silica gel, and the product was recrystallized from ethyl acetate—hexane to afford yellow needles (1.6 g, 73%).

$^1$H-NMR (200 MHz, CDCl$_3$) δ: 3.90(3H,s), 4.25(2H,s), 5.20(1H,brs), 5.46(1H,brs), 6.73(1H,t), 7.32–7.54(7H,m), 7.78(1H,dd), 7.97(1H,dd), 8.12(1H,dd).

IR(KBr)cm$^{-1}$: 3470, 3330, 1695, 1670, 1605, 1580, 1530, 1500, 1450, 1350, 1260, 1120, 1110, 765, 745.

54d) Methyl 3-amino-2-(2'-carbamoylbiphenyl-4-yl)methyl-aminobenzoate

To a suspension of nickel chloride (4 mg) in methanol (20 ml) was added a small amount of NaBH$_4$ was added the compound (1.2 g) obtained in Example (54c) (1.2 g). To the ice-cooling reaction mixture was added NaBH$_4$ (0.45 g) in portions during a period of 30 minutes. After stirring for further 30 minutes, the reaction mixture was partitioned between water and ethyl acetate. The organic layer was washed with water and dried over MgSO$_4$. The solvent was removed in vacuo, and the residue was purified by column chromatography on silica gel to afford a colorless syrup (0.84 g, 76%).

$^1$H-NMR (200 MHz, CDCl$_3$) δ: 3.80(3H,s), 4.25(2H,s), 5.12(1H,brs), 5.42(1H,brs), 6.88–6.94(2H,m), 7.20–7.56(8H,m), 7.78–7.83(1H,m).

IR(neat)cm$^{-1}$: 3450, 3350, 3180, 1700–1660, 1610, 1470, 1380, 1290, 1200, 760.

54e) Methyl 1-[(2'-carbamoylbiphenyl-4-yl)methyl]-2-ethoxybenzimidazole-7-carboxylate To dioxane (2 ml) were added the compound (0.84 g) obtained in Example (54d), tetraethoxymethane (0.63 g) and acetic acid (0.13 g), and the mixture was stirred for 6 hours at 80°–90° C. The solvent was removed in vacuo, and the residue was purified by column chromatography on silica gel. Recrystallization from ethyl acetate—hexane afforded colorless needles (0.61 g, 64%), m.p. 198°–199° C.

Elemental Analysis for $C_{25}H_{23}N_3O_4$:

|  | C(%) | H(%) | N(%) |
|---|---|---|---|
| Calcd.: | 69.92; | 5.40; | 9.78 |
| Found: | 69.96; | 5.68; | 9.81 |

$^1$H-NMR (200 MHz,CDCl$_3$) δ: 1.52(3H,t), 3.78(3H,s), 4.73(2H,q), 5.14(1H,brs), 5.39(1H,brs), 5.66(2H,s), 7.03(2H,d), 7.20(1H,t), 7.30–7.56(6H,m), 7.73–7.81(2H,m).

IR(KBr)cm$^{-1}$: 3400, 3200, 1720, 1660, 1620, 1540, 1475, 1430, 1380, 1350, 1280, 1250, 1040, 755, 740.

54f) Methyl 2-ethoxy-1-[(2'-[ethoxycarboimidoyl]biphenyl-4-yl)methyl]benzimidazole-7-carboxylate To methylene chloride (50 ml) were added the compound (4.3 g) obtained in Example (54e) and triethyl tetrafluoroborate (2.8 g). The mixture was stirred for one hour at room temperature. The reaction mixture was washed with a saturated aqueous solution of $NaHCO_3$ and dried over $MgSO_4$. The solvent was removed in vacuo, and the residue was purified by column chromatography on silica gel. Recrystallization from isopropylether afforded colorless prisms (3.6 g, 78%), m.p. 105–106° C.

Elemental Analysis for $C_{27}H_{27}N_3O_4$:

|  | C(%) | H(%) | N(%) |
|---|---|---|---|
| Calcd.: | 70.88; | 5.95; | 9.18 |
| Found: | 70.66; | 5.96; | 9.16 |

$^1$H-NMR (200 MHz, $CDCl_3$) δ: 0.92(3H,t), 1.50(3H,t), 3.79 (3H,s), 4.01 (2H,q), 4.67 (2H,q), 5.66(2H,s), 7.02 (2H,d), 7.13–7.58(8H,m), 7.73(1H,dd).

IR(KBr)cm$^{-1}$: 3310, 1715, 1640, 1620, 1550, 1480, 1460, 1430, 1390, 1375, 1350, 1330, 1280, 1250, 1220, 1170, 1130, 1110, 1080, 1040, 1005, 870, 760, 750, 740.

54g) Methyl 2-ethoxy-1-[[2'-[(N-methoxycarbonyl)ethoxycarboimidoyl]biphenyl-4-yl]methyl]benzimidazole-7-carboxylate To toluene (10 ml) were added the compound (1.5 g) obtained in Example (54f), ethyl chloroformate (0.41 g) and 2,6-dimethylpyridine (0.46 g), and the mixture was stirred for 3 hours at 80°–90° C. The reaction mixture was diluted with ethyl acetate, washed with a saturated aqueous solution of $NaHCO_3$ and dried over $MgSO_4$. The solvent was removed in vacuo, and the residue was recrystallized from ethyl acetate to afford colorless prisms (1.5 g, 88%), m.p. 157°–158° C.

Elemental Analysis for $C_{29}H_{29}N_3O_6$:

|  | C (%) | H (%) | N (%) |
|---|---|---|---|
| Calcd.: | 67.56; | 5.67; | 8.15 |
| Found: | 67.43; | 5.70; | 8.10 |

$^1$H-NMR (200 MHz, $CDCl_3$) δ: 0.68(3H,t), 1.50(3H,t), 3.57(3H,s), 3.81 (3H,s), 3.87(2H,q), 4.67 (2H,q), 5.67(2H,s), 7.04(2H,d), 7.15(1H,t), 7.23–7.50(6H,m), 7.55(1H,dd), 7.72(1H,dd).

IR(KBr)cm$^{-1}$: 1710, 1650, 1615, 1550, 1475, 1455, 1445, 1430, 1410, 1390, 1375, 1350, 1320, 1270, 1240, 1220, 1140, 1120, 1040, 1010, 800, 765, 755.

54h) Methyl 2-ethoxy-1-[[2'-(2,5-dihydro-5-oxo-1,2,4-oxadiazol-3-yl)biphenyl-4-yl]methyl]benzimidazole-7-carboxylate To methanol (15 ml) were added the compound (1.0 g) obtained in Example (54g), hydroxylamine hydrochloride (0.28 g) and MeONa (0.22 g). The mixture was heated for 6 hours under reflux. To the reaction mixture was added water. Resulting crystalline precipitates were collected by filtration and recrystallized from ethyl acetate—hexane to afford colorless prisms (0.7 g, 77%), m.p.186°–187° C.

$^1$H-NMR (200 MHz, $CDCl_3$) δ: 1.43(3H,t), 3.46(3H,s), 4.39(2H,q), 5.62(2H,s), 6.88–7.01(4H,m), 7.09(2H,d), 7.26–7.30(1H,m), 7.45(1H,dd), 7.54–7.60(2H,m), 7.85–7.89(1H,m), 10.25 (1H,brs).

IR(KBr)cm$^{-1}$: 1780, 1720, 1610, 1550, 1490, 1470, 1435, 1410, 1390, 1350, 1280, 1250, 1220, 1130, 1040, 755.

54i) Methyl 2-ethoxy-1-[[2'-(2,5-dihydro-5-oxo-1,2,4-oxadiazol-3-yl)biphenyl-4-yl]methyl]benzimidazole-7-carboxylate A mixture of the compound (0.23 g) obtained in Example (54g), methyl chloroformate (66 mg) and 2,4,6-trimethylpyridine (85 mg) in toluene (1 ml) was stirred for 16 hours at 80°–90° C. Precipitates were filtered off, and the solvent was removed in vacuo. The residue was added to a mixture of hydroxylamine hydrochloride (42 mg) and NaOMe (32 mg) in methanol (2 ml). The mixture was heated for 5.5 hours under reflux. The reaction mixture was concentrated to dryness, and the residue was dissolved in ethyl acetate, washed with dilute hydrochloric acid and dried over $MgSO_4$. The solvent was evaporated in vacuo, and the residue was crystallized from ethyl acetate—methanol to afford colorless prisms (0.13 g, 55%).

54j) 2-Ethoxy-1-[[2'-(2,5-dihydro-5-oxo-1,2,4-oxadiazol-3-yl)biphenyl4-yl]methyl]benzimidazole-7-carboxylic acid A mixture of the compound (0.47 g) obtained in Example (54h) and 1N NaOH (3 ml) in methan6l (3 ml) was heated for 30 minutes under reflux. The reaction mixture was adjusted to pH 3–4 with 1N HCl. Resulting crystalline precipitates were collected by filtration and recrystallized from ethyl acetate—hexane. The crystals were suspended in water (2 ml), and the suspension was stirred for 2 hours at 60° C. Insoluble materials were collected by filtration and dried to afford colorless crystals (0.25 g, 54%). This product was in agreement with that obtained in Example 1.

$^1$H-NMR (200 MHz, DMSO-$d_6$) δ: 1.38(3H,t), 4.58(2H, q), 5.68(2H,s) 7.04(2H,d), 7.13–7.25(3H,m), 7.45–7.69(6H, m).

EXAMPLE 55

2-Ethyl-3-[[2'-(2,5-dihydro-5-ox0-1,2,4-oxadiazol-3yl)bipenyl-4-yl]methyl]-5,7-dimethylimidazo[4,5-b]pyridine To a solution of 5,7-dimethyl-2-ethylimidazo[4,5b]pyridine (0.7 g) synthesized in accordance with European Patent EP 0400974 A2 in dimethylformamide (10 ml) was added sodium hydride (60% in oil; 0.18 g) under ice-cooling, and the mixture was stirred for 10 minutes. To the ice-cooling reaction mixture was added the compound (2.10 g) obtained in Example (22c), and the mixture was stirred for 30 minutes at room temperature. The reaction mixture was partitioned between water and ethyl acetate. The organic layer was washed with water, dried and concentrated to dryness. The residue was purified by column chromatography on silica gel to give a brown syrup. To a solution of the product in methanol (10 ml) was added an aqueous solution of 1N NaOH (2 ml), and the solution was stirred for 30 minutes at room temperature. The reaction mixture was adjusted to pH 3–4 with 1N HCl and extracted with chloroform. The extract was dried, and the solvent was removed under reduced pressure. The residue was purified by chromatography on silica gel. Crude crystals thus obtained was recrystallized from ethyl acetate—hexane to afford the title compound as colorless crystals (0.35 g, 20%), m.p.149°–152° C.

Elemental Analysis for $C_{25}H_{23}N_5O_2 \cdot 0.1H_2O$ (427.29):

|  | C (%) | H (%) | N (%) |
|---|---|---|---|
| Calcd.: | 70.27; | 5.47; | 16.39 |
| Found: | 70.24; | 5.42; | 16.40 |

¹H-NMR (200 MHz, CDCl₃) δ: 1.24(3H,t), 2.42(3H,s), 2.51(3H,s), 2.64(2H,q), 5.39(2H,s), 6.83(1H,s), 7.05(2H,d), 7.17(2H,d), 7.29–7.34(1H,m), 7.48(1H,dt), 7.57(1H,dt), 7.75–7.80(1H,m).

IR(KBr)cm⁻¹: 1780, 1610, 1595, 1505, 1495, 1465, 1455, 1425, 1390, 765.

EXAMPLE 56

2-Ethyl-3-[[2'-(2,57dihydo-5-oxo-1,2,4-oxadiazol-3yl)biphenyl)-4-yl]methyl]-7-methylimidazo[4,5-b]pyridine-5-carboxylic acid 56a) 4-Methyl-2-nitraminepyridine 2-Amino-4-methylpyridine (25 g) was added gradually to conc. sulfuric acid (150 ml) under ice-cooling. To the mixture was added dropwise a previously ice-cooled mixture of conc. nitric acid (26 ml) and conc. sulfuric acid (19 ml), maintaining at 0° C. The mixture was then stirred for 2.5 hours. The reaction mixture was poured into 300 g of ice, and the mixture was neutralized with aqueous ammonia under ice-cooling. Insoluble materials were filtered off, and the filtrate was concentrated. Resulting crystalline precipitates were collected by filtration and dried to afford the title compound as yellow needles (26.3 g, 74%), m.p.185°–187° C.

¹H-NMR (200 MHz, DMSO-d₆) δ: 2.40(3H,s), 7.02(1H, dd), 7.47(1H,s), 8.05(1H,d).

IR(KBr)cm⁻¹: 1625, 1600, 1520, 1415, 1375, 1365, 1320, 1295, 1260, 1215, 1165.

56b) 2-Amino-4-methyl-3(and 5)-nitropyridine

4-Methyl-2-nitraminepyridine (34.1 g) was added to conc. sulfuric acid (170 ml), maintaining at 0° C. The mixture was stirred for 24 hours at room temperature and poured into ice (500 g), followed by neutralization with aqueous ammonium hydroxide under ice-cooling. The reaction mixture was cooled to give a crystalline product. The crystals were collected by filtration and dried to give a mixture of 3-nitro derivative and 5-nitro derivative as yellow crystals (23,5 g, 3-nitro derivative: 5-nitro derivative=1:1.7). 3-Nitro derivative: ¹H-NMR (200 MHz,DMSO-d₆) δ: 2.36(3H,s), 6.60(1H,d), 7.09(2H,brs), 8.07(1H,d). 5-Nitro derivative: ¹H-NMR (200 MHz,DMSO-d₆) δ: 2.46(3H,s), 6.32(1H,s), 7.30(2H,brs), 8.76(1H,s).

56c) 2-Ethyl-7-methylimidazo[4,5-b]pyridine

A suspension of the compound (23.4 g) obtained in Example (56b) and 5%Pd-C (13 g) in methanol (500 ml) was stirred under hydrogen atmosphere. Insoluble materials were filtered off, and the filtrate was concentrated to dryness to give a brown syrup. The syrup was mixed in polyphosphoric acid (240 g) and propionic acid (40 g), and the mixture was stirred for 20 minutes at 100° C. The reaction mixture was poured into ice-water and neutralized with aqueous ammonium hydroxide. Resulting crystalline precipitates were collected by filtration and recrystallized from chloroform. Resulting crystalline precipitates (byproduct) were collected by filtration. The filtrate and the mother liquor were combined and concentrated, then resulting crystalline precipitates were collected by filtration and washed with chloroform. The filtrates were combined and concentrated to dryness, which was purified by chromatography on silica gel. Crude crystals thus obtained were recrystallized form ethyl acetate—hexane afforded the title compound as pale yellow crystals (4.55 g), m.p.117°–119° C.

¹H-NMR (200 MHz,CDCl₃) δ: 1.56(3H,t), 2.70(3H,s), 3.11(2H,q), 7.05(1H,d), 8.19(1H,d).

IR(KBr)cm⁻¹: 1630, 1540, 1445, 1375, 1365, 890, 820.

56d) 2-Ethyl-7-methylimidazo[4,5-]pyridin-4N-oxide

To an ice-cooling solution of the compound (2.0 g) obtained in Example (56c) in chloroform (30 ml) was added m-chlorobenzoic acid (2.78 g). The mixture was stirred for 10 minutes and then heated for one hour under reflux. The reaction mixture was concentrated to dryness under reduced pressure. The concentrate was purified by chromatography on silica gel to give crude crystals. Recrystallization from ethyl acetate—methanol afforded the title compound as colorless needles (1.92 g, 85%), m.p.189°–191° C.

Elemental Analysis for C₉H₁₁N₃O.0.2H₂O(180.81):

|         | C (%)  | H (%) | N (%)  |
|---------|--------|-------|--------|
| Calcd.: | 59.79; | 6.36; | 23.24  |
| Found:  | 59.94; | 6.61; | 23.23  |

¹H-NMR (200 MHz,CDCl₃) δ: 1.33(3H,t), 2.46(3H,s), 2.86(2H,q), 6.96(1H,d), 8.00(1H,d).

IR(KBr)cm⁻¹: 1480, 1420, 1280, 1250, 1230, 1170, 765.

56e) 5-Cyano-2-ethyl-7-methylimidazo[4,5-b]pyridine

To a suspension of the compound (2.0 g) obtained in Example (56d) in acetonitrile (30 ml) were added trimethylsilyl cyanide (4.5 g) and triethylamine (1.15 g), and the mixture was heated for 16 hours under reflux. The reaction mixture was concentrated to dryness under reduced pressure. The residue was purified by chromatography on silica gel. Crude crystals thus obtained were recrystallized from ethyl acetate to afford the title compound as pale yellow needles (1.40 g, 66%), m.p.216°–218° C. (decomp.).

Elemental Analysis for C₁₀H₁₀N₄(186.22):

|         | C (%)  | H (%) | N (%)  |
|---------|--------|-------|--------|
| Calcd.: | 64.50; | 5.41; | 30.09  |
| Found:  | 64.26; | 5.45; | 29.87  |

¹H-NMR (200 MHz,CDCl₃) δ: 1.54(3H,t), 2.75(3H,s), 3.22(2H,q), 7.50(1H,s).

IR(KBr)cm⁻¹: 2225, 1615, 1600, 1515, 1415, 1395, 1375, 1295, 1270, 785.

56f) Methyl 2-ethyl-7-methylimidazo[4,5-b]pyridine-5-carboxylate

The compound (1.31g) obtained in Example (56e) was suspended in 9N-hydrogen chloride in methanol solution (30 ml). The suspension was heated for 3 hours under reflux. The reaction mixture was concentrated under reduced pressure, and the pH was adjusted to 5 with a saturated aqueous solution of sodium hydrogencarbonate, followed by extraction with chloroform. The extract was dried, and the solvent was removed under reduced pressure to give crude crystals. Recrystallization from ethyl acetate—methanol afforded the title compound as colorless prisms (1.33 g, 86%), m.p.208°–210° C.

Elemental Analysis for C₁₁H₁₃N₃O₂(219.24):

|         | C (%)  | H (%) | N (%)  |
|---------|--------|-------|--------|
| Calcd.: | 60.26; | 5.98; | 19.17  |
| Found:  | 60.14; | 5.99; | 19.07  |

¹H-NMR (200 MHz,CDCl₃) δ: 1.41(3H,t), 2.74(3H,s), 3.14(2H,q), 4.03(3H,s), 7.92(1H,s).

IR(KBr)cm⁻¹: 3240, 1730, 1615, 1510, 1435, 1405, 1385, 1300, 1250, 1200, 750.

56g) Methyl 2-ethyl-3-[[2'-(2,5-dihydro-5-oxo-1,2,4-oxadiazol-3-yl)biphenyl-4-yl]methyl]-7-methylimidazo[4,5-b]pyridine-5-carboxylate To a solution of the compound (1.0 g) obtained in Example (56f) in dimethylformamide (10 ml) was added sodium hydride (60% in oil; 0.21 g) at room temperatures. The mixture was stirred for 5minutes, and to the mixture was added the compound (2.27 g) obtained in Example (22c), followed by stirring for one hour at room temperatures. The reaction mixture was partitioned between water and ethyl acetate. The organic layer was washed with a saturated aqueous saline solution and dried. The solvent was removed under reduced pressure, and the residue was purified by chromatography on silica gel to give colorless crystals. The crystals were dissolved in chloroform (7.5 ml)-methanol (15 ml). To the solution was added an aqueous solution of 1N sodium hydroxide (3.5 ml), and the mixture was stirred for 20 minutes at room temperature. To the reaction mixture was added 1N-HCl to adjust the pH to 3 to 4, followed by extraction with chloroform. The extract was dried, and the solvent was removed under reduced pressure to give crude crystals. Recrystallization from ethyl acetate—methanol afforded the title compound as colorless prisms (1.07 g, 58%), m.p.246°–248° C. (decomp.).

Elemental Analysis for $C_{26}H_{23}N_5O_4(469.50)$:

|  | C (%) | H (%) | N (%) |
|---|---|---|---|
| Calcd.: | 66.51; | 4.94; | 14.92 |
| Found: | 66.37; | 4.97; | 14.84 |

$^1$H-NMR (200 MHz,CDCl$_3$) δ: 1.31(3H,t), 2.63(3H,s), 2.80(2H,q), 3.93(3H,s), 5.52(2H,s), 7.14(2H,d), 7.23(2H,d), 7.35(1H,dd), 7.43–7.63(2H,m), 7.76(1H,dd), 7.92(1H,s), 9.15(1H,brs).

IR(KBr)cm$^{-1}$: 1780, 1705, 1485, 1465, 1435, 1275, 1220, 760.

56h) 2-Ethyl-3-[[2'-(2,5-dihydro-5-oxo-1,2,4-oxadiazol-3-yl)biphenyl-4-yl]methyl]-7-methylimidazo[4,5-b]-pyridine-5-carboxylic acid To a suspension of the compound (0.9 g) obtained in Example (56g) in methanol (20 ml) was added 1N aqueous solution of sodium hydroxide (4.5 ml), and the mixture was stirred for 3 hours at 60° C. To the reaction mixture was added 1N HCl to adjust the pH to 3–4. Resulting crystalline precipitates were collected by filtration and dried. Crude crystals thus obtained were recrystallized from ethyl acetate—methanol afforded the title compound as colorless crystals (0.61 g, 69%), m.p.261–164° C. (decomp.).

Elemental Analysis for $C_{25}H_{21}N_5O_4(455.47)$:

|  | C (%) | H (%) | N (%) |
|---|---|---|---|
| Calcd.: | 65.93; | 4.65; | 15.38 |
| Found: | 65.63; | 4.67; | 15.15 |

$^1$H-NMR (200 MHz,DMSO-d$_6$) δ: 1.25(3H,t), 2.64(3H,s), 2.86(2H,q), 5.62(2H,s), 7.22(2H,d), 7.29(2H,d), 7.48–7.72(4H,m), 7.88(1H,s).

IR(KBr)cm$^{-1}$: 1790, 1695, 1285, 1270.

EXAMPLE 57

Methyl 2-ethoxy-1-[[2'-(2,5-dihydro-5-oxo-1,2,4-oxadiazol-3-yl)biphenyl-4-yl]methyl]benzimidazole-7-carboxylate 57a) Methyl 3-amino-2-[[2'-(ethoxycarbonyloxycarbamimidoyl]biphenyl-4-yl)methylamino]benzoate To a suspension of the compound (7.1 g) obtained in Example (1a) in methanol (120 ml) were added hydroxylamine hydrochloride (5.56 g) and triethylamine (6.06 g). The mixture was stirred for 3 days at 70° C. under nitrogen atmosphere. Methanol was removed in vacuo. The residue was partitioned between ethyl acetate (200 ml) and water (50 ml). The organic layer was washed with water, dried and concentrated to dryness under reduced pressure. To a solution of the residue in tetrahydrofuran (100 ml) was added triethylamine (2 g) under ice-cooling. To the mixture was added dropwise a solution of ethyl chlorocarbonate (1.4 g) in tetrahydrofuran (20 ml). The reaction mixture was stirred for one hour at the same temperature, and the solvent was removed in vacuo. The residue was partitioned between ethyl acetate—water. The organic layer was washed with water, dried and concentrated to dryness to give a pale yellow syrup (8.6 g).

$^1$H-NMR (200 MHz,CDCl$_3$) δ: 1.35(3H,t), 3.80(3H,s), 4.20(2H,s), 4.32(2H,q), 4.57(2H,br s), 6.83–6.93(2H,m), 7.27–7.54(8H,m), 7.64–7.70(1H,m).

IR(CHCl$_3$)cm$^{-1}$: 3520, 3415, 3350, 1765, 1700, 1635.

57b) Methyl 2-ethoxy-1-[[2-(ethoxycarbonyloxycarbamimidoyl)biphenyl-4-yl]methyl]benzimidazole-7-carboxylate The pale brown syrup (8.58 g) obtained in Example (57a) was dissolved in dioxane (20 ml). To the solution were added tetraethoxymethane (8.64 g) and acetic acid (1.56 g). The mixture was stirred for 2 hours at 100° C. The reaction mixture was concentrated to dryness. The residue was crystallized from ethyl acetate (50 ml). Resulting crystalline precipitates were collected by filtration to obtain the title compound.

$^1$H-NMR(200 MHz,CDCl$_3$) δ: 1.50(3H,t), 3.77(3H,s), 4.31(2H,q), 4.69(2H,q), 5.64(2H,s), 7.01(2H,d), 7.17(1H,t), 7.26–7.55(6H,m), 7.72(1H,d).

IR(CHCl$_3$)cm$^{-1}$: 3520, 3410, 1765, 1710, 1635, 1545.

57c) Methyl 2-ethoxy-1-[[2'-(2,5-dihydro-5-oxo-1,2,4-oxadiazol-3-yl)biphenyl-4-yl]methyl]benzimidazole-7-carboxylate The crude crystals (4.0 g) obtained in Example (57b) was dissolved in ethyl acetate (50 ml). To the solution was added 1,8-diazabicyclo[5.4.0]undec-7-ene (DBU, 3.2 g), and the mixture was stirred for 2 hours at 80° C. The reaction mixture was partitioned between ethyl acetate (50 ml) and 1N HCl (20 ml). The organic layer was washed with water, dried and concentrated to dryness. The residue was crystallized from chloroformethyl acetate to afford the title compound as colorless prisms (2.1 g, 45%), which was in agreement with that obtained in Example (1d).

EXAMPLE 58

Methyl 2-ethoxy-1-[[2'-(2,5-dihydro-5-oxo-1,2,4-oxadiazol-3-yl)biphenyl-4-yl]methyl]benzimidazole-7-carboxylate The crude crystals (4.0 g) obtained in Example (57) were dissolved in ethyl acetate (50 ml). To the solution was added potassium carbonate (3 g) (in place of DBU), and the mixture was stirred for 18 hours at 90° C. Resulting crystalline precipitates were collected by filtration and suspended in water (30 ml). The pH of the suspension was adjusted to 3–4 with 2N-HCl. Resulting crystals were collected by filtration and dried to obtain the title compound as colorless crystals (1.81 g, 38%), which were in agreement with those obtained in Example (57).

EXAMPLE 59

2-Ethoxy-1-[[2'-(2,5-dihydro-5-oxo-1,2,4-oxadiazol-3-yl)-biphenyl-4-yl)]methyl]benzimidazole-7-carboxylic acid The compound (3.2 g) obtained according to the procedure of Example (1d) was suspended in 0.5N NaOH (50 ml). The suspension was stirred for 3 hours at 60° C. The reaction mixture was adjusted to pH 3 to 4 with 2N-HCl. Resulting crystals were collected by filtration and washed with water. The crystals thus obtained were stirred in ethanol (45 ml) for one hour to afford colorless prisms (2.9 g, 94%), m.p.212°–214° C.

Elemental Analysis for $C_{25}H_{20}N_4O_4$:

|  | C (%) | H (%) | N (%) |
|---|---|---|---|
| Calcd.: | 65.78; | 4.42; | 12.27 |
| Found: | 65.72; | 4.67; | 12.28 |

$^1$H-NMR (200 MHz,CDCl$_3$) δ: 1.47(3H,t), 4.67(2H,q), 5.77(2H,s), 7.07–7.70 (11H,m), 13.0(1H,br s)

IR(Nujol)cm$^{-1}$: 1780, 1 700, 1555, 1470, 1440, 1290, 1050, 765.

EXAMPLE 60

Methyl 2-ethoxy-1-[[2'-(2,5-dihydro-5-oxo-1,2,4-thiadiazol-3-yl)biphenyl-4-yl]methyl]benzimidazole-7-carboxylate The compound obtained in Example (1c) (0.89 g) was added to tetrahydrofuran (15 ml), to which was added 1,1'-thiocarbonyl diimidazole (0.36 g) while stirring at room temperatures. After stirring for 30 minutes, the reaction mixture was concentrated to dryness. The concentrate was dissolved in ethyl acetate, and the solution was washed with dilute hydrochloric acid and water, and then dried. To a solution of the residue in chloroform-methanol (5:1, 150 ml) was added silica gel (7 g), and the mixture was stirred for 48 hours at room temperature. Insoluble materials were filtered off, and the filtrate was concentrated to dryness to give a syrup. The product was purified by column chromatography on silica gel to give crystals. Recrystallization from ethyl acetate afforded colorless prisms (0. 33 g, 34%), m.p.211°–212° C.

Elemental Analysis for $C_{26}H_{22}N_4O_4S$:

|  | C (%) | H (%) | N (%) | S (%) |
|---|---|---|---|---|
| Calcd.: | 64.18; | 4.56; | 11.52; | 6.59 |
| Found: | 64.44; | 4.56; | 11.44; | 6.42 |

$^1$H-NMR(90 MHz,CDCl$_3$) δ: 1.43(3H,t), 3.70(3H,s), 4.57(2H,q), 5.67(2H,s), 6 .93–7.60 (10H,m), 7.77–7.90(1H, m), 9.43(1H, brs)

IR(Nujol)cm$^{-1}$: 1715, 1665, 1550, 1440, 1430, 1285, 1250, 1040.

EXAMPLE 61

2-Ethoxy-1-[[2'-(2,5-dihydro-5-oxo-1,2,4-thiadiazol-3-yl)biphenyl-4-yl]methyl]benzimidazole-7-carboxylate The compound (0.68 g) obtained in Example (60a) was suspended in a 0.2N aqueous solution of NaOH (10 ml). The suspension was stirred for 20 hours at 60° C., and then the pH was adjusted to 3–4 with 1N-HCl. Resulting crystals were collected by filtration and recrystallized from methanol to afford colorless prisms (0.29 g, 44%), m.p.210°–211° C.

Elemental Analysis for $C_{25}H_{20}N_4O_4S$:

|  | C (%) | H (%) | N (%) | S (%) |
|---|---|---|---|---|
| Calcd.: | 63.55; | 4.27; | 11.86; | 6.79 |
| Found: | 63.26; | 4.32; | 11.84; | 6.59 |

$^1$H-NMR (90 MHz,CDCl$_3$) δ: 1.49(3H,t), 4.64(2H,q), 5.76(2H,s), 7.06–7.70(11H,m), 12.13(1H,brs).

IR (Nujol) cm$^{-1}$: 1720, 1670, 1550, 1425, 1280, 1035.

Working Example 62
Methyl 2-ethoxy-1-[[2'-(2,5-dihydro-5-thioxo-1,2,4-oxadiazol-3-yl)biphenyl-4-yl]methyl]benzimidazole-7-carboxylate A mixture of methyl 2-ethoxy-1-[(2'-hydroxycarbamimidoyl)biphenyl-4-yl]methyl]benzimidazole-7-carboxylate (0.66 g) obtained in Working Example (1c), thiocarbonyldiimidazole (0.3 g) and 1,5-diazabicyclo[4.3.0]non-5-ene (0.56 g) in acetonitrile (15 ml) was stirred at room temperature for 20 hours. After evaporation of the solvent, the residue was dissolved in water and the pH of the solution was adjusted to pH 4–5, followed by extraction with ethylacetate. The extract was dried and concentrated to dryness and the residue was purified by silica gel column chromatography to give crystals. Recrystallization from ethyl acetate-MeOH gave colorless crystals (0.2 g, 20%).

$^1$H-NMR (200 MHz,DMSO-d$_6$) δ: 1.41(3H,t), 3.68(3H, s), 4.61(2H,q), 5.49(2H,s), 6.89(2H,d), 7.15(2H,d), 7.18(1H, t), 7.25–7.61(5H,m), 7.68(1H,dd), 8.81(1H,s)

Working Example 63
Methyl 2-butyl-1-[[2'-(2,5-dihydro-5)thioxo-1,2,4-oxadiazol-3-yl)biphenyl-4-yl]methyl]benzimidazol-7-carboxylate
63a) Methyl 1-[[2'-(N-acetoxycarbamimidoyl]biphenyl-4-yl)methyl]-2-butylbenzimidazole-7-carboxylate To a solution of methyl 2-butyl-1-[[2'-(hydroxycarbamimidoyl)biphenyl-4-yl]methyl]bezimidazole-7-carboxylate (1.83 g) in dichloromethane (20 ml) was added triethylamine (0.46 g) and acetic anhydride (0.46 g), and the reaction mixture was stirred at room temperature for 2 hours. After evaporation of the solvent, the residue was partitioned between ethylacetate and water and the organic layer was washed with an aqueous solution of NaHCO$_3$ and water. The solution was dried and concentrated to dryness to give a pale yellow solid (1.99 g, quant.)

$^1$H-NMR (200 MHz,CDCl$_3$) δ: 0.96(3H,t), 1.38–1.56(2H, m), 1.80–1.95(2H,m), 2.14(3H,s), 2.93(2H,t), 3.74(3H,s), 4.60(2H,brs), 5.76(2H,s), 6.87(2H,d), 7.20–7.50(6H,m), 7.55–7.65(2H,m), 7.93(1H,d)

IR(Nujol)cm$^{-1}$: 3325, 3170, 1750, 1720, 1630, 1280

This compound was used to the next reaction without any purification.
63b) Methyl 2-butyl-1-[[2'-(2,5-dihydro-5-thioxo-1,2,4-oxadiazol-3-yl)biphenyl-4-yl]methyl]benzimidazol-7-carboxylate To a mixture of methyl 2-butyl-1-[[2'-(acetoxycarbamimidoyl)biphenyl-4-yl)methyl]benzimidazole-7-carboxylate (2.0 g) and CS$_2$(1.5 g) in DMF (12 ml) was added sodium hydride (60% in oil, 0.56 g) during a period of 10 minutes and the reaction mixture was stirred at room temperature for 2 hours. The reaction mixture was poured into ice-water and the pH of the solution was adjusted to 3. The mixture was extracted with ethylacetate and the extract was washed with water, dried, and concentrated to dryness. The residue was crystallized from chloroform-methanol to afford pale yellow prisms (0.64 g, 32%). m.p. 180°–181° C.

Elemental Analysis for $C_{28}H_{26}N_4O_3S$:

| | C (%) | H (%) | N (%) |
|---|---|---|---|
| Calcd.: | 67.45; | 5.26; | 11.24 |
| Found: | 67.14; | 5.05; | 10.97 |

$^1$H-NMR (200 MHz,DMSO-$d_6$) δ: 0.90(3H,t), 1.30–1.50 (2H,m), 1.69–1.84(2H,m), 2.90(2H,t), 3.65(3H,S), 5.73(2H,S), 6.89 (2H,d), 7.19 (2H,d), 7.28(1H,t), 7.44–7.72(5H,m), 7.87(2H,d)

IR(Nujol)cm$^{-1}$: 1720, 1430, 1285, 1265, 755.

Working Example 64

2-Butyl-1-[[2'-(2,5-dihydro-5-thioxo-1,2,4-oxadiazol-3-yl)biphenyl-4-yl]methyl]benzimidazole-7-carboxylic acid A solution of methyl ester (0.42g) obtained in Working Example 63 in an aqueous solution of 0.3 N NaOH (8.2 ml) was stirred at 50° C. for 1.5 hours. The pH of the reaction solution was adjusted to 3 with 2N HCl and the solution was extracted with ethylacetate (40 ml). The organic layer was washed with water and concentrated to dryness. The resulting crystals were recrystallized from ethanol-ethylacetate to afford colorless prisms (0.25 g, 61%).

m.p. 178°–180° C.

Elemental Analysis for $C_{27}H_{24}N_4O_3S$:

| | C (%) | H (%) | N (%) |
|---|---|---|---|
| Calcd.: | 66.92; | 4.99; | 11.56 |
| Found: | 66.72; | 4.95; | 11.72 |

$^1$H-NMR (200 MHz,DMSO-$d_6$) δ: 0.88(3H,t), 1.28–1.47(2H,m), 1.65–1.80(2H,m), 2.85(2H,t), 5.90(2H,S), 6,90(2H,d), 7.17(2H,d), 7.26(1H,t), 7.42–7.69(5H,m), 7.85(1H,d).

IR(Nujol) cm$^{-1}$: 3400, 1700, 1430, 1410, 1335, 1230.

Working Example 65

Methyl 2-butyl-1-[[2'-(2,5-dihydro-5-oxo-1,2,4-thiadiazol-3-yl)biphenyl-4-yl]methyl]benzimidazole-7-carboxylate The tile compound (0.22g) was prepared in 44% yield according to the procedure described in Working Example 60 from the hydroxycarbamimidoyl derivative (0.46 g) obtained in Working Example 2. m.p. 178°–179° C.

Elemental Analysis for $C_{28}H_{26}N_4O_3S$:

| | C (%) | H (%) | N (%) |
|---|---|---|---|
| Calcd.: | 67.45; | 5.26; | 11.24 |
| Found: | 67.31; | 5.27; | 11.25 |

$^1$H-NMR (200 MHz,CDCl$_3$) δ: 0.92(3H,t), 1.30–1.50(2H,m), 1.60–1.73 (2H,m), 3.62(3H,s), 5.69(2H,s), 6.72(2H,d), 6.98–7.27 (5H,m), 7.53–7.80 (3H,m), 7.80–7.89 (1H,m), 11.35 (1H,brs)

IR(Nujol)cm$^{-1}$: 1720, 1700, 1660, 1435, 1290, 1280, 1265, 1125, 760, 750

Working Example 66

2-Butyl-1-[[2'-(2,5-dihydro-5-oxo-1,2,4-thiadiazol-3-yl]biphenyl-4-yl]methyl]benzimidazole-7-carboxylic acid The title compound (0.16 g) was prepared in 82% yield according to the procedure for Working Example 61 from the compound (0.2g) obtained in Working Example 65. m.p. 238°–239° C. (dec)

Elemental Analysis for $C_{27}H_{24}N_4O_3S \cdot \frac{1}{3} H_2O$:

| | C (%) | H (%) | N (%) |
|---|---|---|---|
| Calcd.: | 66.11; | 5.07; | 11.42 |
| Found: | 66.29; | 4.98; | 11.58 |

$^1$H-NMR (200 MHz, DMSO-$d_6$) δ: 0.88(3H,t), 1.27–1.45(2H,m), 1.65–1.80(2H,m), 2.83(2H,t), 5.88(2H,s), 6.87(2H,s), 7.14(2H,d), 7.24(1H,t), 7.41–7.64(5H,m), 7.83(2H,d)

IR(Nujol)cm$^{-1}$: 3255, 1675, 1450, 1420, 1240, 1230, 1205, 755

Working Example 67

Methyl 2-ethyl-1-[[2'-(2,5-dihydro-5-oxo-1,2,4-thiadiazol-3-yl)biphenyl-4-yl]methyl]benzimidazole-7-carboxylate The title compound (0.17g) was prepared in 38% yield according to the procedure for Working Example 60 from the compound (0.4g) obtained in Working Example 31. m.p. 203°–205° C.

Elemental Analysis for $C_{26}H_{22}N_4O_3S \cdot 0.5H_2O$:

| | C (%) | H (%) | N (%) |
|---|---|---|---|
| Calcd.: | 65.12; | 4.83; | 11.68 |
| Found: | 65.30 | 4.54; | 11.63; |

$^1$H-NMR (200 MHz,CDCl$_3$) δ: 1.13(3H,t), 2.64(2H,q), 3.53(3H,s), 5.62(2H,s), 6.59(2H,d), 6.8–7.9(7H,m)

IR(KBr)cm$^{-1}$: 1715, 1690, 1600, 1520

Working Example 68

2-Ethyl-1-[[2'-(2,5-dihydro-5-oxo-1,2,4-thiadiazol-3-yl)biphenyl-4-yl]methyl]benzimidazole-7-carboxylic acid The title compound (0.4g) was prepared in 58% yield according to the procedure for Working Example 61 from the ester (0.7g) obtained in Working Example 67.

$^1$H-NMR (200 MHz, DMSO-$d_6$) δ: 1.30(3H,t), 2.86(2H,q), 5.89(2H,s), 6.90(2H,d), 7.15(2H,d), 7.27(1H,t), 7.4–7.7(5H,m), 7.86(1H,d)

IR(KBr)cm$^{-1}$: 1700, 1655, 1570

Working Example 69

Methyl 2-ethyl-1-[[2'-(2,5-dihydro-5-thioxo-1,2,4-oxadiazol-3-yl)biphenyl-4-yl]methyl]benzimidazole-7-carboxylate The title compound (0.12g) was prepared in 22% yield) according to the procedure for Working Example 62 from the compound (0.45 g) obtained in Working Example 31.

$^1$H-NMR (200 MHz, CDCl$_3$) δ: 1.23(3H,t), 2.78(2H,q), 3.76(3H,s), 5.52(2H,s), 6.91(2H,d), 7.10(2H,d), 7.1–7.7(6H, m), 7.93(1H,d)

Working Example 70

Methyl 1-[[2'-(2,5-dihydro-5-thioxo-1,2,4-oxadiazol-3-yl)biphenyl-4-yl]metyl]-2-propylbenzimidazole-7-carboxylate 70a) Methyl 1-[[2'-(N-acetoxycarbamimidoyl)biphenyl-4-yl]methyl]2-propylbenzimidazole-7-carboxylate The title compound (0.95g) was prepared in 86% yield according to the procedure described in Working Example 63 from the hydrocarbamimidoyl derivative (1 g) obtained in Working Example 30. m.p. 177°–178° C.

Elemental Analysis for $C_{28}H_{28}N_4O_4S \cdot 0.1H_2O$ (486.36):

| | C (%) | H (%) | N (%) |
|---|---|---|---|
| Calcd.: | 69.15; | 5.84; | 11.52 |
| Found: | 68.93; | 5.80; | 11.54; |

$^1$H-NMR (200 MHz,CDCl$_3$) δ: 1.07 (3H,t), 1.84–2.03(2H,m), 2.15(3H,s), 2.91(2H,t), 3.74(3H,s), 4.57(2H,brs), 5.76(2H,s), 6.87(2H,d), 7.21–7.52(6H,m), 7.59–7.64(2H,m), 7.94(1H,dd)

IR(KBr)cm$^{-1}$: 3495, 3365, 1745, 1720, 1620, 1285, 1275, 1260, 1230, 1205

70b) Methyl 1-[[2'-(2,5-dihydro-5-thioxo-1,2,4-oxodiazol-3-yl)biphenyl-4-yl]methyl]2-propylbenzimidazole-7-carboxylate The title compound (0.14g) was prepared in 28% yield according to the procedure described in Working Example (63b) from the N-acetoxycarbamimidoyl derivative (0.5 g) obtained in Working Example (70a). m.p. 206°–209° C. (decomp.)

Elemental Analysis for $C_{27}H_{24}N_4O_3S.0.2H_2O$ (488.18):

|  | C (%) | H (%) | N (%) |
| --- | --- | --- | --- |
| Calcd.: | 66.43; | 5.04; | 11.48 |
| Found: | 66.42; | 5.14; | 11.51 |

$^1$H-NMR (200 MHz,DMSO-d$_6$) δ: 0.98(3H,t), 1.71.–1.90(2H,m), 2.88(2H,t), 3.65(3H,s), 5.73(2H,s), 6.89(2H,d), 7.21(2H,d), 7.28(1H,t), 7.44–7.72(5H,m), 7.88(1H,dd)

IR(KBr)cm$^{-1}$: 1725, 1450, 1435, 1410, 1335, 1325, 1285, 1270, 1210, 1125, 770, 760

Working Example 71

Methyl 1-[[2'-(2,5-dihydro-5-oxo-1,2,4-thiadiazol-3-yl)biphenyl-4-yl]methyl]-2-propylbenzimidazole-7-carboxylate The title compound (0.16g) was prepared in 25% yield according to the procedure described in Working Example 60 from the hydroxycarbamimidoyl derivative (0.58 g) obtained in Working Example 30. m.p. 225°–227° C. (decomp.)

Elemental Analysis for $C_{27}H_{24}N_4O_3S.0.2H_2O$

|  | C (%) | H (%) | N (%) |
| --- | --- | --- | --- |
| Calcd: | 66.43; | 5.04 | 11.48 |
| Found: | 66.64; | 5.16; | 11.26 |

$^1$H-NMR(200 MHz, CDCl$_3$) δ: 1.01(3H,t), 1.60–1.80(2H, m), 2.70(3H,t), 3.60(3H,s), 5.69(3H,s), 6,71(2H,d), 6.96–7.05(4H,m), 7.22–7.26(1H,m) 7.50–7.59(3H,m), 7.83–7.87(1H,m), 11.40(1H,brs)

IR(KBr)cm$^{-1}$: 1720, 1700, 1685, 1460, 1435, 1410, 1290, 1270, 1125, 755.

The following compounds are prepared according to the procedures described in Working Examples 1–71.

Working Example 72
1-[[2'-(2,5-dihydro-5-oxo-1,2,4-thiadiazol-3-yl)biphenyl-4-yl]methyl]-2-methoxybenzimidazole-7-carboxylic acid Working Example 73
1-[[2'-(2,5-dihydro-5-oxo-1,2,4-thiadiazol-3-yl)biphenyl-4-yl]methyl]-2-propoxybenzimidazole-7-carboxylic acid Working Example 74
1-[[2'-(2,5-dihydro-5-oxo-1,2,4-thiadiazol-3-yl)biphenyl-4-yl]methyl]-2-isopropoxybenzimidazole-7-carboxylic acid Working Example 75
2-butoxy-1-[[2'-(2,5-dihydro-5-oxo-1,2,4-thiadiazol-3-yl)biphenyl-4-yl]methyl]benzimidazole-7-carboxylic acid Working Example 76
1-[[2'-(2,5-dihydro-5-oxo-1,2,4-thiadiazol-3-yl)biphenyl-4-yl]methyl]-2-methylthiobenzimidazole-7-carboxylic acid Working Example 77
1-[[2'-(2,5-dihydro-5-oxo-1,2,4-thiadiazol-3-yl)biphenyl-4-yl]methyl]-2-ethylthiobenzimidazole-7-carboxylic acid Working Example 78
1-[[2'-(2,5-dihydro-5-oxo-1,2,4-thiadiazol-3-yl)biphenyl-4-yl]methyl]-2-propylthiobenzimidazole-7-carboxylic acid Working Example 79
1-[[2'-(2,5-dihydro-5-oxo-1,2,4-thiadiazol-3-yl)biphenyl-4-yl]methyl]-2-isopropylthiobenzimidazole-7-carboxylic acid Working Example 80
1-[[2'-(2,5-dihydro-5-oxo-1,2,4-thiadiazol-3-yl)biphenyl-4-yl]methyl]-2-methylaminobenzimidazole-7-carboxylic acid Working Example 81
1-[[2'-(2,5-dihydro-5-oxo-1,2,4-thiadiazol-3-yl)biphenyl-4-yl]methyl]-2-ethylaminobenzimidazole-7-carboxylic acid Working Example 82
1-[[2'-(2,5-dihydro-5-oxo-1,2,4-thiadiazol-3-yl)biphenyl-4-yl]methyl]-2-propylaminobenzimidazole-7-carboxylic acid Working Example 83
1-[[2'-(2,5-dihydro-5-oxo-1,2,4-thiadiazol-3-yl)biphenyl-4-yl]methyl]-2-methylbenzimidazole-7-carboxylic acid Working Example 84
2-cyclopropyl-1-[[2'-(2,5-dihydro-5-oxo-1,2,4-thiadiazol-3-yl)biphenyl-4-yl]methyl]benzimidazole-7-carboxylic acid Working Example 85
1-[[2'-(2,5-dihydro-5-oxo-1,2,4-thiadiazol-3-yl)biphenyl-4-yl]methyl]-2,4-dimethylthieno[3,4-d]imidazole-6-carboxylic acid Working Example 86
1-[[2'-(2,5-dihydro-5-oxo-1,2,4-thiadiazol-3-yl)biphenyl-4-yl]methyl]-2-ethyl-4-methylthieno[3,4-d]imidazole-6-carboxylic acid Working Example 87
1-[[2'-(2,5-dihydro-5-oxo-1,2,4-thiadiazol-3-yl)biphenyl-4-yl]methyl]-4-methyl-2-propylthieno[3,4-d]imidazole-6-carboxylic acid Working Example 88
2-cyclopropyl-1-[[2'-(2,5-dihydro-5-oxo-1,2,4-thiadiazol-3-yl)biphenyl-4-yl]methyl]-4-methylthieno[3,4-d]imidazole-6-carboxylic acid Working Example 89
1-[[2'-(2,5-dihydro-5-oxo-1,2,4-thiadiazol-3-yl)biphenyl-4-yl]methyl]-2-methoxy-4-methylthieno[3,4-d]imidazole-6-carboxylic acid Working Example 90
1-[[2'-(2,5-dihydro-5-oxo-1,2,4-thiadiazol-3-yl)biphenyl-4-yl]methyl]-2-ethoxy-4-methylthieno[3,4-d]imidazole-6-carboxylic acid Working Example 91

1-[[2'-(2,5-dihydro-5-oxo-1,2,4-thiadiazol-3-yl)biphenyl-4-yl]methyl]-4-methyl-4-propoxythieno[3,4-d]imidazole-6-carboxylic acid Working Example 92
1-[[2'-(2,5-dihydro-5-oxo-1,2,4-thiadiazol-3-yl)biphenyl-4-yl]methyl]-4-methyl-2methylthiothieno[3,4-d]imidazole-6-carboxylic acid Working Example 93
1-[[2'-(2,5-dihydro-5-oxo-1,2,4-thiadiazol-3-yl)biphenyl-4-yl]methyl]-2-ethylthio-4-methylthieno[3,4-d]imidazole-6-carboxylic acid Working Example 94
1-[[2'-(2,5-dihydro-5-oxo-1,2,4-thiadiazol-3-yl)biphenyl-4-yl]methyl]-4-methyl-2-methylaminothieno[3,4-d]imidazole-6-carboxylic acid Working Example 95
1-[[2'-(2,5-dihydro-5-oxo-1,2,4-thiadiazol-3-yl)biphenyl-4-yl]-methyl]-2-ethylamino-4-methylthieno[3,4-d]imidazole-6-carboxylic acid Working Example 96

1-[[2'-(2,5-dihydro-5-thioxo-1,2,4-oxadiazol-3-yl)biphenyl-4-yl]methyl]-2-methoxybenzimidazole-7-carboxylic acid
Working Example 97
1-[[2'-(2,5-dihydro-5-thioxo-1,2,4-oxadiazol-3-yl)biphenyl-4-yl]methyl]-2-propoxybenzimidazole-7-carboxylic acid
Working Example 98
1-[[2'-(2,5-dihydro-5-thioxo-1,2,4-oxadiazol-3-yl)biphenyl-4-yl]methyl]-2-isopropoxybenzimidazole-7-carboxylic acid
Working Example 99
2-butoxy-1-[[2'-(2,5-dihydro-5-thioxo-1,2,4-oxadiazol-3-yl)biphenyl-4-yl]methyl]benzimidazole-7-carboxylic acid
Working Example 100
1-[[2'-(2,5-dihydro-5-thioxo-1,2,4-oxadiazol-3-yl)biphenyl-4-yl]methyl]-2-methylthiobenzimidazole-7-carboxylic acid
Working Example 101
1-[[2'-(2,5-dihydro-5-thioxo-1,2,4-oxadiazol-3-yl)biphenyl-4-yl]methyl]-2-ethylthiobenzimidazole-7-carboxylic acid
Working Example 102
1-[[2'-(2,5-dihydro-5-thioxo-1,2,4-oxadiazol-3-yl)biphenyl-4-yl]methyl]-2-propylthiobenzimidazole-7-carboxylic acid
Working Example 103
1-[[2'-(2,5-dihydro-5-thioxo-1,2,4-oxadiazol-3-yl)biphenyl-4-yl]methyl]-2-isopropylthiobenzimidazole-7-carboxylic acid
Working Example 104
1-[[2'-(2,5-dihydro-5-thioxo-1,2,4-oxadiazol-3-yl)biphenyl-4-yl]methyl]-2-methylaminobenzimidazole-7-carboxylic acid
Working Example 105
1-[[2'-(2,5-dihydro-5-thioxo-1,2,4-oxadiazol-3-yl)biphenyl-4-yl]methyl]-2-ethylaminobenzimidazole-7-carboxylic acid
Working Example 106
1-[[2'-(2,5-dihydro-5-thioxo-1,2,4-oxadiazol-3-yl)biphenyl-4-yl]methyl]-2-propylaminobenzimidazole-7-carboxylic acid
Working Example 107
1-[[2'-(2,5-dihydro-5-thioxo-1,2,4-oxadiazol-3-yl)biphenyl-4-yl]methyl]-2-methylbenzimidazole-7-carboxylic acid
Working Example 108
2-cyclopropyl-1-[[2'-(2,5-dihydro-5-thioxo-1,2,4-oxadiazol-3-yl)biphenyl-4-yl]methyl]benzimidazole-7-carboxylic acid
Working Example 109
1-[[2'-(2,5-dihydro-5-thioxo-1,2,4-oxadiazol-3-yl)biphenyl-4-yl]methyl]-2,4-dimethylthieno[3,4-d]imidazole-6-carboxylic acid
Working Example 110
1-[[2'-(2,5-dihydro-5-thioxo-1,2,4-oxadiazol-3-yl)biphenyl-4-yl]methyl]-2-ethyl-4-methylthieno[3,4-d]imidazole-6-carboxylic acid
Working Example 111
1-[[2'-(2,5-dihydro-5-thioxo-1,2,4-oxadiazol-3-yl)biphenyl-4-yl]methyl]-4-methyl-2-propylthieno[3,4-d]imidazole-6-carboxylic acid
Working Example 112
2-cyclopropyl-1-[[2'-(2,5-dihydro-5-thioxo-1,2,4-oxadiazol-3-yl)biphenyl-4-yl]methyl]-4-methylthieno[3,4-d]imidazole-6-carboxylic acid
Working Example 113
1-[[2'-(2,5-dihydro-5-thioxo-1,2,4-oxadiazol-3-yl)biphenyl-4-yl]methyl]-2-methoxy-4-methylthieno[3,4-d]imidazole-6-carboxylic acid
Working Example 114
1-[[2'-(2,5-dihydro-5-thioxo-1,2,4-oxadiazol-3-yl)biphenyl-4-yl]methyl]-2-ethoxy-4-methylthieno[3,4-d]imidazole-6-carboxylic acid
Working Example 115
1-[[2'-(2,5-dihydro-5-thioxo-1,2,4-oxadiazol-3-yl)biphenyl-4-yl]methyl]-4-methyl-2-propoxythieno[3,4-d]imidazole-6-carboxylic acid
Working Example 116
1-[[2'-(2,5-dihydro-5-thioxo-1,2,4-oxadiazol-3-yl)biphenyl-4-yl]methyl]-4-methyl-2-methylthiothieno[3,4-d]imidazole-6-carboxylic acid
Working Example 117
1-[[2'-(2,5-dihydro-5-thioxo-1,2,4-oxadiazol-3-yl)biphenyl-4-yl]methyl]-2-ethylthio-4-methylthieno[3,4-d]imidazole-6-carboxylic acid
Working Example 118
1-[[2'-(2,5-dihydro-5-thioxo-1,2,4-oxadiazol-3-yl)biphenyl-4-yl]methyl]-4-methyl-2-methylaminothieno[3,4-d]imidazole-6-carboxylic acid
Working Example 119
1-[[2'-(2,5-dihydro-5-thioxo-1,2,4-oxadiazol-3-yl)biphenyl-4-yl]methyl]-2-ethylamino-4-methylthieno[3,4-d]imidazole-6-carboxylic acid
Working Example 120
1-[[2'-(2,5-dihydro-5-thioxo-1,2,4-thiadiazol-3-yl)biphenyl-4-yl]methyl]-2-methoxybenzimidazole-7-carboxylic acid
Working Example 121
1-[[2'-(2,5-dihydro-5-thioxo-1,2,4-thiadiazol-3-yl)biphenyl-4-yl]methyl]-2-ethoxybenzimidazole-7-carboxylic acid
Working Example 122
2-butyl-1-[[2'-(2,5-dihydro-5-thioxo-1,2,4-thiadiazol-3-yl)biphenyl-4-yl]methyl]benzimidazole-7-carboxylic acid
Working Example 123
1-[[2'-(2,5-dihydro-5-thioxo-1,2,4-thiadiazol-3-yl)biphenyl-4-yl]methyl]-2-ethylthiobenzimidazole-7-carboxylic acid
Working Example 124
1-[[2'-(2,5-dihydro-5-thioxo-1,2,4-thiadiazol-3-yl)biphenyl-4-yl]methyl]-2-methoxy-4-methylthieno[3,4-d]imidazole-6-carboxylic acid
Working Example 125
1-[[2'-(2,5-dihydro-5-thioxo-1,2,4-thiadiazol-3yl)biphenyl-4-yl]methyl]-2-ethoxy-4-methylthieno[3,4-d]imidazole-6-carboxylic acid
Working Example 126
2-butyl-1-[[2'-(2,5-dihydro-5-thioxo-1,2,4-thiadiazol-3-yl)biphenyl-4-yl]methyl]-4-methylthieno[3,4-d]imidazole-6-carboxylic acid
Working Example 127
1-[[2'-(2,5-dihydro-5-thioxo-1,2,4-thiadiazol-3-yl)biphenyl-4-yl]methyl]-2-ethylthio-4-methylthieno[3,4-d]imidazole-6-carboxylic acid
Working Example 128
2-ethyl-3-[[2'-(2,5-dihydro-5-oxo-1,2,4-thiadiazol-3-yl)biphenyl-4-yl]methyl]-5,7-dimethylimidazo[4,5-b]pyridine
Working Example 129
2-propyl-3-[[2'-(2,5-dihydro-5-oxo-1,2,4-thiadiazol-3-yl)biphenyl-4-yl]methyl]-5,7-dimethylimidazo[4,5-b]pyridine
Working Example 130
2-butyl-3-[[2'-(2,5-dihydro-5-oxo-1,2,4-thiadiazol-3-yl)biphenyl-4-yl]methyl]-5,7-dimethylimidazo[4,5-b]pyridine
Working Example 131
2-methoxy-3-[[2'-(2,5-dihydro-5-oxo-1,2,4-thiadiazol-3-yl)biphenyl-4-yl]methyl]-5,7-dimethylimidazo[4,5-b]pyridine
Working Example 132
2-ethoxy-3-[[2'-[2,5-dihydro-5-oxo-1,2,4-thiadiazol-3-yl)biphenyl-4-yl]methyl]-5,7-dimethylimidazo[4,5-b]pyridine
Working Example 133
2-propoxy-3-[[2'-(2,5-dihydro-5-oxo-1,2,4-thiadiazol-3-yl)biphenyl-4-yl]methyl]-5,7-dimethylimidazo[4,5-b]pyridine
Working Example 134
2-cyclopropyl-3-[[2'-(2,5-dihydro-5-oxo-1,2,4-thiadiazol-3-yl)biphenyl-4-yl]methyl]-5,7-dimethylimidazo[4,5-b]pyridine Working Example 135
2-ethyl-3-[[2'-(2,5-dihydro-5-thioxo-1,2,4-oxadiazol-3-yl)biphenyl-4-yl]methyl]-5,7-dimethylimidazo[4,5-b]pyridine Working Example 136
2-propyl-3-[[2'-(2,5-dihydro-5-thioxo-1,2,4-oxadiazol-3-yl)biphenyl-4-yl]methyl]-5,7-dimethylimidazo[4,5-b]pyridine Working Example 137
2-butyl-3-[[2'-(2,5-dihydro-5-thioxo-1,2,4-oxadiazol-3-yl)biphenyl-4-yl]methyl]-5,7-dimethylimidazo[4,5-b]pyridine Working Example 138
2-methoxy-3-[[2-(2,5-dihydro-5-thioxo-1,2,4-oxadiazol-3-yl)biphenyl-4-yl]methyl]-5,7-dimethylimidazo[4,5-b]pyridine Working Example 139
2-ethoxv-3-[[2'-(2,5-dihydro-5-thioxo-1,2,4-oxadiazol-3-yl)biphenyl-4-yl]methyl]-5,7-dimethylimidazo[4,5-b]pyridine Working Example 140
2-propoxy-3-[[2'-(2,5-dihydro-5-thioxo-1,2,4-oxadiazol-3-yl)biphenyl-4-yl]methyl]-5,7-dimethylimidazo[4,5-b]pyridine Working Example 141
2-cyclopropyl-3-[[2'-(2,5-dihydro-5-thioxo-1,2,4-oxadiazol-3-yl)biphenyl-4-yl]methyl]-5,7-dimethylimidazo[4,5-b]pyridine Working Example 142
2-methyl-3-[[2'-(2,5-dihydro-5-thioxo-1,2,4'-thiadiazol-3-yl)biphenyl-4-yl]methyl]-5,7-dimethylimidazo[4,5-b]pyridine Working Example 143
2-ethyl-3-[[2'-(2,5-dihydro-5-thioxo-1,2,4-thiadiazol-3-yl)biphenyl-4-yl]methyl]-5,7-dimethylimidazo[4,5-b]pyridine Working Example 144
2-cyclopropyl-3-[[2'-(2,5-dihydro-5-thioxo-1,2,4-thiadiazol-3-yl)biphenyl-4-yl]methyl]-5,7-dimethylimidazo[4,5-b]pyridine Working Example 145
2-ethoxy-3-[[2'-(2,5-dihydro-5-thioxo-1,2,4-thiadiazol-3-yl)biphenyl-4-yl]methyl]-5,7-dimethylimidazo[4,5-b]pyridine Experimental Example 1
Inhibitory Effect of Binding of Angiotensin-II to Angiotensin Receptor

[Method]

An experiment of inhibition on the binding of angiotensin II (A-II) receptor was conducted by modifying the method of Douglas et al. [Endocrinology, 102, 685–696 (1978)]. An A-II receptor membrane fraction was prepared from bovine adrenal cortex.

The compound of the present invention ($10^{-6}$M or $10^{-7}$M and $^{125}$I-angiotensin II ($^{125}$I-AII) (1.85 kBq/50 microliter) were added to the receptor membrane fraction, and the mixture was incubated at room temperature for one hour. The receptor-bound and free $^{125}$I-AII were separated through a filter (Whatman GF/B filter), and the radioactivity of $^{125}$I-AII bound to the receptor was determined.

[Results]

The results relating to the compounds of the present invention are shown in [Table 1].

Experimental Example 2
Inhibitory Effect of the Compound of the Present Invention on Pressor Action of AII

[Method]

Jcl: SD rat (9 week old, male) were employed. on the day prior to the experiment, these animals were applied with cannulation into the femoral artery and vein under anesthesia with pentobarbital Na. These animals were fasted but allowed to free acess to drinking water until the experiment was started. Just on the day of conducting the experiment, the artery cannula was connected with a blood-pressure transducer, and the average blood pressure was recorded by means of polygraph. Before administration of the drug, the pressor action due to intravenous administration of A-II (100 ng/kg) as the control was determined. The drugs were orally administered, then, at each point of the determination, A-II was administered intravenously, and the pressor action was similarly determined. By comparing the pressor action before and after administration of the drug, the percent inhibition by the drug on A-II-induced pressor action was evaluated.

[Results]

The results relating to the compounds of the present invention are shown in [Table I].

TABLE 1

| Example No. | Chemical Formula | Radioreceptor assay % inhibition | Pressor Response to A II (p.o.) 1 mg/kg | 3 mg/kg |
|---|---|---|---|---|
| 1 | (structure) | 79 ($10^{-6}$M) 34 ($10^{-7}$M) | +++ | +++[a] |

TABLE 1-continued
| Example No. | Chemical Formula | Radioreceptor assay % inhibition | Pressor Response to A II (p.o.) | |
|---|---|---|---|---|
| | | | 1 mg/kg | 3 mg/kg |
| 3 | 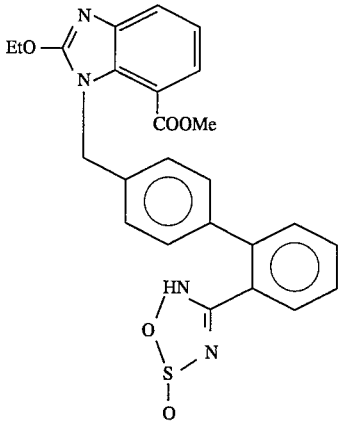 | 75 ($10^{-6}$ M)<br>33 ($10^{-7}$ M) | | +++ |
| 9 | 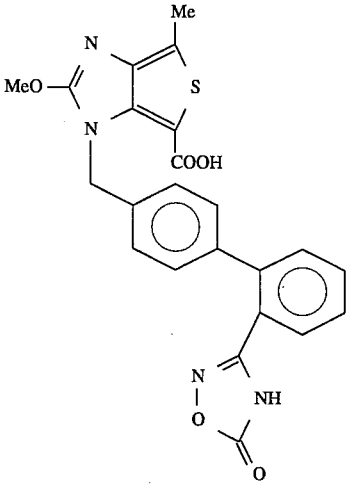 | 55 ($10^{-6}$ M)<br>19 ($10^{-7}$ M) | +++ | +++ |
| 4 | 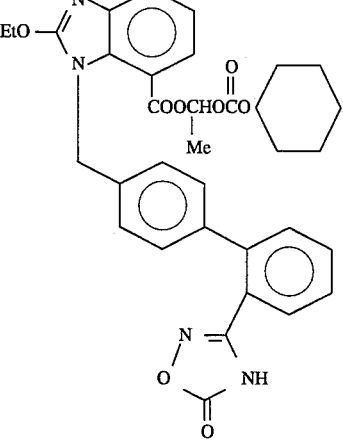 | 44 ($10^{-6}$ M)<br>17 ($10^{-7}$ M) | | +++ |

TABLE 1-continued

| Example No. | Chemical Formula | Radioreceptor assay % inhibition | Pressor Response to A II (p.o.) 1 mg/kg | 3 mg/kg |
|---|---|---|---|---|
| 8 | (structure with EtS-, Me, thiophene-imidazole, COOH, biphenyl, oxadiazolone) | 40 (10$^{-6}$ M) <br> 8 (10$^{-7}$ M) | +++ | |
| 10 | (structure with EtO-, Me, thiophene-imidazole, COOH, biphenyl, oxadiazolone) | 51 (10$^{-6}$ M) <br> 17 (10$^{-7}$ M) | +++ | |
| 11 | (structure with Pro-, Me, thiophene-imidazole, COOH, biphenyl, oxadiazolone) | 41 (10$^{-6}$ M) <br> 10 (10$^{-7}$ M) | +++ | |

TABLE 1-continued

| Example No. | Chemical Formula | Radioreceptor assay % inhibition | Pressor Response to A II (p.o.) 1 mg/kg | 3 mg/kg |
|---|---|---|---|---|
| 12 | (structure) | 78 ($10^{-6}$ M) 46 ($10^{-7}$ M) | + | |
| 13 | (structure) | 69 ($10^{-6}$ M) 31 ($10^{-7}$ M) | +++ | |
| 30 | (structure) | 77 ($10^{-6}$ M) 35 ($10^{-7}$ M) | +++ | |

TABLE 1-continued

| Example No. | Chemical Formula | Radioreceptor assay % inhibition | Pressor Response to A II (p.o.) 1 mg/kg | 3 mg/kg |
|---|---|---|---|---|
| 31 | (structure: 2-ethylbenzimidazole-7-COOH, N-CH2-biphenyl-oxadiazolone) | 79 ($10^{-6}$ M)<br>41 ($10^{-7}$ M) | +++ | |
| 32c | (structure: 2-cyclopropylbenzimidazole-7-COOMe, N-CH2-biphenyl-oxadiazolone) | 79 ($10^{-6}$ M)<br>40 ($10^{-7}$ M) | +++ | |
| 32 | (structure: 2-cyclopropylbenzimidazole-7-COOH, N-CH2-biphenyl-oxadiazolone) | 75 ($10^{-6}$ M)<br>27 ($10^{-7}$ M) | +++ | |

TABLE 1-continued

| Example No. | Chemical Formula | Radioreceptor assay % inhibition | Pressor Response to A II (p.o.) 1 mg/kg | 3 mg/kg |
|---|---|---|---|---|
| 33 | (Bu-benzimidazole-COOH-biphenyl-oxadiazolone structure) | 70 ($10^{-6}$ M)<br>23 ($10^{-7}$ M) | ++ | |
| 35 | (MeO-benzimidazole-COOH-biphenyl-oxadiazolone structure) | 79 ($10^{-6}$ M)<br>38 ($10^{-7}$ M) | +++ | |
| 36 | (Pro-benzimidazole-COOH-biphenyl-oxadiazolone structure) | 60 ($10^{-6}$ M)<br>18 ($10^{-7}$ M) | +++ | |

TABLE 1-continued

| Example No. | Chemical Formula | Radioreceptor assay % inhibition | Pressor Response to A II (p.o.) | |
|---|---|---|---|---|
| | | | 1 mg/kg | 3 mg/kg |
| 56 | 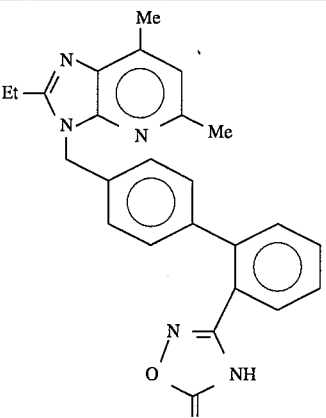 | 94 ($10^{-6}$ M)<br>80 ($10^{-7}$ M) | +++ | |
| 60 | 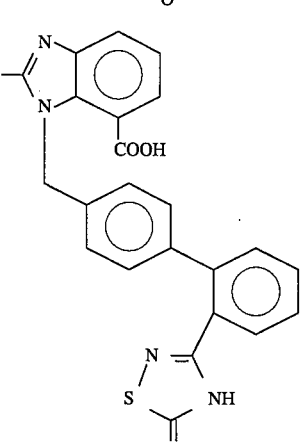 | 84 ($10^{-6}$ M)<br>43 ($10^{-7}$ M) | +++ | |

[a] +++ ≧ 70% > ++ ≧ 50% > +

What is claimed is:

1. A compound or a salt thereof:

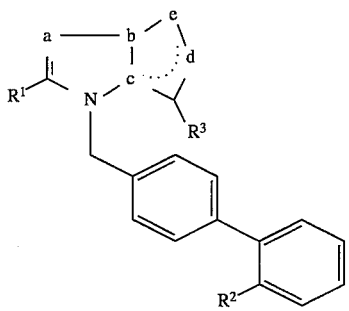

wherein $R^1$ is an optionally substituted hydrocarbon residue which is optionally bound through a hetero-atom;

$R^2$ is a group of the formula:

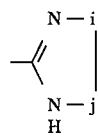

wherein i is —O— or —S— and j is >c=0 or >c=S;

$R^3$ is optionally esterified or amidated carboxyl, tetrazolyl, trifluoromethanesulfonic amide, phosphoric acid or sulfonic acid, which may be protected with optionally substituted lower alkyl or acyl and the group of the formula

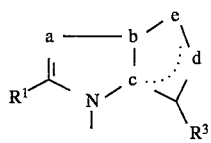

has a structure selected from the group consisting of

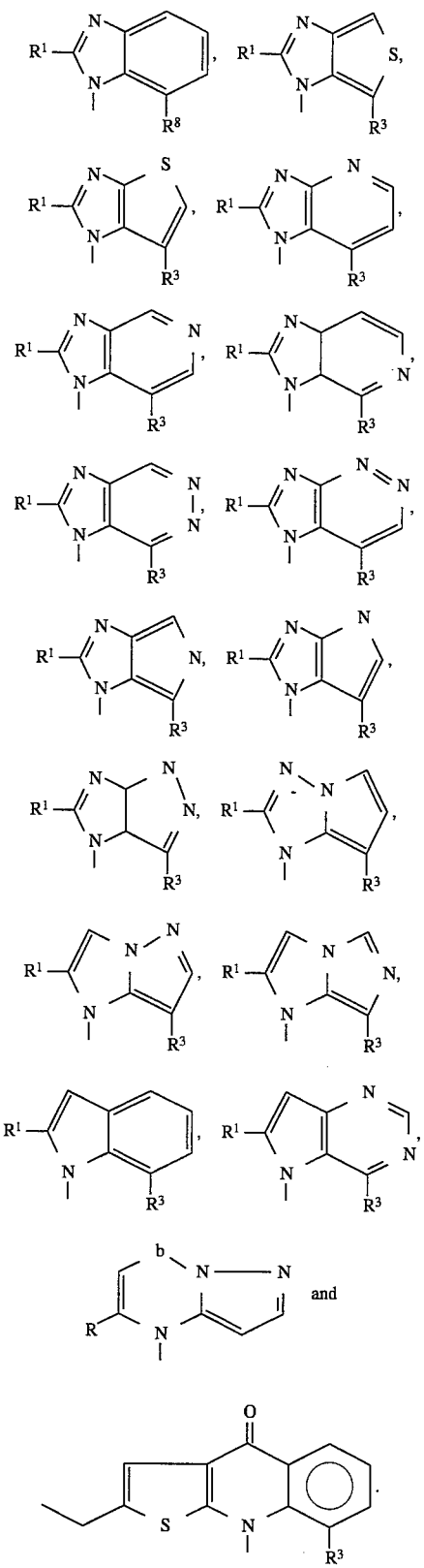

wherein in addition to $R^1$ and $R^3$, a methyl substituent may be provided, and wherein h is $CH_2$, $C=O$, $C=S$, $S-(O)_m$, $NR^9$ and O wherein m denotes an integer of 0–2 and $R^9$ is hydrogen or lower(1–4C)alkyl, and excluding the compound 2-ethoxy-1-[[2'-(2,5-dihydro-5-oxo-1,2,4-oxadiazol-3-yl)biphenyl-4-yl]methyl]benzimidazole-7-carboxylic acid and its physiologically acceptable salts.

2. A compound or a salt thereof according to claim 1, wherein $R^1$ is lower ($C_{2-4}$) alkyl which may be bound through —O—, —NH— or —S—.

3. A compound or a salt thereof according to claim 1, wherein $R^3$ is a group of the formula: —CO—D wherein D is hydroxy, amino, N-lower ($C_{1-4}$) alkylamino, N, N-di-lower ($C_{1-4}$) alkylamino, lower ($C_{1-6}$) alkoxy, lower ($C_{1-6}$) alkylthio or optionally substituted dioxolenyl, or a group of the formula: —O—CH($R^4$)—OCOR$^5$ wherein $R^4$ is hydrogen, lower ($C_{1-6}$) alkyl, lower ($C_{2-6}$) alkenyl or lower ($C_{3-8}$) cycloalkyl; and $R^5$ is lower ($C_{1-6}$) alkyl, lower ($C_{2-6}$) alkenyl, lower ($C_{3-8}$) cycloalkyl, lower ($C_{1-3}$) alkyl substituted with lower ($C_{3-8}$) cycloalkyl or aryl, lower ($C_{2-3}$) alkenyl optionally substituted with lower ($C_{3-8}$) cycloalkyl or aryl, aryl, lower ($C_{1-6}$) alkoxy, lower ($C_{2-8}$) alkenyloxy, lower ($C_{3-8}$) cycloalkyloxy, lower ($C_{1-3}$) alkoxy substituted with lower ($C_{3-8}$) cycloalkyl or aryl, lower ($C_{2-3}$) alkenyloxy substituted with lower ($C_{3-8}$) cycloalkyl or aryl, or aryloxy.

4. A compound or a salt thereof according to claim 1, wherein $R^3$ is a group of the formula: —CO—D" wherein D" is hydroxy, amino, N-lower ($C_{1-4}$) alkylamino, N,N-di-lower ($C_{1-4}$) alkylamino or lower ($C_{1-4}$) alkoxy whose alkyl moiety may be substituted by hydroxy, amino, halogen, lower ($C_{2-6}$) alkanoyloxy, 1-lower ($C_{1-6}$) alkoxycarbonyl or lower ($C_{1-4}$) alkoxy, or tetrazolyl optionally protected with lower ($C_{1-4}$) alkyl or acyl.

5. A compound or a salt thereof according to claim 1, wherein $R^3$ is optionally esterified carboxyl.

6. A compound or a salt thereof according to claim 1, wherein the group of the formula:

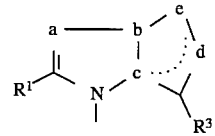

is benzimidazole, thienoimidazole or imidazopyridine structure.

7. A compound or a salt thereof according to claim 1, wherein the group

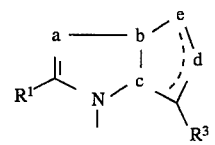

is

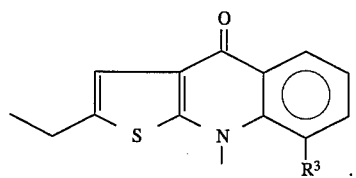

8. A compound or a salt thereof according to claim 1, wherein $R^3$ is optionally esterified or amidated carboxyl.

9. A compound or a salt thereof according to claim 8, wherein $R^3$ is a group of the formula: —CO—D wherein D is hydroxy, optionally substituted amino or optionally substituted alkoxy.

10. A compound or a salt thereof according to claim 9, wherein the optionally substituted alkoxy is lower ($C_{1-6}$) alkoxy whose alkyl moiety may be substituted by hydroxy, optionally substituted amino, halogen, lower ($C_{1-6}$) alkoxy, lower ($C_{1-6}$) alkylthio or optionally substituted dioxolenyl, or a group of the formula: —O—CH($R^4$)—OCOR$^5$ wherein $R^4$ is hydrogen, lower ($C_{1-6}$) alkyl, lower ($C_{2-6}$) alkenyl or lower ($C_{3-8}$) cycloalkyl; and $R^5$ is lower ($C_{1-6}$) alkyl, lower ($C_{2-6}$) alkenyl, lower ($C_{3-8}$) cycloalkyl, lower ($C_{1-3}$) alkyl substituted with lower ($C_{3-8}$) cycloalkyl or aryl, lower ($C_{2-3}$) alkenyl optionally substituted with lower ($C_{3-8}$) cycloalkyl or aryl, aryl, lower ($C_{1-6}$) alkoxy, lower ($C_{2-8}$) alkenyloxy, lower ($C_{3-8}$) cycloalkyloxy, lower ($C_{1-3}$) alkoxy substituted with lower ($C_{3-8}$) cycloalkyl or aryl, lower ($C_{2-3}$) alkenyloxy substituted with lower ($C_{3-8}$) cycloalkyl or aryl, or aryloxy.

11. A compound or a salt thereof according to claim 8, wherein $R^3$ is carboxyl.

12. A compound or a salt thereof according to claim 1, wherein $R^1$ is alkyl, alkenyl, alkynyl or cycloalkyl which may be bound through a group of the formula: —N($R^9$)— wherein $R^9$ is hydrogen or lower ($C_{1-4}$) alkyl, —O— or —S(O)$_m$— wherein m is an integer of 0 to 2 and which may be substituted with hydroxy, optionally substituted amino, halogen, lower ($C_{1-4}$) alkoxy or lower ($C_{1-4}$) alkylthio.

13. A compound or a salt thereof according to claim 1, wherein $R^1$ is aryl or aralkyl which may be bound through a group of the formula: —N($R^9$)— wherein $R^9$ is hydrogen or lower ($C_{1-4}$) alkyl, —O— or —S(O)$_m$— wherein m is an integer of 0 to 2 and which may be substituted with halogen, nitro, optionally substituted amino, lower ($C_{1-4}$) alkoxy, lower ($C_{1-4}$) alkylthio or lower ($C_{1-4}$) alkyl.

14. A compound or a salt thereof according to claim 1, wherein $R^1$ is lower ($C_{1-8}$) alkyl or lower ($C_{2-8}$) alkenyl which may be bound through a group of the formula: —N($R^9$)— wherein $R^9$ is hydrogen or lower ($C_{1-4}$) alkyl, —O— or —S(O)$_m$ wherein m is an integer of 0 to 2 and which may be substituted with hydroxy, amino, N-lower ($C_{1-4}$) alkylamino, N,N-dilower ($C_{1-4}$) alkylamino, halogen, lower ($C_{1-4}$) alkoxy or lower ($C_{1-4}$) alkylthio.

15. A compound or a salt thereof according to claim 1, wherein $R^1$ is lower ($C_{1-5}$) alkyl or lower ($C_{2-5}$) alkenyl which may be bound through a group of the formula: —N($R^9$)— wherein $R^9$ is hydrogen or lower ($C_{1-4}$) alkyl, —O— or —S(O)$_m$— wherein m is an integer of 0 to 2 and which may be substituted with hydroxy, amino, halogen or lower ($C_{1-4}$) alkoxy.

16. A compound or a salt thereof according to claim 1, wherein $R^2$ is 2,5-dihydro-5-oxo-1,2,4-oxadiazol-3-yl group.

17. A compound or a salt thereof according to claim 1, wherein $R^2$ is 2,5-dihydro-5-oxo-1,2,4-thiadiazol-3-yl group.

18. A compound or a salt thereof according to claim 1, wherein $R^2$ is 2,5-dihydro-5-thioxo-1,2,4-oxadiazol-3-yl group.

19. A compound or a salt according to claim 1, wherein the group of the formula:

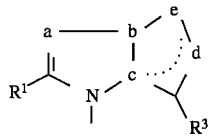

is benzimidazole or imidazopyridine.

20. A compound or a salt according to claim 19, wherein $R^2$ is 2,5-dihydro-5-oxo-1,2,4-oxadiazol-3-yl or 2,5-dihydro-5-oxo-1,2,4-thiadiazol-3-yl.

21. A compound or a salt according to claim 1, wherein the group of the formula:

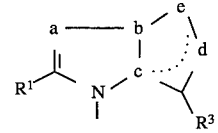

has a structure selected from the group consisting of

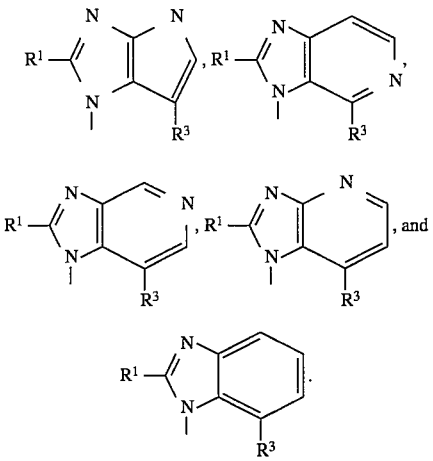

22. A compound or a salt according to claim 21, wherein $R^2$ is 2,5-dihydro-5-oxo-1,2,4-oxadiazol-3-yl or 2,5-dihydro-5-oxo-1,2,4-thiadiazol-3-yl.

23. A compound or a salt thereof of formula:

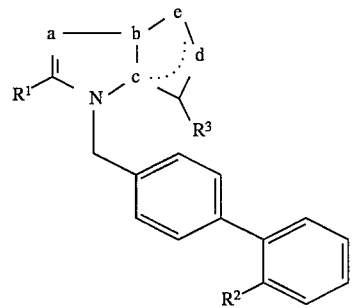

wherein $R^1$ is lower ($C_{1-5}$) alkyl which may be bound through —O—, —NH— or —S— and which may be substituted with hydroxy, amino, N-lower ($C_{1-4}$) alkylamino, N,N-di-lower ($C_{1-4}$) alkylamino, halogen, lower ($C_{1-4}$) alkoxy or lower ($C_{1-4}$) alkylthio;

$R^2$ is a group of the formula:

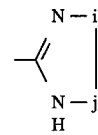

wherein i is —O— or —S— and j is >c=O or >c=S;

$R^3$ is optionally esterified or amidated carboxyl, tetrazolyl, trifluoromethanesulfonic amide, phosphoric acid or sulfonic acid, which may be protected with optionally substituted lower alkyl or acyl and the group of the formula

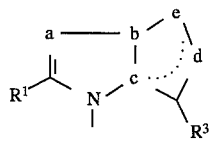

has a structure selected from the group consisting of

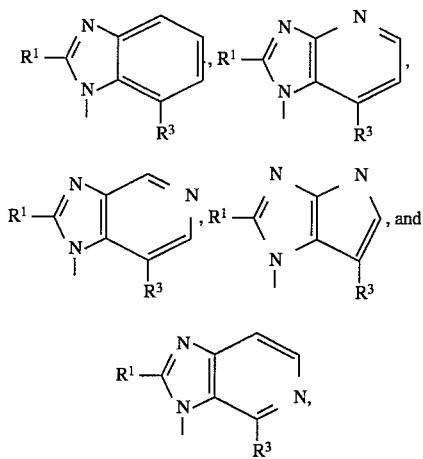

wherein in addition to $R^1$ and $R^3$, a methyl substituent may be provided, and excluding the compound 2-ethoxy-1-[[2'-(2,5-dihydro-5-oxo-1,2,4-oxadiazol-3-yl)biphenyl-4-yl]methyl]benzimidazole-7-carboxylic acid and its physiologically acceptable salts thereof.

24. A compound according to claim 1, which is 1-(cyclohexyloxycarbonyloxy)ethyl 2-ethoxy-1-[[2'-(2,5-dihydro-5-oxo-1,2,4-oxadiazol-3-yl)biphenyl-4-yl]methyl]benzimidazole-7-carboxylate.

25. A compound according to claim 1, which is 1-[2'-(2,5-dihydro-5-oxo-1,2,4-oxadiazol-3-yl)biphenyl-4-yl]methyl-4-methyl-2-propoxythieno[3,4-d]imidazole-6-carboxylic acid.

26. A compound according to claim 1, which is 2-ethyl-1-[[2'-(2,5-dihydro-5-oxo-1,2,4-oxadiazol-3-yl)biphenyl-4-yl]methyl]benzimidazole-7-carboxylic acid.

27. A compound according to claim 1, which is 2-ethoxy-1-[[2'-(2,5-dihydro-5-oxo-1,2,4-thiadiazol-3-yl)biphenyl-4-yl]methyl]benzimidazole-7-carboxylic acid.

28. A compound according to claim 1, which is 2-ethyl-3-[[2'-(2,5-dihydro-5-oxo-1,2,4-oxadiazol-3-yl)biphenyl-4-yl]methyl]-5,7-dimethylimidazo[4.5-b]pyridine.

29. A compound according to claim 1, which is 1-[[2'-(2,5-dihydro-5-oxo-1,2,4-oxadiazol-3-yl)biphenyl-4-yl]methyl]2-methoxy-4-methylthieno[3,4-d]imidazole-6-carboxylic acid.

30. A compound according to claim 1, which is 2-cyclopropyl-1-[[2'-(2,5-dihydro-5-oxo-1,2,4-oxadiazol-3-yl)biphenyl-4-yl]methyl]benzimidazole-7-carboxylic acid.

31. A pharmaceutical composition for antagonizing angiotensin II which comprises a therapeutically effective amount of a compound according to claim 1 or a pharmaceutically acceptable salt thereof in admixture with a pharmaceutical acceptable carrier, excipient or diluent.

32. A method for antagonizing angiotensin II in a mammal which comprises administering to said mammal a therapeutically effective amount of a compound according to claim 1 or a pharmaceutically acceptable salt thereof.

* * * * *

UNITED STATES PATENT AND TRADEMARK OFFICE
CERTIFICATE OF CORRECTION

Page 1 of 3

PATENT NO. : 5,583,141
DATED : December 10, 1996
INVENTOR(S) : Takehiko NAKA et al.

It is certified that error appears in the above-indentified patent and that said Letters Patent is hereby corrected as shown below:

Please note that Column 22, line 6, contains a typographical error wherein "alkoxycarbonyl" should read --alkoxycarbonyloxy--.

Column 137, between lines 2-8, delete

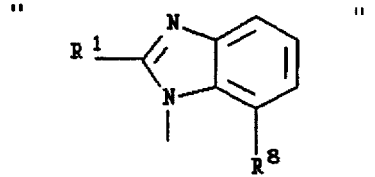

and insert

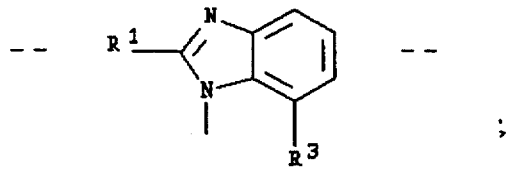

;

UNITED STATES PATENT AND TRADEMARK OFFICE
CERTIFICATE OF CORRECTION

Page 2 of 3

PATENT NO. : 5,583,141
DATED : December 10, 1996
INVENTOR(S) : Takehiko NAKA et al.

It is certified that error appears in the above-indentified patent and that said Letters Patent is hereby corrected as shown below:

between lines 50-55, delete

"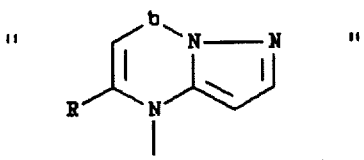"

and insert

--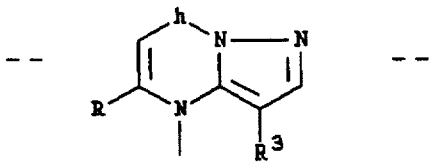--

Column 137, line 66, claim 1, wherein "and" (first occurrence) should read --or--.

UNITED STATES PATENT AND TRADEMARK OFFICE
CERTIFICATE OF CORRECTION

PATENT NO. : 5,583,141
DATED : December 10, 1996
INVENTOR(S) : Takehiko NAKA et al.

It is certified that error appears in the above-indentified patent and that said Letters Patent is hereby corrected as shown below:

Column 138, line 10, claim 3, after "alkoxy" insert -- whose alkyl moiety is optionally substituted with hydroxyl group, amino, dimethylamino, diethylamino, piperidino, morpholino, halogen, lower ($C_{1-6}$) alkoxy,--;
  line 27, claim 4, wherein "alkoxycarbonyl" should read --alkoxycarbonyloxy--.

Column 142, line 14, claim 28, "according to claim 1" should read --or a salt thereof--;
  line 20, claim 29, "thyl]2-methoxy" should read --thyl]-2-methoxy--;
  line 28, claim 31, "pharmaceutical" should read --pharmaceutically--.

Signed and Sealed this

Sixteenth Day of December, 1997

Attest:

BRUCE LEHMAN

*Attesting Officer*    *Commissioner of Patents and Trademarks*